United States Patent
Schreiber et al.

(10) Patent No.: US 12,145,975 B2
(45) Date of Patent: Nov. 19, 2024

(54) FUSION PROTEINS FOR THE TREATMENT OF CARDIOMETABOLIC DISEASES

(71) Applicant: Shattuck Labs, Inc., Austin, TX (US)

(72) Inventors: Taylor Schreiber, Austin, TX (US); George Fromm, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 0 days.

(21) Appl. No.: 18/599,583

(22) Filed: Mar. 8, 2024

(65) Prior Publication Data

US 2024/0218040 A1 Jul. 4, 2024

Related U.S. Application Data

(63) Continuation of application No. PCT/US2023/082572, filed on Dec. 5, 2023.

(60) Provisional application No. 63/579,243, filed on Aug. 28, 2023, provisional application No. 63/386,107, filed on Dec. 5, 2022.

(51) Int. Cl.
| | |
|---|---|
| *C07K 14/605* | (2006.01) |
| *A61K 38/00* | (2006.01) |
| *A61P 3/04* | (2006.01) |
| *A61P 3/10* | (2006.01) |
| *C07K 14/575* | (2006.01) |
| *C07K 14/645* | (2006.01) |
| *A61K 39/00* | (2006.01) |

(52) U.S. Cl.
CPC ........... *C07K 14/605* (2013.01); *A61P 3/04* (2018.01); *A61P 3/10* (2018.01); *C07K 14/575* (2013.01); *C07K 14/645* (2013.01); *A61K 38/00* (2013.01); *A61K 2039/505* (2013.01); *C07K 2319/30* (2013.01); *C07K 2319/31* (2013.01); *C07K 2319/50* (2013.01)

(58) Field of Classification Search
CPC ............... C07K 14/605; C07K 14/575; C07K 2319/31; C07K 14/645
See application file for complete search history.

(56) References Cited

U.S. PATENT DOCUMENTS

| | | |
|---|---|---|
| 5,120,712 A | 6/1992 | Habener |
| 5,188,666 A | 2/1993 | Boccardo |
| 5,512,549 A | 4/1996 | Chen et al. |
| 5,523,549 A | 6/1996 | Tenzer |
| 5,977,071 A | 11/1999 | Galloway et al. |
| 6,191,102 B1 | 2/2001 | DiMarchi et al. |
| 6,506,724 B1 | 1/2003 | Hiles et al. |
| 6,703,359 B1 | 3/2004 | Young et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,921,748 B1 | 7/2005 | O'Harte et al. |
| 6,956,026 B2 | 10/2005 | Beeley et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,271,149 B2 | 9/2007 | Glaesner et al. |
| 7,452,966 B2 | 11/2008 | Glaesner et al. |
| 7,833,531 B2 | 11/2010 | O'Neil et al. |
| 8,034,770 B2 | 10/2011 | Belouski et al. |
| 8,497,240 B2 | 7/2013 | Levy et al. |
| 8,795,985 B2 | 8/2014 | Belouski et al. |
| 8,809,499 B2 | 8/2014 | Fan et al. |
| 8,835,385 B2 | 9/2014 | Belouski et al. |
| 9,006,400 B2 | 4/2015 | Boettcher et al. |
| 9,161,953 B2 | 10/2015 | Osei |
| 9,453,062 B2 | 9/2016 | Ma et al. |
| 9,458,214 B2 | 10/2016 | Boettcher et al. |
| 10,086,042 B2 | 10/2018 | Schreiber et al. |
| 10,183,060 B2 | 1/2019 | Schreiber et al. |
| 10,188,701 B2 | 1/2019 | Schreiber et al. |
| 10,253,078 B2 | 4/2019 | Shelton et al. |
| 10,449,233 B2 | 10/2019 | Schreiber et al. |
| 10,493,128 B2 | 12/2019 | Schreiber et al. |
| 10,513,548 B2 | 12/2019 | Schreiber et al. |
| 10,525,102 B2 | 1/2020 | Schreiber et al. |
| 10,543,253 B2 | 1/2020 | Schreiber et al. |
| 10,646,545 B2 | 5/2020 | Schreiber et al. |
| 10,653,748 B2 | 5/2020 | Schreiber et al. |
| 10,660,936 B2 | 5/2020 | Schreiber et al. |
| 10,780,121 B2 | 9/2020 | Schreiber et al. |
| 10,899,817 B2 | 1/2021 | Schreiber et al. |
| 10,927,159 B2 | 2/2021 | Schreiber et al. |
| 10,988,517 B2 | 4/2021 | Schreiber et al. |

(Continued)

FOREIGN PATENT DOCUMENTS

| | | |
|---|---|---|
| KR | 20220069610 A | 5/2022 |
| WO | WO 1998/05351 A1 | 2/1998 |

(Continued)

OTHER PUBLICATIONS

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*

(Continued)

*Primary Examiner* — Vanessa L. Ford
*Assistant Examiner* — Sandra Carter
(74) *Attorney, Agent, or Firm* — Morgan, Lewis & Bockius LLP

(57) ABSTRACT

The present disclosure relates to, inter alia, compositions and pharmaceutical compositions, including heterologous chimeric proteins that find use, inter alia, in the treatment of diabetes, obesity, or metabolic syndrome.

1 Claim, 27 Drawing Sheets

Specification includes a Sequence Listing.

(56) References Cited

U.S. PATENT DOCUMENTS

| | | |
|---|---|---|
| 10,995,127 B2 | 5/2021 | Schreiber et al. |
| 11,045,522 B2 | 6/2021 | Wei et al. |
| 11,098,093 B2 | 8/2021 | Schreiber et al. |
| 11,136,364 B2 | 10/2021 | Kim et al. |
| 11,192,933 B2 | 12/2021 | Schreiber et al. |
| 11,192,934 B2 | 12/2021 | Schreiber et al. |
| 11,267,856 B2 | 3/2022 | Schreiber et al. |
| 11,267,857 B2 | 3/2022 | Schreiber et al. |
| 11,332,509 B2 | 5/2022 | Schreiber et al. |
| 11,547,742 B1 | 1/2023 | Schreiber et al. |
| 11,643,447 B2 | 5/2023 | Schreiber et al. |
| 11,654,180 B2 | 5/2023 | Schreiber et al. |
| 11,780,897 B2 | 10/2023 | Schreiber et al. |
| 11,834,488 B2 | 12/2023 | Schreiber et al. |
| 11,896,618 B2 | 2/2024 | Schreiber et al. |
| 2003/0036504 A1 | 2/2003 | Kolterman et al. |
| 2003/0232761 A1 | 12/2003 | Hinke et al. |
| 2006/0094652 A1 | 5/2006 | Levy et al. |
| 2008/0312157 A1 | 12/2008 | Levy et al. |
| 2011/0136737 A1 | 6/2011 | Levy et al. |
| 2014/0162945 A1 | 6/2014 | Ma et al. |
| 2015/0329611 A1 | 11/2015 | Jung et al. |
| 2017/0240609 A1 | 8/2017 | Shelton et al. |
| 2017/0342121 A1 | 11/2017 | Agoram et al. |
| 2019/0085043 A1 | 3/2019 | Boscheinen et al. |
| 2021/0062227 A1 | 3/2021 | Qi et al. |
| 2022/0106373 A1 | 4/2022 | Mumm |
| 2022/0340635 A1 | 10/2022 | Huang |
| 2023/0265152 A1 | 8/2023 | Boscheinen et al. |
| 2023/0382970 A1 | 11/2023 | Kim et al. |

FOREIGN PATENT DOCUMENTS

| | | | |
|---|---|---|---|
| WO | WO 1999/07404 A1 | 2/1998 | |
| WO | WO 1998/008871 A1 | 3/1998 | |
| WO | WO 1999/25727 A2 | 5/1999 | |
| WO | WO 1999/25728 A1 | 5/1999 | |
| WO | WO 1999/40788 A1 | 8/1999 | |
| WO | WO 2000/034331 A2 | 6/2000 | |
| WO | WO 2000/41546 A2 | 7/2000 | |
| WO | WO 2000/41548 A2 | 7/2000 | |
| WO | WO 2000/069911 A1 | 11/2000 | |
| WO | WO 2000/73331 A2 | 12/2000 | |
| WO | WO 2001/004156 A1 | 1/2001 | |
| WO | WO 2001/51078 A1 | 7/2001 | |
| WO | WO 2003/018516 A2 | 3/2003 | |
| WO | WO 2003/099314 A1 | 12/2003 | |
| WO | WO 2010/091122 A1 | 8/2010 | |
| WO | WO-2011068810 A1 * | 6/2011 | A61K 31/7105 |
| WO | WO-2013192131 A1 * | 12/2013 | A61K 47/68 |
| WO | WO 2017/059168 A1 | 4/2017 | |
| WO | WO 2018/157162 A1 | 8/2018 | |
| WO | WO 2018/157163 A1 | 8/2018 | |
| WO | WO 2018/157164 A1 | 8/2018 | |
| WO | WO 2018/157165 A1 | 8/2018 | |
| WO | WO 2019/246508 A1 | 12/2019 | |
| WO | WO 2020/047319 A1 | 3/2020 | |
| WO | WO 2020/047322 A1 | 3/2020 | |
| WO | WO 2020/047325 A1 | 3/2020 | |
| WO | WO 2020/047327 A2 | 3/2020 | |
| WO | WO 2020/047328 A1 | 3/2020 | |
| WO | WO 2020/047329 A1 | 3/2020 | |
| WO | WO 2020/146393 A1 | 6/2020 | |
| WO | WO 2020/176718 A1 | 9/2020 | |
| WO | WO 2020/232365 A1 | 11/2020 | |
| WO | WO 2020/257762 A1 | 12/2020 | |
| WO | WO 2021/041958 A1 | 3/2021 | |
| WO | WO 2022/061124 A1 | 3/2022 | |
| WO | WO 2022/093310 A1 | 3/2022 | |
| WO | WO 2022/109110 A1 | 5/2022 | |
| WO | WO 2022/120187 A2 | 6/2022 | |
| WO | WO 2022/120191 A1 | 6/2022 | |
| WO | WO 2022/187488 A2 | 9/2022 | |
| WO | WO 2022/187583 A1 | 9/2022 | |
| WO | WO 2022/187584 A1 | 9/2022 | |
| WO | WO 2022/192236 A1 | 9/2022 | |
| WO | WO 2022/197821 A1 | 9/2022 | |
| WO | WO 2022/212845 A2 | 10/2022 | |
| WO | WO 2022/077152 A2 | 5/2023 | |
| WO | WO 2023/077156 A1 | 5/2023 | |
| WO | WO 2023/137143 A1 | 7/2023 | |

OTHER PUBLICATIONS

Whisstock et al. Prediction of proteinfunction fromprotein sequence and structure. Quarterly Reviews in Biophysics. 36(3):307-340, 2007 (Year: 2007).*

Davidsohn, et al., "A single combination gene therapy treats multiple age-related diseases," PNAS, vol. 116, No. 47, pp. 23505-23511, Nov. 19, 2019.

Gilroy, et al., "Sustained release of a GLP-1 and FGF21 dual agonist from an injectable depot protects mice from obesity and hyperglycemia," Sci. Adv., vol. 6, Aug. 20, 2020, 12 pages.

Kaufman, et al., "AKR-001, an Fc-FGF21 Analog, Showed Sustained Pharmacodynamic Effects on Insulin Sensitivity and Lipid Metabolism in Type 2 Diabetes Patients," Cell Reports Medicine 1, 100057, Jul. 21, 2020, 19 pages.

Pan, et al., "A novel GLP-1 and FGF21 dual agonist has therapeutic potential for diabetes and non-alcoholic steatohepatitis," EBioMedicine 63 (2021) 103202, 14 pages.

International Search Report issued in International Application No. PCT/US2023/082572, dated Apr. 8, 2024, 6 pages.

Written Opinion issued in International Application No. PCT/US2023/082572, dated Feb. 23, 2024, 10 pages.

Zhao, et al., "Structural insights into multiplexed pharmacological actions of tirzepatide and peptide 20 at the GIP, GLP-1 or glucagon receptors," Nature Communications, Feb. 25, 2022 (Feb. 25, 2022), vol. 13, No. 1057, pp. 1-16, entire document.

Adriaenssens, et al., "Glucose-Dependent Insulinotropic Polypeptide Receptor-Expressing Cells in the Hypothalamus Regulate Food Intake", Cell Metabolism 30, 987-996 (2019).

Alana, et al., "NMR and Alanine Scan Studies of Glucose-dependent Insulinotropic Polypeptide in Water", The Journal of Biological Chemistry, vol. 281, No. 24 (2006).

Boylan, et al., "Gastric inhibitory polypeptide immunoneutralization attenuates development of obesity in mice", Am J Physiol Endocrinol Metab 309 (2015).

Crawley, et al., "Direct medical costs of obesity in the United States and the most populous states", JMCP.org, vol. 27, No. 3 (2021).

Chalasani, et al., "The Diagnosis and management of Nonalcoholic Fatty Liver Disease: Practice Guidance From the American association for the Study of Liver Diseases", Hepatology, vol. 67, No. 1 (2018).

Chang, et al., "Structure and folding of glucagon-like peptide-1-(7-36)-amide in aqueous trifluoroethanol studied by NMR spectroscopy", Magnetic Resonance in Chemistry 39: 477-483 (2001).

Fulurija, et al., "Vaccination against GIP for the Treatment of Obesity", PLoS One, vol. 3, Issue 9, (2008).

Gasbjerg, et al., "Evaluation of the incretin effect in humans using GIP and GLP-1 receptor antagonists", Peptides 125 (2020).

Lu, et al., "GIPR antagonist antibodies conjugated to GLP-1 peptide are bispecific molecules that decrease weight in obsess mice and monkeys", Cell Reports Medicine 2 (2021).

McClean, et al., "GIP receptor antagonism reverses obesity, insulin resistance, and associated metabolic disturbances induced in mice by prolonged consumption of high-fat diet", Am J Physiol Endocrinol Metab 293 (2007).

Nauck, et al., "The evolving story of incretins (GIP and GLP-1) in metabolic and cardiovascular disease: A pathophysiological update", Diabetes Obes Metab (2021).

Parthier, et al., "Crystal structure of the incretin-bound extracellular domain of a G protein-coupled receptor", PNAS vol. 104, No. 35 (2007).

Tatarkiewicz, et al., "A novel long-acting glucose-dependent insulinotropic peptide analogue: enhanced efficacy in normal and diabetic rodents", Diabetes, Obesity and Metabolism 16: 75-85, (2014).

(56) References Cited

OTHER PUBLICATIONS

Underwood, et al., "Crystal Structure of Glucagon-like Peptide-1 in Complex with the Extracellular Domain of the Glucagon-like Peptide-1 Receptor", The Journal of Biological Chemistry, vol. 285, No. 1, (2010).

Zhang, et al., "Differential GLP-1R Binding and Activation by Peptide and Non-peptide Agonists", Molecular Cell 80, 485-500 (2020).

\* cited by examiner

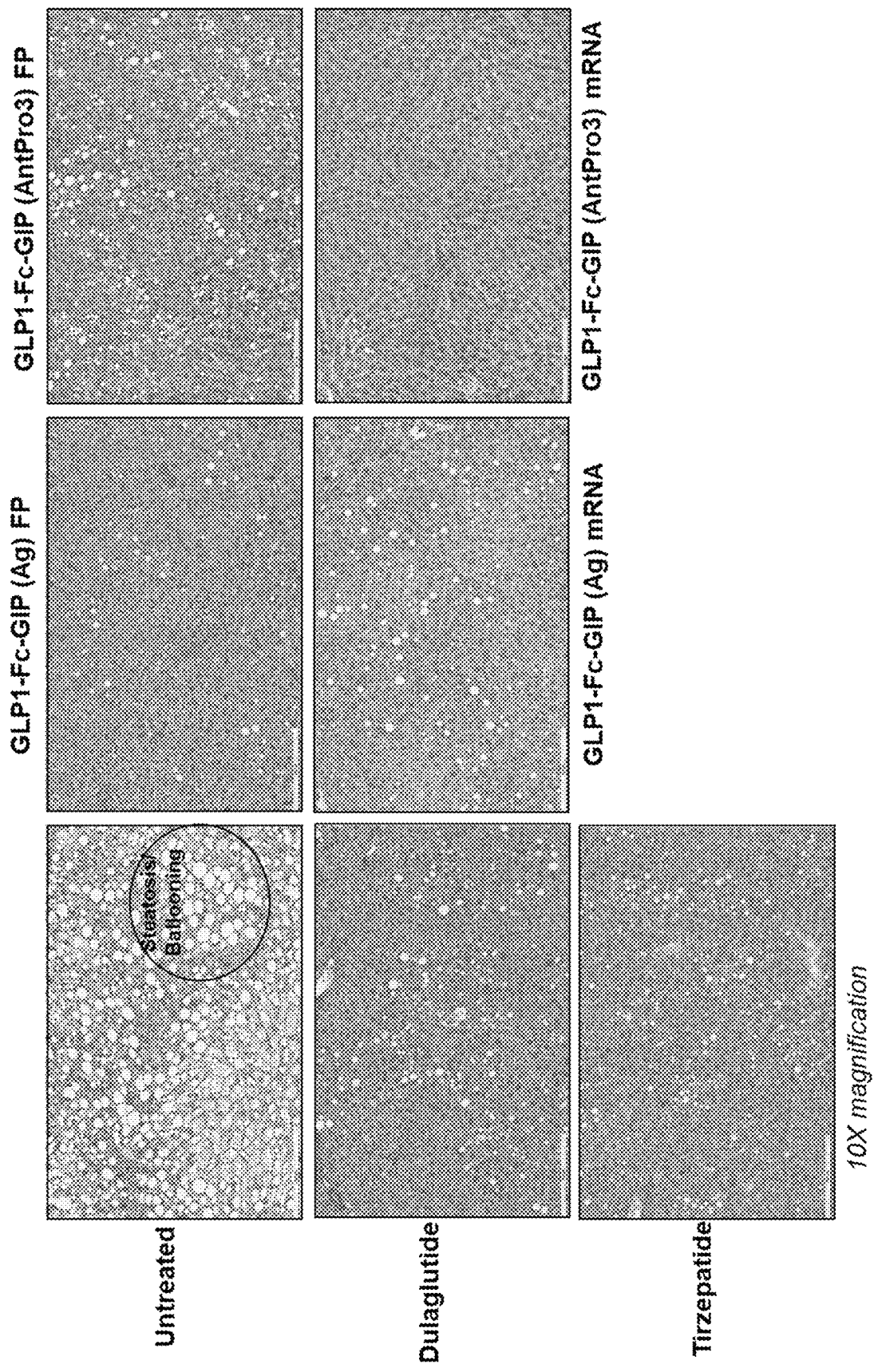

12,145,975 B2

SEQUENCE LISTING

```
Sequence total quantity: 154
SEQ ID NO: 1              moltype = AA  length = 217
FEATURE                   Location/Qualifiers
REGION                    1..217
                          note = Synthetic Polypeptide
source                    1..217
                          mol_type = protein
                          organism = synthetic construct
SEQUENCE: 1
APEFLGGPSV FLFPPKPKDT LMISRTPEVT CVVVDVSQED PEVQFNWYVD GVEVHNAKTK   60
PREEQFNSTY RVVSVLTVLH QDWLSGKEYK CKVSSKGLPS SIEKTISNAT GQPREPQVYT  120
LPPSQEEMTK NQVSLTCLVK GFYPSDIAVE WESNGQPENN YKTTPPVLDS DGSFFLYSRL  180
TVDKSSWQEG NVFSCSVMHE ALHNHYTQKS LSLSLGK                           217

SEQ ID NO: 2              moltype = AA  length = 217
FEATURE                   Location/Qualifiers
REGION                    1..217
                          note = Synthetic Polypeptide
source                    1..217
                          mol_type = protein
                          organism = synthetic construct
SEQUENCE: 2
APEFLGGPSV FLFPPKPKDQ LMISRTPEVT CVVVDVSQED PEVQFNWYVD GVEVHNAKTK   60
PREEQFNSTY RVVSVLTTPH SDWLSGKEYK CKVSSKGLPS SIEKTISNAT GQPREPQVYT  120
LPPSQEEMTK NQVSLTCLVK GFYPSDIAVE WESNGQPENN YKTTPPVLDS DGSFFLYSRL  180
TVDKSSWQEG NVFSCSVLHE ALHNHYTQKS LSLSLGK                           217

SEQ ID NO: 3              moltype = AA  length = 217
FEATURE                   Location/Qualifiers
REGION                    1..217
                          note = Synthetic Polypeptide
source                    1..217
                          mol_type = protein
                          organism = synthetic construct
SEQUENCE: 3
APEFLGGPSV FLFPPKPKDQ LMISRTPEVT CVVVDVSQED PEVQFNWYVD GVEVHNAKTK   60
PREEQFNSTY RVVSVLTVLH QDWLSGKEYK CKVSSKGLPS SIEKTISNAT GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVLHE ALHNHYTQKS LSLSLGK                           217

SEQ ID NO: 4              moltype = AA  length = 11
FEATURE                   Location/Qualifiers
REGION                    1..11
                          note = Synthetic Polypeptide
source                    1..11
                          mol_type = protein
                          organism = synthetic construct
SEQUENCE: 4
SKYGPPCPSC P                                                        11

SEQ ID NO: 5              moltype = AA  length = 11
FEATURE                   Location/Qualifiers
REGION                    1..11
                          note = Synthetic Polypeptide
source                    1..11
                          mol_type = protein
                          organism = synthetic construct
SEQUENCE: 5
SKYGPPCPPC P                                                        11

SEQ ID NO: 6              moltype = AA  length = 6
FEATURE                   Location/Qualifiers
REGION                    1..6
                          note = Synthetic Polypeptide
source                    1..6
                          mol_type = protein
                          organism = synthetic construct
SEQUENCE: 6
SKYGPP                                                               6

SEQ ID NO: 7              moltype = AA  length = 6
FEATURE                   Location/Qualifiers
REGION                    1..6
                          note = Synthetic Polypeptide
source                    1..6
                          mol_type = protein
                          organism = synthetic construct
SEQUENCE: 7
```

```
IEGRMD                                                                                 6

SEQ ID NO: 8            moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 8
GGGVPRDCG                                                                              9

SEQ ID NO: 9            moltype = AA   length = 15
FEATURE                 Location/Qualifiers
REGION                  1..15
                        note = Synthetic Polypeptide
source                  1..15
                        mol_type = protein
                        organism = synthetic construct
SEQUENCE: 9
IEGRMDGGGG AGGGG                                                                      15

SEQ ID NO: 10           moltype = AA   length = 8
FEATURE                 Location/Qualifiers
REGION                  1..8
                        note = Synthetic Polypeptide
source                  1..8
                        mol_type = protein
                        organism = synthetic construct
SEQUENCE: 10
GGGSGGGS                                                                               8

SEQ ID NO: 11           moltype = AA   length = 12
FEATURE                 Location/Qualifiers
REGION                  1..12
                        note = Synthetic Polypeptide
source                  1..12
                        mol_type = protein
                        organism = synthetic construct
SEQUENCE: 11
GGGSGGGGSG GG                                                                         12

SEQ ID NO: 12           moltype = AA   length = 14
FEATURE                 Location/Qualifiers
REGION                  1..14
                        note = Synthetic Polypeptide
source                  1..14
                        mol_type = protein
                        organism = synthetic construct
SEQUENCE: 12
EGKSSGSGSE SKST                                                                       14

SEQ ID NO: 13           moltype = AA   length = 4
FEATURE                 Location/Qualifiers
REGION                  1..4
                        note = Synthetic Polypeptide
source                  1..4
                        mol_type = protein
                        organism = synthetic construct
SEQUENCE: 13
GGSG                                                                                   4

SEQ ID NO: 14           moltype = AA   length = 12
FEATURE                 Location/Qualifiers
REGION                  1..12
                        note = Synthetic Polypeptide
source                  1..12
                        mol_type = protein
                        organism = synthetic construct
SEQUENCE: 14
GGSGGGSGGG SG                                                                         12

SEQ ID NO: 15           moltype = AA   length = 15
FEATURE                 Location/Qualifiers
REGION                  1..15
                        note = Synthetic Polypeptide
source                  1..15
                        mol_type = protein
                        organism = synthetic construct
```

```
SEQUENCE: 15
EAAAKEAAAK EAAAK                                                               15

SEQ ID NO: 16           moltype = AA  length = 20
FEATURE                 Location/Qualifiers
REGION                  1..20
                        note = Synthetic Polypeptide
source                  1..20
                        mol_type = protein
                        organism = synthetic construct
SEQUENCE: 16
EAAAREAAAR EAAAREAAAR                                                          20

SEQ ID NO: 17           moltype = AA  length = 17
FEATURE                 Location/Qualifiers
REGION                  1..17
                        note = Synthetic Polypeptide
source                  1..17
                        mol_type = protein
                        organism = synthetic construct
SEQUENCE: 17
GGGGSGGGGS GGGGSAS                                                             17

SEQ ID NO: 18           moltype = AA  length = 9
FEATURE                 Location/Qualifiers
REGION                  1..9
                        note = Synthetic Polypeptide
source                  1..9
                        mol_type = protein
                        organism = synthetic construct
SEQUENCE: 18
GGGGAGGGG                                                                      9

SEQ ID NO: 19           moltype =     length =
SEQUENCE: 19
000

SEQ ID NO: 20           moltype = AA  length = 6
FEATURE                 Location/Qualifiers
REGION                  1..6
                        note = Synthetic Polypeptide
source                  1..6
                        mol_type = protein
                        organism = synthetic construct
SEQUENCE: 20
GSGSGS                                                                         6

SEQ ID NO: 21           moltype = AA  length = 10
FEATURE                 Location/Qualifiers
REGION                  1..10
                        note = Synthetic Polypeptide
source                  1..10
                        mol_type = protein
                        organism = synthetic construct
SEQUENCE: 21
GSGSGSGSGS                                                                     10

SEQ ID NO: 22           moltype = AA  length = 7
FEATURE                 Location/Qualifiers
REGION                  1..7
                        note = Synthetic Polypeptide
source                  1..7
                        mol_type = protein
                        organism = synthetic construct
SEQUENCE: 22
GGGGSAS                                                                        7

SEQ ID NO: 23           moltype = AA  length = 20
FEATURE                 Location/Qualifiers
REGION                  1..20
                        note = Synthetic Polypeptide
source                  1..20
                        mol_type = protein
                        organism = synthetic construct
SEQUENCE: 23
APAPAPAPAP APAPAPAPAP                                                          20

SEQ ID NO: 24           moltype = AA  length = 4
FEATURE                 Location/Qualifiers
```

```
                          -continued

REGION                    1..4
                          note = Synthetic Polypeptide
source                    1..4
                          mol_type = protein
                          organism = synthetic construct
SEQUENCE: 24
CPPC                                                                     4

SEQ ID NO: 25             moltype = AA  length = 5
FEATURE                   Location/Qualifiers
REGION                    1..5
                          note = Synthetic Polypeptide
source                    1..5
                          mol_type = protein
                          organism = synthetic construct
SEQUENCE: 25
GGGGS                                                                    5

SEQ ID NO: 26             moltype = AA  length = 10
FEATURE                   Location/Qualifiers
REGION                    1..10
                          note = Synthetic Polypeptide
source                    1..10
                          mol_type = protein
                          organism = synthetic construct
SEQUENCE: 26
GGGGSGGGGS                                                              10

SEQ ID NO: 27             moltype = AA  length = 15
FEATURE                   Location/Qualifiers
REGION                    1..15
                          note = Synthetic Polypeptide
source                    1..15
                          mol_type = protein
                          organism = synthetic construct
SEQUENCE: 27
GGGGSGGGGS GGGGS                                                        15

SEQ ID NO: 28             moltype = AA  length = 20
FEATURE                   Location/Qualifiers
REGION                    1..20
                          note = Synthetic Polypeptide
source                    1..20
                          mol_type = protein
                          organism = synthetic construct
SEQUENCE: 28
GGGGSGGGGS GGGGSGGGGS                                                   20

SEQ ID NO: 29             moltype = AA  length = 25
FEATURE                   Location/Qualifiers
REGION                    1..25
                          note = Synthetic Polypeptide
source                    1..25
                          mol_type = protein
                          organism = synthetic construct
SEQUENCE: 29
GGGGSGGGGS GGGGSGGGGS GGGGS                                             25

SEQ ID NO: 30             moltype = AA  length = 30
FEATURE                   Location/Qualifiers
REGION                    1..30
                          note = Synthetic Polypeptide
source                    1..30
                          mol_type = protein
                          organism = synthetic construct
SEQUENCE: 30
GGGGSGGGGS GGGGSGGGGS GGGGSGGGGS                                        30

SEQ ID NO: 31             moltype = AA  length = 35
FEATURE                   Location/Qualifiers
REGION                    1..35
                          note = Synthetic Polypeptide
source                    1..35
                          mol_type = protein
                          organism = synthetic construct
SEQUENCE: 31
GGGGSGGGGS GGGGSGGGGS GGGGSGGGGS GGGGS                                  35

SEQ ID NO: 32             moltype = AA  length = 40
```

```
FEATURE                 Location/Qualifiers
REGION                  1..40
                        note = Synthetic Polypeptide
source                  1..40
                        mol_type = protein
                        organism = synthetic construct
SEQUENCE: 32
GGGGSGGGGS GGGGSGGGGS GGGGSGGGGS GGGGSGGGGS                              40

SEQ ID NO: 33           moltype = AA  length = 16
FEATURE                 Location/Qualifiers
REGION                  1..16
                        note = Synthetic Polypeptide
source                  1..16
                        mol_type = protein
                        organism = synthetic construct
SEQUENCE: 33
GGSGGSGGGG SGGGGS                                                        16

SEQ ID NO: 34           moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 34
GGGGGGGG                                                                 8

SEQ ID NO: 35           moltype = AA  length = 6
FEATURE                 Location/Qualifiers
REGION                  1..6
                        note = Synthetic Polypeptide
source                  1..6
                        mol_type = protein
                        organism = synthetic construct
SEQUENCE: 35
GGGGGG                                                                   6

SEQ ID NO: 36           moltype = AA  length = 5
FEATURE                 Location/Qualifiers
REGION                  1..5
                        note = Synthetic Polypeptide
source                  1..5
                        mol_type = protein
                        organism = synthetic construct
SEQUENCE: 36
EAAAK                                                                    5

SEQ ID NO: 37           moltype = AA  length = 10
FEATURE                 Location/Qualifiers
REGION                  1..10
                        note = Synthetic Polypeptide
source                  1..10
                        mol_type = protein
                        organism = synthetic construct
SEQUENCE: 37
EAAAKEAAAK                                                               10

SEQ ID NO: 38           moltype = AA  length = 15
FEATURE                 Location/Qualifiers
REGION                  1..15
                        note = Synthetic Polypeptide
source                  1..15
                        mol_type = protein
                        organism = synthetic construct
SEQUENCE: 38
EAAAKEAAAK EAAAK                                                         15

SEQ ID NO: 39           moltype = AA  length = 12
FEATURE                 Location/Qualifiers
REGION                  1..12
                        note = Synthetic Polypeptide
source                  1..12
                        mol_type = protein
                        organism = synthetic construct
SEQUENCE: 39
AEAAAKEAAA KA                                                            12
```

```
SEQ ID NO: 40            moltype = AA   length = 17
FEATURE                  Location/Qualifiers
REGION                   1..17
                         note = Synthetic Polypeptide
source                   1..17
                         mol_type = protein
                         organism = synthetic construct
SEQUENCE: 40
AEAAAKEAAA KEAAAKA                                                   17

SEQ ID NO: 41            moltype = AA   length = 22
FEATURE                  Location/Qualifiers
REGION                   1..22
                         note = Synthetic Polypeptide
source                   1..22
                         mol_type = protein
                         organism = synthetic construct
SEQUENCE: 41
AEAAAKEAAA KEAAAKEAAA KA                                             22

SEQ ID NO: 42            moltype = AA   length = 27
FEATURE                  Location/Qualifiers
REGION                   1..27
                         note = Synthetic Polypeptide
source                   1..27
                         mol_type = protein
                         organism = synthetic construct
SEQUENCE: 42
AEAAAKEAAA KEAAAKEAAA KEAAAKA                                        27

SEQ ID NO: 43            moltype = AA   length = 46
FEATURE                  Location/Qualifiers
REGION                   1..46
                         note = Synthetic Polypeptide
source                   1..46
                         mol_type = protein
                         organism = synthetic construct
SEQUENCE: 43
AEAAAKEAAA KEAAAKEAAA KALEAEAAAK EAAAKEAAAK EAAAKA                   46

SEQ ID NO: 44            moltype = AA   length = 5
FEATURE                  Location/Qualifiers
REGION                   1..5
                         note = Synthetic Polypeptide
source                   1..5
                         mol_type = protein
                         organism = synthetic construct
SEQUENCE: 44
PAPAP                                                                 5

SEQ ID NO: 45            moltype = AA   length = 18
FEATURE                  Location/Qualifiers
REGION                   1..18
                         note = Synthetic Polypeptide
source                   1..18
                         mol_type = protein
                         organism = synthetic construct
SEQUENCE: 45
KESGSVSSEQ LAQFRSLD                                                  18

SEQ ID NO: 46            moltype = AA   length = 12
FEATURE                  Location/Qualifiers
REGION                   1..12
                         note = Synthetic Polypeptide
source                   1..12
                         mol_type = protein
                         organism = synthetic construct
SEQUENCE: 46
GSAGSAAGSG EF                                                        12

SEQ ID NO: 47            moltype = AA   length = 5
FEATURE                  Location/Qualifiers
REGION                   1..5
                         note = Synthetic Polypeptide
source                   1..5
                         mol_type = protein
                         organism = synthetic construct
SEQUENCE: 47
GGGSE                                                                 5
```

```
SEQ ID NO: 48              moltype = AA   length = 5
FEATURE                    Location/Qualifiers
REGION                     1..5
                           note = Synthetic Polypeptide
source                     1..5
                           mol_type = protein
                           organism = synthetic construct
SEQUENCE: 48
GSESG                                                                      5

SEQ ID NO: 49              moltype = AA   length = 5
FEATURE                    Location/Qualifiers
REGION                     1..5
                           note = Synthetic Polypeptide
source                     1..5
                           mol_type = protein
                           organism = synthetic construct
SEQUENCE: 49
GSEGS                                                                      5

SEQ ID NO: 50              moltype = AA   length = 35
FEATURE                    Location/Qualifiers
REGION                     1..35
                           note = Synthetic Polypeptide
source                     1..35
                           mol_type = protein
                           organism = synthetic construct
SEQUENCE: 50
GEGGSGEGSS GEGSSSEGGG SEGGGSEGGG SEGGS                                     35

SEQ ID NO: 51              moltype = AA   length = 234
FEATURE                    Location/Qualifiers
REGION                     1..234
                           note = Synthetic Polypeptide
source                     1..234
                           mol_type = protein
                           organism = synthetic construct
SEQUENCE: 51
SKYGPPCPSC PAPEFLGGPS VFLFPPKPKD TLMISRTPEV TCVVVDVSQE DPEVQFNWYV           60
DGVEVHNAKT KPREEQFNST YRVVSVLTVL HQDWLSGKEY KCKVSSKGLP SSIEKTISNA          120
TGQPREPQVY TLPPSQEEMT KNQVSLTCLV KGFYPSDIAV EWESNGQPEN NYKTTPPVLD          180
SDGSFFLYSR LTVDKSSWQE GNVFSCSVMH EALHNHYTQK SLSLSLGKIE GRMD                234

SEQ ID NO: 52              moltype = AA   length = 234
FEATURE                    Location/Qualifiers
REGION                     1..234
                           note = Synthetic Polypeptide
source                     1..234
                           mol_type = protein
                           organism = synthetic construct
SEQUENCE: 52
SKYGPPCPSC PAPEFLGGPS VFLFPPKPKD QLMISRTPEV TCVVVDVSQE DPEVQFNWYV           60
DGVEVHNAKT KPREEQFNST YRVVSVLTTP HSDWLSGKEY KCKVSSKGLP SSIEKTISNA          120
TGQPREPQVY TLPPSQEEMT KNQVSLTCLV KGFYPSDIAV EWESNGQPEN NYKTTPPVLD          180
SDGSFFLYSR LTVDKSSWQE GNVFSCSVLH EALHNHYTQK SLSLSLGKIE GRMD                234

SEQ ID NO: 53              moltype = AA   length = 234
FEATURE                    Location/Qualifiers
REGION                     1..234
                           note = Synthetic Polypeptide
source                     1..234
                           mol_type = protein
                           organism = synthetic construct
SEQUENCE: 53
SKYGPPCPSC PAPEFLGGPS VFLFPPKPKD QLMISRTPEV TCVVVDVSQE DPEVQFNWYV           60
DGVEVHNAKT KPREEQFNST YRVVSVLTVL HQDWLSGKEY KCKVSSKGLP SSIEKTISNA          120
TGQPREPQVY TLPPSQEEMT KNQVSLTCLV KGFYPSDIAV EWESNGQPEN NYKTTPPVLD          180
SDGSFFLYSR LTVDKSRWQE GNVFSCSVLH EALHNHYTQK SLSLSLGKIE GRMD                234

SEQ ID NO: 54              moltype = AA   length = 234
FEATURE                    Location/Qualifiers
REGION                     1..234
                           note = Synthetic Polypeptide
source                     1..234
                           mol_type = protein
                           organism = synthetic construct
SEQUENCE: 54
SKYGPPCPPC PAPEFLGGPS VFLFPPKPKD TLMISRTPEV TCVVVDVSQE DPEVQFNWYV           60
```

```
DGVEVHNAKT KPREEQFNST YRVVSVLTVL HQDWLSGKEY KCKVSSKGLP SSIEKTISNA    120
TGQPREPQVY TLPPSQEEMT KNQVSLTCLV KGFYPSDIAV EWESNGQPEN NYKTTPPVLD    180
SDGSFFLYSR LTVDKSSWQE GNVFSCSVMH EALHNHYTQK SLSLSLGKIE GRMD          234

SEQ ID NO: 55           moltype = AA  length = 234
FEATURE                 Location/Qualifiers
REGION                  1..234
                        note = Synthetic Polypeptide
source                  1..234
                        mol_type = protein
                        organism = synthetic construct
SEQUENCE: 55
SKYGPPCPPC PAPEFLGGPS VFLFPPKPKD QLMISRTPEV TCVVVDVSQE DPEVQFNWYV    60
DGVEVHNAKT KPREEQFNST YRVVSVLTTP HSDWLSGKEY KCKVSSKGLP SSIEKTISNA    120
TGQPREPQVY TLPPSQEEMT KNQVSLTCLV KGFYPSDIAV EWESNGQPEN NYKTTPPVLD    180
SDGSFFLYSR LTVDKSSWQE GNVFSCSVLH EALHNHYTQK SLSLSLGKIE GRMD          234

SEQ ID NO: 56           moltype = AA  length = 234
FEATURE                 Location/Qualifiers
REGION                  1..234
                        note = Synthetic Polypeptide
source                  1..234
                        mol_type = protein
                        organism = synthetic construct
SEQUENCE: 56
SKYGPPCPPC PAPEFLGGPS VFLFPPKPKD QLMISRTPEV TCVVVDVSQE DPEVQFNWYV    60
DGVEVHNAKT KPREEQFNST YRVVSVLTVL HQDWLSGKEY KCKVSSKGLP SSIEKTISNA    120
TGQPREPQVY TLPPSQEEMT KNQVSLTCLV KGFYPSDIAV EWESNGQPEN NYKTTPPVLD    180
SDGSFFLYSR LTVDKSRWQE GNVFSCSVLH EALHNHYTQK SLSLSLGKIE GRMD          234

SEQ ID NO: 57           moltype = AA  length = 180
FEATURE                 Location/Qualifiers
source                  1..180
                        mol_type = protein
                        organism = synthetic construct
SEQUENCE: 57
MKSIYFVAGL FVMLVQGSWQ RSLQDTEEKS RSFSASQADP LSDPDQMNED KRHSQGTFTS    60
DYSKYLDSRR AQDFVQWLMN TKRNRNNIAK RHDEFERHAE GTFTSDVSSY LEGQAAKEFI    120
AWLVKGRGRR DFPEEVAIVE ELGRRHADGS FSDEMNTILD NLAARDFINW LIQTKITDRK    180

SEQ ID NO: 58           moltype = AA  length = 37
FEATURE                 Location/Qualifiers
source                  1..37
                        mol_type = protein
                        organism = synthetic construct
SEQUENCE: 58
HDEFERHAEG TFTSDVSSYL EGQAAKEFIA WLVKGRG                              37

SEQ ID NO: 59           moltype = AA  length = 36
FEATURE                 Location/Qualifiers
source                  1..36
                        mol_type = protein
                        organism = synthetic construct
SEQUENCE: 59
HDEFERHAEG TFTSDVSSYL EGQAAKEFIA WLVKGR                               36

SEQ ID NO: 60           moltype = AA  length = 30
FEATURE                 Location/Qualifiers
source                  1..30
                        mol_type = protein
                        organism = synthetic construct
SEQUENCE: 60
HAEGTFTSDV SSYLEGQAAK EFIAWLVKGR                                      30

SEQ ID NO: 61           moltype = AA  length = 39
FEATURE                 Location/Qualifiers
source                  1..39
                        mol_type = protein
                        organism = synthetic construct
SEQUENCE: 61
HGEGTFTSDL SKQMEEEAVR LFIEWLKNGG PSSGAPPPS                            39

SEQ ID NO: 62           moltype = AA  length = 44
FEATURE                 Location/Qualifiers
source                  1..44
                        mol_type = protein
                        organism = synthetic construct
SEQUENCE: 62
HGEGTFTSDL SKQMEEEAVR LFIEWLKNGG PSSGAPPSKK KKKK                      44
```

```
SEQ ID NO: 63              moltype = AA   length = 30
FEATURE                    Location/Qualifiers
source                     1..30
                           mol_type = protein
                           organism = synthetic construct
SEQUENCE: 63
HGEGTFTSDV SSYLEGQAAK EFIAWLVKGR                                    30

SEQ ID NO: 64              moltype = AA   length = 38
FEATURE                    Location/Qualifiers
source                     1..38
                           mol_type = protein
                           organism = synthetic construct
SEQUENCE: 64
HGEGTFTSDL SKQMEEEAVR LFEWLKNGGP SSGAPPPS                           38

SEQ ID NO: 65              moltype = AA   length = 275
FEATURE                    Location/Qualifiers
source                     1..275
                           mol_type = protein
                           organism = synthetic construct
SEQUENCE: 65
HGEGTFTSDV SSYLEEQAAK EFIAWLVKGG GGGGGSGGGG SGGGGSAESK YGPPCPPCPA   60
PEAAGGPSVF LFPPKPKDTL MISRTPEVTC VVVDVSQEDP EVQFNWYVDG VEVHNAKTKP  120
REEQFNSTYR VVSVLTVLHQ DWLNGKEYKC KVSNKGLPSS IEKTISKAKG QPREPQVYTL  180
PPSQEEMTKN QVSLTCLVKG FYPSDIAVEW ESNGQPENNY KTTPPVLDSD GSFFLYSRLT  240
VDKSRWQEGN VFSCSVMHEA LHNHYTQKSL SLSLG                             275

SEQ ID NO: 66              moltype = AA   length = 31
FEATURE                    Location/Qualifiers
source                     1..31
                           mol_type = protein
                           organism = synthetic construct
SEQUENCE: 66
HGEGTFTSDV SSYLEEQAAK EFIAWLVKGG G                                  31

SEQ ID NO: 67              moltype = AA   length = 153
FEATURE                    Location/Qualifiers
source                     1..153
                           mol_type = protein
                           organism = synthetic construct
SEQUENCE: 67
MVATKTFALL LLSLFLAVGL GEKKEGHFSA LPSLPVGSHA KVSSPQPRGP RYAEGTFISD   60
YSIAMDKIHQ QDFVNWLLAQ KGKKNDWKHN ITQREARALE LASQANRKEE EAVEPQSSPA  120
KNPSDEDLLR DLLIQELLAC LLDQTNLCRL RSR                               153

SEQ ID NO: 68              moltype = AA   length = 42
FEATURE                    Location/Qualifiers
source                     1..42
                           mol_type = protein
                           organism = synthetic construct
SEQUENCE: 68
YAEGTFISDY SIAMDKIHQQ DFVNWLLAQK GKKNDWKHNI TQ                      42

SEQ ID NO: 69              moltype = AA   length = 28
FEATURE                    Location/Qualifiers
source                     1..28
                           mol_type = protein
                           organism = synthetic construct
SEQUENCE: 69
YAEGTFISDY SIAMDKIHQQ DFVNWLLA                                      28

SEQ ID NO: 70              moltype = AA   length = 6
FEATURE                    Location/Qualifiers
source                     1..6
                           mol_type = protein
                           organism = synthetic construct
SEQUENCE: 70
HSSKLQ                                                              6

SEQ ID NO: 71              moltype = AA   length = 7
FEATURE                    Location/Qualifiers
source                     1..7
                           mol_type = protein
                           organism = synthetic construct
SEQUENCE: 71
GPLGVRG                                                             7
```

```
SEQ ID NO: 72            moltype = AA   length = 8
FEATURE                  Location/Qualifiers
source                   1..8
                         mol_type = protein
                         organism = synthetic construct
SEQUENCE: 72
IPVSLRSG                                                                     8

SEQ ID NO: 73            moltype = AA   length = 8
FEATURE                  Location/Qualifiers
source                   1..8
                         mol_type = protein
                         organism = synthetic construct
SEQUENCE: 73
VPLSLYSG                                                                     8

SEQ ID NO: 74            moltype = AA   length = 10
FEATURE                  Location/Qualifiers
source                   1..10
                         mol_type = protein
                         organism = synthetic construct
SEQUENCE: 74
SGESPAYYTA                                                                  10

SEQ ID NO: 75            moltype = AA   length = 4
FEATURE                  Location/Qualifiers
source                   1..4
                         mol_type = protein
                         organism = synthetic construct
SEQUENCE: 75
RFRS                                                                         4

SEQ ID NO: 76            moltype = AA   length = 220
FEATURE                  Location/Qualifiers
source                   1..220
                         mol_type = protein
                         organism = synthetic construct
SEQUENCE: 76
PCPAPEAAGG PSVFLFPPKP KDTLMISRTP EVTCVVVDVS HEDPEVKFNW YVDGVEVHNA            60
KTKPREEQYN STYRVVSVLT VLHQDWLNGK EYKCKVSNKA LPAPIEKTIS KAKGQPREPQ           120
VYTLPPSRDE LTKNQVSLTC LVKGFYPSDI AVEWESNGQP ENNYKTTPPV LDSDGSFFLY           180
SKLTVDKSRW QQGNVFSCSV MHEALHNHYT QKSLSLSPGK                                 220

SEQ ID NO: 77            moltype = AA   length = 31
FEATURE                  Location/Qualifiers
source                   1..31
                         mol_type = protein
                         organism = synthetic construct
SEQUENCE: 77
HAEGTFTSDV SSYLEGQAAK EFIAWLVRGR G                                           31

SEQ ID NO: 78            moltype = AA   length = 192
FEATURE                  Location/Qualifiers
source                   1..192
                         mol_type = protein
                         organism = synthetic construct
SEQUENCE: 78
LAFSDAGPHV HYGWGDPIRL RHLYTSGPHG LSSCFLRIRA DGVVDCARGQ SAHSLLEIKA            60
VALRTVAIKG VHSVRYLCMG ADGKMQGLLQ YSEEDCAFEE EIRPDGYNVY RSEKHRLPVS           120
LSSAKQRQLY KNRGFLPLSH FLPMLPMVPE EPEDLRGHLE SDMFSSPLET DSMDPFGLVT           180
GLEAVRSPSF EK                                                               192

SEQ ID NO: 79            moltype = AA   length = 190
FEATURE                  Location/Qualifiers
source                   1..190
                         mol_type = protein
                         organism = synthetic construct
SEQUENCE: 79
MRDSSPLVHY GWGDPIRLRH LYTSGPHGLS SCFLRIRADG VVDCARGQSA HSLLEIKAVA            60
LRTVAIKGVH SVRYLCMGAD GKMQGLLQYS EEDCAFEEEI RPDGYNVYRS EKHRLPVSLS           120
SAKQRQLYKN RGFLPLSHFL PMLPMVPEEP EDLRGHLESD MFSSPLETDS MDPFGLVTGL           180
EAVRSPSFEK                                                                  190

SEQ ID NO: 80            moltype = AA   length = 181
FEATURE                  Location/Qualifiers
source                   1..181
                         mol_type = protein
                         organism = synthetic construct
SEQUENCE: 80
```

```
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHLPG 120
NKSPHRDPAP RGPARFLPLP GLPPALPEPP GILAPQPPDV GSSDPLSMVG PSQGRSPSYA 180
S                                                                181

SEQ ID NO: 81           moltype = AA   length = 181
FEATURE                 Location/Qualifiers
source                  1..181
                        mol_type = protein
                        organism = synthetic construct
SEQUENCE: 81
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRERLL EDGYNVYQSE AHGLPLHLPG 120
NKSPHRDPAP RGPARFLPLP GLPPAPPEPP GILAPQPPDV GSSDPLSMVG GSQGRSPSYE 180
S                                                                181

SEQ ID NO: 82           moltype = AA   length = 424
FEATURE                 Location/Qualifiers
source                  1..424
                        mol_type = protein
                        organism = synthetic construct
SEQUENCE: 82
MDKTHTCPPC PAPELLGGPS VFLFPPKPKD TLMISRTPEV TCVVVDVSHE DPEVKFNWYV  60
DGVEVHNAKT KPREEQYNST YRVVSVLTVL HQDWLNGKEY KCKVSNKALP APIEKTISKA 120
KGQPREPQVY TLPPSRDELT KNQVSLTCLV KGFYPSDIAV EWESNGQPEN NYKTTPPVLD 180
SDGSFFLYSK LTVDKSRWQQ GNVFSCSVMH EALHNHYTQK SLSLSPGKGG GGSGGGGSGG 240
GGSHPIPDSS PLLQFGGQVR QRYLYTDDAQ QTEAHLEIRE DGTVGGAADQ SPESLLQLKA 300
LKPGVIQILG VKTSRFLCQR PDGALYGSLH FDPEACSFRE RLLEDGYNVY QSEAHGLPLH 360
LPGNKSPHRD PAPRGPARFL PLPGLPPAPP EPPGILAPQP PDVGSSDPLS MVGGSQGRSP 420
SYES                                                             424

SEQ ID NO: 83           moltype = AA   length = 177
FEATURE                 Location/Qualifiers
source                  1..177
                        mol_type = protein
                        organism = synthetic construct
SEQUENCE: 83
DSSPLLQFGG QVRQRYLYTD DAQQTEAHLE IREDGTVGGA ADQSPESLLQ LKALKPGVIQ  60
ILGVKTSRFL CQRPDGALYG SLHFDPEACS FRELLLEDGY NVYQSEAHGL PLHCPGNKSP 120
HRDPAPRGPC RFLPLPGLPP ALPEPPGILA PQPPDVGSSD PLAMVGPSQG RSPSYAS    177

SEQ ID NO: 84           moltype = AA   length = 181
FEATURE                 Location/Qualifiers
source                  1..181
                        mol_type = protein
                        organism = synthetic construct
SEQUENCE: 84
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRERLL EDGYNVYQSE AHGLPLHLPG 120
NKSPHRDPAP RGPARFLPLP GLPPALPEPP GILAPQPPDV GSSDPLSMVG GSQGRSPSYE 180
S                                                                181

SEQ ID NO: 85           moltype = AA   length = 181
FEATURE                 Location/Qualifiers
source                  1..181
                        mol_type = protein
                        organism = synthetic construct
SEQUENCE: 85
HPIPDSSPLL QFGGQVRQRY LYTDDAQQTE AHLEIREDGT VGGAADQSPE SLLQLKALKP  60
GVIQILGVKT SRFLCQRPDG ALYGSLHFDP EACSFRELLL EDGYNVYQSE AHGLPLHPPG 120
NKSPHRDPAP RGPARFLPLP GLPPALPEPP GILAPQPPDV GSSDPLSMVG PSQGRSPSYA 180
S                                                                181

SEQ ID NO: 86           moltype = AA   length = 311
FEATURE                 Location/Qualifiers
source                  1..311
                        mol_type = protein
                        organism = synthetic construct
SEQUENCE: 86
HGEGTFTSDV SSYLEEQAAK EFIAWLVKGR GEPKSVDKTH TCPPCPAPEA AGGPSVFLFP  60
PKPKDTLMIS RTPEVTCVVV DVSHEDPEVK FNWYVDGVEV HNAKTKPREE QYNSTYRVVS 120
VLTVLHQDWL NGKEYKCKVS NKALPAPIEK TISKAKGQPR EPQVYTLPPS RDELTKNQVS 180
LTCLVKGFYP SDIAVEWESN GQPENNYKTT PPVLDSDGSF FLYSKLTVDK SRWQQGNVFS 240
CSVMHEALHN HYTQKSLSLS PGKIEGRMDY AEGTFISDYS IAMDKIHQQD FVNWLLAQKG 300
KKNDWKHNIT Q                                                     311

SEQ ID NO: 87           moltype = AA   length = 315
FEATURE                 Location/Qualifiers
source                  1..315
```

```
                        mol_type = protein
                        organism = synthetic construct
SEQUENCE: 87
HGEGTFTSDV  SSYLEEQAAK  EFIAWLVKGR  GRFRSEPKSC  DKTHTCPPCP  APEAAGGPSV   60
FLFPPKPKDT  LMISRTPEVT  CVVVDVSHED  PEVKFNWYVD  GVEVHNAKTK  PREEQYNSTY  120
RVVSVLTVLH  QDWLNGKEYK  CKVSNKALPA  PIEKTISKAK  GQPREPQVYT  LPPSRDELTK  180
NQVSLTCLVK  GFYPSDIAVE  WESNGQPENN  YKTTPPVLDS  DGSFFLYSKL  TVDKSRWQQG  240
NVFSCSVMHE  ALHNHYTQKS  LSLSPGKIEG  RMDYAEGTFI  SDYSIAMDKI  HQQDFVNWLL  300
AQKGKKNDWK  HNITQ                                                      315

SEQ ID NO: 88           moltype = AA  length = 457
FEATURE                 Location/Qualifiers
source                  1..457
                        mol_type = protein
                        organism = synthetic construct
SEQUENCE: 88
YAEGTFISDY  SIAMDKIHQQ  DFVNWLLAQK  GKKNDWKHNI  TQPCPAPEAA  GGPSVFLFPP   60
KPKDTLMISR  TPEVTCVVVD  VSHEDPEVKF  NWYVDGVEVH  NAKTKPREEQ  YNSTYRVVSV  120
LTVLHQDWLN  GKEYKCKVSN  KALPAPIEKT  ISKAKGQPRE  PQVYTLPPSR  DELTKNQVSL  180
TCLVKGFYPS  DIAVEWESNG  QPENNYKTTP  PVLDSDGSFF  LYSKLTVDKS  RWQQGNVFSC  240
SVMHEALHNH  YTQKSLSLSP  GKIEGRMDRD  SSPLVHYGWG  DPIRLRHLYT  SGPHGLSSCF  300
LRIRADGVVD  CARGQSAHSL  LEIKAVALRT  VAIKGVHSVR  YLCMGADGKM  QGLLQYSEED  360
CAFEEEIRPD  GYNVYRSEKH  RLPVSLSSAK  QRQLYKNRGF  LPLSHFLPML  PMVPEEPEDL  420
RGHLESDMFS  SPLETDSMDP  FGLVTGLEAV  RSPSFEK                            457

SEQ ID NO: 89           moltype = AA  length = 484
FEATURE                 Location/Qualifiers
source                  1..484
                        mol_type = protein
                        organism = synthetic construct
SEQUENCE: 89
MEFGLSWVFL  VAIIKGVQCY  AEGTFISDYS  IAMDKIHQQD  FVNWLLAQKG  KKNDWKHNIT   60
QRFRSEPKSC  DKTHTCPPCP  APEAAGGPSV  FLFPPKPKDT  LMISRTPEVT  CVVVDVSHED  120
PEVKFNWYVD  GVEVHNAKTK  PREEQYNSTY  RVVSVLTVLH  QDWLNGKEYK  CKVSNKALPA  180
PIEKTISKAK  GQPREPQVYT  LPPSRDELTK  NQVSLTCLVK  GFYPSDIAVE  WESNGQPENN  240
YKTTPPVLDS  DGSFFLYSKL  TVDKSRWQQG  NVFSCSVMHE  ALHNHYTQKS  LSLSPGKIEG  300
RMDHPIPDSS  PLLQFGGQVR  QRYLYTDDAQ  QTEAHLEIRE  DGTVGGAADQ  SPESLLQLKA  360
LKPGVIQILG  VKTSRFLCQR  PDGALYGSLH  FDPEACSFRE  RLLEDGYNVY  QSEAHGLPLH  420
LPGNKSPHRD  PAPRGPARFL  PLPGLPPALP  EPPGILAPQP  PDVGSSDPLS  MVGGSQGRSP  480
SYES                                                                   484

SEQ ID NO: 90           moltype = AA  length = 480
FEATURE                 Location/Qualifiers
source                  1..480
                        mol_type = protein
                        organism = synthetic construct
SEQUENCE: 90
MEFGLSWVFL  VAIIKGVQCY  AEGTFISDYS  IAMDKIHQQD  FVNWLLAQKG  KKNDWKHNIT   60
QEPKSVDKTH  TCPPCPAPEA  AGGPSVFLFP  PKPKDTLMIS  RTPEVTCVVV  DVSHEDPEVK  120
FNWYVDGVEV  HNAKTKPREE  QYNSTYRVVS  VLTVLHQDWL  NGKEYKCKVS  NKALPAPIEK  180
TISKAKGQPR  EPQVYTLPPS  RDELTKNQVS  LTCLVKGFYP  SDIAVEWESN  GQPENNYKTT  240
PPVLDSDGSF  FLYSKLTVDK  SRWQQGNVFS  CSVMHEALHN  HYTQKSLSLS  PGKIEGRMDH  300
PIPDSSPLLQ  FGGQVRQRYL  YTDDAQQTEA  HLEIREDGTV  GGAADQSPES  LLQLKALKPG  360
VIQILGVKTS  RFLCQRPDGA  LYGSLHFDPE  ACSFRELLLE  DGYNVYQSEA  HGLPLHPPGN  420
KSPHRDPAPR  GPARFLPLPG  LPPALPEPPG  ILAPQPPDVG  SSDPLSMVGP  SQGRSPSYAS  480

SEQ ID NO: 91           moltype = AA  length = 31
FEATURE                 Location/Qualifiers
source                  1..31
                        mol_type = protein
                        organism = synthetic construct
SEQUENCE: 91
HGEGTFTSDV  SSYLEEQAAK  EFIAWLVKGR  G                                   31

SEQ ID NO: 92           moltype = AA  length = 12
FEATURE                 Location/Qualifiers
source                  1..12
                        mol_type = protein
                        organism = synthetic construct
SEQUENCE: 92
EPKSCDKTHT  CP                                                          12

SEQ ID NO: 93           moltype = AA  length = 330
FEATURE                 Location/Qualifiers
source                  1..330
                        mol_type = protein
                        organism = synthetic construct
SEQUENCE: 93
MEFGLSWVFL  VAIIKGVQCH  GEGTFTSDVS  SYLEEQAAKE  FIAWLVKGRG  EPKSVDKTHT   60
```

```
CPPCPAPEAA GGPSVFLFPP KPKDTLMISR TPEVTCVVVD VSHEDPEVKF NWYVDGVEVH    120
NAKTKPREEQ YNSTYRVVSV LTVLHQDWLN GKEYKCKVSN KALPAPIEKT ISKAKGQPRE    180
PQVYTLPPSR DELTKNQVSL TCLVKGFYPS DIAVEWESNG QPENNYKTTP PVLDSDGSFF    240
LYSKLTVDKS RWQQGNVFSC SVMHEALHNH YTQKSLSLSP GKIEGRMDYA EGTFISDYSI    300
AMDKIHQQDF VNWLLAQKGK KNDWKHNITQ                                    330

SEQ ID NO: 94           moltype = AA   length = 315
FEATURE                 Location/Qualifiers
source                  1..315
                        mol_type = protein
                        organism = synthetic construct
SEQUENCE: 94
MEFGLSWVFL VAIIKGVQCH GEGTFTSDVS SYLEEQAAKE FIAWLVKGRG EPKSVDKTHT     60
CPPCPAPEAA GGPSVFLFPP KPKDTLMISR TPEVTCVVVD VSHEDPEVKF NWYVDGVEVH    120
NAKTKPREEQ YNSTYRVVSV LTVLHQDWLN GKEYKCKVSN KALPAPIEKT ISKAKGQPRE    180
PQVYTLPPSR DELTKNQVSL TCLVKGFYPS DIAVEWESNG QPENNYKTTP PVLDSDGSFF    240
LYSKLTVDKS RWQQGNVFSC SVMHEALHNH YTQKSLSLSP GKIEGRMDEG TFISDYSIAM    300
DKIHQQDFVN WLLAQ                                                    315

SEQ ID NO: 95           moltype = AA   length = 330
FEATURE                 Location/Qualifiers
source                  1..330
                        mol_type = protein
                        organism = synthetic construct
SEQUENCE: 95
MEFGLSWVFL VAIIKGVQCH GEGTFTSDVS SYLEEQAAKE FIAWLVKGRG EPKSVDKTHT     60
CPPCPAPEAA GGPSVFLFPP KPKDTLMISR TPEVTCVVVD VSHEDPEVKF NWYVDGVEVH    120
NAKTKPREEQ YNSTYRVVSV LTVLHQDWLN GKEYKCKVSN KALPAPIEKT ISKAKGQPRE    180
PQVYTLPPSR DELTKNQVSL TCLVKGFYPS DIAVEWESNG QPENNYKTTP PVLDSDGSFF    240
LYSKLTVDKS RWQQGNVFSC SVMHEALHNH YTQKSLSLSP GKIEGRMDYA PGTFISDYSI    300
AMDKIHQQDF VNWLLAQKGK KNDWKHNITQ                                    330

SEQ ID NO: 96           moltype = AA   length = 315
FEATURE                 Location/Qualifiers
source                  1..315
                        mol_type = protein
                        organism = synthetic construct
SEQUENCE: 96
MEFGLSWVFL VAIIKGVQCH GEGTFTSDVS SYLEEQAAKE FIAWLVKGRG EPKSVDKTHT     60
CPPCPAPEAA GGPSVFLFPP KPKDTLMISR TPEVTCVVVD VSHEDPEVKF NWYVDGVEVH    120
NAKTKPREEQ YNSTYRVVSV LTVLHQDWLN GKEYKCKVSN KALPAPIEKT ISKAKGQPRE    180
PQVYTLPPSR DELTKNQVSL TCLVKGFYPS DIAVEWESNG QPENNYKTTP PVLDSDGSFF    240
LYSKLTVDKS RWQQGNVFSC SVMHEALHNH YTQKSLSLSP GKIEGRMDPG TFISDYSIAM    300
DKIHQQDFVN WLLAQ                                                    315

SEQ ID NO: 97           moltype = AA   length = 42
FEATURE                 Location/Qualifiers
source                  1..42
                        mol_type = protein
                        organism = synthetic construct
SEQUENCE: 97
YAPGTFISDY SIAMDKIHQQ DFVNWLLAQK GKKNDWKHNI TQ                        42

SEQ ID NO: 98           moltype = AA   length = 27
FEATURE                 Location/Qualifiers
source                  1..27
                        mol_type = protein
                        organism = synthetic construct
SEQUENCE: 98
EGTFISDYSI AMDKIHQQDF VNWLLAQ                                        27

SEQ ID NO: 99           moltype = AA   length = 27
FEATURE                 Location/Qualifiers
source                  1..27
                        mol_type = protein
                        organism = synthetic construct
SEQUENCE: 99
PGTFISDYSI AMDKIHQQDF VNWLLAQ                                        27

SEQ ID NO: 100          moltype = AA   length = 21
FEATURE                 Location/Qualifiers
source                  1..21
                        mol_type = protein
                        organism = synthetic construct
SEQUENCE: 100
YSIAMDKIHQ QDFVNWLLAQ K                                              21

SEQ ID NO: 101          moltype = AA   length = 21
FEATURE                 Location/Qualifiers
```

| | | |
|---|---|---|
| source | 1..21<br>mol_type = protein<br>organism = synthetic construct | |
| SEQUENCE: 101 | | |
| YSIAMDKIRQ QDFVNWLLAQ K | | 21 |
| | | |
| SEQ ID NO: 102<br>FEATURE<br>source | moltype = AA  length = 39<br>Location/Qualifiers<br>1..39<br>mol_type = protein<br>organism = synthetic construct | |
| SEQUENCE: 102 | | |
| YXEGTFISDY SIALEKIRQQ EFVNWLLKQK PSSGAPPKS | | 39 |
| | | |
| SEQ ID NO: 103<br>FEATURE<br>source | moltype = AA  length = 30<br>Location/Qualifiers<br>1..30<br>mol_type = protein<br>organism = synthetic construct | |
| SEQUENCE: 103 | | |
| YAEGTFISDY SIAMDKIHQQ DFVNWLLAQK | | 30 |
| | | |
| SEQ ID NO: 104<br>FEATURE<br>source | moltype = AA  length = 31<br>Location/Qualifiers<br>1..31<br>mol_type = protein<br>organism = synthetic construct | |
| SEQUENCE: 104 | | |
| YAEGTFISDY SIAMDKIHQQ DFVNWLLAQK G | | 31 |
| | | |
| SEQ ID NO: 105<br>FEATURE<br>source | moltype = AA  length = 494<br>Location/Qualifiers<br>1..494<br>mol_type = protein<br>organism = synthetic construct | |
| SEQUENCE: 105 | | |
| MEFGLSWVFL VAIIKGVQCY AEGTFISDYS IAMDKIHQQD FVNWLLAQKG KKNDWKHNIT | | 60 |
| QRFRSEPKSC DKTHTCPPPC PAPEAAGGPS VFLFPPKPKD TLMISRTPEV TCVVVDVSHE | | 120 |
| DPEVKFNWYV DGVEVHNAKT KPREEQYNST YRVVSVLTVL HQDWLNGKEY KCKVSNKALP | | 180 |
| APIEKTISKA KGQPREPQVY TLPPSRDELT KNQVSLTCLV KGFYPSDIAV EWESNGQPEN | | 240 |
| NYKTTPPVLD SDGSFFLYSK LTVDKSRWQQ GNVFSCSVMH EALHNHYTQK SLSLSPGKIE | | 300 |
| GRMDMRDSSP LVHYGWGDPI RLRHLYTSGP HGLSSCFLRI RADGVVDCAR GQSAHSLLEI | | 360 |
| KAVALRTVAI KGVHSVRYLC MGADGKMQGL LQYSEEDCAF EEEIRPDGYN VYRSEKHRLP | | 420 |
| VSLSSAKQRQ LYKNRGFLPL SHFLPMLPMV PEEPEDLRGH LESDMFSSPL ETDSMDPFGL | | 480 |
| VTGLEAVRSP SFEK | | 494 |
| | | |
| SEQ ID NO: 106<br>FEATURE<br>source | moltype = AA  length = 485<br>Location/Qualifiers<br>1..485<br>mol_type = protein<br>organism = synthetic construct | |
| SEQUENCE: 106 | | |
| MEFGLSWVFL VAIIKGVQCY AEGTFISDYS IAMDKIHQQD FVNWLLAQKG KKNDWKHNIT | | 60 |
| QRFRSEPKSC DKTHTCPPPC PAPEAAGGPS VFLFPPKPKD TLMISRTPEV TCVVVDVSHE | | 120 |
| DPEVKFNWYV DGVEVHNAKT KPREEQYNST YRVVSVLTVL HQDWLNGKEY KCKVSNKALP | | 180 |
| APIEKTISKA KGQPREPQVY TLPPSRDELT KNQVSLTCLV KGFYPSDIAV EWESNGQPEN | | 240 |
| NYKTTPPVLD SDGSFFLYSK LTVDKSRWQQ GNVFSCSVMH EALHNHYTQK SLSLSPGKIE | | 300 |
| GRMDHPIPDS SPLLQFGGQV RQRYLYTDDA QQTEAHLEIR EDGTVGGAAD QSPESLLQLK | | 360 |
| ALKPGVIQIL GVKTSRFLCQ RPDGALYGSL HFDPEACSFR ERLLEDGYNV YQSEAHGLPL | | 420 |
| HLPGNKSPHR DPAPRGPARF LPLPGLPPAL PEPPGILAPQ PPDVGSSDPL SMVGGSQGRS | | 480 |
| PSYES | | 485 |
| | | |
| SEQ ID NO: 107<br>FEATURE<br>source | moltype = AA  length = 484<br>Location/Qualifiers<br>1..484<br>mol_type = protein<br>organism = synthetic construct | |
| SEQUENCE: 107 | | |
| MEFGLSWVFL VAIIKGVQCY AEGTFISDYS IAMDKIHQQD FVNWLLAQKG KKNDWKHNIT | | 60 |
| QRFRSEPKSC DKTHTCPPCP APEAAGGPSV FLFPPKPKDT LMISRTPEVT CVVVDVSHED | | 120 |
| PEVKFNWYVD GVEVHNAKTK PREEQYNSTY RVVSVLTVLH QDWLNGKEYK CKVSNKALPA | | 180 |
| PIEKTISKAK GQPREPQVYT LPPSRDELTK NQVSLTCLVK GFYPSDIAVE WESNGQPENN | | 240 |
| YKTTPPVLDS DGSFFLYSKL TVDKSRWQQG NVFSCSVMHE ALHNHYTQKS LSLSPGKIEG | | 300 |
| RMDHPIPDSS PLLQFGGQVR QRYLYTDDAQ QTEAHLEIRE DGTVGGAADQ SPESLLQLKA | | 360 |
| LKPGVIQILG VKTSRFLCQR PDGALYGSLH FDPEACSFRE LLLEDGYNVY QSEAHGLPLH | | 420 |
| PPGNKSPHRD PAPRGPARFL PLPGLPPALP EPPGILAPQP PDVGSSDPLS MVGPSQGRSP | | 480 |
| SYAS | | 484 |
| | | |
| SEQ ID NO: 108 | moltype = AA  length = 311 | |

```
FEATURE              Location/Qualifiers
source               1..311
                     mol_type = protein
                     organism = synthetic construct
SEQUENCE: 108
HGEGTFTSDV SSYLEEQAAK EFIAWLVKGR GEPKSCDKTH TCPPCPAPEA AGGPSVFLFP  60
PKPKDTLMIS RTPEVTCVVV DVSHEDPEVK FNWYVDGVEV HNAKTKPREE QYNSTYRVVS 120
VLTVLHQDWL NGKEYKCKVS NKALPAPIEK TISKAKGQPR EPQVYTLPPS RDELTKNQVS 180
LTCLVKGFYP SDIAVEWESN GQPENNYKTT PPVLDSDGSF FLYSKLTVDK SRWQQGNVFS 240
CSVMHEALHN HYTQKSLSLS PGKIEGRMDY AEGTFISDYS IAMDKIHQQD FVNWLLAQKG 300
KKNDWKHNIT Q                                                     311

SEQ ID NO: 109       moltype = AA  length = 334
FEATURE              Location/Qualifiers
source               1..334
                     mol_type = protein
                     organism = synthetic construct
SEQUENCE: 109
MEFGLSWVFL VAIIKGVQCH GEGTFTSDVS SYLEEQAAKE FIAWLVKGRG RFRSEPKSCD  60
KTHTCPPCPA PEAAGGPSVF LFPPKPKDTL MISRTPEVTC VVVDVSHEDP EVKFNWYVDG 120
VEVHNAKTKP REEQYNSTYR VVSVLTVLHQ DWLNGKEYKC KVSNKALPAP IEKTISKAKG 180
QPREPQVYTL PPSRDELTKN QVSLTCLVKG FYPSDIAVEW ESNGQPENNY KTTPPVLDSD 240
GSFFLYSKLT VDKSRWQQGN VFSCSVMHEA LHNHYTQKSL SLSPGKIEGR MDYAEGTFIS 300
DYSIAMDKIH QQDFVNWLLA QKGKKNDWKH NITQ                            334

SEQ ID NO: 110       moltype = AA  length = 330
FEATURE              Location/Qualifiers
source               1..330
                     mol_type = protein
                     organism = synthetic construct
SEQUENCE: 110
MEFGLSWVFL VAIIKGVQCH GEGTFTSDVS SYLEEQAAKE FIAWLVKGRG EPKSVDKTHT  60
CPPCPAPEAA GGPSVFLFPP KPKDTLMISR TPEVTCVVVD VSHEDPEVKF NWYVDGVEVH 120
NAKTKPREEQ YNSTYRVVSV LTVLHQDWLN GKEYKCKVSN KALPAPIEKT ISKAKGQPRE 180
PQVYTLPPSR DELTKNQVSL TCLVKGFYPS DIAVEWESNG QPENNYKTTP PVLDSDGSFF 240
LYSKLTVDKS RWQQGNVFSC SVMHEALHNH YTQKSLSLSP GKIEGRMDYA EGTFISDYSI 300
AMDKIHQQDF VNWLLAQKGK KNDWKHNITQ                                 330

SEQ ID NO: 111       moltype = AA  length = 484
FEATURE              Location/Qualifiers
source               1..484
                     mol_type = protein
                     organism = synthetic construct
SEQUENCE: 111
MEFGLSWVFL VAIIKGVQCY AEGTFISDYS IAMDKIHQQD FVNWLLAQKG KKNDWKHNIT  60
QRFRSEPKSV DKTHTCPPCP APEAAGGPSV FLFPPKPKDT LMISRTPEVT CVVVDVSHED 120
PEVKFNWYVD GVEVHNAKTK PREEQYNSTY RVVSVLTVLH QDWLNGKEYK CKVSNKALPA 180
PIEKTISKAK GQPREPQVYT LPPSRDELTK NQVSLTCLVK GFYPSDIAVE WESNGQPENN 240
YKTTPPVLDS DGSFFLYSKL TVDKSRWQQG NVFSCSVMHE ALHNHYTQKS LSLSPGKIEG 300
RMDHPIPDSS PLLQFGGQVR QRYLYTDDAQ QTEAHLEIRE DGTVGGAADQ SPESLLQLKA 360
LKPGVIQILG VKTSRFLCQR PDGALYGSLH FDPEACSFRE LLEDGYNVY QSEAHGLPLH 420
LPGNKSPHRD PAPRGPARFL PLPGLPPALP EPPGILAPQP PDVGSSDPLS MVGGSQGRSP 480
SYES                                                             484

SEQ ID NO: 112       moltype = AA  length = 484
FEATURE              Location/Qualifiers
source               1..484
                     mol_type = protein
                     organism = synthetic construct
SEQUENCE: 112
MEFGLSWVFL VAIIKGVQCY AEGTFISDYS IAMDKIHQQD FVNWLLAQKG KKNDWKHNIT  60
QRFRSEPKSV DKTHTCPPCP APEAAGGPSV FLFPPKPKDT LMISRTPEVT CVVVDVSHED 120
PEVKFNWYVD GVEVHNAKTK PREEQYNSTY RVVSVLTVLH QDWLNGKEYK CKVSNKALPA 180
PIEKTISKAK GQPREPQVYT LPPSRDELTK NQVSLTCLVK GFYPSDIAVE WESNGQPENN 240
YKTTPPVLDS DGSFFLYSKL TVDKSRWQQG NVFSCSVMHE ALHNHYTQKS LSLSPGKIEG 300
RMDHPIPDSS PLLQFGGQVR QRYLYTDDAQ QTEAHLEIRE DGTVGGAADQ SPESLLQLKA 360
LKPGVIQILG VKTSRFLCQR PDGALYGSLH FDPEACSFRE LLLEDGYNVY QSEAHGLPLH 420
PPGNKSPHRD PAPRGPARFL PLPGLPPALP EPPGILAPQP PDVGSSDPLS MVGPSQGRSP 480
SYAS                                                             484

SEQ ID NO: 113       moltype = AA  length = 12
FEATURE              Location/Qualifiers
source               1..12
                     mol_type = protein
                     organism = synthetic construct
SEQUENCE: 113
EPKSVDKTHT CP                                                     12

SEQ ID NO: 114       moltype = DNA  length = 235
```

```
FEATURE                 Location/Qualifiers
source                  1..235
                        mol_type = other DNA
                        organism = synthetic construct
SEQUENCE: 114
gctcgctttc ttgctgtcca atttctatta aaggttcctt tgttccctaa gtccaactac    60
taaactgggg gatattatga agggccttga gcatctggat tctgcctaat aaaaaacatt   120
tattttcatt gcaattgcca tgtgtatgtg ggttcgccca catactctga tgatccccaa   180
tcgtggcgtg tcggcctgct tcggcaggca ctggcgccgg gatcattcat ggcaa        235

SEQ ID NO: 115          moltype = DNA   length = 451
FEATURE                 Location/Qualifiers
source                  1..451
                        mol_type = other DNA
                        organism = synthetic construct
SEQUENCE: 115
aaagcaaaac taacatgaaa caaggctaga agtcaggtcg gattaagcca tagtacggaa    60
aaaactatgc tacctgtgag ccccgtccaa ggacgttaaa agaagtcagg ccatcataaa   120
tgccatagct tgagtaaact atgcagcctg tagctccacc tgagaaggtg taaaaaatcc   180
gggaggccac aaaccatgga agctgtacgc atggcgtagt ggactagcgg ttagaggaga   240
cccctccctt acaaatcgca gcaacaatgg gggcccaagg cgagatgaag ctgtagtctc   300
gctggaagga ctagaggtta gaggagaccc ccccgaacaa aaaaacagca tattgacgct   360
gggaaagacc agagatcctg ctgtctcctc agcatcattc caggcacaga acgccagaaa   420
atggaatggt gctgttgaat caacaggttc t                                  451

SEQ ID NO: 116          moltype = DNA   length = 111
FEATURE                 Location/Qualifiers
source                  1..111
                        mol_type = other DNA
                        organism = synthetic construct
SEQUENCE: 116
gctggagcct cggtggccta gcttcttgcc ccttgggcct cccccccagcc cctcctcccc    60
ttcctgcacc cgtaccccg tggtctttga ataaagtctg agtgggcggc a              111

SEQ ID NO: 117          moltype = RNA   length = 209
FEATURE                 Location/Qualifiers
source                  1..209
                        mol_type = other RNA
                        organism = synthetic construct
SEQUENCE: 117
ttctagagcg gccgcttcga gccggttgaa tcgctgatct cacgccgtgg tgagctcgct    60
ttcttgctgt ccaatttcta ttaaaggttc ctttgttccc taagtccaac tactaaactg   120
gggatatta tgaagggcct tgagcatctg gattctgcct aataaaaaac atttattttc    180
attgcaaagt tccgcgtacg tacggcgtc                                     209

SEQ ID NO: 118          moltype = DNA   length = 295
FEATURE                 Location/Qualifiers
source                  1..295
                        mol_type = other DNA
                        organism = synthetic construct
SEQUENCE: 118
ctcgagctgg tactgcatgc acgcaatgct agctgcccct ttcccgtcct gggtaccccg    60
agtctccccc gacctcgggt cccaggtatg ctcccacctc cacctgcccc actcaccacc   120
tctgctagtt ccagacacct cccaagcacg cagcaatgca gctcaaaacg cttagcctag   180
ccacaccccc acgggaaaca gcagtgatta acctttagca ataaacgaaa gtttaactaa   240
gctatactaa ccccagggtt ggtcaatttc gtgccagcca caccctggag ctagc         295

SEQ ID NO: 119          moltype = RNA   length = 94
FEATURE                 Location/Qualifiers
source                  1..94
                        mol_type = other RNA
                        organism = synthetic construct
SEQUENCE: 119
gctgccttct gcggggcttg ccttctggcc atgcccttct tctctcccctt gcacctgtac    60
ctcttggtct ttgaataaag cctgagtagg aagt                                94

SEQ ID NO: 120          moltype = DNA   length = 260
FEATURE                 Location/Qualifiers
source                  1..260
                        mol_type = other DNA
                        organism = synthetic construct
SEQUENCE: 120
gggccttttcc aagattgctg tttttgtttt ggagcttcaa gactttgcat ttcctagtat    60
ttctgtttgt cagttctcaa tttcctgtgt ttgcaatgtt gaaatttttt ggtgaagtac   120
tgaacttgct tttttttccgg tttctacatg cagagatgaa tttatactgc catcttacga   180
ctatttcttc tttttaatac acttaactca ggccatttttt taagttggtt acttcaaagt   240
aaataaactt taaaattcaa                                                260

SEQ ID NO: 121          moltype = DNA   length = 319
```

```
FEATURE              Location/Qualifiers
source               1..319
                     mol_type = other DNA
                     organism = synthetic construct
SEQUENCE: 121
ccgctacgcc ccaatgaccc gaccagcaaa actcgacgta ctaccgagga accgatgtgc    60
ataacgcatc gggctggtac attagatccc cgtcatcaga cgggctcata gcgacgctaa   120
aactcgacgt attcccgagg aagtgcagtg cataatgctg agcagcgtcg tcatatattc   180
acttattatt caatatagag tagacaccaa aactcaatgt attttctgagg aagcgtggtg   240
cataatgcca cgcagtgtct acataatcaa tttattattt tcttttattt tattcacata   300
attttgtttt taatatttc                                                 319

SEQ ID NO: 122       moltype = DNA  length = 154
FEATURE              Location/Qualifiers
source               1..154
                     mol_type = other DNA
                     organism = synthetic construct
SEQUENCE: 122
catcacattt aaaagcatct cagcctacca tgagaataag agaaagaaaa tgaagatcaa    60
aagcttattc atctgttttt cttttcgtt ggtgtaaagc caacaccctg tctaaaaaac   120
ataaatttct ttaatcattt tgcctctttt ctct                                154

SEQ ID NO: 123       moltype = DNA  length = 295
FEATURE              Location/Qualifiers
source               1..295
                     mol_type = other DNA
                     organism = synthetic construct
SEQUENCE: 123
atattatccc taatacctgc caccccactc ttaatcagtg gtggaagaac ggtctcagaa    60
ctgttttgttt caattggcca tttaagttta gtagtaaaag actggttaat gataacaatg   120
catcgtaaaa ccttcagaag gaaaggagaa tgtttgtgg accactttgg ttttctttt    180
tgcgtgtggc agtttaagt tattagtttt taaaatcagt acttttaat ggaaacaact    240
tgaccaaaaa tttgtcacag aattttgaga cccattaaaa aagttaaatg agaaa         295

SEQ ID NO: 124       moltype = DNA  length = 337
FEATURE              Location/Qualifiers
source               1..337
                     mol_type = other DNA
                     organism = synthetic construct
SEQUENCE: 124
gcgcctgccc acctgccacc gactgctgga acccagccag tgggagggcc tggcccacca    60
gagtcctgct ccctcactcc tcgccccgcc cctgtcccca gagtcccacc tggggggctct   120
ctccacccctt ctcagagttc cagtttcaac cagagttcca accaatgggc tccatcctct   180
ggattctggc caatgaaata tctccctggc agggtcctct tcttttccca gagctccacc   240
ccaaccagga gctctagtta tggagagct cccagcacac tcggagcttg tgctttgtct   300
ccacgcaaag cgataaataa aagcattggt ggcctta                             337

SEQ ID NO: 125       moltype = DNA  length = 159
FEATURE              Location/Qualifiers
source               1..159
                     mol_type = other DNA
                     organism = synthetic construct
SEQUENCE: 125
gtgtgtggag gacaccctga accccccgct ttcaaacaag ttttcaaatt gtttgaggtc    60
aggatttctc aaaactgattc cttctttgc atatgagtat ttgaaaataa atattttccc   120
agaatataaa taaatcatca catgattatt ttaactata                           159

SEQ ID NO: 126       moltype = DNA  length = 111
FEATURE              Location/Qualifiers
source               1..111
                     mol_type = other DNA
                     organism = synthetic construct
SEQUENCE: 126
gctggagcct cggtggccta gcttcttgcc ccttgggcct cccccagcc cctcctcccc     60
ttcctgcacc cgtaccccg tggtctttga ataaagtctg agtgggcggc a              111

SEQ ID NO: 127       moltype = RNA  length = 209
FEATURE              Location/Qualifiers
source               1..209
                     mol_type = other RNA
                     organism = synthetic construct
SEQUENCE: 127
ttctagagcg gccgcttcga gccggttgaa tcgctgatct cacgccgtgg tgagctcgct    60
ttcttgctgt ccaatttcta ttaaaggttc ctttgttgcc taagtccaac tactaaactg   120
ggggatatta tgaagggcct tgagcatctg gattctgcct aataaaaaac atttattttc   180
attgcaaagt tccgcgtacg tacggcgtc                                      209

SEQ ID NO: 128       moltype = DNA  length = 50
FEATURE              Location/Qualifiers
```

|                        |                                                            |     |
|------------------------|------------------------------------------------------------|-----|
| source                 | 1..50<br>mol_type = other DNA<br>organism = synthetic construct |     |
| SEQUENCE: 128          |                                                            |     | acatttgctt ctgacacaac tgtgttcact agcaacctca aacagacacc           50

| SEQ ID NO: 129<br>FEATURE<br>source | moltype = DNA   length = 69<br>Location/Qualifiers<br>1..69<br>mol_type = other DNA<br>organism = synthetic construct |     |
|---|---|---|
| SEQUENCE: 129 | | | acatttgctt ctgacacaac tgtgttcact agcaacctca aacagacacc ccccggcgcc   60
gccaccatg                                                           69

| SEQ ID NO: 130<br>FEATURE<br>source | moltype = DNA   length = 69<br>Location/Qualifiers<br>1..69<br>mol_type = other DNA<br>organism = synthetic construct |     |
|---|---|---|
| SEQUENCE: 130 | | | acatttgctt ctgacacaac tgtgttcact agcaacctca aacagacacc ggggcgcccg   60
gccaccatg                                                           69

| SEQ ID NO: 131<br>FEATURE<br>source | moltype = DNA   length = 398<br>Location/Qualifiers<br>1..398<br>mol_type = other DNA<br>organism = synthetic construct |     |
|---|---|---|
| SEQUENCE: 131 | | | ttggggcga cactccacca tagatcactc ccctgtgagg aactactgtc ttcacgcaga    60
aagcgtctag ccatggcgtt agtatgagtg tcgtgcagcc tccaggaccc ccctcccgg   120
gagagccata gtggtctgcg aaccggtga gtacaccgga attgccagga cgaccgggtc   180
ctttcttgga ttaacccgct caatgcctgg agatttgggc gtgccccgc gagactgcta   240
gccgagtagt gttgggtcgc gaaaggcctt gtggtactgc ctgatagggt gcttgcgagt   300
gccccgggag gtctcgtaga ccgtgcatca tgagcacaaa tcctaaacct caaagaaaaa   360
ccaaacgtaa caagggcgaa ttcgttggta aagccacc                          398

| SEQ ID NO: 132<br>FEATURE<br>source | moltype = DNA   length = 408<br>Location/Qualifiers<br>1..408<br>mol_type = other DNA<br>organism = synthetic construct |     |
|---|---|---|
| SEQUENCE: 132 | | | ttggggcga cactccacca tagatcactc ccctgtgagg aactactgtc ttcacgcaga    60
aagcgtctag ccatggcgtt agtatgagtg tcgtgcagcc tccaggaccc ccctcccgg   120
gagagccata gtggtctgcg aaccggtga gtacaccgga attgccagga cgaccgggtc   180
ctttcttgga ttaacccgct caatgcctgg agatttgggc gtgccccgc gagactgcta   240
gccgagtagt gttgggtcgc gaaaggcctt gtggtactgc ctgatagggt gcttgcgagt   300
gccccgggag gtctcgtaga ccgtgcatca tgagcacaaa tcctaaacct caaagaaaaa   360
ccaaacgtaa caagggcgaa ttcgttggta accccggcg ccgccacc                408

| SEQ ID NO: 133<br>FEATURE<br>source | moltype = DNA   length = 408<br>Location/Qualifiers<br>1..408<br>mol_type = other DNA<br>organism = synthetic construct |     |
|---|---|---|
| SEQUENCE: 133 | | | ttggggcga cactccacca tagatcactc ccctgtgagg aactactgtc ttcacgcaga    60
aagcgtctag ccatggcgtt agtatgagtg tcgtgcagcc tccaggaccc ccctcccgg   120
gagagccata gtggtctgcg aaccggtga gtacaccgga attgccagga cgaccgggtc   180
ctttcttgga ttaacccgct caatgcctgg agatttgggc gtgccccgc gagactgcta   240
gccgagtagt gttgggtcgc gaaaggcctt gtggtactgc ctgatagggt gcttgcgagt   300
gccccgggag gtctcgtaga ccgtgcatca tgagcacaaa tcctaaacct caaagaaaaa   360
ccaaacgtaa caagggcgaa ttcgttggta aagggcgcgc cggccacc               408

| SEQ ID NO: 134<br>FEATURE<br>source | moltype = DNA   length = 57<br>Location/Qualifiers<br>1..57<br>mol_type = other DNA<br>organism = synthetic construct |     |
|---|---|---|
| SEQUENCE: 134 | | | gggaaataag agagaaaaga agagtaagaa gaaatataag accccggcgc cgccacc     57

| SEQ ID NO: 135<br>FEATURE<br>source | moltype = RNA   length = 53<br>Location/Qualifiers<br>1..53<br>mol_type = other RNA<br>organism = synthetic construct |     |
|---|---|---|

```
SEQUENCE: 135
gggacatttg cttctgacac aactgtgttc actagcaacc tcaaacagac acc          53

SEQ ID NO: 136         moltype = DNA   length = 225
FEATURE                Location/Qualifiers
source                 1..225
                       mol_type = other DNA
                       organism = synthetic construct
SEQUENCE: 136
tttaaaatct gtgtggctgt cactcggctg cttgcttagt gcactcacgc agtataatta    60
ataactaatt actgtcgttg acaggacacg agtaactcgt ctatcttctg caggctgctt   120
acggtttcgt ccgtgttgca gccgatcatc agcacatcta ggtttcgtcc gggtgtgacc   180
gaaaggtaag ttggagagcc ttgtccctgg tttcaacgag aaaac                   225

SEQ ID NO: 137         moltype = DNA   length = 47
FEATURE                Location/Qualifiers
source                 1..47
                       mol_type = other DNA
                       organism = synthetic construct
SEQUENCE: 137
gggaaataag agagaaaaga agagtaagaa gaaatataag agccacc                  47

SEQ ID NO: 138         moltype = DNA   length = 54
FEATURE                Location/Qualifiers
source                 1..54
                       mol_type = other DNA
                       organism = synthetic construct
SEQUENCE: 138
gagaataaac tagtattctt ctggtcccca cagactcaga gagaacccgc cacc          54

SEQ ID NO: 139         moltype = DNA   length = 43
FEATURE                Location/Qualifiers
source                 1..43
                       mol_type = other DNA
                       organism = synthetic construct
SEQUENCE: 139
gggaaaaaga gagaaaagaa gagaagaaga aaaagagcc acc                       43

SEQ ID NO: 140         moltype = DNA   length = 222
FEATURE                Location/Qualifiers
source                 1..222
                       mol_type = other DNA
                       organism = synthetic construct
SEQUENCE: 140
aacggctagc ctgaggagct gctgcgacag tccactacct ttttcgagag tgactcccgt    60
tgtcccaagg cttcccagag cgaacctgtg cggctgcagg caccggcgcg tcgagtttcc   120
ggcgtccgga aggaccgagc tcttctcgcg gatccagtgt tccgtttcca gccccaatc    180
tcagagcgga gccgacagag agcagggaac cggcccgcca cc                      222

SEQ ID NO: 141         moltype = DNA   length = 56
FEATURE                Location/Qualifiers
source                 1..56
                       mol_type = other DNA
                       organism = synthetic construct
SEQUENCE: 141
tagtcagtgt aatatacagt aactgaccaa accacatcca ccgtaaaccc gccacc        56

SEQ ID NO: 142         moltype = DNA   length = 50
FEATURE                Location/Qualifiers
source                 1..50
                       mol_type = other DNA
                       organism = synthetic construct
SEQUENCE: 142
gagacccaag ctggctagcg ggagaaagct taccggctag cgccgccacc               50

SEQ ID NO: 143         moltype = DNA   length = 231
FEATURE                Location/Qualifiers
source                 1..231
                       mol_type = other DNA
                       organism = synthetic construct
SEQUENCE: 143
tttaaaatct gtgtggctgt cactcggctg cttgcttagt gcactcacgc agtataatta    60
ataactaatt actgtcgttg acaggacacg agtaactcgt ctatcttctg caggctgctt   120
acggtttcgt ccgtgttgca gccgatcatc agcacatcta ggtttcgtcc gggtgtgacc   180
gaaaggtaag ttggagagcc ttgtccctgg tttcaacgag aaaacgccac c             231

SEQ ID NO: 144         moltype = DNA   length = 73
FEATURE                Location/Qualifiers
source                 1..73
```

```
                         mol_type = other DNA
                         organism = synthetic construct
SEQUENCE: 144
gggtcagtgt cacctccagg atacagacag ccccccttca gcccagccca gccaggtctc      60
ctacaccgcc acc                                                         73

SEQ ID NO: 145           moltype = DNA   length = 61
FEATURE                  Location/Qualifiers
source                   1..61
                         mol_type = other DNA
                         organism = synthetic construct
SEQUENCE: 145
actcctcccc atcctctccc tctgtccctc tgtccctctg accctgcact gtcccagcac      60
c                                                                      61

SEQ ID NO: 146           moltype = DNA   length = 37
FEATURE                  Location/Qualifiers
source                   1..37
                         mol_type = other DNA
                         organism = synthetic construct
SEQUENCE: 146
gggactcccg ggctggcagc agggccccag cggcacc                               37

SEQ ID NO: 147           moltype = DNA   length = 58
FEATURE                  Location/Qualifiers
source                   1..58
                         mol_type = other DNA
                         organism = synthetic construct
SEQUENCE: 147
agcaatcctt tctttcagct ggagtgctcc tcaggagcca gccccaccct tagaaaag        58

SEQ ID NO: 148           moltype = DNA   length = 73
FEATURE                  Location/Qualifiers
source                   1..73
                         mol_type = other DNA
                         organism = synthetic construct
SEQUENCE: 148
gggtcagtgt cacctccagg atacagacag ccccccttca gcccagccca gccaggtctc      60
ctacaccgcc acc                                                         73

SEQ ID NO: 149           moltype = DNA   length = 231
FEATURE                  Location/Qualifiers
source                   1..231
                         mol_type = other DNA
                         organism = synthetic construct
SEQUENCE: 149
tttaaaatct gtgtggctgt cactcggctg cttgcttagt gcactcacgc agtataatta      60
ataactaatt actgtcgttg acaggacacg agtaactcgt ctatcttctg caggctgctt     120
acggtttcgt ccgtgttgca gccgatcatc agcacatcta ggtttcgtcc gggtgtgacc     180
gaaaggtaag ttggagagcc ttgtccctgg tttcaacgag aaaacgccac c               231

SEQ ID NO: 150           moltype = DNA   length = 10
FEATURE                  Location/Qualifiers
source                   1..10
                         mol_type = other DNA
                         organism = synthetic construct
SEQUENCE: 150
ccccggcgcc                                                             10

SEQ ID NO: 151           moltype = DNA   length = 10
FEATURE                  Location/Qualifiers
source                   1..10
                         mol_type = other DNA
                         organism = synthetic construct
SEQUENCE: 151
ggggcgcccg                                                             10

SEQ ID NO: 152           moltype = AA    length = 512
FEATURE                  Location/Qualifiers
source                   1..512
                         mol_type = protein
                         organism = Homo sapiens
SEQUENCE: 152
MTAPWVALAL LWGSLCAGSG RGEAETRECI YYNANWELER TNQSGLERCE GEQDKRLHCY      60
ASWRNSSGTI ELVKKGCWLD DFNCYDRQEC VATEENPQVY FCCCEGNFCN ERFTHLPEAG     120
GPEVTYEPPP TAPTLLTVLA YSLLPIGGLS LIVLLAFWMY RHRKPPYGHV DIHEDPGPPP     180
PSPLVGLKPL QLLEIKARGR FGCVWKAQLM NDFVAVKIFP LQDKQSWQSE REIFSTPGMK     240
HENLLQFIAA EKRGSNLEVE LWLITAFHDK GSLTDYLKGN IITWNELCHV AETMSRGLSY     300
LHEDVPWCRG EGHKPSIAHR DFKSKNVLLK SDLTAVLADF GLAVRFEPGK PPGDTHGQVG     360
```

```
TRRYMAPEVL EGAINFQRDA FLRIDMYAMG LVLWELVSRC KAADGPVDEY MLPFEEEIGQ   420
HPSLEELQEV VVHKKMRPTI KDHWLKHPGL AQLCVTIEEC WDHDAEARLS AGCVEERVSL   480
IRRSVNGTTS DCLVSLVTSV TNVDLPPKES SI                                 512

SEQ ID NO: 153          moltype = AA  length = 119
FEATURE                 Location/Qualifiers
source                  1..119
                        mol_type = protein
                        organism = synthetic construct
SEQUENCE: 153
SGRGEAETRE CIYYNANWEL ERTNQSGLER CEGEQDKRLH CYASWRNSSG TIELVKKGCW    60
LDDFNCYDRQ ECVATEENPQ VYFCCCEGNF CNERFTHLPE AGGPEVTYEP PPTAPTLLT    119

SEQ ID NO: 154          moltype = AA  length = 407
FEATURE                 Location/Qualifiers
source                  1..407
                        mol_type = protein
                        organism = synthetic construct
SEQUENCE: 154
MEFGLSWVFL VAIIKGVQCH GEGTFTSDVS SYLEEQAAKE FIAWLVKGRG EPKSVDKTHT    60
CPPCPAPEAA GGPSVFLFPP KPKDTLMISR TPEVTCVVVD VSHEDPEVKF NWYVDGVEVH   120
NAKTKPREEQ YNSTYRVVSV LTVLHQDWLN GKEYKCKVSN KALPAPIEKT ISKAKGQPRE   180
PQVYTLPPSR DELTKNQVSL TCLVKGFYPS DIAVEWESNG QPENNYKTTP PVLDSDGSFF   240
LYSKLTVDKS RWQQGNVFSC SVMHEALHNH YTQKSLSLSP GKIEGRMDSG RGEAETRECI   300
YYNANWELER TNQSGLERCE GEQDKRLHCY ASWRNSSGTI ELVKKGCWLD DFNCYDRQEC   360
VATEENPQVY FCCCEGNFCN ERFTHLPEAG GPEVTYEPPP TAPTLLT                 407
```

FUSION PROTEINS FOR THE TREATMENT OF CARDIOMETABOLIC DISEASES

PRIORITY

This application is a continuation of International Application No. PCT/US2023/082572, filed Dec. 5, 2023, which claims the benefit of, and priority to, U.S. Provisional Application No. 63/386,107, filed Dec. 5, 2022, and U.S. Provisional Application No. 63/579,243, filed Aug. 28, 2023, the contents of each of which are hereby incorporated by reference in their entirety.

TECHNICAL FIELD

The present disclosure relates to, inter alia, compositions and methods, including heterologous chimeric proteins that find use, inter alia, in the treatment management of hyperglycemia, diabetes, including type II diabetes, obesity, metabolic syndrome and the reduction of cardiovascular risk.

SEQUENCE LISTING

The instant application contains a sequence listing, which has been submitted in XML format via Patent Center. The contents of the XML copy named "SHK-073_116981-5073 Sequence Listing", which was created on Feb. 28, 2024, and is 173,442 bytes in size, are incorporated herein by reference in their entirety.

BACKGROUND

Diabetes mellitus, obesity, diabesity, which is a term used to describe the combined harmful health outcomes of obesity and diabetes mellitus, are major health hazards affecting people worldwide. Ng et al., Diabesity: the combined burden of obesity and diabetes on heart disease and the role of imaging *Nature Reviews Cardiology* 2021; 18: 291-304. Based on an estimate from the World Health Organization (WHO), the people with diabetes rose from 108 million in 1980 to 422 million in 2014. According to the Center for Disease Control (CDC), diabetes affects about 37.3 million people in the US, which is 11.3% of the US population, and this number includes about 8.5 million people that have undiagnosed diabetes. Similarly, obesity has nearly tripled worldwide since 1975, with more than 1.9 billion overweight, and over 650 million obese adults worldwide as of 2016. likewise, US obesity prevalence increased from about 30.5% in year 2000 to about 41.9% in 2017 according to the CDC. Currently, over 20% children and over 40% adults suffer from obesity. Obesity is estimated to cost health services US $990 billion, which is 13% healthcare expenditure, per year globally. For example, the aggregate medical cost due to obesity among adults in the United States was $260.6 billion in 2016. Cawley et al., Direct medical costs of obesity in the United States and the most populous states, *J Manag Care Spec Pharm* 2021; 27(3):354-366.

Diabetes is linked to a number of health problems, including microvascular complications, such as retinopathy, neuropathy, nephropathy, blindness in working-age adults, end-stage renal disease, peripheral artery disease (PAD), cardiovascular complications, and cardiovascular disease (CVD). Similarly, obesity itself increases risk for many serious diseases, including hypertension, dyslipidemia, type 2 diabetes, coronary heart disease, metabolic syndrome, fatty liver disease, stroke, gallstones, cholecystitis, osteoarthritis, kidney disease, sleep apnea and breathing problems, clinical depression, anxiety, and many types of cancers. The current standard of care for T2D includes diet, life-style changes and exercise along with regular insulin injections and/or available oral and injectable glucose lowering drugs. Nonetheless, many patients with T2D still remain inadequately controlled. The current standard of care for obesity includes diet, life-style changes and exercise along with medication such as phentermine, diethylpropion, bupropion-naltrexone, liraglutide, orlistat, phentermine-topiramate, setmelanotide, and semaglutide. These drugs, delay gastric emptying, reduce appetite and food cravings, stimulate insulin release, and/or reduce fat absorption. However, each of them are associated with some side effects and contraindications. Many of these agents have short exposure profiles in humans, and thus need to be taken daily and often after fasting. This leads to frequent spikes in the serum concentration of these agents, which are associated with prolonged delays in gastric emptying, nausea and vomiting, and in some cases, gastroparesis. In addition, disproportional and undesirable loss of lean body mass occurs with some agents. As a result of these combined adverse events, many patients discontinue therapy within one year.

GLP-1 and GIP are incretin hormones which have both been described to have effects on glucose tolerance and body weight. GLP-1 receptor agonists such as liraglutide and semaglutide are approved and have been shown to reduce appetite, food intake and body weight. No GIP receptor modulating agents have been approved, and GIP receptor agonists were shown to reduce food intake and body weight in rodent studies, however contradictory findings have been reported from studies in humans. Moreover, recent studies have shown that GIP receptor antagonists can also reduce food intake and body weight in rodents. These paradoxical observations with GIP receptor agonists and antagonists within rodents, and the unpredictable relevance of these findings to human subjects has created uncertainty as to whether the beneficial effects of GIP receptor agonists and antagonists could be related to inter-species differences, the starting body weight of treated subjects, the presence of insulin resistance in treated subjects, the half-life and duration of exposure of the GIP receptor targeted agents, or a variety of these factors.

Therefore, there remains a need for more effective and accessible methods of treating diabetes, obesity, diabesity and related diseases.

SUMMARY

In various aspects, the present disclosure provides compositions and methods that are useful, inter alia, in the treatment or prevention of hyperglycemia, diabetes, including type II diabetes, obesity, metabolic syndrome and the reduction of cardiovascular risk.

Accordingly, in aspects, the present disclosure provides a chimeric protein having a general structure of: N terminus-(a)-(b)-(c)-C terminus, wherein: (A) (a) is a first domain comprising a glucagon-like peptide-1 (GLP-1) receptor agonist, (b) is a linker adjoining the first domain and a second domain, wherein the linker comprises one or more protease-cleavable polypeptide linkers, and optionally a hinge-CH2-CH3 Fc domain, and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a pharmaceutical composition comprising a pharmaceutically acceptable carrier and a modified mRNA (mmRNA) encoding a chimeric protein having a general structure of: N terminus-(a)-(b)-(c)-C terminus, wherein: (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNPs), a lipoplex, or a liposome. In embodiments, the pharmaceutical composition is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA. In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In aspects, the present disclosure provides a pharmaceutical composition comprising: (A) (a) a contiguous nucleic acid comprising a 5' translatable region encoding: (i) a glucagon-like peptide-1 (GLP-1) receptor agonist, or (ii) a fibroblast growth factor 19 (FGF19), FGF21 or a variant thereof, or an analog thereof; and (b) a contiguous nucleic acid comprising a 3' translatable region encoding glucose-dependent insulinotropic polypeptide (GIP) receptor (GIPR) modulator; or (B) (a) a contiguous nucleic acid comprising a 5' translatable region encoding a glucose-dependent insulinotropic polypeptide (GIP) receptor (GIPR) modulator; and (b) a contiguous nucleic acid comprising a 3' translatable region encoding: (i) a glucagon-like peptide-1 (GLP-1) receptor agonist, or (ii) a fibroblast growth factor 19 (FGF19), FGF21 or a variant thereof, or an analog thereof, wherein the 5' translatable region and the 3' translatable region are adjoined by an in-frame linker, optionally wherein the linker encodes one or more protease-cleavable polypeptide linkers, and/or a hinge-CH2-CH3 Fc domain.

In embodiments, the pharmaceutical composition is formulated for parenteral administration. In embodiments, the pharmaceutical composition is formulated for intradermal, intramuscular, intraperitoneal, intraarticular, intravenous, subcutaneous, intraarterial or transdermal administration.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition comprising a chimeric protein, or a polynucleotide encoding the chimeric protein, wherein the chimeric protein comprises a general structure of: N terminus-(a)-(b)-(c)-C terminus, wherein: (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a chimeric protein comprising a general structure of: N terminus-(a)-(b)-(c)-C terminus, wherein: (A) (a) is a first domain comprising a glucagon-like peptide-1 (GLP-1) receptor agonist, (c) is a second domain comprising a portion of activin receptor type-2B (ACVR2B), and (b) is a linker adjoining the first domain and a second domain, optionally wherein the linker comprises a hinge-CH2-CH3 Fc domain; or (B) (a) is a second domain comprising a portion of activin receptor type-2B (ACVR2B), (c) is a first domain comprising a glucagon-like peptide-1 (GLP-1) receptor agonist, and (b) is a linker adjoining the first domain and a second domain, optionally a hinge-CH2-CH3 Fc domain. In embodiments, the portion of ACVR2B is capable of binding activin A and/or GDF-8. In embodiments, the portion of ACVR2B comprises substantially the entire extracellular domain of ACVR2B. In embodiments, the portion of ACVR2B comprises the entire extracellular domain of ACVR2B. In embodiments, the portion of ACVR2B comprises an amino acid sequence that is at least about 90%, or at least about 95% identical to the amino acid sequence of SEQ ID NO: 153.

In embodiments, the GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77, 91, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the fibroblast growth factor comprises FGF19, or an analog thereof. In embodiments, the analog of FGF19 is aldafermin (NGM282). In embodiments, the fibroblast growth factor is capable of activating FGFR4, optionally wherein the activating requires R-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence of SEQ ID NOs: 78 or 79.

In embodiments, the fibroblast growth factor comprises FGF21, or an analog thereof. In embodiments, the analog of FGF21 is selected from efruxifermin, LY2405319, FGF21 (RGE) and FGF21 (L146P). In embodiments, the fibroblast growth factor is capable of activating FGFR1c, optionally wherein the activating requires β-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence selected from SEQ ID NOs: 80-85.

In embodiments, the GIPR modulator comprises GIP (SEQ ID NO: 68), or a variant or analog thereof. In embodiments, the analog of GIP has an amino acid sequence that is selected from the amino acid sequence of SEQ ID NO: 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the GIPR modulator is capable of binding a GIP receptor (GIPR). In embodiments, the GIPR modulator is capable of activating the GIPR. In embodiments, the GIPR modulator is capable of inhibiting the GIPR. In embodiments, the GIPR modulator is capable of modulating the GIPR on the surface of the endocrine pancreas. In embodiments, the GIPR modulator is capable of activating the hypothalamic GIPR. In embodiments, the GIPR modulator comprises an amino acid sequence selected from the amino acid sequence of SEQ ID NOs: 68 or 74 or a variant or an analog thereof having about 1, 2, 3, 4, 5, 6, 7, 8, 9, or 10 or more amino acid mutations independently selected from substitutions, insertions, deletions, and truncations.

In embodiments, the linker comprises a protease-cleavable polypeptide linker. In embodiments, the protease-cleavable polypeptide linker cleavable by a protease that is endogenous to a mammalian expressed in liver, skin and/or muscle. In embodiments, the protease-cleavable linker is cleavable by a protease selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the protease-cleavable linker comprises a consensus recognition and/or cleavage site of a protease selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain.

In embodiments, the chimeric protein comprises two protease-cleavable polypeptide linkers. In embodiments, wherein the first protease-cleavable polypeptide linker is C terminal to the first domain and the second protease-cleavable polypeptide linker is N terminal to the second domain.v In embodiments, the two protease-cleavable polypeptide linkers are cleavable by a protease that is endogenous to a mammalian expressed in liver, skin and/or muscle. In embodiments, the two protease-cleavable polypeptide linkers are cleavable by a protease independently selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the two protease-cleavable polypeptide linkers comprise consensus recognition and/or cleavage sites of a proteases independently selected from, caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the two protease-cleavable polypeptide linkers are cleavable by a protease independently comprises an amino acid sequence selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75), or a variant thereof having about 1, 2, 3, 4, or more amino acid mutations with respect to an amino acid sequence selected from SEQ ID NOs: 70 to 75.

In embodiments, the first domain comprises a glucagon-like peptide-1 (GLP-1) receptor agonist and the protease-cleavable polypeptide linker is C terminal to the first domain; or the second domain comprises a glucagon-like peptide-1 (GLP-1) receptor agonist and the protease-cleavable polypeptide linker is N terminal to the second domain. In embodiments, the chimeric protein comprises two protease-cleavable polypeptide linkers, such protease-cleavable polypeptide linker independently selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the first protease-cleavable polypeptide linker is C terminal to the first domain and the second domain is protease-cleavable polypeptide linker is N terminal to the second domain.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof. In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127.

In embodiments, the polynucleotide is DNA. In embodiments, the polynucleotide comprises a liver, skin and/or muscle-specific control element. In embodiments, the liver-specific control element is a liver-specific promoter selected from albumin promoter, thyroxine-binding globulin (TBG) promoter, hybrid liver-specific promoter (HLP), human α1-antitrypsin promoter, LP1 promoter, and hemopexin promoter.

In aspects, the present disclosure provides a vector comprising the polynucleotide of any of the embodiments disclosed herein.

In aspects, the present disclosure provides a host cell comprising the mmRNA of any of the embodiments disclosed herein. In aspects, the present disclosure provides a host cell comprising the vector of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the isolated polynucleotide of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the modified mRNA of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the pharmaceutical composition of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the vector of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the host cell of any of the embodiments disclosed herein.

Any aspect or embodiment disclosed herein can be combined with any other aspect or embodiment as disclosed herein.

BRIEF DESCRIPTION OF THE DRAWINGS

FIG. 2A shows a western blot of the human GLP-1-Fc-GIP chimeric protein probed with anti-GIP antibody. FIG. 2B shows the Western blots showing characterization of the GLP-1-Fc-GIP(Ag) chimeric protein. FIG. 2C shows the Western blots showing characterization of the GLP-1-Fc-GIP(AntPro3) chimeric protein. FIG. 2D shows the Western blots showing characterization of the GLP-1-Fc-GIP(Ant 3-30) chimeric protein. FIG. 2E shows the Western blots showing characterization of the GLP-1-Fc-GIP(Ant 3-30, Pro3) chimeric protein. In case of the blots shown in FIG. 2B to FIG. 2E, a molecular weight ladder is loaded in first lane of each gel. The samples of the GLP-1-Fc-GIP(Ag) chimeric protein that were not reduced or deglycosylated but only boiled with SDS were loaded into the lane marked as NR of each of the blots. Samples in the lane marked as R were treated with a reducing agent, R-mercaptoethanol and boiled. Samples in the lane marked as DG were treated with a deglycosylation agent, the reducing agent, and boiled. Each individual domain of the chimeric protein was probed using an anti-human GLP antibody (left blot), an anti-Fc antibody (center blot), or an anti-human GIP antibody (right blot).

FIG. 3A shows the schematic representation of the reporter assay. FIG. 3B demonstrates the activation of GIPR by the purified chimeric proteins.

FIG. 4A demonstrates the activation of GIPR and accumulation of cAMP as evidenced by a decrease in signal as ATP is utilized in the rat insulinoma INS-1 cells harboring a cAMP-luciferase reporter gene, by the GIP-Fc fusion protein, the GIP-Fc-FGF19 or GIP-Fc-FGF21 chimeric proteins, or tirzepatide. FIG. 4B demonstrates the glucose-stimulated insulin secretion (GSIS) by the upon the treatment with dulaglutide, tirzepatide, the GIP-Fc-FGF19 or GIP(Ag)-Fc-FGF19 chimeric proteins, or a X-Fc-FGF19 chimeric protein.

FIG. 5A shows the results of an assay for the screening of various GIP derivatives for their agonistic and antagonistic activity. Two GIP antagonist peptides, namely GIP(AntPro3) and GIP(AntPro3NH2), demonstrated more potent inhibition of GIP agonist signaling than the others tested. FIG. 5B shows the activation of GIPR by a GIP agonist (GIP(Ag)), and inhibition of a fixed concentration of GIP(Ag) by a titration of two GIP antagonists (GIP (AntPro3) and GIP (AntPro3NH2)).

FIG. 7A shows the results of a glucose tolerance test. Shown is a time course of changes in serum glucose following glucose administration. FIG. 7B shows an area under curve (AUC) of glucose following glucose administration. FIG. 7C shows a time course of changes in insulin following glucose administration. FIG. 7D shows an area under curve (AUC) of insulin following glucose administration.

FIG. 8A to FIG. 8K demonstrate the efficacy of the GLP-1-Fc-GIP (Ag) and GLP-1-Fc-GIP(AntPro3) chimeric proteins or mRNA encoding them in a mouse model of obesity, hepatic steatosis and early-stage liver fibrosis The mouse obesity model of FIG. 6A (bottom right) was treated with tirzepatide, dulaglutide. the GLP-1-Fc-GIP (Ag) and GLP-1-Fc-GIP(AntPro3) chimeric proteins ("FP"), or mRNA encoding the GLP-1-Fc-GIP (Ag) and GLP-1-Fc-GIP(AntPro3) chimeric proteins and the control of body weight (FIG. 8A and FIG. 8B), plasma insulin (FIG. 8C), food intake (FIG. 8D), blood glucose (FIG. 8E), liver adiposity (FIG. 8F), liver weight (FIG. 8G), subcutaneous white adipose tissue (sWAT) weight (FIG. 8H), steatosis, ballooning and fibrosis of liver (FIG. 8I, FIG. 8J and FIG. 8K). Liver histology was performed to determine the degree of hepatic steatosis in mice treated with the indicated recombinant proteins or mmRNA/LNP encoding the indicated recombinant protein (FIG. 8I stained with picrosirius red, and FIG. 8J and FIG. 8K stained with H&E).

FIG. 11A is a bar graph comparing the production of the GLP-1-Fc-ACVR2B chimeric protein by cells transfected with mRNA constructs encoding the GLP-1-Fc-ACVR2B chimeric protein and harboring different 5' UTR sequences and 3'UTR sequences. FIG. 11B is a line graph showing the binding by increasing amounts of purified recombinant human ACVR2B-Fc fusion protein to recombinant human Activin A as measured using a Meso Scale Discovery (MSD) platform-based assay. FIG. 11C is a line graph showing the binding to recombinant human Activin A by the GLP-1-Fc-ACVR2B chimeric protein increasing dilutions of the culture supernatants of HEK293T cells transfected with mRNA constructs encoding the GLP-1-Fc-ACVR2B chimeric protein and harboring different 5' UTR sequences and 3'UTR sequences. FIG. 11D is a line graph showing the binding by increasing amounts of purified recombinant human ACVR2B-Fc fusion protein to recombinant human GDF-8 as measured using a Meso Scale Discovery (MSD) platform-based assay. FIG. 11E is a line graph showing the binding to recombinant human GDF-8 by the GLP-1-Fc-ACVR2B chimeric protein increasing dilutions of the culture supernatants of HEK293T cells transfected with mRNA constructs encoding the GLP-1-Fc-ACVR2B chimeric protein and harboring different 5' UTR sequences and 3'UTR sequences.

DETAILED DESCRIPTION

Figure 1A:
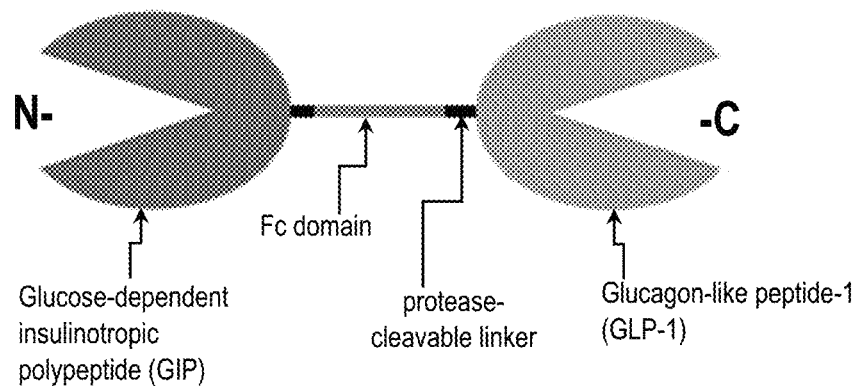
FIG. 1A to FIG. 1B show the non-limiting schematic illustrations of the chimeric proteins glucose-dependent insulinotropic polypeptide (GIP)-Fc-protease-cleavable linker-GLP-1 (FIG. 1A) and GLP-1-protease-cleavable linker-Fc-GIP (FIG. 1B).

The present disclosure is based, in part, on the creation of a fusion protein comprising a glucagon-like peptide-1 (GLP-1) receptor agonist or fibroblast growth factor 19 (FGF19), FGF21, FGF23, or a variant thereof, which is connected via an optional protease-cleavable linker to a polypeptide comprising a hinge-CH2-CH3 Fc domain-glucose-dependent insulinotropic polypeptide (GIP) receptor (GIPR) modulator. The present disclosure is based, in part, on the delivery of a nucleic acid encoding the fusion protein to liver, expression of the fusion protein in expressed in liver, skin and/or muscle, cleavage of the protease-cleavable linker in the expressed in liver, skin and/or muscle, leading to the release of the glucagon-like peptide-1 (GLP-1) receptor agonist in the circulation.

The present disclosure is based, in part, on the discovery that the chimeric proteins disclosed herein and the nucleic acids (without limitation, e.g., mmRNA) encoding the chimeric proteins disclosed herein control body weight, plasma insulin, food intake, blood glucose, liver adiposity, liver weight, intrahepatic lipid content, subcutaneous white adipose tissue (sWAT), hepatocellular ballooning, steatosis, and liver fibrosis. The data shown herein indicate, inter alia, show that the chimeric proteins disclosed herein and the nucleic acids (without limitation, e.g., mmRNA) encoding the chimeric proteins disclosed herein are useful to treat diabetes, obesity, Type II diabetes, metabolic syndrome and related ailments. The data shown herein indicate, inter alia, show that the chimeric proteins disclosed herein and the nucleic acids (without limitation, e.g., mmRNA) encoding the chimeric proteins disclosed herein do not reduce food intake or water consumption as significantly as prior art agents that are associated with nausea and GI distress.

The present disclosure is based, in part, on the discovery that the chimeric proteins disclosed herein and especially the nucleic acids (without limitation, e.g., mmRNA) encoding the chimeric proteins disclosed herein provide a prolonged exposure to the fusion proteins disclosed herein leading to efficacy. The data shown herein indicate, inter alia, show that the nucleic acids (without limitation, e.g., mmRNA) encoding the chimeric proteins disclosed herein provide for one or more of sustained delivery of the chimeric proteins, increased $C_{max}$ and increased area under curve (AUC).

GLP-1 and GIP are incretin hormones which have both been described to have effects on glucose tolerance and body weight. GLP-1 receptor agonists such as liraglutide and semaglutide are approved and have been shown to reduce appetite, food intake and body weight. Many of these agents have short exposure profiles in humans, and thus need to be taken daily and often after fasting. This leads to frequent spikes in the serum concentration of these agents, which are associated with prolonged delays in gastric emptying and the accompanying nausea and vomiting. GLP-1 agonist agents have demonstrated reduced delays in gastric emptying, improved side-effect profiles, and improved glycemic efficacy by restoring insulin sensitivity and glucagon secretion. No GIP receptor modulating agents have been approved, and GIP receptor agonists were shown to reduce food intake and body weight in rodent studies, however contradictory findings have been reported from studies in humans. Moreover, recent studies have shown that GIP receptor antagonists can also reduce food intake and body weight in rodents. These paradoxical observations with GIP receptor agonists and antagonists within rodents, and the unpredictable relevance of these findings to human subjects has prompted questions as to whether the beneficial effects of GIP receptor agonists and antagonists could be related to inter-species differences, the starting body weight of treated subjects, the presence of insulin resistance in treated subjects, the half-life and duration of exposure of the GIP receptor targeted agents, or a variety of these factors. In addition, GLP-1 suppresses in a glucose-dependent manner, but GIP increases glucagon secretion in a glucose-dependent manner. The insulinotropic effects of GLP-1 are slightly impaired in type 2 diabetes, and GIP has lost much of its acute insulinotropic activity in type 2 diabetes. Moreover, stimulation of the GIP receptor, but not the GLP-1 receptor, increases triglyceride storage in white adipose tissue not only through stimulating insulin secretion, but also by interacting with regional blood vessels and GIP receptors. Nauck et al., The evolving story of incretins (GIP and GLP-1) in metabolic and cardiovascular disease: A pathophysiological update, *Diabetes Obes Metab* 2021; 23 Suppl 3: 5-29.

As a result of the potential complementary effects of GLP-1 and GIP, constructs combining GLP-1 receptor agonism and GIP receptor agonists or antagonists have been proposed. Pre-clinical studies have not yet clarified the state of the art however, as studies have reported that combinations of GLP-1 agonists with either GIP receptor agonists or antagonists have been shown to reduce food intake, stimulate weight loss, and in some cases improve insulin resistance. For example, multi-specific antibodies specific to using GIP and GLP-1 receptor have been tried. Lu et al., GIPR antagonist antibodies conjugated to GLP-1 peptide are bispecific molecules that decrease weight in obese mice and monkeys *Cell Reports Medicine* 2021; 2: 100263. However, the half-life of these molecules far exceeds the half-life of GLP-1 secretion following food intake, and the health consequences of disrupting the cyclical nature of the incretin effect with these types of agents is currently unknown. Moreover, these molecules are manufactured using a complex process, wherein both the antibody and GLP-1 peptide must be produced and then coupled to one another with high fidelity. Such a process could produce non-native epitopes which could result in an anti-drug antibody response that would limit the chronic administration of such a therapeutic. Peptides having GIP and GLP-1 receptor antagonist activities have been attempted. Gasbjerg et al., Evaluation of the incretin effect in humans using GIP and GLP-1 receptor antagonists, *Peptides* 2020; 125:170183. However, these molecules have undesirably short half-lives, which results in both rapid accumulation and elimination of the peptide in serum, which is associated with undesirable side-effects including nausea and vomiting, and in a frequent schedule of administration. In embodiments, the molecule disclosed herein is a fusion protein comprising a glucagon-like peptide-1 (GLP-1) receptor agonist, which is connected via a to a protease-cleavable linker to a polypeptide comprising a hinge-CH2-CH3 Fc domain-glucose-dependent insulinotropic polypeptide (GIP) receptor (GIPR) modulator. In embodiments, this fusion protein is easy to synthesize. In embodiments, the linker disclosed herein increase the serum half-life of the fusion protein. In embodiments, the protease cleavage sites in the molecule facilitate cleavage of the fusion protein, facilitating the release the GLP-1 receptor agonist (without limitation, e.g., GLP-1) and/or GIPR modulator (without limitation, e.g., GIP).

In embodiments, the chimeric protein and/or the nucleic acids encoding the chimeric protein disclosed herein accumulate in the serum over time, and then provide sustained amounts of GLP-1 and/or GIP for longer duration. In embodiments, the chimeric protein disclosed herein and/or the nucleic acids encoding the chimeric protein disclosed herein result in prolonged accumulation of GLP-1 and/or GIP in a manner which reduces one or more adverse events associated with very rapid accumulation of GLP-1 or GIP. In embodiments, the chimeric protein and/or the nucleic acids encoring the chimeric protein disclosed herein result in extended exposure of GLP-1 and/or GIP due to continuous production of those peptides in a subject and/or decreasing renal clearance. Increase the half-lives of GLP-1 and/or GIP by decreasing renal clearance. In embodiments, the renal clearance is decreased because of fusion with the linker disclosed herein. In embodiments, the chimeric protein and/or the nucleic acids encoding the chimeric protein disclosed herein provide sustained synthesis of GLP-1 and/or GIP for longer duration based on nucleic acid-based delivery disclosed herein, which enables sustained biosynthesis of the chimeric protein in the patient's body. In embodiments, the nucleic acid is DNA or modified mRNA (mmRNA).

Moreover, in embodiments, the present molecules may be delivered in the form of nucleic acids harboring control elements that enable controllable synthesis of the fusion protein by patient's own liver, muscle or subcutaneous tissue. In these embodiments, the fusion protein synthesis may be controlled.

Accordingly, In aspects, the present disclosure provides a chimeric protein having a general structure of: N terminus-(a)-(b)-(c)-C terminus, wherein: (A) (a) is a first domain comprising a glucagon-like peptide-1 (GLP-1) receptor agonist, (b) is a linker adjoining the first domain and a second domain, optionally wherein the linker comprises one or more protease-cleavable polypeptide linkers, and/or a hinge-CH2-CH3 Fc domain, and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof.

In embodiments, the chimeric proteins disclosed herein have a general structure of: N terminus-(a)-(b)-(c)-C terminus, wherein (a) is a first domain comprising a glucagon-like peptide-1 (GLP-1) receptor agonist. In these embodiments, (b) is a linker adjoining the first domain and a second domain, optionally wherein the linker comprises one or more protease-cleavable polypeptide linkers, and/or a hinge-CH2-CH3 Fc domain.

In these embodiments, (c) is the second domain comprising a glucose-dependent insulinotropic polypeptide (GIP) receptor (GIPR) modulator.

In alternative embodiments, the chimeric proteins disclosed herein have a general structure of: N terminus-(a)-(b)-(c)-C terminus, wherein (c) is a first domain comprising a glucose-dependent insulinotropic polypeptide (GIP) receptor (GIPR) modulator. In these embodiments, (b) is a linker adjoining the first domain and a second domain, optionally wherein the linker comprises one or more protease-cleavable polypeptide linkers, and/or a hinge-CH2-CH3 Fc domain. In these embodiments, (a) is a first domain comprising (i) a glucagon-like peptide-1 (GLP-1) receptor agonist, or (ii) a fibroblast growth factor 19 (FGF19), FGF21 or a variant thereof, or an analog thereof.

Fusion Proteins of the Present Disclosure

In aspects, the present disclosure provides a chimeric protein having a general structure of: N terminus-(a)-(b)-(c)-C terminus, wherein: (A) (a) is a first domain comprising a glucagon-like peptide-1 (GLP-1) receptor agonist, (b) is a linker adjoining the first domain and a second domain, optionally wherein the linker comprises one or more protease-cleavable polypeptide linkers, and/or a hinge-CH2-CH3 Fc domain, and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof. In embodiments, the chimeric protein is administered to a patient. In embodiments, a nucleic acid encoding the chimeric protein (e.g., modified mRNA or DNA) is administered to a patient. In embodiments, the nucleic acid encoding harbors control elements that enable the expression of the chimeric protein (e.g., modified mRNA or DNA) is the expressed in liver, skin and/or muscle.

In aspects, the present disclosure provides a chimeric protein having a general structure of: N terminus-(a)-(b)-(c)-C terminus, wherein (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor 19 (FGF19), FGF21 or a variant thereof, or an analog thereof. In embodiments, the chimeric protein is administered to a patient.

In embodiments, a nucleic acid encoding the chimeric protein (e.g., modified mRNA or DNA) is administered to a patient. In embodiments, the nucleic acid encoding harbors control elements that enable the expression of the chimeric protein (e.g., modified mRNA or DNA) is the expressed in liver, skin and/or muscle.

In aspects, the present disclosure provides a chimeric protein having a general structure of: N terminus-(a)-(b)-(c)-C terminus, wherein (a) is the second domain comprising fibroblast growth factor 19 (FGF19), FGF21 or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is a second domain comprising a glucose-dependent insulinotropic polypeptide (GIP) receptor (GIPR) modulator. In embodiments, the chimeric protein is administered to a patient. In embodiments, a nucleic acid encoding the chimeric protein (e.g., modified mRNA or DNA) is administered to a patient. In embodiments, the nucleic acid encoding harbors control elements that enable the expression of the chimeric protein (e.g., modified mRNA or DNA) is the expressed in liver, skin and/or muscle.

In aspects, the present disclosure provides a chimeric protein having a general structure of: N terminus-(a)-(b)-(c)-C terminus, wherein (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a chimeric protein having a general structure of: N terminus-(a)-(b)-(c)-C terminus, wherein (a) is a first domain comprising a glucagon-like peptide-1 (GLP-1) receptor agonist, glucose-dependent insulinotropic polypeptide (GIP) receptor (GIPR) modulator and/or a glucagon receptor (GCGR) agonist and/or the Fibroblast growth factor 19 (FGF19), FGF21 or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a portion of activin receptor type-2B (ACVR2B). In embodiments, the portion of ACVR2B is capable of binding activin A and/or GDF-8. In embodiments, the portion of ACVR2B is the extracellular domain of ACVR2B. In embodiments, the first domain comprises the GLP-1 receptor agonist of any of the embodiments disclosed herein. In embodiments, the first domain comprises the GIP receptor modulator of any of the embodiments disclosed herein. In embodiments, the first domain comprises the GIP receptor modulator of any of the embodiments disclosed herein. In embodiments, the first domain comprises the Fibroblast growth factor 19 (FGF19), FGF21 or a variant thereof, or an analog thereof of any of the embodiments disclosed herein. In embodiments, the chimeric protein is administered to a patient. In embodiments, a nucleic acid encoding the chimeric protein (e.g., modified mRNA or DNA) is administered to a patient. In embodiments, the nucleic acid encoding harbors control elements that enable the expression of the chimeric protein (e.g., modified mRNA or DNA) is the expressed in liver, skin and/or muscle.

In aspects, the present disclosure provides a chimeric protein having a general structure of: N terminus-(a)-(b)-(c)-C terminus, wherein (a) is the second domain comprising a portion of activin receptor type-2B (ACVR2B), (b) is a linker adjoining the first domain and a second domain, optionally wherein the linker comprises one or more protease-cleavable polypeptide linkers, and/or a hinge-CH2-CH3 Fc domain, and (c) is a first domain comprising a glucagon-like peptide-1 (GLP-1) receptor agonist, glucose-dependent insulinotropic polypeptide (GIP) receptor (GIPR) modulator and/or a glucagon receptor (GCGR) agonist and/or the Fibroblast growth factor 19 (FGF19), FGF21 or a variant thereof, or an analog thereof. In embodiments, the portion of ACVR2B is capable of binding activin A and/or GDF-8. In embodiments, the portion of ACVR2B is the extracellular domain of ACVR2B. In embodiments, the first domain comprises the GLP-1 receptor agonist of any of the embodiments disclosed herein. In embodiments, the first domain comprises the GIP receptor modulator of any of the embodiments disclosed herein. In embodiments, the first domain comprises the GIP receptor modulator of any of the embodiments disclosed herein. In embodiments, the first domain comprises the Fibroblast growth factor 19 (FGF19), FGF21 or a variant thereof, or an analog thereof of any of the embodiments disclosed herein. In embodiments, the chimeric protein is administered to a patient. In embodiments, a nucleic acid encoding the chimeric protein (e.g., modified mRNA or DNA) is administered to a patient. In embodiments, the nucleic acid encoding harbors control elements that enable the expression of the chimeric protein (e.g., modified mRNA or DNA) is the expressed in liver, skin and/or muscle.

In embodiments, the GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77, 91, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the fibroblast growth factor comprises FGF19, or an analog thereof. In embodiments, the analog of FGF19 is aldafermin (NGM282). In embodiments, the fibroblast growth factor is capable of activating FGFR4, optionally wherein the activating requires R-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence of SEQ ID NOs: 78 or 79.

In embodiments, the fibroblast growth factor comprises FGF21, or an analog thereof. In embodiments, the analog of FGF21 is selected from efruxifermin, LY2405319, FGF21 (RGE) and FGF21 (L146P). In embodiments, the fibroblast growth factor is capable of activating FGFR1c, optionally wherein the activating requires β-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence selected from SEQ ID NOs: 80-85.

In embodiments, the GIPR modulator comprises GIP (SEQ ID NO: 68), or a variant or analog thereof. In embodiments, the analog of GIP has an amino acid sequence that is selected from the amino acid sequence of SEQ ID NO: 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the GIPR modulator is capable of binding a GIP receptor (GIPR). In embodiments, the GIPR modulator is capable of activating the GIPR. In embodiments, the GIPR modulator is capable of inhibiting the GIPR. In embodiments, the GIPR modulator is capable of modulating the GIPR on the surface of the endocrine pancreas. In embodiments, the GIPR modulator is capable of activating the hypothalamic GIPR. In embodiments, the GIPR modulator comprises an amino acid sequence selected from the amino acid sequence of SEQ ID NOs: 68 or 74 or a variant or an analog thereof having about 1, 2, 3, 4, 5, 6, 7, 8, 9, or 10 or more amino acid mutations independently selected from substitutions, insertions, deletions, and truncations.

In embodiments, the linker comprises a protease-cleavable polypeptide linker. In embodiments, the protease-cleavable polypeptide linkers are cleavable by a protease, wherein the protease is endogenous to a mammalian liver, skin, and/or muscle. In embodiments, the protease is selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain. In embodiments, the protease-cleavable polypeptide linker is N- or C-terminal to the first domain comprising a glucagon-like peptide-1 (GLP-1) receptor agonist. In embodiments, the protease-cleavable polypeptide linker is N- or C-terminal to the first domain comprising a fibroblast growth factor 19 (FGF19), FGF21 or a variant thereof, or an analog thereof. In embodiments, the protease-cleavable polypeptide linker is N- or C-terminal to the second domain comprising glucose-dependent insulinotropic polypeptide (GIP) receptor (GIPR) modulator. In embodiments, the chimeric protein comprises two protease-cleavable polypeptide linkers, such protease-cleavable polypeptide linker independently selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the first protease-cleavable polypeptide linker is C terminal to the first domain and the second domain is protease-cleavable polypeptide linker is N terminal to the second domain.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In aspects, the present disclosure provides an isolated polynucleotide encoding the chimeric protein of any of the embodiments disclosed herein. In embodiments, the polynucleotide is selected from mRNA, circular RNA (circRNA) and self-amplifying RNA (saRNA), optionally wherein the polynucleotide is modified. In embodiments, the polynucleotide is an mmRNA. In embodiments, the mmRNA comprises one or more nucleoside modifications, optionally wherein the mmRNA comprises one or more of 1-methylpseudouridine nucleotides.

In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthioadenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof. In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127. In embodiments, the mmRNA further comprises 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) or 3' UTR_6 (SEQ ID NO: 119); 5' UTR_14 (SEQ ID NO: 141) and 3' UTR_10 (SEQ ID NO: 123).

In embodiments, the polynucleotide is DNA. In embodiments, the polynucleotide comprises a liver, skin and/or muscle-specific control element. In embodiments, the liver-specific control element is a liver-specific promoter selected from albumin promoter, thyroxine-binding globulin (TBG) promoter, hybrid liver-specific promoter (HLP), human α1-antitrypsin promoter, LP1 promoter, and hemopexin promoter.

In aspects, the present disclosure provides a vector comprising the polynucleotide of any of the embodiments disclosed herein.

In aspects, the present disclosure provides a host cell comprising the mmRNA of any of the embodiments disclosed herein. In aspects, the present disclosure provides a host cell comprising the vector of any of the embodiments disclosed herein.

In aspects, the present disclosure provides a pharmaceutical composition comprising the chimeric protein of any of the embodiments disclosed herein, and a pharmaceutically acceptable carrier. In aspects, the present disclosure provides a pharmaceutical composition comprising the isolated polynucleotide of any of the embodiments disclosed herein and a pharmaceutically acceptable carrier. In aspects, the present disclosure provides a pharmaceutical composition comprising the vector of any of the embodiments disclosed herein, and a pharmaceutically acceptable carrier. In aspects, the present disclosure provides a pharmaceutical composition comprising the host cell of any of the embodiments disclosed herein, and a pharmaceutically acceptable carrier.

In aspects, the present disclosure provides a pharmaceutical composition comprising the mmRNA of any of the embodiments disclosed herein, and a pharmaceutically acceptable carrier. In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNPs), a lipoplex, or a liposome. In embodiments, the pharmaceutical composition is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA. In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In embodiments, the pharmaceutical composition is formulated for parenteral administration. In embodiments, the pharmaceutical composition is formulated for intradermal, intramuscular, intraperitoneal, intraarticular, intravenous, subcutaneous, intraarterial or transdermal administration.

Glucagon-Like Peptide 1 (GLP-1) Receptor Agonists

Glucagon-like peptide 1 (GLP-1) is a 30-amino acid peptide hormone produced in the intestine. GLP-1 is normally produced after meals and stimulates insulin secretion and inhibits glucagon secretion. It is also involved in the regulation of R-cell growth and survival, gastric emptying, and appetite. In the body, GLP-1 is degraded by dipeptidyl peptidase IV and has a short half-life of around 2 minutes. Reduced GLP-1 secretion is associated with type 2 diabetes and the development of obesity.

In embodiments, the chimeric proteins disclosed herein have a general structure of: N terminus-(a)-(b)-(c)-C terminus, wherein (a) is a first domain comprising a glucagon-like peptide-1 (GLP-1) receptor agonist. In these embodiments, (b) is a linker adjoining the first domain and a second domain, optionally wherein the linker comprises one or more protease-cleavable polypeptide linkers, and/or a hinge-CH2-CH3 Fc domain. In these embodiments, (c) is the second domain comprising a glucose-dependent insulinotropic polypeptide (GIP) receptor (GIPR) modulator.

In alternative embodiments, the chimeric proteins disclosed herein have a general structure of: N terminus-(a)-(b)-(c)-C terminus, wherein (c) is a first domain comprising a glucose-dependent insulinotropic polypeptide (GIP) receptor (GIPR) modulator. In these embodiments, (b) is a linker adjoining the first domain and a second domain, optionally wherein the linker comprises one or more protease-cleavable polypeptide linkers, and/or a hinge-CH2-CH3 Fc domain. In these embodiments, (a) is a first domain comprising (i) a glucagon-like peptide-1 (GLP-1) receptor agonist, or (ii) a fibroblast growth factor 19 (FGF19), FGF21 or a variant thereof, or an analog thereof.

In embodiments, the GLP-1 receptor agonist signals through its receptor, GLP-1 receptor (GLP-1R), a G-protein coupled receptor. In embodiments, the GLP-1 receptor agonist activates the GLP-1R on the surface of pancreatic β-cells. In embodiments, the GLP-1 receptor agonist induces increased insulin production by the pancreatic β-cells in a glucose dependent manner in response to the GLP-1R activation. In embodiments, the GLP-1 receptor agonist activates the GLP-1R on the surface of pancreatic α-cells. In embodiments, the GLP-1 receptor agonist activates GLP-1R suppresses glucose-dependent glucagon secretion by the pancreatic α-cells in response to the GLP-1R activation.

In embodiments, any of a number of drugs that mimic the action of GLP-1 by binding and activating the GLP-1 receptor is suitable. In embodiments, the GLP-1 receptor agonist is a short acting form (without limitation, e.g., exenatide). In embodiments, the GLP-1 receptor agonist is a long-acting forms (without limitation, e.g., dulaglutide and liraglutide). In embodiments, the GLP-1 receptor agonist is GLP-1.

GLP-1 is produced by the alpha cells of the pancreas and in the intestinal L cells in the distal ileum and colon in form of a precursor called preglucagon that is cleaved in different organs into glicentin, glicentin-related pancreatic polypeptide (GRPP), oxyntomodulin, glucagon, glucagon-like peptide 1 (GLP-1, indicated in a boldface-underlined font), and glucagon-like peptide 2 (GLP-2). Preglucagon has the following sequence:

(SEQ ID NO: 57)
MKSIYFVAGLFVMLVQGSWQRSLQDTEEKSRSFSASQADPLSDPDQMNE

DKRHSQGTFTSDYSKYLDSRRAQDFVQWLMNTKRNRNNIAKRHDEFERH

AEGTFTSDVSSYLEGQAAKEFIAWLVKGRGRRDFPEEVAIVEELGRRHA

DGSFSDEMNTILDNLAARDFINWLIQTKITDRK

In embodiments, the GLP-1 receptor agonist is wild-type human GLP-1. In embodiments, the GLP-1 receptor agonist is GLP-1 receptor agonists. In embodiments, the GLP-1 receptor agonist is variant of these peptides that can activate the GLP-1 receptor. Suitable GLP-1 receptor agonists are disclosed in U.S. Pat. Nos. 5,188,666, 5,120,712, 5,523,549, 5,512,549, 5,977,071, 6,191,102; 6,956,026; 6,506,724; 6,703,359; 6,858,576; 6,872,700; 6,902,744; 7,157,555; 7,223,725; 7,220,721; 9,161,953; PCT International Patent Application Publication Nos: WO 1998/008871; WO 1998/05351; WO 1999/07404; WO 1999/25727; WO 1999/25728; WO 1999/40788; WO 2000/034331; WO 2000/41546; WO 2000/41548; WO 2000/069911; WO 2000/73331; WO 2001/004156; WO 2001/51078; WO 2003/018516; WO 2003/099314; U.S. Patent Application Publication Nos. 2003/0036504; and 2006/0094652, the entire contents of which are hereby incorporated by reference in their entirety.

In embodiments, the GLP-1 receptor agonist is GLP-1 having the following sequence, and is also referred to herein as GLP-1 (1-37):

(SEQ ID NO: 58)
HDEFERHAEGTFTSDVSSYLEGQAAKEFIAWLVKGRG

In embodiments, the GLP-1 receptor agonist is a GLP-1 variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 58.

In embodiments, the GLP-1 receptor agonist is GLP-1 having the following sequence, and is also referred to herein as GLP-1 (1-36):

(SEQ ID NO: 59)
HDEFERHAEGTFTSDVSSYLEGQAAKEFIAWLVKGR

In embodiments, the GLP-1 receptor agonist is a GLP-1 variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 59.

In embodiments, the GLP-1 receptor agonist is GLP-1 having the following sequence, and is also referred to herein as GLP-1 (7-36) or GLP-1:

(SEQ ID NO: 60)
HAEGTFTSDVSSYLEGQAAKEFIAWLVKGR

In embodiments, the GLP-1 receptor agonist is a GLP-1 variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 60.

In embodiments, the GLP-1 receptor agonist is GLP-1, or a variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from SEQ ID NO: 60.

In embodiments, the GLP-1 receptor agonist is exenatide having the following sequence:

(SEQ ID NO: 61)
HGEGTFTSDLSKQMEEEAVRLFIEWLKNGGPSSGAPPPS

In embodiments, the GLP-1 receptor agonist is an exenatide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 61.

In embodiments, the GLP-1 receptor agonist lixisenatide is having the following sequence:

(SEQ ID NO: 62)
HGEGTFTSDLSKQMEEEAVRLFIEWLKNGGPSSGAPPSKKKKKK

In embodiments, the GLP-1 receptor agonist is a lixisenatide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 62.

In embodiments, the GLP-1 receptor agonist is the GLP-1 receptor agonist portion of albiglutide having the following sequence:

(SEQ ID NO: 63)
HGEGTFTSDVSSYLEGQAAKEFIAWLVKGR

In embodiments, the GLP-1 receptor agonist is an albiglutide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 63.

In embodiments, the GLP-1 receptor agonist is liraglutide having the following sequence:

(SEQ ID NO: 77)
HAEGTFTSDVSSYLEGQAAKEFIAWLVRGRG

In embodiments, the GLP-1 receptor agonist is an liraglutide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 77.

In embodiments, the GLP-1 receptor agonist is exendin-4 having the following sequence:

(SEQ ID NO: 64)
HGEGTFTSDLSKQMEEEAVRLFEWLKNGGPSSGAPPPS

In embodiments, the GLP-1 receptor agonist is an exendin-4 variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 64.

Dulaglutide (GLP-1 moiety-Fc fusion protein; GLP-1 moiety underlined, (GGGGS)$_3$ shown in a boldface font) has the following sequence:

(SEQ ID NO: 65)
HGEGTFTSDVSSYLEEQAAKEFIAWLVKGGGGGGGSGGGGSGGGGSAES

KYGPPCPPCPAPEAAGGPSVFLFPPKPKDTLMISRTPEVTCVVVDVSQE

DPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTC

LVKGFYPSDIAVEWESNGQPENNYKTTPPVLDSDGSFFLYSRLTVDKSR

WQEGNVFSCSVMHEALHNHYTQKSLSLSLG

In embodiments, the GLP-1 receptor agonist is an GLP-1 moiety of dulaglutide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 65.

In embodiments, the GLP-1 receptor agonist is the GLP-1 moiety of dulaglutide having the following sequence:

(SEQ ID NO: 66)
HGEGTFTSDVSSYLEEQAAKEFIAWLVKGGG

In embodiments, the GLP-1 receptor agonist is an GLP-1 moiety of dulaglutide variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 66.

In embodiments, the GLP-1 receptor agonist is GLP-1 derivative that is resistant to DPP4 degradation. In embodiments, the GLP-1 receptor agonist comprises a mutation that confers resistance to DPP4. In embodiments, the GLP-1 receptor agonist is DPP4 degradation resistant GLP-1 (7-37, A8G) having the following sequence:

(SEQ ID NO: 91)
HGEGTFTSDVSSYLEEQAAKEFIAWLVKGRG

In embodiments, the GLP-1 receptor agonist is a GLP-1, or a variant thereof having one or more amino acid mutations, independently selected from substitutions, insertions, deletions, and truncations. In embodiments, the GLP-1 receptor agonist has an amino acid sequence having about 1, 2, 3, 4, 5, 6, 7, 8, 9, or 10 or more amino acid mutations with respect to an amino acid sequence selected from the amino acid sequence of SEQ ID NO: 91.

In embodiments, the GLP-1 receptor agonist is an GLP-1 moiety of liraglutide, or an amino acid sequence having about 1, 2, 3, 4, 5, 6, 7, 8, 9, or 10 or more amino acid mutations with respect to an amino acid sequence of the GLP-1 moiety of liraglutide. In embodiments, the GLP-1 receptor agonist is an GLP-1 moiety of semaglutide, or an amino acid sequence having about 1, 2, 3, 4, 5, 6, 7, 8, 9, or 10 or more amino acid mutations with respect to an amino acid sequence of the GLP-1 moiety of semaglutide. In embodiments, the GLP-1 receptor agonist is an GLP-1 moiety of taspoglutide, or an amino acid sequence having about 1, 2, 3, 4, 5, 6, 7, 8, 9, or 10 or more amino acid mutations with respect to an amino acid sequence of the GLP-1 moiety of taspoglutide.

In embodiments, the chimeric protein of the disclosure binds to human GLP-1 receptor with a K$_D$ of less than about 1 µM, about 900 nM, about 800 nM, about 700 nM, about 600 nM, about 550 nM, about 530 nM, about 500 nM, about 400 nM, about 300 nM, about 200 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to human GLP-1 receptor with a K$_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry). In embodiments, the chimeric protein binds to human GLP-1 receptor with a $K_D$ of from about 300 pM to about 700 pM.

GLP-1 derivatives can be constructed from available structural data, including that described by Chang et al., Structure and Folding of Glucagon-like Peptide-1-(7-36)-amide in Trifluoroethanol Studied by NMR, *Magn Reson Chem* 39: 477-483 (2001); Underwood et al., Crystal structure of glucagon-like peptide-1 in complex with the extracellular domain of the glucagon-like peptide-1 receptor, *J Biol Chem* 285: 723-730 (2010); Lau et al., Discovery of the Once-Weekly Glucagon-Like Peptide-1 (GLP-1) Analogue Semaglutide, *J Med Chem* 58: 7370-7380 (2015); Oddo et al., alpha-Helix or beta-Turn? An Investigation into N-Terminally Constrained Analogues of Glucagon-like Peptide 1 (GLP-1) and Exendin-4, *Biochemistry* 57: 4148-4154 (2018); Zhang et al., Cryo-EM structure of the activated GLP-1 receptor in complex with a G protein, *Nature* 546: 248-253 (2017); Bueno et al., Structural insights into probe-dependent positive allosterism of the GLP-1 receptor, *Nat Chem Biol* 16: 1105-1110 (2020); Zhang et al., Differential GLP-1R Binding and Activation by Peptide and Non-peptide Agonists, *Mol Cell* 80: 485 (2020).

In embodiments, the GLP-1 receptor agonist is selected from GLP-1 (1-37), GLP-1 (1-36) GLP-1 (7-36), exenatide, lixisenatide, exendin-4, albiglutide, liraglutide, dulaglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77, 91, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the mutations are independently selected from substitutions, insertions, deletions, and truncations. In embodiments, first domain is capable of binding a GLP-1 receptor. In embodiments, the GLP-1 receptor agonist is capable of stimulating and/or increasing insulin secretion, and/or inhibiting and/or decreasing glucagon secretion. In embodiments, the GLP-1 receptor agonist is capable of stimulating and/or increasing insulin secretion, and/or inhibiting and/or decreasing glucagon secretion, compared to a chimeric protein lacking the first domain (e.g., having a structure: (a) a second domain comprising a glucose-dependent insulinotropic polypeptide (GIP) receptor (GIPR) modulator of any of the embodiments disclosed herein and optionally (b) a linker comprising one or more protease-cleavable polypeptide linkers and/or a hinge-CH2-CH3 Fc domain.

Glucose-Dependent Insulinotropic Polypeptide (GIP) Receptor Modulators

Glucose-dependent insulinotropic polypeptide (GIP) is a biologically active 42-amino acid-long gastro-intestinal peptide hormone, having a very short half-life (2-5 min) in circulation, which is synthesized and secreted into the blood stream by intestinal endocrine K cells within minutes of ingesting a meal. GIP binds to a specific glucose-dependent insulinotropic polypeptide receptor (GIPR), which is a class B G-protein-coupled receptor (GPCR) expressed in the endocrine pancreas, gastrointestinal tract, brain, immune and cardiovascular systems, testis, pituitary, lung, kidney, thyroid, several regions of the central nervous system and adipose tissue. GIP is believed to induce insulin secretion, which is stimulated primarily by hyperosmolarity of glucose in the duodenum. The amount of insulin secreted is greater when glucose is administered orally than intravenously. GIP is also believed to reduce food intake upon signaling via the hypothalamic GIPR. Adriaenssens, et al., Glucose-Dependent Insulinotropic Polypeptide Receptor-Expressing Cells in the Hypothalamus Regulate Food Intake, *Cell Metabolism* 2019; 30(5): 987-996. GIP is known to inhibit apoptosis of the pancreatic beta cells and to promote their proliferation. It also stimulates glucagon secretion and fat accumulation. Both GIP receptor (GIPR) agonism and antagonism are effective strategies for inhibiting weight gain. Miyawaki et al., Inhibition of gastric inhibitory polypeptide signaling prevents obesity, *Nat. Med.*, 2002; 8: 738-742; McClean et al., GIP receptor antagonism reverses obesity, insulin resistance, and associated metabolic disturbances induced in mice by prolonged consumption of high-fat diet, *Am. J. Physiol. Endocrinol. Metab.*, 2007; 293: E1746-E1755. Boylan et al., Gastric inhibitory polypeptide immunoneutralization attenuates development of obesity in mice, *Am. J. Physiol. Endocrinol. Metab.*, 309: E1008-E1018; Fulurija et al., Vaccination against GIP for the treatment of obesity, *PLoS One* 2008; 3: e3163. Accordingly, in embodiments, the GIPR modulator is a GIPR agonist. In embodiments, the GIPR modulator is a GIPR antagonist.

In embodiments, the chimeric proteins disclosed herein have a general structure of: N terminus-(a)-(b)-(c)-C terminus, wherein (a) is a first domain comprising a glucagon-like peptide-1 (GLP-1) receptor agonist. In these embodiments, (b) is a linker adjoining the first domain and a second domain, optionally wherein the linker comprises one or more protease-cleavable polypeptide linkers, and/or a hinge-CH2-CH3 Fc domain. In these embodiments, (c) is the second domain comprising a glucose-dependent insulinotropic polypeptide (GIP) receptor (GIPR) modulator. In embodiments, the GIPR modulator is a GIPR agonist. In embodiments, the GIPR modulator is a GIPR antagonist.

In alternative embodiments, the chimeric proteins disclosed herein have a general structure of: N terminus-(a)-(b)-(c)-C terminus, wherein (c) is a first domain comprising a glucose-dependent insulinotropic polypeptide (GIP) receptor (GIPR) modulator. In these embodiments, (b) is a linker adjoining the first domain and a second domain, optionally wherein the linker comprises one or more protease-cleavable polypeptide linkers, and/or a hinge-CH2-CH3 Fc domain. In these embodiments, (a) is a first domain comprising (i) a glucagon-like peptide-1 (GLP-1) receptor agonist, or (ii) a fibroblast growth factor 19 (FGF19), FGF21 or a variant thereof, or an analog thereof. In embodiments, the GIPR modulator is a GIPR agonist. In embodiments, the GIPR modulator is a GIPR antagonist.

In embodiments, the GIPR modulator signals through its receptor, a specific glucose-dependent insulinotropic polypeptide receptor (GIPR), which is a class B G-protein-coupled receptor (GPCR). In embodiments, the GIPR modulator modulates the GIPR on the surface of the endocrine pancreas. In embodiments, the GIPR modulator activates hypothalamic GIPR. In embodiments, the GIPR modulator induces increased insulin production by the pancreatic β-cells in a glucose dependent manner in response to the GIPR activation. In embodiments, the GIPR modulator inhibits apoptosis of the pancreatic β-cells. In embodiments, the GIPR modulator inhibits food intake. In embodiments, the GIPR modulator inhibits triglyceride storage in adipose tissue. In embodiments, the GIPR modulator activates the GIPR on the surface of pancreatic α-cells. In embodiments, the GIPR modulator activates GIPR suppresses glucose-dependent glucagon secretion by the pancreatic α-cells in response to the GIPR activation.

In embodiments, any of a number of drugs that mimic the action of GIP by binding and activating the GIPR is suitable. In embodiments, the GIPR modulator is a GIPR agonist. In embodiments, the GIPR modulator is a GIPR antagonist. GIP, which is encoded by the GIP gene, is derived from a 153-amino acid proprotein having the following sequence (GIP is shown in a boldface-underlined font):

(SEQ ID NO: 67)
MVATKTFALLLLSLFLAVGLGEKKEGHFSALPSLPVGSHAKVSSPQPRG

PRYAEGTFISDYSIAMDKIHQQDFVNWLLAQKGKKNDWKHNITQREARA

LELASQANRKEEEAVEPQSSPAKNPSDEDLLRDLLIQELLACLLDQTNL

CRLRSR

In embodiments, the GIPR modulator, which is also referred to herein as GIP Agonist (amino acids 1-42) or GIP (Ag), is GIP having the following sequence:

(SEQ ID NO: 68)
YAEGTFISDYSIAMDKIHQQDFVNWLLAQKGKKNDWKHNITQ

In embodiments, the GIPR modulator is GIP or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence selected from the amino acid sequence of SEQ ID NO: 68.

In embodiments, the GIPR modulator is GIP (1-28) having the following sequence:

(SEQ ID NO: 69)
YAEGTFISDYSIAMDKIHQQDFVNWLLA

In embodiments, the GIPR modulator is GIP (1-28) or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence selected from the amino acid sequence of SEQ ID NO: 69.

In embodiments, the GIPR modulator is GIP (1-30) having the following sequence:

(SEQ ID NO: 103)
YAEGTFISDYSIAMDKIHQQDFVNWLLAQK

In embodiments, the GIPR modulator is GIP (1-30) or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence selected from the amino acid sequence of SEQ ID NO: 103.

In embodiments, the GIPR modulator is GIP (1-31) having the following sequence:

(SEQ ID NO: 104)
YAEGTFISDYSIAMDKIHQQDFVNWLLAQKG

In embodiments, the GIPR modulator is GIP (1-31) or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence selected from the amino acid sequence of SEQ ID NO: 104.

In embodiments, the GIPR modulator is GIP (10-28) having the following sequence the following sequence:

(SEQ ID NO: 100)
YSIAMDKIHQQDFVNWLLAQK

In embodiments, the GIPR modulator is GIP (10-28) or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence selected from the amino acid sequence of SEQ ID NO: 100.

In embodiments, the GIPR modulator has the following sequence:

(SEQ ID NO: 101)
YSIAMDKIRQQDFVNWLLAQK

In embodiments, the GIPR modulator has an amino acid sequence of SEQ ID NO: 101 or a variant thereof having one or more amino acid mutations, independently selected from substitutions, insertions, deletions, and truncations. In embodiments, GIPR modulator has an amino acid sequence having about 1, 2, 3, 4, 5, 6, 7, 8, 9, or 10 or more amino acid mutations with respect to an amino acid sequence of SEQ ID NO: 101.

In embodiments, the GIPR modulator has the following sequence:

(SEQ ID NO: 102)
YXEGTFISDYSIALEKIRQQEFVNWLLKQKPSSGAPPKS, wherein X is any amino acid.

In embodiments, the GIPR modulator has an amino acid sequence of SEQ ID NO: 102 or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence of SEQ ID NO: 102.

In embodiments, the GIPR modulator, which is also referred to herein as GIP Antagonist (amino acids 1-42, having a E3P substitution) or GIP (AntPro3), is GIP having the following sequence:

(SEQ ID NO: 97)
YAPGTFISDYSIAMDKIHQQDFVNWLLAQKGKKNDWKHNITQ

In embodiments, the GIPR modulator is GIP or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence of SEQ ID NO: 97.

In embodiments, the GIPR modulator, which is also referred to herein as GIP Antagonist (amino acids 3-30) or GIP (Ant3-30), is GIP having the following sequence:

```
                                      (SEQ ID NO: 98)
EGTFISDYSIAMDKIHQQDFVNWLLAQ
```

In embodiments, the GIPR modulator is GIP or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence of SEQ ID NO: 98.

In embodiments, the GIPR modulator, which is also referred to herein as GIP Antagonist (amino acids 3-30, having a E1P substitution) or GIP (Ant3-30, E1P), is GIP having the following sequence:

```
                                      (SEQ ID NO: 99)
PGTFISDYSIAMDKIHQQDFVNWLLAQ
```

In embodiments, the GIPR modulator is GIP or a variant thereof having one or more amino acid mutations, independently selected from substitutions, insertions, deletions, and truncations. In embodiments, the GIPR modulator has an amino acid sequence having about 1, 2, 3, 4, 5, 6, 7, 8, 9, or 10 or more amino acid mutations with respect to an amino acid sequence of SEQ ID NO: 99.

In embodiments, the chimeric protein of the disclosure binds to human GIP receptor with a $K_D$ of less than about 1 µM, about 900 nM, about 800 nM, about 700 nM, about 600 nM, about 550 nM, about 530 nM, about 500 nM, about 400 nM, about 300 nM, about 200 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to human GIP receptor with a $K_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry). In embodiments, the chimeric protein binds to human GIP receptor with a $K_D$ of from about 300 pM to about 700 pM.

GIP derivatives can be constructed from available structural data, including that described by Hinke et al., Structure-activity relationships of glucose-dependent insulinotropic polypeptide (GIP), *Biol Chem* 2003; 384(3):403-7; Parthier et al., Crystal structure of the incretin-bound extracellular domain of a G protein-coupled receptor, *Proc. Natal. Acad. Sci. USA* 2007; 104 (35) 13942-13947; Zhao et al., Structural insights into hormone recognition by the human glucose-dependent insulinotropic polypeptide receptor, *Elife* 2021 13; 10:e68719; Alana et al., NMR and alanine scan studies of glucose-dependent insulinotropic polypeptide in water. *J Biol Chem* 2006; 281: 16370-16376; Gault et al., Glucose-dependent insulinotropic polypeptide analogues and their therapeutic potential for the treatment of obesity-diabetes, *Biochem Biophys Res Commun* 2003; 308 (2):207-13; Tatarkiewicz et al., A novel long-acting glucose-dependent insulinotropic peptide analogue: enhanced efficacy in normal and diabetic rodents, *Diabetes Obes Metab.* 2014; 16(1):75-85.

Suitable GIPR modulators (without limitations, e.g., GIP analogs, GIP agonists, and GIP antagonists) are disclosed in U.S. Pat. Nos. 6,921,748; 8,497,240; 9,453,062; 10,253,078 and US Patent Application Publication Nos. 2003/0232761; 2008/0312157; 2011/0136737; 2014/0162945; 2015/0329611; 2017/0240609; 2017/0240609, the entire contents of which are hereby incorporated by reference in their entirety.

In embodiments, the GIPR modulator has an amino acid sequence that is selected from the amino acid sequence of SEQ ID NO: 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104, wherein the amino acid mutations are independently selected from substitutions, insertions, deletions, and truncations. In embodiments, the GIPR modulator has an amino acid sequence of any one of SEQ ID NOs: 67 to 74, or a variant having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the mutations are independently selected from substitutions, insertions, deletions, and truncations. In embodiments, second domain is capable of binding a GLP-1 receptor. In embodiments, the second domain is capable of stimulating and/or increasing insulin secretion. In embodiments, the second domain is capable of stimulating and/or increasing insulin secretion, compared to a chimeric protein lacking the second domain (e.g., having a structure: (a) a first domain comprising a glucagon-like peptide-1 (GLP-1) receptor agonist of any of the embodiments disclosed herein and optionally (b) a linker comprising one or more protease-cleavable polypeptide linkers and/or a hinge-CH2-CH3 Fc domain. In embodiments, the second domain is capable of stimulating and/or increasing glucagon secretion at fasting glucose concentrations. Therefore, in embodiments, the second domain is capable of enhancing glucagon secretion to limit hypoglycemia and/or stimulating insulin secretion to lower hyperglycemia.

FGF19 and FGF21

Fibroblast growth factors (FGFs) are signaling proteins involved in development and metabolism. In humans, there are three endocrine FGFs: FGF19, FGF21, and FGF23.

In aspects, the present disclosure provides a chimeric protein having a general structure of: N terminus-(a)-(b)-(c)-C terminus, wherein (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor 19 (FGF19), FGF21 or a variant thereof, or an analog thereof.

In aspects, the present disclosure provides a chimeric protein having a general structure of: N terminus-(a)-(b)-(c)-C terminus, wherein (a) is the second domain comprising fibroblast growth factor 19 (FGF19), FGF21 or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is a second domain comprising a glucose-dependent insulinotropic polypeptide (GIP) receptor (GIPR) modulator.

In embodiments, the FGF19, FGF21 or a variant thereof, or an analog thereof is the murine FGF15, the ortholog of human FGF19. In embodiments, the FGF19, FGF21 or a variant thereof lack the heparin binding domain common in other FGFs. In embodiments, the FGF19, FGF21 or a variant thereof has low heparan sulphate affinity. Accordingly, in embodiments, the FGF19, FGF21 or a variant thereof enter into the circulatory system and perform endocrine signaling functions.

In embodiments, the FGF19, FGF21 or a variant thereof activate the fibroblast growth factor receptors (FGFRs). In embodiments, the FGF19, FGF21 or a variant thereof require the transmembrane proteins α-Klotho or β-Klotho as a cofactor for signaling. While FGFR proteins are widely expressed, α-Klotho and β-Klotho exhibit tissue specific expression patterns, limiting the tissues where the endocrine FGFs are active. α-Klotho is expressed predominantly in the kidney and brain, and ß-Klotho is predominantly expressed in the liver, adipose tissue, and pancreas. Accordingly, in embodiments, the FGF19, FGF21 or a variant thereof binds FGFR-Klotho complexes in an FGF-specific manner (e.g., FGF19 and variants primarily act through FGFR4 and β-Klotho; FGF21 and variants act through FGFR1c and β-Klotho; and FGF23 and variants through FGFR1c with α-Klotho).

FGF19 is produced in the ileum in response to bile acid absorption there. In embodiments, the FGF19 or a variant thereof regulates the production of bile acid. Bile acid is produced and released in the liver, stored in the gall bladder, and released into the duodenum, where it helps emulsify and solubilize fat. In embodiments, the FGF19 or a variant thereof enter circulation, and, in the liver, reduces the expression of the cholesterol 7 alpha-hydroxylase (CYP71A) enzyme, the rate limiting enzyme in bile acid production.

In embodiments, the FGF19, FGF21 or a variant thereof are wild-type human FGF19, FGF21 or FGF23. Suitable FGF19, FGF21 are disclosed in U.S. Pat. Nos. 7,576,190; 8,012,931; 8,541,369; 8,535,912; 8,741,841; 8,883,726; 8,927,492; 8,951,966; 9,089,525; 9,422,353; 9,493,530; 9,889,177; 9,889,178; 9,895,416; 9,974,833; 9,963,494; 9,925,242, and US Publication No. 2007/0237768, the contents of which are hereby incorporated by reference in their entirety.

In embodiments, the FGF19 or a variant thereof is the FGF19 having the following sequence:

```
                                          (SEQ ID NO: 78)
LAFSDAGPHVHYGWGDPIRLRHLYTSGPHGLSSCFLRIRADGVVDCARG

QSAHSLLEIKAVALRTVAIKGVHSVRYLCMGADGKMQGLLQYSEEDCAF

EEEIRPDGYNVYRSEKHRLPVSLSSAKQRQLYKNRGFLPLSHFLPMLPM

VPEEPEDLRGHLESDMFSSPLETDSMDPFGLVTGLEAVRSPSFEK.
```

In embodiments, the present chimeric protein comprises FGF19 which has the amino acid sequence of SEQ ID NO: 78. In embodiments, the present chimeric proteins may comprise the FGF19 as described herein, or a variant or functional fragment thereof. For instance, the chimeric protein may comprise a sequence of the FGF19 as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF19 as described herein.

In embodiments, the FGF19 reduces bile acid-induced liver damage in cholestatic liver diseases. In embodiments, the FGF19 reduces fat absorption into the body.

In embodiments, the FGF19 or a variant thereof is the adafermin (as M70 or NGM282) having the following sequence:

```
                                          (SEQ ID NO: 79)
MRDSSPLVHYGWGDPIRLRHLYTSGPHGLSSCFLRIRADGVVDCARGQS

AHSLLEIKAVALRTVAIKGVHSVRYLCMGADGKMQGLLQYSEEDCAFEE

EIRPDGYNVYRSEKHRLPVSLSSAKQRQLYKNRGFLPLSHELPMLPMVP

EEPEDLRGHLESDMFSSPLETDSMDPFGLVTGLEAVRSPSFEK
```

In embodiments, the present chimeric protein comprises FGF19, FGF21 or a variant thereof is adafermin, which has the amino acid sequence of SEQ ID NO: 79. In embodiments, the present chimeric proteins may comprise adafermin as described herein, or a variant or functional fragment thereof. For instance, the chimeric protein may comprise a sequence of adafermin as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of adafermin as described herein.

In embodiments, the FGF19 or a variant thereof reduces liver fat content (without limitation, e.g., in human NASH patients. In embodiments, the FGF19 or a variant thereof reduces production of bile acid. In embodiments, the second domain comprises FGF19, or an analog thereof. In embodiments, the analog of FGF19 is aldafermin (NGM282). In embodiments, the second domain is capable of activating FGFR4, optionally wherein the activating requires R-Klotho as a coreceptor. In embodiments, the second domain comprises an amino acid sequence that is at least about 90%, or at least about 95%, or at least about 97%, or at least about 98%, or at least about 99% identical to an amino acid sequence of SEQ ID NOs: 78 or 79.

FGF19 derivatives can be constructed from available structural data, including that described by Harmer et al., The crystal structure of fibroblast growth factor (FGF) 19 reveals novel features of the FGF family and offers a structural basis for its unusual receptor affinity, *Biochemistry* 43: 629-640 (2004); Goetz et al., Molecular insights into the klotho-dependent, endocrine mode of action of fibroblast growth factor 19 subfamily members, *Mol Cell Biol* 27: 3417-3428 (2007); Liu et al., Novel Abs targeting the N-terminus of fibroblast growth factor 19 inhibit hepatocellular carcinoma growth without bile-acid-related side-effects, Cancer Sci 111: 1750-1760 (2020); Kuzina et al., Structures of ligand-occupied beta-Klotho complexes reveal a molecular mechanism underlying endocrine FGF specificity and activity, Proc Natl Acad Sci USA 116: 7819-7824 (2019).

FGF21 is predominantly expressed in the liver and helps regulate glucose and lipid homeostasis. In embodiments, the chimeric protein reduces weight without decreased caloric intake and improved hepatosteatosis. In embodiments, the chimeric protein reduces glucose levels, body weight, insulin, and cholesterol and triglycerides. Pegbelfermin (BMS-986036) has been shown to reduce liver fat content in human NASH patients.

In embodiments, the FGF21 has the following sequence:

```
                                           (SEQ ID NO: 80)
HPIPDSSPLLQFGGQVRQRYLYTDDAQQTEAHLEIREDGTVGGAADQSP

ESLLQLKALKPGVIQILGVKTSRFLCQRPDGALYGSLHFDPEACSFREL

LLEDGYNVYQSEAHGLPLHLPGNKSPHRDPAPRGPARFLPLPGLPPALP

EPPGILAPQPPDVGSSDPLSMVGPSQGRSPSYAS
```

In embodiments, the present chimeric protein comprises FGF21 which has the amino acid sequence of SEQ ID NO: 80. In embodiments, the present chimeric proteins may comprise the FGF21 as described herein, or a variant or functional fragment thereof. For instance, the chimeric protein may comprise a sequence of the FGF21 as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF21 as described herein.

In embodiments, the FGF21 or a variant thereof is the FGF21 moiety from efruxifermin (AMG876) having the following sequence:

```
                                           (SEQ ID NO: 81)
HPIPDSSPLLQFGGQVRQRYLYTDDAQQTEAHLEIREDGTVGGAADQSP

ESLLQLKALKPGVIQILGVKTSRFLCQRPDGALYGSLHFDPEACSFRER

LLEDGYNVYQSEAHGLPLHLPGNKSPHRDPAPRGPARFLPLPGLPPAPP

EPPGILAPQPPDVGSSDPLSMVGGSQGRSPSYES
```

In embodiments, the present chimeric protein comprises FGF21 moiety from efruxifermin (AMG876) which has the amino acid sequence of SEQ ID NO: 81. In embodiments, the present chimeric proteins may comprise the FGF21 moiety from efruxifermin (AMG876) as described herein, or a variant or functional fragment thereof. For instance, the chimeric protein may comprise a sequence of the FGF21 moiety from efruxifermin (AMG876) as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF21 moiety from efruxifermin (AMG876) as described herein.

Efruxifermin has the following amino acid sequence (AMG876; FGF21 moiety underlined, (GGGGS)₃ shown in a boldface font):

```
                                           (SEQ ID NO: 82)
MDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQ

GNVFSCSVMHEALHNHYTQKSLSLSPGKGGGGSGGGGSGGGGSHPIPDSS

PLLQFGGQVRQRYLYTDDAQQTEAHLEIREDGTVGGAADQSPESLLQLKA

LKPGVIQILGVKTSRFLCQRPDGALYGSLHFDPEACSFRERLLEDGYNVY

QSEAHGLPLHLPGNKSPHRDPAPRGPARFLPLPGLPPAPPEPPGILAPQP

PDVGSSDPLSMVGGSQGRSPSYES
```

In embodiments, the present chimeric protein comprises FGF21 moiety from efruxifermin (AMG876) which has the amino acid sequence of SEQ ID NO: 82. In embodiments, the present chimeric proteins may comprise the FGF21 moiety from efruxifermin (AMG876) as described herein, or a variant or functional fragment thereof. For instance, the chimeric protein may comprise a sequence of the FGF21 moiety from efruxifermin (AMG876) as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF21 moiety from efruxifermin (AMG876) as described herein.

In embodiments, the FGF21 or a variant thereof is LY2405319 having the following amino acid sequence:

(SEQ ID NO: 83)
DSSPLLQFGGQVRQRYLYTDDAQQTEAHLEIREDGTVGGAADQSPESLLQ

LKALKPGVIQILGVKTSRFLCQRPDGALYGSLHFDPEACSFRELLLEDGY

NVYQSEAHGLPLHCPGNKSPHRDPAPRGPCRFLPLPGLPPALPEPPGILA

PQPPPDVGSSDPLAMVGPSQGRSPSYAS

In embodiments, the present chimeric protein comprises LY2405319, which has the amino acid sequence of SEQ ID NO: 83. In embodiments, the present chimeric proteins may comprise the LY2405319 as described herein, or a variant or functional fragment thereof. For instance, the chimeric protein may comprise a sequence of the LY2405319 as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the LY2405319 as described herein.

In embodiments, the FGF21 (RGE), which has the substitutions in comparison with SEQ ID NO: 66 indicated with a boldface font, has the following sequence:

(SEQ ID NO: 84)
HPIPDSSPLLQFGGQVRQRYLYTDDAQQTEAHLEIREDGTVGGAADQSPE

SLLQLKALKPGVIQILGVKTSRFLCQRPDGALYGSLHFDPEACSFRERLL

EDGYNVYQSEAHGLPLHLPGNKSPHRDPAPRGPARFLPLPGLPPALPEPP

GILAPQPPDVGSSDPLSMVGGSQGRSPSYES

In embodiments, the present chimeric protein comprises FGF21 which has the amino acid sequence of SEQ ID NO: 84. In embodiments, the present chimeric proteins may comprise the FGF21 (RGE) as described herein, or a variant or functional fragment thereof. For instance, the chimeric protein may comprise a sequence of the FGF21 (RGE) as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF21 (RGE) as described herein.

In embodiments, the FGF21 (L146P), which has the substitution in comparison with SEQ ID NO: 80 indicated with a boldface font, has the following sequence:

(SEQ ID NO: 85)
HPIPDSSPLLQFGGQVRQRYLYTDDAQQTEAHLEIREDGTVGGAADQS

PESLLQLKALKPGVIQILGVKTSRFLCQRPDGALYGSLHFDPEACSFR

ELLLEDGYNVYQSEAHGLPLHPPGNKSPHRDPAPRGPARFLPLPGLPP

ALPEPPGILAPQPPDVGSSDPLSMVGPSQGRSPSYAS

In embodiments, the present chimeric protein comprises FGF21 which has the amino acid sequence of SEQ ID NO: 85. In embodiments, the present chimeric proteins may comprise the FGF21 as described herein, or a variant or functional fragment thereof. For instance, the chimeric protein may comprise a sequence of the FGF21 (L146P) as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the FGF21 (L146P) as described herein.

In embodiments, the second domain comprises FGF21, or an analog thereof. In embodiments, the analog of FGF21 is selected from efruxifermin, LY2405319, FGF21 (RGE) and FGF21 (L146P). In embodiments, the second domain is capable of activating FGFR1c, optionally wherein the activating requires R-Klotho as a coreceptor. In embodiments, the second domain comprises an amino acid sequence that is at least about 90%, or at least about 95%, or at least about 97%, or at least about 98%, or at least about 99% identical to an amino acid sequence selected from the amino acid sequence of SEQ ID NOs: 80 to 85.

In embodiments, the analog of FGF21 is the FGF21 moiety from pegbelfermin (BMS-986036) or an amino acid sequence that is at least about 90%, or at least about 95%, or at least about 97%, or at least about 98%, or at least about 99% identity thereto.

FGF21 derivatives can be constructed from available structural data, including that described by Lee et al., Structures of beta-klotho reveal a 'zip code'-like mechanism for endocrine FGF signaling, Nature 553: 501-505 (2018); Kharitonenkov et al., Rational Design of a Fibroblast Growth Factor 21-Based Clinical Candidate, LY2405319. PLoS ONE 8(3):e58575 (2013); and Huang, J. et al., Development of a Novel Long-Acting Antidiabetic FGF21 Mimetic by Targeted Conjugation to a Scaffold Antibody, *The Journal Of Pharmacology And Experimental Therapeutics* 346(2):270-280 (2013).

Activin Receptor Type-2B (ACVR2B)

Activin receptor type-2B is a transmembrane serine/threonine kinase activin type-2 receptor, which transduces regulates muscle physiology, neuron physiology, hair follicle development and cycling, FSH production, wound healing, extracellular matrix production, etc. ACVR2B ligands include activin A and GDF-8/myostatin, both of which negatively regulate the muscle size. McPherron et al., Regulation of skeletal muscle mass in mice by a new TGF-beta superfamily member, *Nature* 387, 83-90 (1997); Chen et al. Elevated expression of activins promotes muscle wasting and cachexia. FASEB J. 28, 1711-1723 (2014). Concomitant inhibition of activin A and GDF8 has been shown to synergistically increase muscle mass in mice and non-human primates. Nissinen et al., Systemic blockade of ACVR2B ligands prevents chemotherapy-induced muscle wasting by restoring muscle protein synthesis without affecting oxidative capacity or atrogenes, *Sci Rep* 6: 32695 (2016); Latres et al., Activin A more prominently regulates muscle mass in primates than does GDF8, *Nat Commun.* 8: 15153 (2017).

Accordingly, in aspects, the present disclosure provides a chimeric protein, or a polynucleotide encoding the chimeric protein, that inhibition of the activin receptor type-2B (ACVR2B), that contemporaneously causes an modulation of one or more of the GLP-1 receptor (GLP-1R), GIP receptor (GIPR), and glucagon receptor (GCGR) same. In embodiments, the chimeric protein causes the activation of GLP-1R and/or GCGR. In embodiments, the chimeric protein causes the activation of GIPR. In embodiments, the chimeric protein causes the inhibition or antagonism of GIPR. In embodiments, the chimeric protein comprises a portion of activin receptor type-2B (ACVR2B). In embodiments, the portion of ACVR2B is capable of binding activin A and/or GDF-8. In embodiments, the portion of ACVR2B is the extracellular domain of ACVR2B.

In aspects, the present disclosure provides a chimeric protein comprising a general structure of: N terminus-(a)-(b)-(c)-C terminus, wherein: (A) (a) is a first domain comprising a glucagon-like peptide-1 (GLP-1) receptor agonist, (c) is a second domain comprising a portion of activin receptor type-2B (ACVR2B), and (b) is a linker adjoining the first domain and a second domain, optionally wherein the linker comprises a hinge-CH2-CH3 Fc domain; or (B) (a) is a second domain comprising a portion of activin receptor type-2B (ACVR2B), (c) is a first domain comprising a glucagon-like peptide-1 (GLP-1) receptor agonist, and (b) is a linker adjoining the first domain and a second domain, optionally a hinge-CH2-CH3 Fc domain.

In embodiments, the GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77 and 91 or a variant having about 1, 2, 3, 4, 5, 6, 7, 8, 9, or 10 or more amino acid mutations with respect to an amino acid sequence selected from the amino acid sequence of SEQ ID NOs: 58 to 66, 77 and 91. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the portion of ACVR2B is capable of binding activin A and/or GDF-8. In embodiments, the portion of ACVR2B comprises substantially the entire extracellular domain of ACVR2B. In embodiments, the portion of ACVR2B comprises the entire extracellular domain of ACVR2B. In embodiments, the portion of ACVR2B comprises an amino acid sequence that is at least about 90%, or at least about 95% identical to the amino acid sequence of SEQ ID NO: 153.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In aspects, the present disclosure provides an isolated polynucleotide encoding the chimeric protein of any of the embodiments disclosed herein. In embodiments, the polynucleotide is selected from mRNA, circular RNA (circRNA) and self-amplifying RNA (saRNA), optionally wherein the polynucleotide is modified. In embodiments, the polynucleotide is an mmRNA. In embodiments, the mmRNA comprises one or more nucleoside modifications, optionally wherein the mmRNA comprises one or more of 1-methylpseudouridine nucleotides.

In embodiments, the chimeric protein comprises a portion of the full length human activin receptor type-2B (ACVR2B), which comprises the following illustrative amino acid sequence:

(SEQ ID NO: 152)
MTAPWVALALLWGSLCAGSGRGEAETRECIYYNANWELERTNQSGLER

CEGEQDKRLHCYASWRNSSGTIELVKKGCWLDDFNCYDRQECVATEEN

PQVYFCCCEGNFCNERFTHLPEAGGPEVTYEPPPTAPTLLTVLAYSLL

PIGGLSLIVLLAFWMYRHRKPPYGHVDIHEDPGPPPPSPLVGLKPLQL

LEIKARGRFGCVWKAQLMNDFVAVKIFPLQDKQSWQSEREIFSTPGMK

HENLLQFIAAEKRGSNLEVELWLITAFHDKGSLTDYLKGNIITWNELC

HVAETMSRGLSYLHEDVPWCRGEGHKPSIAHRDFKSKNVLLKSDLTAV

```
-continued
LADFGLAVRFEPGKPPGDTHGQVGTRRYMAPEVLEGAINFQRDAFLRI

DMYAMGLVLWELVSRCKAADGPVDEYMLPFEEEIGQHPSLEELQEVVV

HKKMRPTIKDHWLKHPGLAQLCVTIEECWDHDAEARLSAGCVEERVSL

IRRSVNGTTSDCLVSLVTSVTNVDLPPKESSI.
```

In embodiments, the chimeric protein comprises a portion of the full length ACVR2B, which comprises a variant or functional fragment SEQ ID NO: 152. For instance, the chimeric protein may comprise a portion of the full length ACVR2B having a sequence as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of SEQ ID NO: 152.

In embodiments, the chimeric protein comprises an extracellular domain of human activin receptor type-2B (ACVR2B), which comprises the following illustrative amino acid sequence:

```
                                        (SEQ ID NO: 153)
SGRGEAETRECIYYNANWELERTNQSGLERCEGEQDKRLHCYASWRNS

SGTIELVKKGCWLDDFNCYDRQECVATEENPQVYFCCCEGNFCNERFT

HLPEAGGPEVTYEPPPTAPTLLT.
```

In embodiments, the chimeric protein comprises an extracellular domain of ACVR2B, which comprises a variant or functional fragment SEQ ID NO: 153. For instance, the chimeric protein may comprise an extracellular domain of ACVR2B having a sequence as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of SEQ ID NO: 153.

ACVR2B derivatives can be constructed from available structural data, including a homology model described by Goebel et al., Structures of activin ligand traps using natural sets of type I and type II TGFβ receptors, *iScience* 25(1): 103590 (2022); Morvan et al., Blockade of activin type II receptors with a dual anti-ActRIIA/IIB antibody is critical to promote maximal skeletal muscle hypertrophy, *Proc Natl Acad Sci USA* 114(47): 12448-12453 (2017); Townson et al., Specificity and structure of a high affinity activin receptor-like kinase 1 (ALK1) signaling complex, *J Biol Chem* 2 287(33): 27313-25 (2012); Han et al., Crystal structure of activin receptor type IIB kinase domain from human at 2.0 Angstrom resolution, *Protein Sci* 16(10): 2272-2277 (2007); and Weber et al., A silent H-bond can be mutationally activated for high-affinity interaction of BMP-2 and activin type IIB receptor, *BMC Struct Biol* 7: 6 (2007).

In aspects, the present disclosure provides a chimeric protein having a general structure of: N terminus-(a)-(b)-(c)-C terminus, wherein (a) is a first domain comprising a glucagon-like peptide-1 (GLP-1) receptor agonist, glucose-dependent insulinotropic polypeptide (GIP) receptor (GIPR) modulator and/or a glucagon receptor (GCGR) agonist and/or the Fibroblast growth factor 19 (FGF19), FGF21 or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a portion of activin receptor type-2B (ACVR2B). In embodiments, the portion of ACVR2B is capable of binding activin A and/or GDF-8. In embodiments, the portion of ACVR2B is the extracellular domain of ACVR2B. In embodiments, the first domain comprises the GLP-1 receptor agonist of any of the embodiments disclosed herein. In embodiments, the first domain comprises the GIP receptor modulator of any of the embodiments disclosed herein. In embodiments, the first domain comprises the GIP receptor modulator of any of the embodiments disclosed herein. In embodiments, the first domain comprises the Fibroblast growth factor 19 (FGF19), FGF21 or a variant thereof, or an analog thereof of any of the embodiments disclosed herein.

In aspects, the present disclosure provides a chimeric protein having a general structure of: N terminus-(a)-(b)-(c)-C terminus, wherein (a) is the second domain comprising a portion of activin receptor type-2B (ACVR2B), (b) is a linker adjoining the first domain and a second domain, optionally wherein the linker comprises one or more protease-cleavable polypeptide linkers, and/or a hinge-CH2-CH3 Fc domain, and (c) is a first domain comprising a glucagon-like peptide-1 (GLP-1) receptor agonist, glucose-dependent insulinotropic polypeptide (GIP) receptor (GIPR) modulator and/or a glucagon receptor (GCGR) agonist and/or the Fibroblast growth factor 19 (FGF19), FGF21 or a variant thereof, or an analog thereof. In embodiments, the portion of ACVR2B is capable of binding activin A and/or GDF-8. In embodiments, the portion of ACVR2B is the extracellular domain of ACVR2B. In embodiments, the first domain comprises the GLP-1 receptor agonist of any of the embodiments disclosed herein. In embodiments, the first domain comprises the GIP receptor modulator of any of the embodiments disclosed herein. In embodiments, the first domain comprises the GIP receptor modulator of any of the embodiments disclosed herein. In embodiments, the first domain comprises the Fibroblast growth factor 19 (FGF19), FGF21 or a variant thereof, or an analog thereof of any of the embodiments disclosed herein.

An illustrative GLP-1-Fc-ACVR2B chimeric protein has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and an extracellular domain of ACVR2B is shown in an italic font):

(SEQ ID NO: 154)
MEFGLSWVFLVAIIKGVQCHGEGTFTSDVSSYLEE

QAAKEFIAWLVKGRGEPKSVDKTHTCPPCPAPEAAGGPSVFLFPPKP

KDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQP

REPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQK

SLSLSPGKIEGRMDSGRGEAETRECIYYNANWELERTNQSGLERCEGE

QDKRLHCYASWRNSSGTIELVKKGCWLDDFNCYDRQECVATEENPQVY

FCCCEGNFCNERFTHLPEAGGPEVTYEPPPTAPTLLT.

In embodiments, the chimeric protein comprises a variant of the GLP-1-Fc-ACVR2B chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of SEQ ID NO: 154.

Linker

In embodiments, the chimeric protein comprises a linker.

In embodiments, the chimeric proteins disclosed herein have a general structure of: N terminus-(a)-(b)-(c)-C terminus, wherein (a) is a first domain comprising a glucagon-like peptide-1 (GLP-1) receptor agonist and (b) is a linker adjoining the first domain and a second domain, optionally wherein the linker comprises one or more protease-cleavable polypeptide linkers, and/or a hinge-CH2-CH3 Fc domain. In these embodiments, (c) is the second domain comprising a glucose-dependent insulinotropic polypeptide (GIP) receptor (GIPR) modulator.

In alternative embodiments, the chimeric proteins disclosed herein have a general structure of: N terminus-(a)-(b)-(c)-C terminus, wherein (c) is a first domain comprising a glucagon-like peptide-1 (GLP-1) receptor agonist, and (b) is a linker adjoining the first domain and a second domain, optionally wherein the linker comprises one or more protease-cleavable polypeptide linkers, and/or a hinge-CH2-CH3 Fc domain. In these embodiments, (a) is the second domain comprising a glucose-dependent insulinotropic polypeptide (GIP) receptor (GIPR) modulator.

In embodiments, the present chimeric proteins may comprise variants of the protease-cleavable polypeptide linkers disclosed in Table 1, below. For instance, a linker may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of any one of SEQ ID NOs: 4 to 50, 92 and 113.

TABLE 1

Illustrative protease-cleavable polypeptide linkers

| SEQ ID NO. | Sequence |
|---|---|
| 70 | HSSKLQ |
| 71 | GPLGVRG |
| 72 | IPVSLRSG |
| 73 | VPLSLYSG |
| 74 | SGESPAYYTA |
| 75 | RFRS |

In embodiments, the linker comprises a protease-cleavable polypeptide linker. In embodiments, the protease-cleavable polypeptide linker cleavable by a protease that is endogenous to a mammalian expressed in liver, skin and/or muscle. In embodiments, the protease-cleavable linker is cleavable by a protease selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the protease-cleavable linker comprises a consensus recognition and/or cleavage site of a protease selected from, caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain.

In embodiments, the chimeric protein comprises two protease-cleavable polypeptide linkers. In embodiments, wherein the first protease-cleavable polypeptide linker is C terminal to the first domain and the second protease-cleavable polypeptide linker is N terminal to the second domain. In embodiments, the two protease-cleavable polypeptide linkers are cleavable by a protease that is endogenous to a mammalian expressed in liver, skin and/or muscle. In embodiments, the two protease-cleavable polypeptide linkers are cleavable by a protease independently selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the two protease-cleavable polypeptide linkers comprise consensus recognition and/or cleavage sites of a proteases independently selected from, caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the two protease-cleavable polypeptide linkers are cleavable by a protease independently comprises an amino acid sequence selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75), or a variant thereof having about 1, 2, 3, 4, or more amino acid mutations with respect to an amino acid sequence selected from SEQ ID NOs: 70 to 75.

In embodiments, the protease-cleavable polypeptide linkers are cleavable by a protease that is endogenous to mammalian expressed in liver, skin and/or muscle. In embodiments, the protease is selected from, caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. Accordingly, in embodiments, the protease that cleaves the protease-cleavable polypeptide linkers is already present in the subject and an exogenous protease need not be administered. In embodiments, levels of the protease are elevated by liver injury, diabetes, and/or fibrosis. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain. Additional suitable protease-cleavable polypeptide linkers are disclosed in US Publication Nos. 2009/0042787 and 2021/0130430, the contents of which are hereby incorporated by reference in their entirety.

In embodiments, the first domain comprises a glucagon-like peptide-1 (GLP-1) receptor agonist and the protease-cleavable polypeptide linker is C terminal to the first domain; or the second domain comprises a glucagon-like peptide-1 (GLP-1) receptor agonist and the protease-cleavable polypeptide linker is N terminal to the second domain. In embodiments, the chimeric protein comprises two protease-cleavable polypeptide linkers, such protease-cleavable polypeptide linker independently selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the first protease-cleavable polypeptide linker is C terminal to the first domain and the second domain is protease-cleavable polypeptide linker is N terminal to the second domain.

In embodiments, the linker comprises at least one cysteine residue capable of forming a disulfide bond. The at least one cysteine residue is capable of forming a disulfide bond between a pair (or more) of chimeric proteins. Without wishing to be bound by theory, such disulfide bond forming is responsible for maintaining a useful multimeric state of chimeric proteins. This allows for efficient production of the chimeric proteins; it allows for desired activity in vitro and in vivo.

In a chimeric protein of the present disclosure, the linker is a polypeptide selected from a flexible amino acid sequence, an IgG hinge region, or an antibody sequence. In embodiments, the linker comprises hinge-CH2-CH3 Fc domain derived from IgG4, optionally human IgG4. In embodiments, the linker comprises hinge-CH2-CH3 Fc domain derived from IgG1, optionally human IgG1.

In embodiments, the linker may be derived from naturally occurring multi-domain proteins or is an empirical linker as described, for example, in Chichili et al., (2013), Protein Sci. 22(2):153-167, Chen et al., (2013), Adv Drug Deliv Rev. 65(10):1357-1369, the entire contents of which are hereby incorporated by reference. In embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In embodiments, the linker is a synthetic linker such as PEG.

In embodiments, the linker comprises a polypeptide. In embodiments, the polypeptide is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long.

In embodiments, the linker is flexible.

In embodiments, the linker is rigid.

In embodiments, the linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100% glycines and serines).

In embodiments, the linker comprises a hinge region of an antibody (e.g., of IgG, IgA, IgD, and IgE, inclusive of subclasses (e.g., IgG1, IgG2, IgG3, and IgG4, and IgA1, and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence CPPC (SEQ ID NO: 24) which, when dimerized by disulfide bond formation, results in a cyclic octapeptide believed to act as a pivot, thus conferring flexibility. In embodiments, the present linker comprises, one, or two, or three of the upper hinge regions, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In embodiments, the linker of the present disclosure comprises one or more glycosylation sites.

In embodiments, the linker comprises an Fc domain of an antibody (e.g., of IgG, IgA, IgD, and IgE, inclusive of subclasses (e.g., IgG1, IgG2, IgG3, and IgG4, and IgA1 and IgA2)).

In a chimeric protein of the present disclosure, the linker comprises a hinge-CH2-CH3 Fc domain derived from IgG4. In embodiments, the linker comprises a hinge-CH2-CH3 Fc domain derived from a human IgG4. In embodiments, the linker has at least about 95%, or at least about 97%, or at least about 97%, or at least about 98% sequence identity with the amino acid sequence of any one of SEQ ID NO: 1 to SEQ ID NO: 3, e.g., at least 95% identical to the amino acid sequence of SEQ ID NO: 2. In embodiments, the linker comprises one or more joining linkers, such joining linkers independently selected from SEQ ID NOs: 4-50 (or a variant thereof). In embodiments, the linker comprises two or more joining linkers each joining linker independently selected from SEQ ID NOs: 4-50 (or a variant thereof); wherein one joining linker is N terminal to the hinge-CH2-CH3 Fc domain and another joining linker is C terminal to the hinge-CH2-CH3 Fc domain.

In embodiments, the linker comprises a hinge-CH2-CH3 Fc domain derived from a human IgG1 antibody. In embodiments, the Fc domain exhibits increased affinity for and enhanced binding to the neonatal Fc receptor (FcRn). In embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In embodiments, the Fc domain in a linker contains one or more amino acid substitutions at amino acid residue 250, 252, 254, 256, 308, 309, 311, 416, 428, 433 or 434 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference), or equivalents thereof. In embodiments, the amino acid substitution at amino acid residue 250 is a substitution with glutamine. In embodiments, the amino acid substitution at amino acid residue 252 is a substitution with tyrosine, phenylalanine, tryptophan or threonine. In embodiments, the amino acid substitution at amino acid residue 254 is a substitution with threonine. In embodiments, the amino acid substitution at amino acid residue 256 is a substitution with serine, arginine, glutamine, glutamic acid, aspartic acid, or threonine. In embodiments, the amino acid substitution at amino acid residue 308 is a substitution with threonine. In embodiments, the amino acid substitution at amino acid residue 309 is a substitution with proline. In embodiments, the amino acid substitution at amino acid residue 311 is a substitution with serine. In embodiments, the amino acid substitution at amino acid residue 385 is a substitution with arginine, aspartic acid, serine, threonine, histidine, lysine, alanine or glycine. In embodiments, the amino acid substitution at amino acid residue 386 is a substitution with threonine, proline, aspartic acid, serine, lysine, arginine, isoleucine, or methionine. In embodiments, the amino acid substitution at amino acid residue 387 is a substitution with arginine, proline, histidine, serine, threonine, or alanine. In embodiments, the amino acid substitution at amino acid residue 389 is a substitution with proline, serine or asparagine. In embodiments, the amino acid substitution at amino acid residue 416 is a substitution with serine. In embodiments, the amino acid substitution at amino acid residue 428 is a substitution with leucine. In embodiments, the amino acid substitution at amino acid residue 433 is a substitution with arginine, serine, isoleucine, proline, or glutamine. In embodiments, the amino acid substitution at amino acid residue 434 is a substitution with histidine, phenylalanine, or tyrosine.

In embodiments, the Fc domain linker (e.g., comprising an IgG constant region) comprises one or more mutations such as substitutions at amino acid residue 252, 254, 256, 433, 434, or 436 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). In embodiments, the IgG constant region includes a triple M252Y/S254T/T256E mutation or YTE mutation. In embodiments, the IgG constant region includes a triple H433K/N434F/Y436H mutation or KFH mutation. In embodiments, the IgG constant region includes an YTE and KFH mutation in combination.

In embodiments, the linker comprises an IgG constant region that contains one or more mutations at amino acid residues 250, 253, 307, 310, 380, 428, 433, 434, and 435 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). Illustrative mutations include T250Q, M428L, T307A, E380A, I253A, H310A, M428L, H433K, N434A, N434F, N434S, and H435A. In embodiments, the IgG constant region comprises a M428L/N434S mutation or LS mutation. In embodiments, the IgG constant region comprises a T250Q/M428L mutation or QL mutation. In embodiments, the IgG constant region comprises an N434A mutation. In embodiments, the IgG constant region comprises a T307A/E380A/N434A mutation or AAA mutation. In embodiments, the IgG constant region comprises an I253A/H310A/H435A mutation or IHH mutation. In embodiments, the IgG constant region comprises a H433K/N434F mutation. In embodiments, the IgG constant region comprises a M252Y/S254T/T256E and a H433K/N434F mutation in combination.

Additional exemplary mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys eta. Journal of Immunology. (2015), 194(11):5497-508, and U.S. Pat. No. 7,083,784, the entire contents of which are hereby incorporated by reference.

In embodiments, the Fc domain in a linker comprises the amino acid sequence of SEQ ID NO: 1 (see the below table), or at least about 90%, or at least about 93%, or at least about 95%, or at least about 97%, or at least about 98%, or at least about 99% identity thereto. In embodiments, mutations are made to SEQ ID NO: 1 to increase stability and/or half-life. For instance, in embodiments, the Fc domain in a linker comprises the amino acid sequence of SEQ ID NO: 2 (see the below table), or at least about 90%, or at least about 93%, or at least about 95%, or at least about 97%, or at least about 98%, or at least about 99% identity thereto. An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants.

In embodiments, the chimeric protein binds to FcRn with high affinity. In embodiments, the chimeric protein may bind to FcRn with a $K_D$ of about 1 nM to about 80 nM. For example, the chimeric protein may bind to FcRn with a $K_D$ of about 1 nM, about 2 nM, about 3 nM, about 4 nM, about 5 nM, about 6 nM, about 7 nM, about 8 nM, about 9 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 71 nM, about 72 nM, about 73 nM, about 74 nM, about 75 nM, about 76 nM, about 77 nM, about 78 nM, about 79 nM, or about 80 nM. In embodiments, the chimeric protein may bind to FcRn with a $K_D$ of about 9 nM. In embodiments, the chimeric protein does not substantially bind to other Fc receptors (i.e., other than FcRn) with effector function.

In embodiments, the Fc domain in a linker has the amino acid sequence of SEQ ID NO: 1 (see Table 2, below), or at least at least about 90%, or at least about 93%, or at least about 95%, or at least about 97%, or at least about 98%, or at least about 99% identity thereto. In embodiments, mutations are made to SEQ ID NO: 1 to increase stability and/or half-life. For instance, in embodiments, the Fc domain in a linker comprises the amino acid sequence of SEQ ID NO: 2 (see Table 2, below), or at least at least about 90%, or at least about 93%, or at least about 95%, or at least about 97%, or at least about 98%, or at least about 99% identity thereto. For instance, in embodiments, the Fc domain in a linker comprises the amino acid sequence of SEQ ID NO: 3 (see Table 2, below), or at least at least about 90%, or at least about 93%, or at least about 95%, or at least about 97%, or at least about 98%, or at least about 99% identity thereto.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

Further, one or more joining linkers may be employed to connect an Fc domain in a linker (e.g., one of SEQ ID NO: 1, SEQ ID NO: 2, SEQ ID NO: 3 or at least at least about 90%, or at least about 93%, or at least about 95%, or at least about 97%, or at least about 98%, or at least about 99% identity thereto) and the extracellular domains. For example, any one of SEQ ID NO: 4, SEQ ID NO: 5, SEQ ID NO: 6, SEQ ID NO: 7, SEQ ID NO: 8, SEQ ID NO: 9, or variants thereof may connect an extracellular domain as disclosed herein and an Fc domain in a linker as disclosed herein. Optionally, any one of SEQ ID NOs: 4 to 50, 92 and 113, or variants thereof are located between an extracellular domain as disclosed herein and an Fc domain as disclosed herein.

In embodiments, the present chimeric proteins may comprise variants of the joining linkers disclosed in Table 2, below. For instance, a linker may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of any one of SEQ ID NO& 4 to 50, 92 and 113.

In embodiments, the first and second joining linkers may be different, or they may be the same.

Without wishing to be bound by theory, including a linker comprising at least a part of an Fc domain in a chimeric protein, helps avoid formation of insoluble and, likely, non-functional protein concatamers and/or aggregates. This is in part due to the presence of cysteines in the Fc domain which are capable of forming disulfide bonds between chimeric proteins.

In embodiments, a chimeric protein may comprise one or more joining linkers, as disclosed herein, and lack an Fc domain linker, as disclosed herein.

In embodiments, the first and/or second joining linkers are independently selected from the amino acid sequences of SEQ ID NOs: 4 to 50, 92 and 113 and are provided in Table 2 below:

TABLE 2

Illustrative linkers
(Fc domain linkers and joining linkers)

| SEQ ID NO. | Sequence |
|---|---|
| 1 | APEFLGGPSVFLFPPKPKDTLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGK |
| 2 | APEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGK |
| 3 | APEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK |
| 76 | PCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 4 | SKYGPPCPSCP |
| 5 | SKYGPPCPPCP |
| 6 | SKYGPP |
| 7 | IEGRMD |
| 8 | GGGVPRDCG |
| 9 | IEGRMDGGGGAGGGG |
| 10 | GGGSGGGS |
| 11 | GGGSGGGGSGGG |
| 12 | EGKSSGSGSESKST |
| 13 | GGSG |
| 14 | GGSGGGSGGGSG |
| 15 | EAAAKEAAAKEAAAK |
| 16 | EAAAREAAAREAAAREAAAR |
| 17 | GGGGSGGGGSGGGGSAS |
| 18 | GGGGAGGGG |
| 19 | GGS |
| 20 | GSGSGS |
| 21 | GSGSGSGSGS |
| 22 | GGGGSAS |
| 23 | APAPAPAPAPAPAPAPAP |
| 24 | CPPC |
| 25 | GGGGS |
| 26 | GGGGSGGGGS |
| 27 | GGGGSGGGGSGGGGS |
| 28 | GGGGSGGGGSGGGGSGGGGS |
| 29 | GGGGSGGGGSGGGGSGGGGSGGGGS |
| 30 | GGGGSGGGGSGGGGSGGGGSGGGGSGGGGS |
| 31 | GGGGSGGGGSGGGGSGGGGSGGGGSGGGGSGGGGS |
| 32 | GGGGSGGGGSGGGGSGGGGSGGGGSGGGGSGGGGSGGGGS |
| 33 | GGSGGSGGGGSGGGGS |
| 34 | GGGGGGGG |
| 35 | GGGGGG |
| 36 | EAAAK |
| 37 | EAAAKEAAAK |
| 38 | EAAAKEAAAKEAAAK |
| 39 | AEAAAKEAAAKA |
| 40 | AEAAAKEAAAKEAAAKA |
| 41 | AEAAAKEAAAKEAAAKEAAAKA |
| 42 | AEAAAKEAAAKEAAAKEAAAKEAAAKA |
| 43 | AEAAAKEAAAKEAAAKEAAAKALEAEAAAKEAAAKEAAAKEAAAKA |
| 44 | PAPAP |
| 45 | KESGSVSSEQLAQFRSLD |
| 46 | GSAGSAAGSGEF |
| 47 | GGGSE |
| 48 | GSESG |
| 49 | GSEGS |
| 50 | GEGGSGEGSSGEGSSSEGGGSEGGGSEGGGSEGGS |
| 92 | EPKSCDKTHTCP |
| 113 | EPKSVDKTHTCP |

In embodiments, the joining linker substantially comprises glycine and serine residues (e.g., about 30%, or about 40%, or about 50%, or about 60%, or about 70%, or about 80%, or about 90%, or about 95%, or about 97%, or about 98%, or about 99%, or about 100% glycines and serines). For example, in embodiments, the joining linker is (Gly$_4$Ser)$_n$, where n is from about 1 to about 8, e.g., 1, 2, 3, 4, 5, 6, 7, or 8 (SEQ ID NO: 25 to SEQ ID NO: 32, respectively). In embodiments, the joining linker sequence is GGSGGSGGGGSGGGGS (SEQ ID NO: 33). Additional illustrative joining linkers include, but are not limited to, linkers having the sequence LE, (EAAAK)$_n$ (n=1-3) (SEQ ID NO: 36 to SEQ ID NO: 38), A(EAAAK)$_n$A (n=2-5) (SEQ ID NO: 39 to SEQ ID NO: 42), A(EAAAK)$_4$ALEA (EAAAK)$_4$A (SEQ ID NO: 43), PAPAP (SEQ ID NO: 44), KESGSVSSEQLAQFRSLD (SEQ ID NO: 45), GSAGSAAGSGEF (SEQ ID NO: 46), and (XP)$_n$, with X designating any amino acid, e.g., Ala, Lys, or Glu. In embodiments, a joining linker has the sequence (Gly)$_n$ where n is any number from 1 to 100, for example: (Gly)$_8$ (SEQ ID NO: 34) and (Gly)$_6$ (SEQ ID NO: 35). In embodiments, the joining linker has the amino acid sequence GGS (SEQ ID NO: 3), or GS or LE. In embodiments, the joining linker has the amino acid sequence EPKSCDKTHTCP (SEQ ID NO: 92). In embodiments, the joining linker has the amino acid sequence EPKSCDKTHTCP EPKSVDKTH-TCP (SEQ ID NO: 113).

In embodiments, the joining linker is one or more of GGGSE (SEQ ID NO: 47), GSESG (SEQ ID NO: 48), GSEGS (SEQ ID NO: 49), GEGGSGEGSSGEGSSSEGGGSEGGGSEGGGSEGGS (SEQ ID NO: 50), and a joining linker of randomly placed G, S, and E every 4 amino acid intervals.

In embodiments, where a chimeric protein comprises a glucagon-like peptide-1 (GLP-1), a protease-cleavable linker preceding the Fc domain, an Fc domain, a joining linker following the Fc domain, and GIP, the chimeric protein may comprise the following structure:

Glucagon-like peptide-1 (GLP-1)-a protease-cleavable linker-Fc Domain-Joining Linker-GIP In embodiments, where a chimeric protein comprises GIP, a joining linker preceding the Fc domain, an Fc domain, a protease-cleavable linker following the Fc domain, a glucagon-like peptide-1 (GLP-1), and the chimeric protein may comprise the following structure:

GIP-Joining Linker-Fc Domain-a protease-cleavable linker-glucagon-like peptide-1 (GLP-1)

In embodiments, where a chimeric protein comprises a glucagon-like peptide-1 (GLP-1), a protease-cleavable linker preceding the Fc domain, an Fc domain, a joining linker following the Fc domain, and GIP, the chimeric protein may comprise the following structure:

Glucagon-like peptide-1 (GLP-1)-a protease-cleavable linker-Fc Domain-Joining Linker-GIP In embodiments, where a chimeric protein comprises GIP, a joining linker preceding the Fc domain, an Fc domain, a protease-cleavable linker following the Fc domain, a glucagon-like peptide-1 (GLP-1), and the chimeric protein may comprise the following structure:

GIP-Joining Linker-Fc Domain-a protease-cleavable linker-glucagon-like peptide-1 (GLP-1)

In embodiments, a chimeric protein comprises only one joining linkers. In embodiments, a chimeric protein comprises only two joining linkers. In embodiments, a chimeric protein lacks joining linkers.

An illustrative GLP-1-Fc-GIP chimeric protein has the following sequence (a secretion signal sequence is shown in double underline, GLP-1 is shown by an underline, a linker comprising a mutant Fc domain of human IgG1 is shown in boldface font, joining linkers are shown in a boldface-underlined font, and GIP is shown in an italic font):

(SEQ ID NO: 86)
<u>MEFGLSWVFLVAIIKGVQCHGEGTFTSDVSSYLEEQAAKEFIAWLV</u>

KGRGEPKSCDKTHTCPPCPAPEAAGGPSVFLFPPKPKDTLMISRTP

EVTCVVVDVSHEDPEVKFNWYVDGVEVHNAKTKPREEQYNSTYRVV

SVLTVLHQDWLNGKEYKCKVSNKALPAPIEKTISKAKGQPREPQVY

TLPPSRDELTKNQVSLTCLVKGFYPSDIAVEWESNGQPENNYKTTP

PVLDSDGSFFLYSKLTVDKSRWQQGNVFSCSVMHEALHNHYTQKSL

SLSPGK<u>IEGRMD</u>_YAEGTFISDYSIAMDKIHQQDFVNWLLAQKGKKN_

_DWKHNITQ_

In embodiments, the chimeric protein comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 86.

An illustrative GLP-1-Fc-GIP chimeric protein has the following sequence (a secretion signal sequence is shown in double underline, GLP-1 is shown by an underline, a linker comprising a mutant Fc domain of human IgG1 is shown in boldface font, joining linkers are shown in a boldface-underlined font, and GIP is shown in an italic font):

(SEQ ID NO: 110)
<u>MEFGLSWVFLVAIIKGVQCHGEGTFTSDVSSYLEEQAAKEFIAWLV</u>

KGRGEPKSVDKTHTCPPCPAPEAAGGPSVFLFPPKPKDTLMISRTP

EVTCVVVDVSHEDPEVKFNWYVDGVEVHNAKTKPREEQYNSTYRVV

SVLTVLHQDWLNGKEYKCKVSNKALPAPIEKTISKAKGQPREPQVY

TLPPSRDELTKNQVSLTCLVKGFYPSDIAVEWESNGQPENNYKTTP

PVLDSDGSFFLYSKLTVDKSRWQQGNVFSCSVMHEALHNHYTQKSL

SLSPGK<u>IEGRMD</u>_YAEGTFISDYSIAMDKIHQQDFVNWLLAQKGKKN_

_DWKHNITQ_

In embodiments, the chimeric protein comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 110.

An illustrative GLP-1-RFRS-Fc-GIP chimeric protein has the following sequence (a secretion signal sequence is shown in double underline, GLP-1 is shown by an underline, a linker comprising a mutant Fc domain of human IgG1 is shown in boldface font, joining linkers are shown in a boldface-underlined font, a protease-cleavable linker is shown in an unmarked font, a joining linker is shown in an underlined-boldface-italic font, and GIP is shown in an italic font):

(SEQ ID NO: 87)
MEFGLSWVFLVAIIKGVQCHGEGTFTSDVSSYLEEQAAKEFIAWLV

KGRGRFRSEPKSCDKTHTCPPCPAPEAAGGPSVFLFPPKPKDTLMI

SRTPEVTCVVVDVSHEDPEVKFNWYVDGVEVHNAKTKPREEQYNST

YRVVSVLTVLHQDWLNGKEYKCKVSNKALPAPIEKTISKAKGQPRE

PQVYTLPPSRDELTKNQVSLTCLVKGFYPSDIAVEWESNGQPENNY

KTTPPVLDSDGSFFLYSKLTVDKSRWQQGNVFSCSVMHEALHNHYT

QKSLSLSPGKIEGRMD*YAEGTFISDYSIAMDKIHQQDFVNWLLAQK*

*GKKNDWKHNITQ*

In embodiments, the chimeric protein comprises a variant of the GLP-1-RFRS-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 87.

An illustrative GLP-1-RFRS-Fc-GIP chimeric protein has the following sequence (a secretion signal sequence is shown in double underline, GLP-1 is shown by an underline, a protease-cleavable polypeptide linker is shown in an italicized-boldface font, a linker comprising a mutant Fc domain of human IgG1 is shown in boldface font, joining linkers are shown in a boldface-underlined font, a protease-cleavable linker is shown in an unmarked font, a joining linker is shown in an underlined-boldface-italic font, and GIP is shown in an italic font):

(SEQ ID NO: 109)
MEFGLSWVFLVAIIKGVQCHGEGTFTSDVSSYLEEQAAKEFIAWLV

KGRG*RFRS*EPKSCDKTHTCPPCPAPEAAGGPSVFLFPPKPKDTLMI

SRTPEVTCVVVDVSHEDPEVKFNWYVDGVEVHNAKTKPREEQYNST

YRVVSVLTVLHQDWLNGKEYKCKVSNKALPAPIEKTISKAKGQPRE

PQVYTLPPSRDELTKNQVSLTCLVKGFYPSDIAVEWESNGQPENNY

KTTPPVLDSDGSFFLYSKLTVDKSRWQQGNVFSCSVMHEALHNHYT

QKSLSLSPGKIEGRMD*YAEGTFISDYSIAMDKIHQQDFVNWLLAQK*

*GKKNDWKHNITQ*

In embodiments, the chimeric protein comprises a variant of the GLP-1-RFRS-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 109.

An illustrative GIP-Fc-FGF19 chimeric protein has the following sequence (a secretion signal sequence is shown in double underline, GIP is shown by an underline, a linker comprising a mutant Fc domain of human IgG1 is shown in boldface font, joining linkers are shown in a boldface-underlined font, and FGF19 is shown in an italic font):

(SEQ ID NO: 88)
MEFGLSWVFLVAIIKGVQCYAEGTFISDYSIAMDKIHQQDFVNWLL

AQKGKKNDWKHNITQEPKSCDKTHTCPPCPAPEAAGGPSVFLFPPK

PKDTLMISRTPEVTCVVVDVSHEDPEVKFNWYVDGVEVHNAKTKPR

EEQYNSTYRVVSVLTVLHQDWLNGKEYKCKVSNKALPAPIEKTISK

AKGQPREPQVYTLPPSRDELTKNQVSLTCLVKGFYPSDIAVEWESN

GQPENNYKTTPPVLDSDGSFFLYSKLTVDKSRWQQGNVFSCSVMHE

ALHNHYTQKSLSLSPGKIEGRMDM*RDSSPLVHYGWGDPIRLRHLYT*

*SGPHGLSSCFLRIRADGVVDCARGQSAHSLLEIKAVALRTVAIKGV*

*HSVRYLCMGADGKMQGLLQYSEEDCAFEEEIRPDGYNVYRSEKHRL*

*PVSLSSAKQRQLYKNRGFLPLSHELPMLPMVPEEPEDLRGHLESDM*

*FSSPLETDSMDPFGLVTGLEAVRSPSFEK*

In embodiments, the chimeric protein comprises a variant of the GIP-Fc-FGF19 chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 88.

An illustrative GIP-RFRS-Fc-FGF19 chimeric protein has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF19 is shown in an italic font):

(SEQ ID NO: 105)
MEFGLSWVFLVAIIKGVQCYAEGTFISDYSIAMDKIHQQDFVNWLL

AQKGKKNDWKHNITQRFRS*EPKSCD*K*THTCP*PCPAPEAAGGPSVFL

FPPKPKDTLMISRTPEVTCVVVDVSHEDPEVKFNWYVDGVEVHNAK

TKPREEQYNSTYRVVSVLTVLHQDWLNGKEYKCKVSNKALPAPIEK

TISKAKGQPREPQVYTLPPSRDELTKNQVSLTCLVKGFYPSDIAVE

WESNGQPENNYKTTPPVLDSDGSFFLYSKLTVDKSRWQQGNVFSCS

VMHEALHNHYTQKSLSLSPGKIEGRMD*MRDSSPLVHYGWGDPIRLR*

*HLYTSGPHGLSSCFLRIRADGVVDCARGQSAHSLLEIKAVALRTVA*

*IKGVHSVRYLCMGADGKMQGLLQYSEEDCAFEEEIRPDGYNVYRSE*

*KHRLPVSLSSAKQRQLYKNRGFLPLSHELPMLPMVPEEPEDLRGHL*

*ESDMFSSPLETDSMDPFGLVTGLEAVRSPSFEK*

In embodiments, the chimeric protein comprises a variant of the GIP-RFRS-Fc-FGF19 chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 105.

An illustrative GIP-Fc-FGF21(RGE) chimeric protein has the following sequence (a secretion signal sequence is shown in double underline, GIP is shown by an underline, a linker comprising a mutant Fc domain of human IgG1 is shown in boldface font, joining linkers are shown in a boldface-underlined font, and FGF21(RGE) is shown in an italic font):

(SEQ ID NO: 89)
MEFGLSWVFLVAIIKGVQCYAEGTFISDYSIAMDKIHQQDFVNWLL

AQKGKKNDWKHNITQ*EPKSCD*K*THTCP*PCPAPEAAGGPSVFLFPPK

PKDTLMISRTPEVTCVVVDVSHEDPEVKFNWYVDGVEVHNAKTKPR

EEQYNSTYRVVSVLTVLHQDWLNGKEYKCKVSNKALPAPIEKTISK

AKGQPREPQVYTLPPSRDELTKNQVSLTCLVKGFYPSDIAVEWESN

GQPENNYKTTPPVLDSDGSFFLYSKLTVDKSRWQQGNVFSCSVMHE

ALHNHYTQKSLSLSPGKIEGRMD*HPIPDSSPLLQFGGQVRQRYLYT*

*DDAQQTEAHLEIREDGTVGGAADQSPESLLQLKALKPGVIQILGVK*

*TSRFLCQRPDGALYGSLHFDPEACSFRERLLEDGYNVYQSEAHGLP*

*LHLPGNKSPHRDPAPRGPARFLPLPGLPPALPEPPGILAPQPPDVG*

*SSDPLSMVGGSQGRSPSYES*

In embodiments, the chimeric protein comprises a variant of the GIP-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 89.

An illustrative GIP-RFRS-Fc-FGF21(RGE) chimeric protein has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(RGE) is shown in an italic font):

(SEQ ID NO: 106)
MEFGLSWVFLVAIIKGVQCYAEGTFISDYSIAMDKIHQQDFVNWLL

AQKGKKNDWKHNITQRFRS*EPKSCD*K*THTCP*PCPAPEAAGGPSVFL

FPPKPKDTLMISRTPEVTCVVVDVSHEDPEVKFNWYVDGVEVHNAK

TKPREEQYNSTYRVVSVLTVLHQDWLNGKEYKCKVSNKALPAPIEK

TISKAKGQPREPQVYTLPPSRDELTKNQVSLTCLVKGFYPSDIAVE

WESNGQPENNYKTTPPVLDSDGSFFLYSKLTVDKSRWQQGNVFSCS

VMHEALHNHYTQKSLSLSPGKIEGRMD*HPIPDSSPLLQFGGQVRQR*

*YLYTDDAQQTEAHLEIREDGTVGGAADQSPESLLQLKALKPGVIQI*

*LGVKTSRFLCQRPDGALYGSLHFDPEACSFRERLLEDGYNVYQSEA*

*HGLPLHLPGNKSPHRDPAPRGPARFLPLPGLPPALPEPPGILAPQP*

*PDVGSSDPLSMVGGSQGRSPSYES*

In embodiments, the chimeric protein comprises a variant of the GIP-RFRS-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 106.

An illustrative GIP-RFRS-Fc-FGF21(RGE) chimeric protein has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(RGE) is shown in an italic font):

(SEQ ID NO: 111)
MEFGLSWVFLVAIIKGVQCYAEGTFISDYSIAMDKIHQQDFVNWLL

AQKGKKNDWKHNITQ*RFRSEPKSVDKTHTCP*PCPAPEAAGGPSVFL

FPPKPKDTLMISRTPEVTCVVVDVSHEDPEVKFNWYVDGVEVHNAK

TKPREEQYNSTYRVVSVLTVLHQDWLNGKEYKCKVSNKALPAPIEK

TISKAKGQPREPQVYTLPPSRDELTKNQVSLTCLVKGFYPSDIAVE

WESNGQPENNYKTTPPVLDSDGSFFLYSKLTVDKSRWQQGNVFSCS

VMHEALHNHYTQKSLSLSPGKIEGRMD*HPIPDSSPLLQFGGQVRQR*

*YLYTDDAQQTEAHLEIREDGTVGGAADQSPESLLQLKALKPGVIQI*

*LGVKTSRFLCQRPDGALYGSLHFDPEACSFRERLLEDGYNVYQSEA*

*HGLPLHLPGNKSPHRDPAPRGPARFLPLPGLPPALPEPPGILAPQP*

*PDVGSSDPLSMVGGSQGRSPSYES*

In embodiments, the chimeric protein comprises a variant of the GIP-RFRS-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 111.

An illustrative GIP-Fc-FGF21(L146P) chimeric protein has the following sequence (a secretion signal sequence is shown in double underline, GIP is shown by an underline, a linker comprising a mutant Fc domain of human IgG1 is shown in boldface font, joining linkers are shown in a boldface-underlined font, and FGF21(L146P) is shown in an italic font):

(SEQ ID NO: 90)
MEFGLSWVFLVAIIKGVQCYAEGTFISDYSIAMDKIHQQDFVNWLL

AQKGKKNDWKHNITQ*EPKSVDKTHTCP*PCPAPEAAGGPSVFLFPPPK

PKDTLMISRTPEVTCVVVDVSHEDPEVKFNWYVDGVEVHNAKTKPR

EEQYNSTYRVVSVLTVLHQDWLNGKEYKCKVSNKALPAPIEKTISK

AKGQPREPQVYTLPPSRDELTKNQVSLTCLVKGFYPSDIAVEWESN

GQPENNYKTTPPVLDSDGSFFLYSKLTVDKSRWQQGNVFSCSVMHE

ALHNHYTQKSLSLSPGKIEGRMD*HPIPDSSPLLQFGGQVRQRYLYT*

*DDAQQTEAHLEIREDGTVGGAADQSPESLLQLKALKPGVIQILGVK*

*TSRFLCQRPDGALYGSLHFDPEACSFRELLLEDGYNVYQSEAHGLP*

*LHPPGNKSPHRDPAPRGPARFLPLPGLPPALPEPPGILAPQPPDVG*

*SSDPLSMVGPSQGRSPSYAS*

In embodiments, the chimeric protein comprises a variant of the GIP-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 90.

An illustrative GIP-RFRS-Fc-FGF21(L146P) chimeric protein has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font and FGF21 L146P is shown in an italic font):

(SEQ ID NO: 107)
MEFGLSWVFLVAIIKGVQCYAEGTFISDYSIAMDKIHQQDFVNWLLAQK

GKKNDWKHNITQ*RFRSEPKSCDKTHTCP*PCPAPEAAGGPSVFLFPPKPK

DTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLS

PGKIEGRMD*HPIPDSSPLLQFGGQVRQRYLYTDDAQQTEAHLEIREDGT*

-continued

VGGAADQSPESLLQLKALKPGVIQILGVKTSRFLCQRPDGALYGSLHFD

PEACSFRELLLEDGYNVYQSEAHGLPLHPPGNKSPHRDPAPRGPARFLP

LPGLPPALPEPPGILAPQPPDVGSSDPLSMVGPSQGRSPSYAS

In embodiments, the chimeric protein comprises a variant of the GIP-RFRS-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 107.

An illustrative GIP-RFRS-Fc-FGF21(L146P) chimeric protein has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(L146P) is shown in an italic font):

(SEQ ID NO: 112)
MEFGLSWVFLVAIIKGVQCYAEGTFISDYSIAMDKIHQQDFVNWLLAQK

GKKNDWKHNITQ*RFR**SEPKSVDKTHTCP*PCPAPEAAGGPSVFLFPPKPK

DTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLS

PGK*IEGRMD*HPIPDSSPLLQFGGQVRQRYLYTDDAQQTEAHLEIREDGT

VGGAADQSPESLLQLKALKPGVIQILGVKTSRFLCQRPDGALYGSLHFD

PEACSFRELLLEDGYNVYQSEAHGLPLHPPGNKSPHRDPAPRGPARFLP

LPGLPPALPEPPGILAPQPPDVGSSDPLSMVGPSQGRSPSYAS

In embodiments, the chimeric protein comprises a variant of the GIP-RFRS-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 112.

An illustrative GLP-1-Fc-GIP(Ag) chimeric protein has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ag1-42) is shown in an italic font):

(SEQ ID NO: 93)
MEFGLSWVFLVAIIKGVQCH*HGEGTFTSDVSSYLE*

*EQAAKEFIAWLVKGRGEPKSVDKTHTCP*PCPAPEAAGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSP

GKIEGRMD*YAEGTFISDYSIAMDKIHQQDFVNWLLAQKGKKNDWKHNIT*

*Q*

In embodiments, the chimeric protein comprises a variant of the GLP-1-Fc-GIP(Ag) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 93.

An illustrative GLP-1-Fc-GIP(Ant 3-30) chimeric protein has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ant3-30) is shown in an italic font):

(SEQ ID NO: 94)
MEFGLSWVFLVAIIKGVQC*HGEGTFTSDVSSYLEE*

*QAAKEFIAWLVKGRGEPKSVDKTHTCP*PCPAPEAAGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSP

GKIEGRMDEGTFISDYSIAMDKIHQQDFVNWLLAQ

In embodiments, the chimeric protein comprises a variant of the GLP-1-Fc-GIP(Ant 3-30) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 94.

An illustrative GLP-1-Fc-GIP(AntPro3) chimeric protein has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP AntPro3 is shown in an italic font):

(SEQ ID NO: 95)
MEFGLSWVFLVAIIKGVQC*HGEGTFTSDVSSYLEE*

*QAAKEFIAWLVKGRGE*PKSVDKTHTCPPCPAPEAAGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSP

GKIEGRMD*YAPGTFISDYSIAMDKIHQQDFVNWLLAQKGKKNDWKHNIT*

*Q*

In embodiments, the chimeric protein comprises a variant of the GLP-1-Fc-GIP(AntPro3)) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 95.

An illustrative GLP-1-Fc-GIP(Ant 3-30, Pro3) chimeric protein has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ant3-30P3) is shown in an italic font):

(SEQ ID NO: 96)
MEFGLSWVFLVAIIKGVQC*HGEGTFTSDVSSYLEE*

*QAAKEFIAWLVKGRGE*PKSVDKTHTCPPCPAPEAAGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSP

GKIEGRMD*PGTFISDYSIAMDKIHQQDFVNWLLAQ*.

In embodiments, the chimeric protein comprises a variant of the GLP-1-Fc-GIP(Ant 3-30, Pro3) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 96.

Isolated Polynucleotide Encoding the Chimeric Protein

In aspects, the present disclosure provides an isolated polynucleotide encoding the chimeric protein of any one of the embodiments disclosed herein.

Accordingly, In aspects, the present disclosure provides an isolated polynucleotide encoding a chimeric protein having a general structure of: N terminus-(a)-(b)-(c)-C terminus, wherein: (A) (a) is a first domain comprising a glucagon-like peptide-1 (GLP-1) receptor agonist, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator, GIP, or a variant thereof, or an analog thereof; or (B) (a) is a first domain comprising a glucose-dependent insulinotropic polypeptide (GIP) receptor (GIPR) modulator, GIP, or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof. In embodiments, the chimeric protein is administered to a patient. In embodiments, a nucleic acid encoding the chimeric protein (e.g., modified mRNA or DNA) is administered to a patient. In embodiments, the chimeric protein the glucagon-like peptide-1 (GLP-1) receptor agonist of any of the embodiments disclosed herein. In embodiments, the chimeric protein the glucose-dependent insulinotropic polypeptide (GIP), GIP, or a variant thereof, or an analog thereof of any of the embodiments disclosed herein. In embodiments, the nucleic acid encoding harbors control elements that enable the expression of the chimeric protein (e.g., modified mRNA or DNA) is the expressed in liver, skin and/or muscle.

Without wishing to be bound by theory, both glucagon-like peptide-1 (GLP-1) and glucose-dependent insulinotropic polypeptide (GIP) have a very short half-life, limiting their potential direct use as therapeutics. For example, GLP-1 secreted in the blood has a very short half-life of less than 2 minutes, which is caused by a loss of activity due to the cleavage of amino acids at the N-terminus by the enzyme dipeptidyl peptidase-4 (DPP-4). Similarly, GIP has a very short half-life of 2-5 minutes, which is caused by its rapid degradation in the bloodstream to the inactive form GIP(3-42) by the DPP-4. Therefore, novel approaches to deliver GLP-1 and/or GIP are required. The present disclosure addresses this need by delivering pharmaceutical compositions which can contain nucleic acids such as modified mRNA (mmRNA) or DNA.

In aspects, the present disclosure provides an isolated polynucleotide encoding a chimeric protein having a general structure of: N terminus-(a)-(b)-(c)-C terminus, wherein: (a) is a first domain comprising a glucose-dependent insulinotropic polypeptide (GIP) receptor (GIPR) modulator, GIP, or a variant thereof, or an analog thereof; (b) is a linker adjoining the first domain and a second domain comprising a hinge-CH2-CH3 Fc domain, and (c) is a glucose-dependent insulinotropic polypeptide (GIP). In embodiments, the isolated polynucleotide encodes a chimeric protein comprises a glucagon-like peptide-1 (GLP-1), a protease-cleavable linker preceding the Fc domain, an Fc domain, a joining linker following the Fc domain, and GIP.

In embodiments, the isolated polynucleotide encodes a chimeric protein comprising a glucagon-like peptide-1 (GLP-1), a protease-cleavable linker preceding the Fc domain, an Fc domain, a joining linker following the Fc domain, and GIP, the chimeric protein may comprise the following structure:

Glucagon-like peptide-1 (GLP-1)-a protease-cleavable linker-Fc Domain-Joining Linker-GIP In aspects, the present disclosure provides an isolated polynucleotide encoding a chimeric protein having a general structure of: N terminus-(a)-(b)-(c)-C terminus, wherein: (a) is a first domain comprising a glucose-dependent insulinotropic polypeptide (GIP); (b) is a linker adjoining the first domain and a second domain comprising a hinge-CH2-CH3 Fc domain, and (c) is a glucagon-like peptide-1 (GLP-1). In embodiments, the isolated polynucleotide encodes a chimeric protein comprises, a glucose-dependent insulinotropic polypeptide (GIP), a protease-cleavable linker following the Fc domain, an Fc domain, a joining linker following the Fc domain, and a glucagon-like peptide-1 (GLP-1).

In embodiments, the isolated polynucleotide encodes a chimeric protein comprising a glucagon-like peptide-1 (GLP-1), a protease-cleavable linker preceding the Fc domain, an Fc domain, a joining linker following the Fc domain, and GIP, the chimeric protein may comprise the following structure:

GIP-Joining Linker-Fc Domain-a protease-cleavable linker-glucagon-like peptide-1 (GLP-1)

In aspects, the present disclosure provides an isolated polynucleotide encoding a chimeric protein having a general structure of: N terminus-(a)-(b)-(c)-C terminus, wherein: (a) is a first domain comprising) a glucagon-like peptide-1 (GLP-1); (b) is a linker adjoining the first domain and a second domain comprising a hinge-CH2-CH3 Fc domain, and (c) is a glucose-dependent insulinotropic polypeptide (GIP. In embodiments, the isolated polynucleotide encodes a chimeric protein comprises, a glucose-dependent insulinotropic polypeptide (GIP), a protease-cleavable linker preceding the Fc domain, an Fc domain, a joining linker following the Fc domain, and a glucagon-like peptide-1 (GLP-1).

In embodiments, the isolated polynucleotide encodes a chimeric protein comprising a glucagon-like peptide-1 (GLP-1), a protease-cleavable linker preceding the Fc domain, an Fc domain, a joining linker following the Fc domain, and GIP, the chimeric protein may comprise the following structure:

Glucagon-like peptide-1 (GLP-1)-a protease-cleavable linker-Fc Domain-Joining Linker-GIP In aspects, the present disclosure provides an isolated polynucleotide encoding a chimeric protein having a general structure of: N terminus-(a)-(b)-(c)-C terminus, wherein: (a) is a first domain comprising a glucose-dependent insulinotropic polypeptide (GIP); (b) is a linker adjoining the first domain and a second domain comprising a hinge-CH2-CH3 Fc domain, and (c) is a glucagon-like peptide-1 (GLP-1). In embodiments, the isolated polynucleotide encodes a chimeric protein comprises, a glucose-dependent insulinotropic polypeptide (GIP), a protease-cleavable linker preceding the Fc domain, an Fc domain, a joining linker following the Fc domain, and a glucagon-like peptide-1 (GLP-1).

In embodiments, the isolated polynucleotide encodes a chimeric protein comprising a glucagon-like peptide-1 (GLP-1), a protease-cleavable linker preceding the Fc domain, an Fc domain, a joining linker following the Fc domain, and GIP, the chimeric protein may comprise the following structure:

GIP-a protease-cleavable linker-Joining Linker-Fc Domain-glucagon-like peptide-1 (GLP-1)

In embodiments, a chimeric protein comprises only one joining linkers. In embodiments, a chimeric protein comprises only two joining linkers. In embodiments, a chimeric protein lacks joining linkers.

In embodiments, the isolated polynucleotide encodes a chimeric protein comprising a fibroblast growth factor 19 (FGF19), FGF21 or a variant thereof, or an analog thereof, a protease-cleavable linker preceding the Fc domain, an Fc domain, a joining linker following the Fc domain, and GIP, the chimeric protein may comprise the following structure:

FGF19/FGF21 or variant/analog-a protease-cleavable linker-Fc Domain-Joining Linker-GIP In aspects, the present disclosure provides an isolated polynucleotide encoding a chimeric protein having a general structure of: N terminus-(a)-(b)-(c)-C terminus, wherein: (a) is a first domain comprising a glucose-dependent insulinotropic polypeptide (GIP); (b) is a linker adjoining the first domain and a second domain comprising a hinge-CH2-CH3 Fc domain, and (c) is a fibroblast growth factor 19 (FGF19), FGF21 or a variant thereof, or an analog thereof. In embodiments, the isolated polynucleotide encodes a chimeric protein comprises, a glucose-dependent insulinotropic polypeptide (GIP), a protease-cleavable linker following the Fc domain, an Fc domain, a joining linker following the Fc domain, and a fibroblast growth factor 19 (FGF19), FGF21 or a variant thereof, or an analog thereof.

In embodiments, the isolated polynucleotide encodes a chimeric protein comprising a fibroblast growth factor 19 (FGF19), FGF21 or a variant thereof, or an analog thereof, a protease-cleavable linker preceding the Fc domain, an Fc domain, a joining linker following the Fc domain, and GIP, the chimeric protein may comprise the following structure:

GIP-Joining Linker-Fc Domain-a protease-cleavable
linker-FGF19/FGF21 or variant/analog In aspects, the present disclosure provides an isolated polynucleotide encoding a chimeric protein having a general structure of: N terminus-(a)-(b)-(c)-C terminus, wherein: (a) is a first domain comprising) a fibroblast growth factor 19 (FGF19), FGF21 or a variant thereof, or an analog thereof; (b) is a linker adjoining the first domain and a second domain comprising a hinge-CH2-CH3 Fc domain, and (c) is a glucose-dependent insulinotropic polypeptide (GIP. In embodiments, the isolated polynucleotide encodes a chimeric protein comprises, a glucose-dependent insulinotropic polypeptide (GIP), a protease-cleavable linker preceding the Fc domain, an Fc domain, a joining linker following the Fc domain, and a fibroblast growth factor 19 (FGF19), FGF21 or a variant thereof, or an analog thereof.

In embodiments, the isolated polynucleotide encodes a chimeric protein comprising a fibroblast growth factor 19 (FGF19), FGF21 or a variant thereof, or an analog thereof, a protease-cleavable linker preceding the Fc domain, an Fc domain, a joining linker following the Fc domain, and GIP, the chimeric protein may comprise the following structure:

FGF19/FGF21 or variant/analog-a protease-cleavable
linker-Fc Domain-Joining Linker-GIP In aspects, the present disclosure provides an isolated polynucleotide encoding a chimeric protein having a general structure of: N terminus-(a)-(b)-(c)-C terminus, wherein: (a) is a first domain comprising a glucose-dependent insulinotropic polypeptide (GIP); (b) is a linker adjoining the first domain and a second domain comprising a hinge-CH2-CH3 Fc domain, and (c) is a fibroblast growth factor 19 (FGF19), FGF21 or a variant thereof, or an analog thereof. In embodiments, the isolated polynucleotide encodes a chimeric protein comprises, a glucose-dependent insulinotropic polypeptide (GIP), a protease-cleavable linker preceding the Fc domain, an Fc domain, a joining linker following the Fc domain, and a fibroblast growth factor 19 (FGF19), FGF21 or a variant thereof, or an analog thereof.

In embodiments, the isolated polynucleotide encodes a chimeric protein comprising a fibroblast growth factor 19 (FGF19), FGF21 or a variant thereof, or an analog thereof, a protease-cleavable linker preceding the Fc domain, an Fc domain, a joining linker following the Fc domain, and GIP, the chimeric protein may comprise the following structure:

GIP-a protease-cleavable linker-Joining Linker-Fc
Domain-FGF19/FGF21 or variant/analog In embodiments, a chimeric protein comprises only one joining linkers. In embodiments, a chimeric protein comprises only two joining linkers. In embodiments, a chimeric protein lacks joining linkers.

In aspects, the present disclosure provides an isolated polynucleotide encoding a chimeric protein having a general structure of: N terminus-(a)-(b)-(c)-C terminus, wherein: (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

An illustrative GLP-1-Fc-GIP chimeric protein that an isolated polynucleotide of the present disclosure encodes has the following sequence (GLP-1 is shown by an underline, a linker comprising a mutant Fc domain of human IgG1 is shown in boldface font, joining linkers are shown in a boldface-underlined font, and GIP is shown in an italic font):

(SEQ ID NO: 86)
HGEGTFTSDVSSYLEEQAAKEFIAWLVKGRG*EPKSVDKTHTCP*PCPAPE

AAGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMH

EALHNHYTQKSLSLSPGKIEGRMDYAEGTFISDYSIAMDKIHQQDFVNW

LLAQKGKKNDWKHNITQ

In embodiments, the chimeric protein that an isolated polynucleotide of the present disclosure encodes comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 86.

An illustrative GLP-1-Fc-GIP chimeric protein that an isolated polynucleotide of the present disclosure encodes has the following sequence (a secretion signal sequence is shown in double underline, GLP-1 is shown by an underline, a linker comprising a mutant Fc domain of human IgG1 is shown in boldface font, joining linkers are shown in a boldface-underlined font, and GIP is shown in an italic font):

(SEQ ID NO: 110)
MEFGLSWVFLVAIIKGVQCHGEGTFTSDVSSYLEEQAAKEFIAWLVKGR

GEPKSVDKTHTCPPCPAPEAAGGPSVFLFPPKPKDTLMISRTPEVTCVV

-continued

VDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKN

QVSLTCLVKGFYPSDIAVEWESNGQPENNYKTTPPVLDSDGSFFLYSKL

TVDKSRWQQGNVFSCSVMHEALHNHYTQKSLSLSPGKIEGRMD*YAEGTF*

*ISDYSIAMDKIHQQDFVNWLLAQKGKKNDWKHNITQ*

In embodiments, the chimeric protein that an isolated polynucleotide of the present disclosure encodes comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 110.

An illustrative GLP-1-Fc-GIP chimeric protein that an isolated polynucleotide of the present disclosure encodes has the following sequence (GLP-1 is shown by an underline, a human IgG1-LALA hinge sequence is shown in an underlined-italicized-boldface font, a linker comprising a mutant Fc domain of human IgG1 is shown in boldface font, joining linkers are shown in a boldface-underlined font, and GIP is shown in an italic font):

(SEQ ID NO: 108)
HGEGTFTSDVSSYLEEQAAKEFIAWLVKGRG***EPKSCDKTHTCPP*CPAPE**

AAGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAP

IEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMH

EALHNHYTQKSLSLSPGKIEGRMD*YAEGTFISDYSIAMDKIHQQDFVNW*

*LLAQKGKKNDWKHNITQ*

In embodiments, the chimeric protein that an isolated polynucleotide of the present disclosure encodes comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 108.

An illustrative GLP-1-RFRS-Fc-GIP chimeric protein that an isolated polynucleotide of the present disclosure encodes has the following sequence (GLP-1 is shown by an underline, a linker comprising a mutant Fc domain of human IgG1 is shown in boldface font, joining linkers are shown in a boldface-underlined font, a protease-cleavable linker is shown in an unmarked font, a joining linker is shown in an underlined-boldface-italic font, and GIP is shown in an italic font):

(SEQ ID NO: 87)
MEFGLSWVFLVAIIKGVQCHGEGTFTSDVSSYLEEQAAKEFIAWLVKGR

GRFRS***EPKSCDKTHTCPP*CPAPEAAGGPSVFLFPPKPKDTLMISRTPEV**

TCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFL

YSKLTVDKSRWQQGNVFSCSVMHEALHNHYTQKSLSLSPGKIEGRMD*YA*

*WGTFISDYSIAMDKIHQQDFVNWLLAQKGKKNDWKHNITQ*

In embodiments, the chimeric protein that an isolated polynucleotide of the present disclosure encodes comprises a variant of the GLP-1-RFRS-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 87.

An illustrative GLP-1-RFRS-Fc-GIP chimeric protein that an isolated polynucleotide of the present disclosure encodes has the following sequence (GLP-1 is shown by an underline, a protease-cleavable polypeptide linker is shown in an italicized-boldface font, a linker comprising a mutant Fc domain of human IgG1 is shown in boldface font, joining linkers are shown in a boldface-underlined font, a protease-cleavable linker is shown in an unmarked font, a joining linker is shown in an underlined-boldface-italic font, and GIP is shown in an italic font):

(SEQ ID NO: 109)
MEFGLSWVFLVAIIKGVQCHGEGTFTSDVSSYLEEQAAKEFIAWLVKGR

G***RFRS*EPKSCDKTHTCPPCPAPEAAGGPSVFLFPPKPKDTLMISRTPEV**

TCVVVDVSHEDPEVKFNWYVDGVEVHNAKTKPREEQYNSTYRVVSVLTV

-continued
LHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFL

YSKLTVDKSRWQQGNVFSCSVMHEALHNHYTQKSLSLSPGK<u>IEGRMD</u>*YA*

*EGTFISDYSIAMDKIHQQDFVNWLLAQKGKKNDWKHNITQ*

In embodiments, the chimeric protein that an isolated polynucleotide of the present disclosure encodes comprises a variant of the GLP-1-RFRS-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 109.

An illustrative GIP-Fc-FGF19 chimeric protein that an isolated polynucleotide of the present disclosure encodes has the following sequence (a secretion signal sequence is shown in double underline, GIP is shown by an underline, a linker comprising a mutant Fc domain of human IgG1 is shown in boldface font, joining linkers are shown in a boldface-underlined font, and FGF19 is shown in an italic font):

(SEQ ID NO: 88)
<u>MEFGLSWVFLVAIIKGVQCY</u>AEGTFISDYSIAMDKIHQQDFVNWLLAQK

GKKNDWKHNITQEPKSCDKTHTCPPCPAPEAAGGPSVFLFPPKPKDTLM

ISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK<u>I</u>

<u>EGRMD</u>*MRDSSPLVHYGWGDPIRLRHLYTSGPHGLSSCFLRIRADGVVDC*

*ARGQSAHSLLEIKAVALRTVAIKGVHSVRYLCMGADGKMQGLLQYSEED*

*CAFEEEIRPDGYNVYRSEKHRLPVSLSSAKQRQLYKNRGFLPLSHELPM*

*LPMVPEEPEDLRGHLESDMFSSPLETDSMDPFGLVTGLEAVRSPSFEK*

In embodiments, the chimeric protein that an isolated polynucleotide of the present disclosure encodes comprises a variant of the GIP-Fc-FGF19 chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 88.

An illustrative GIP-RFRS-Fc-FGF19 chimeric protein that an isolated polynucleotide of the present disclosure encodes has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF19 is shown in an italic font):

(SEQ ID NO: 105)
<u>MEFGLSWVFLVAIIKGVQCY</u>AEGTFISDYSIAMDKIHQQDFVNWLLAQK

GKKNDWKHNITQ*RFRSEPKSCDKTHTC*PPCPAPEAAGGPSVFLFPPKPK

DTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTP

PVLDSDGSFFLYSKLTVDKSRWQQGNVFSCSVMHEALHNHYTQKSLSLS

PGK<u>IEGRMD</u>*MRDSSPLVHYGWGDPIRLRHLYTSGPHGLSSCFLRIRADG*

*VVDCARGQSAHSLLEIKAVALRTVAIKGVHSVRYLCMGADGKMQGLLQY*

*SEEDCAFEEEIRPDGYNVYRSEKHRLPVSLSSAKQRQLYKNRGFLPLSH*

*ELPMLPMVPEEPEDLRGHLESDMFSSPLETDSMDPFGLVTGLEAVRSPS*

*FEK*

In embodiments, the chimeric protein that an isolated polynucleotide of the present disclosure encodes comprises a variant of the GIP-RFRS-Fc-FGF19 chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 105.

An illustrative GIP-Fc-FGF21(RGE) chimeric protein that an isolated polynucleotide of the present disclosure encodes has the following sequence (a secretion signal sequence is shown in double underline, GIP is shown by an underline, a linker comprising a mutant Fc domain of human IgG1 is shown in boldface font, joining linkers are shown in a boldface-underlined font, and FGF21(RGE) is shown in an italic font):

(SEQ ID NO: 89)
MEFGLSWVFLVAIIKGVQCYAEGTFISDYSIAMDKIHQQDFVNWLLAQK

GKKNDWKHNITQ*__EPKSCDKTHTCP__*PCPAPEAAGGPSVFLFPPKPKD

TLMISRTPEVTCVVVDVSHEDPEVKFNWYVDGVEVHNAKTKPREEQYN

STYRVVSVLTVLHQDWLNGKEYKCKVSNKALPAPIEKTISKAKGQPRE

PQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSL

SLSPGK__IEGRMD__HPIPDSSPLLQFGGQVRQRYLYTDDAQQTEAHLEIR

EDGTVGGAADQSPESLLQLKALKPGVIQILGVKTSRFLCQRPDGALYG

SLHFDPEACSFRERLLEDGYNVYQSEAHGLPLHLPGNKSPHRDPAPRG

PARFLPLPGLPPALPEPPGILAPQPPDVGSSDPLSMVGGSQGRSPSYE

S

In embodiments, the chimeric protein that an isolated polynucleotide of the present disclosure encodes comprises a variant of the GIP-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 89.

An illustrative GIP-RFRS-Fc-FGF21(RGE) chimeric protein that an isolated polynucleotide of the present disclosure encodes has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(RGE) is shown in an italic font):

(SEQ ID NO: 106)
MEFGLSWVFLVAIIKGVQCYAEGTFISDYSIAMDKIHQQDFVNWLLAQK

GKKNDWKHNITQ*__RFRS____RFRS____EPKSCDKTHTCP__*PCPAPEAAGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK__IEGRMD__HPIPDSSPLLQFGGQVRQRYLYTDDAQQTEAHLE

IREDGTVGGAADQSPESLLQLKALKPGVIQILGVKTSRFLCQRPDGALY

GSLHFDPEACSFRERLLEDGYNVYQSEAHGLPLHLPGNKSPHRDPAPRG

PARFLPLPGLPPALPEPPGILAPQPPDVGSSDPLSMVGGSQGRSPSYES

In embodiments, the chimeric protein that an isolated polynucleotide of the present disclosure encodes comprises a variant of the GIP-RFRS-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 106.

An illustrative GIP-RFRS-Fc-FGF21(RGE) chimeric protein that an isolated polynucleotide of the present disclosure encodes has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(RGE) is shown in an italic font):

(SEQ ID NO: 111)
MEFGLSWVFLVAIIKGVQCYAEGTFISDYSIAMDKIHQQDFVNWLLAQKG

KKNDWKHNITQ*__RFRS__**__EPKSVDKTHTCP__*PCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK__IEG

RMD__HPIPDSSPLLQFGGQVRQRYLYTDDAQQTEAHLEIREDGTVGGAADQ

SPESLLQLKALKPGVIQILGVKTSRFLCQRPDGALYGSLHFDPEACSFRE

RLLEDGYNVYQSEAHGLPLHLPGNKSPHRDPAPRGPARFLPLPGLPPALP

EPPGILAPQPPDVGSSDPLSMVGGSQGRSPSYES

In embodiments, the chimeric protein that an isolated polynucleotide of the present disclosure encodes comprises a variant of the GIP-RFRS-Fc-FGF21(RGE) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 111.

An illustrative GIP-Fc-FGF21(RGE) chimeric protein that an isolated polynucleotide of the present disclosure encodes has the following sequence (a secretion signal sequence is shown in double underline, GIP is shown by an underline, a linker comprising a mutant Fc domain of human IgG1 is shown in boldface font, joining linkers are shown in a boldface-underlined font, and FGF21(L146P) is shown in an italic font):

(SEQ ID NO: 90)
<u>MEFGLSWVFLVAIIKGVQCYAEGTFISDYSIAMDKIHQQDFVNWLLAQKG KKNDWKHNITQ</u>EPKSVDKTHTCPPCPAPEAAGGPSVFLFPPKPKDTLMIS RTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSF FLYSKLTVDKSRWQQGNVFSCSVMHEALHNHYTQKSLSLSPGK<u>IEGRMD</u>*H PIPDSSPLLQFGGQVRQRYLYTDDAQQTEAHLEIREDGTVGGAADQSPES LLQLKALKPGVIQILGVKTSRFLCQRPDGALYGSLHFDPEACSFRELLLE DGYNVYQSEAHGLPLHPPGNKSPHRDPAPRGPARFLPLPGLPPALPEPPG ILAPQPPDVGSSDPLSMVGPSQGRSPSYAS*

In embodiments, the chimeric protein that an isolated polynucleotide of the present disclosure encodes comprises a variant of the GIP-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 90.

An illustrative GIP-RFRS-Fc-FGF21(L146P) chimeric protein that an isolated polynucleotide of the present disclosure encodes has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(L146P) is shown in an italic font):

(SEQ ID NO: 107)
<u>MEFGLSWVFLVAIIKGVQCYAEGTFISDYSIAMDKIHQQDFVNWLLAQKG KKNDWKHNITQ</u>*<u>RFRS</u>**<u>EPKSCDKTHTCP</u>PCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK<u>IEG RMD</u>*HPIPDSSPLLQFGGQVRQRYLYTDDAQQTEAHLEIREDGTVGGAADQ SPESLLQLKALKPGVIQILGVKTSRFLCQRPDGALYGSLHFDPEACSFRE LLLEDGYNVYQSEAHGLPLHPPGNKSPHRDPAPRGPARFLPLPGLPPALP EPPGILAPQPPDVGSSDPLSMVGPSQGRSPSYAS*

In embodiments, the chimeric protein that an isolated polynucleotide of the present disclosure encodes comprises a variant of the GIP-RFRS-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 107.

An illustrative GIP-RFRS-Fc-FGF21(L146P) chimeric protein that an isolated polynucleotide of the present disclosure encodes has the following sequence (a secretion signal sequence is shown in double underline, GIP is shown by an underline, a protease-cleavable polypeptide linker is shown in an italicized-boldface font, a human IgG1-LALA hinge sequence is shown in an underlined-italicized-boldface font, a linker comprising a mutant Fc domain of human IgG1 is shown in boldface font, joining linkers are shown in a boldface-underlined font, and FGF21(L146P) is shown in an italic font):

(SEQ ID NO: 112)
<u>MEFGLSWVFLVAIIKGVQCYAEGTFISDYSIAMDKIHQQDFVNWLLAQKG KKNDWKHNITQ</u>*<u>RFRS</u>**<u>EPKSVDKTHTCP</u>PCPAPEAAGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDS DGSFFLYSKLTVDKSRWQQGNVFSCSVMHEALHNHYTQKSLSLSPGK<u>IEG RMD</u>*HPIPDSSPLLQFGGQVRQRYLYTDDAQQTEAHLEIREDGTVGGAADQ SPESLLQLKALKPGVIQILGVKTSRFLCQRPDGALYGSLHFDPEACSFRE*

-continued

LLLEDGYNVYQSEAHGLPLHPPGNKSPHRDPAPRGPARFLPLPGLPPALP

EPPGILAPQPPDVGSSDPLSMVGPSQGRSPSYAS

In embodiments, the chimeric protein that an isolated polynucleotide of the present disclosure encodes comprises a variant of the GIP-RFRS-Fc-FGF21(L146P) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 112.

An illustrative GLP-1-Fc-GIP chimeric protein that an isolated polynucleotide of the present disclosure encodes has the following sequence (GLP-1 is shown by an underline, a human IgG1-LALA hinge sequence is shown in an underlined-italicized-boldface font, a linker comprising a mutant Fc domain of human IgG1 is shown in boldface font, joining linkers are shown in a boldface-underlined font, and GIP is shown in an italic font):

(SEQ ID NO: 108)
HGEGTFTSDVSSYLEEQAAKEFIAWLVKGRG*EPKSCDKTHTCP*PCPAPEA

AGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEK

TISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHN

HYTQKSLSLSPGKIEGRMDYAEGTFISDYSIAMDKIHQQDFVNWLLAQKG

KKNDWKHNITQ

In embodiments, the chimeric protein that an isolated polynucleotide of the present disclosure encodes comprises a variant of the GLP-1-Fc-GIP chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 108.

An illustrative GLP-1-Fc-GIP(Ag) chimeric protein that an isolated polynucleotide of the present disclosure encodes has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ag1-42) is shown in an italic font):

(SEQ ID NO: 93)
<u>MEFGLSWVFLVAIIKGVQC</u>*HGEGTFTSDVSSYLEEQAAKEFIAWLVKGRG*

EPKSVDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKIEGRMDYAEGTFISDYSI

AMDKIHQQDFVNWLLAQKGKKNDWKHNITQ

In embodiments, the chimeric protein that an isolated polynucleotide of the present disclosure encodes comprises a variant of the GLP-1-Fc-GIP(Ag) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 93.

An illustrative GLP-1-Fc-GIP(Ant 3-30) chimeric protein that an isolated polynucleotide of the present disclosure encodes has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ant3-30) is shown in an italic font):

(SEQ ID NO: 94)
<u>MEFGLSWVFLVAIIKGVQC</u>*HGEGTFTSDVSSYLEEQAAKEFIAWLVKGRG*

EPKSVDKTHTCPPCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKIEGRMDEGTFISDYSIAM

DKIHQQDFVNWLLAQ

In embodiments, the chimeric protein that an isolated polynucleotide of the present disclosure encodes comprises a variant of the GLP-1-Fc-GIP(Ant 3-30) chimeric protein.

As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 94.

An illustrative GLP-1-Fc-GIP(AntPro3)) chimeric protein that an isolated polynucleotide of the present disclosure encodes has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(AntPro3) is shown in an italic font):

(SEQ ID NO: 95)
<u>MEFGLSWVFLVAIIKGVQC</u>*HGEGTFTSDVSSYLEEQAAKEFIAWLVKGRG*

<u>EPKSVDKTHTCP</u>PCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK<u>IEGRMD</u>*YAPGTFISDYSI*

*AMDKIHQQDFVNWLLAQKGKKNDWKHNITQ*

In embodiments, the chimeric protein that an isolated polynucleotide of the present disclosure encodes comprises a variant of the GLP-1-Fc-GIP(AntPro3)) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 95.

An illustrative GLP-1-Fc-GIP(Ant 3-30, Pro3) chimeric protein that an isolated polynucleotide of the present disclosure encodes has the following sequence (a secretion signal sequence is shown in double underline. GLP-1 is shown by an boldface-italicized font, a linker comprising a mutant Fc domain of human IgG1 is shown in an unmarked font, joining linkers are shown in a boldface-underlined font, and GIP(Ant3-30P3) is shown in an italic font):

(SEQ ID NO: 96)
<u>MEFGLSWVFLVAIIKGVQC</u>*HGEGTFTSDVSSYLEEQAAKEFIAWLVKGRG*

<u>EPKSVDKTHTCP</u>PCPAPEAAGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK<u>IEGRMD</u>*PGTFISDYSIAM*

*DKIHQQDFVNWLLAQ*

In embodiments, the chimeric protein that an isolated polynucleotide of the present disclosure encodes comprises a variant of the GLP-1-Fc-GIP(Ant 3-30, Pro3) chimeric protein. As examples, the variant may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with SEQ ID NO: 96.

In aspects, the present disclosure provides an isolated polynucleotide encoding a chimeric protein comprising a general structure of: N terminus-(a)-(b)-(c)-C terminus, wherein: (A) (a) is a first domain comprising a glucagon-like peptide-1 (GLP-1) receptor agonist, (c) is a second domain comprising a portion of activin receptor type-2B (ACVR2B), and (b) is a linker adjoining the first domain and a second domain, optionally wherein the linker comprises a hinge-CH2-CH3 Fc domain; or (B) (a) is a second domain comprising a portion of activin receptor type-2B (ACVR2B), (c) is a first domain comprising a glucagon-like peptide-1 (GLP-1) receptor agonist, and (b) is a linker adjoining the first domain and a second domain, optionally a hinge-CH2-CH3 Fc domain.

In embodiments, the isolated polynucleotide encodes a GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the isolated polynucleotide encodes a portion of ACVR2B is capable of binding activin A and/or GDF-8. In embodiments, the portion of ACVR2B comprises substantially the entire extracellular domain of ACVR2B. In embodiments, the portion of ACVR2B comprises the entire extracellular domain of ACVR2B. In embodiments, the portion of ACVR2B comprises an amino acid sequence that is at least about 90%, or at least about 95% identical to the amino acid sequence of SEQ ID NO: 153.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In embodiments, the polynucleotide is RNA, optionally, an mRNA. In embodiments, the polynucleotide is codon optimized.

In embodiments, the polynucleotide is selected from mRNA, circular RNA (circRNA) and self-amplifying RNA (saRNA), optionally wherein the polynucleotide is modified. In embodiments, the polynucleotide may include a polynucleotide modification including, but not limited to, a nucleoside modification. In embodiments, the polynucleotide is an mmRNA. In embodiments, the mmRNA comprises one or more nucleoside modifications. In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethyl-guanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues of the mmRNA are replaced by modified cytosine residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the uracil residues of the mmRNA are replaced by modified uracil residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the adenine residues of the mmRNA are replaced by modified adenine residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the guanine residues of the mmRNA are replaced by modified guanine residues.

In aspects, the present disclosure provides an isolated polynucleotide encoding a chimeric protein comprising a general structure of: N terminus-(a)-(b)-(c)-C terminus, wherein: (A) (a) is a first domain comprising a glucagon-like peptide-1 (GLP-1) receptor agonist, (c) is a second domain comprising a portion of activin receptor type-2B (ACVR2B), and (b) is a linker adjoining the first domain and a second domain, optionally wherein the linker comprises a hinge-CH2-CH3 Fc domain; or (B) (a) is a second domain comprising a portion of activin receptor type-2B (ACVR2B), (c) is a first domain comprising a glucagon-like peptide-1 (GLP-1) receptor agonist, and (b) is a linker adjoining the first domain and a second domain, optionally a hinge-CH2-CH3 Fc domain.

In embodiments, the isolated polynucleotide encodes a GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the isolated polynucleotide encodes a portion of ACVR2B is capable of binding activin A and/or GDF-8. In embodiments, the portion of ACVR2B comprises substantially the entire extracellular domain of ACVR2B. In embodiments, the portion of ACVR2B comprises the entire extracellular domain of ACVR2B. In embodiments, the portion of ACVR2B comprises an amino acid sequence that is at least about 90%, or at least about 95% identical to the amino acid sequence of SEQ ID NO: 153.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In embodiments, the polynucleotide is RNA, optionally, an mRNA. In embodiments, the polynucleotide is codon optimized.

In embodiments, the polynucleotide is selected from mRNA, circular RNA (circRNA) and self-amplifying RNA (saRNA), optionally wherein the polynucleotide is modified. In embodiments, the polynucleotide may include a polynucleotide modification including, but not limited to, a nucleoside modification. In embodiments, the polynucleotide is an mmRNA. In embodiments, the mmRNA comprises one or more nucleoside modifications. In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

In embodiments, the polypeptide the at least one chemically modified nucleoside is selected from pseudouridine (Ψ), N1-methylpseudouridine (m1Ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1Ψ), 5-methoxy-uridine (mo5U), 5-methyl-cytidine (m5C). alpha-thio-guanosine, alpha.-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, and two or more combinations thereof.

In embodiments, the mmRNA does not cause a substantial induction of the innate immune response of a cell into which the mmRNA is introduced. In embodiments, the modification in the mmRNA enhance one or more of the efficiency of production of the chimeric protein, intracellular retention of the mmRNA, and viability of contacted cells, and possess reduced immunogenicity.

In embodiments, the mmRNA has a length sufficient to include an open reading frame encoding the chimeric protein of the present disclosure.

In embodiments, the mmRNA is not uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least about 50% modified nucleotides, at least about 80% modified nucleotides, or at least about 90% modified nucleotides.

In embodiments, the mmRNA may contain a modified pyrimidine such as uracil or cytosine. In embodiments, at least about 5%, at least about 10%, at least about 25%, at least about 50%, In embodiments, the modified uracil may be replaced by a compound having a single unique structure or can be replaced by a plurality of compounds having different structures disclosed above (e.g., same mmRNA may contain 2, 3, 4 or more types of uniquely modified uracil). In embodiments, at least about 5%, at least about 10%, at least about 25%, at least about 50%, at least about 80%, at least about 90% or 100% of the cytosine in the nucleic acid may be replaced with a modified cytosine. The modified cytosine can be replaced by a compound having a single unique structure or can be replaced by a plurality of compounds having different structures disclosed above (e.g., same mmRNA may contain 2, 3, 4 or more types of uniquely modified cytosine).

In embodiments, the mmRNA comprises at least one chemically modified nucleoside. In embodiments, wherein the at least one chemically modified nucleoside is selected from pseudouridine (Ψ), N1-methylpseudouridine (m1Ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1Ψ), 5-methoxy-uridine (mo5U), 5-methyl-cytidine (m5C). alpha-thio-guanosine, alpha.-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, and two or more combinations thereof. In embodiments, the mmRNA comprises at least one chemically modified nucleoside, wherein the at least one chemically modified nucleoside is selected from pseudouridine, N1-methylpseudouridine, 5-methylcytosine, 5-methoxyuridine, and a combination thereof. In embodiments, the mmRNA comprises at least one chemically modified nucleoside is N1-methylpseudouridine. In embodiments, the mmRNA is fully modified with chemically-modified uridines. In embodiments, the mmRNA is a fully modified N1-methylpseudouridine mRNA. Additional chemical modifications are disclosed in US Patent Application Publication No. 2019/0111003, the entire contents of which are hereby incorporated by reference.

In embodiments, modified nucleosides include pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In embodiments, modified nucleosides include 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In embodiments, the nucleotide can be modified on the major groove face and can include replacing hydrogen on C-5 of uracil with a methyl group or a halo group.

In embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

Further examples of modified nucleotides and modified nucleotide combinations are disclosed in U.S. Pat. Nos. 8,710,200; 8,822,663; 8,999,380; 9,181,319; 9,254,311; 9,334,328; 9,464,124; 9,950,068; 10,626,400; 10,808,242; 11,020,477, and US Patent Application Publication Nos. 2022/0001026, 2021/0318817, 2021/0283262, 2020/0360481, 2020/0113844, 2020/0085758, 2017/0204152, 2019/0114089, 2019/0114090, 2018/0369374, 2018/0318385, 2019/0111003, and PCT International Application Publication Nos. WO/2017112943, WO 2014/028429, WO 2017/201325 the entire contents of which are hereby incorporated by reference. The methods for synthesizing the modified mRNA are disclosed, e.g., in US Patent Application Publication Nos. 2017/0204152, the entire contents of which are hereby incorporated by reference.

In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues of the mmRNA are replaced by modified cytosine residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the uracil residues of the mmRNA are replaced by modified uracil residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the adenine residues of the mmRNA are replaced by modified adenine residues. In embodiments, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the guanine residues of the mmRNA are replaced by modified guanine residues.

In embodiments, the mmRNA further comprises a 5' untranslated region (UTR) and/or a 3'UTR, wherein either or both may independently contain one or more different nucleoside modifications. In such embodiments, nucleoside modifications may also be present in the translatable region. In embodiments, the mmRNA further comprises a Kozak sequence. In embodiments, the mmRNA further comprises a internal ribosome entry site (IRES).

In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127. In embodiments, the mmRNA further comprises 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) or 3' UTR_6 (SEQ ID NO: 119); 5' UTR_14 (SEQ ID NO: 141) and 3' UTR_10 (SEQ ID NO: 123).

In embodiments, the 5'-cap contains a 5'-5'-triphosphate linkage between the 5'-most nucleotide and guanine nucleotide. In embodiments, the 5'-cap comprises a methylation of the ultimate and penultimate most 5'-nucleotides on the 2'-hydroxyl group. In embodiments, the 5'-cap facilitates binding the mRNA Cap Binding Protein (CBP), confers mRNA stability in the cell and/or confers translation competency.

In embodiments, the poly-A tail is greater than about 30 nucleotides, or greater than about 40 nucleotides in length. In embodiments, the poly-A tail at least about 40 nucleotides, or at least about 45 nucleotides, or at least about 55 nucleotides, or at least about 60 nucleotides, or at least about 80 nucleotides, or at least about 90 nucleotides, or at least about 100 nucleotides, or at least about 120 nucleotides, or at least about 140 nucleotides, or at least about 160 nucleotides, or at least about 180 nucleotides, or at least about 200 nucleotides, or at least about 250 nucleotides, or at least about 300 nucleotides, or at least about 350 nucleotides, or at least about 400 nucleotides, or at least about 450 nucleotides, or at least about 500 nucleotides, or at least about 600 nucleotides, or at least about 700 nucleotides, or at least about 800 nucleotides, or at least about 900 nucleotides, or at least about 1000 nucleotides in length.

In embodiments, the mmRNA comprises a 3' untranslated region (UTR). In embodiments, the 3' UTR comprises a nucleic acid sequence at least about 90%, or at least about 95%, or at least about 96%, or at least about 97%, or at least about 98%, or at least about 99%, or about 100% identical to a sequence listed in Table 4A or Table 4B of US Patent Application Publication No. 2019/0114089, which is incorporated herein in its entirety. In embodiments, the 3' UTR comprises at least one microRNA-122 (miR-122) binding site, wherein the miR-122 binding site is a miR-122-3p binding site or a miR-122-5-binding site. In embodiments, the mmRNA comprises a nucleic acid sequence comprising a miRNA binding site. In some embodiments, the miRNA binding site binds to miR-122. In a particular embodiment, the miRNA binding site binds to miR-122-3p or miR-122-5p. In embodiments, the mmRNA comprises at least two, at least three, at least four, at least five, at least six, at least seven, at least eight, at least nine, or at least ten miRNA binding sites.

In embodiments, the 3' UTR sequence is 3' UTR_1 having the following nucleotide sequence:

```
                                        (SEQ ID NO: 114)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTGGAT

TCTGCCTAATAAAAAACATTTATTTTCATTGCAATTGCCATGTGTATGTG

GGTTCGCCCACATACTCTGATGATCCCCAATCGTGGCGTGTCGGCCTGCT

TCGGCAGGCACTGGCGCCGGGATCATTCATGGCAA.
```

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 114. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 114 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 114 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 114 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_2 having the following nucleotide sequence:

(SEQ ID NO: 115)
AAAGCAAAACTAACATGAAACAAGGCTAGAAGTCAGGTCGGATTAAGCCA

TAGTACGGAAAAAACTATGCTACCTGTGAGCCCCGTCCAAGGACGTTAAA

AGAAGTCAGGCCATCATAAATGCCATAGCTTGAGTAAACTATGCAGCCTG

TAGCTCCACCTGAGAAGGTGTAAAAAATCCGGGAGGCCACAAACCATGGA

AGCTGTACGCATGGCGTAGTGGACTAGCGGTTAGAGGAGACCCCTCCCTT

ACAAATCGCAGCAACAATGGGGGCCCAAGGCGAGATGAAGCTGTAGTCTC

GCTGGAAGGACTAGAGGTTAGAGGAGACCCCCCCGAAACAAAAAACAGCA

TATTGACGCTGGGAAAGACCAGAGATCCTGCTGTCTCCTCAGCATCATTC

CAGGCACAGAACGCCAGAAAATGGAATGGTGCTGTTGAATCAACAGGTTC

T.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 115. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 115 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 115 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 115 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_3 having the following nucleotide sequence:

(SEQ ID NO: 116)
GCTGGAGCCTCGGTGGCCTAGCTTCTTGCCCCTTGGGCCTCCCCCCAGCC

CCTCCTCCCCTTCCTGCACCCGTACCCCCGTGGTCTTTGAATAAAGTCTG

AGTGGGGGGCA.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 116. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 116 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 116 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 116 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_4 having the following nucleotide sequence:

(SEQ ID NO: 117)
UUCUAGAGCGGCCGCUUCGAGCCGGUUGAAUCGCUGAUCUCACGCCGUGG

UGAGCUCGCUUUCUUGCUGUCCAAUUUCUAUUAAAGGUUCCUUUGUUCCC

UAAGUCCAACUACUAAACUGGGGGAUAUUAUGAAGGGCCUUGAGCAUCUG

GAUUCUGCCUAAUAAAAAACAUUUAUUUUCAUUGCAAAGUUCCGCUACG

UACGGCGUC.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 117. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 117, with at least about 10%, or at least about 20%, or at least about 30%, or at least about 40%, or at least about 50%, or at least about 60%, or about 100% U residues replaced with T residues, modified U residues or a combination thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 117 with one or more U and/or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 117 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% U or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 117 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_5 having the following nucleotide sequence:

```
                                          (SEQ ID NO: 118)
CTCGAGCTGGTACTGCATGCACGCAATGCTAGCTGCCCCTTTCCCGTCCT

GGGTACCCCGAGTCTCCCCCGACCTCGGGTCCCAGGTATGCTCCCACCTC

CACCTGCCCCACTCACCACCTCTGCTAGTTCCAGACACCTCCCAAGCACG

CAGCAATGCAGCTCAAAACGCTTAGCCTAGCCACACCCCACGGGAAACA

GCAGTGATTAACCTTTAGCAATAAACGAAAGTTTAACTAAGCTATACTAA

CCCCAGGGTTGGTCAATTTCGTGCCAGCCACACCCTGGAGCTAGC.
```

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 118. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 118 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 118 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 118 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments the 3' UTR sequence is 3' UTR 6 having the following nucleotide sequence:

```
                                          (SEQ ID NO: 119)
GCUGCCUUCUGCGGGGCUUGCCUUCUGGCCAUGCCCUUCUUCUCUCCCUU

GCACCUGUACCUCUUGGUCUUUGAAUAAAGCCUGAGUAGGAAGU.
```

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 119. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 119, with at least about 10%, or at least about 20%, or at least about 30%, or at least about 40%, or at least about 50%, or at least about 60%, or about 100% U residues replaced with T residues, modified U residues or a combination thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 119 with one or more U or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 119 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% U or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 119 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_7 having the following nucleotide sequence:

(SEQ ID NO: 120)
GGGCCTTTCCAAGATTGCTGTTTTTGTTTTGGAGCTTCAAGACTTTGCA

TTTCCTAGTATTTCTGTTTGTCAGTTCTCAATTTCCTGTGTTTGCAATG

TTGAAATTTTTTGGTGAAGTACTGAACTTGCTTTTTTTCCGGTTTCTAC

ATGCAGAGATGAATTTATACTGCCATCTTACGACTATTTCTTCTTTTTA

ATACACTTAACTCAGGCCATTTTTTAAGTTGGTTACTTCAAAGTAAATA

AACTTTAAAATTCAA.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 120. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 120 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 120 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 120 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_8 having the following nucleotide sequence:

(SEQ ID NO: 121)
CCGCTACGCCCCAATGACCCGACCAGCAAAACTCGACGTACTACCGAGG

AACCGATGTGCATAACGCATCGGGCTGGTACATTAGATCCCCGTCATCA

GACGGGCTCATAGCGACGCTAAAACTCGACGTATTCCCGAGGAAGTGCA

GTGCATAATGCTGAGCAGCGTCGTCATATATTCACTTATTATTCAATAT

AGAGTAGACACCAAAACTCAATGTATTTCTGAGGAAGCGTGGTGCATAA

TGCCACGCAGTGTCTACATAATCAATTTATTATTTTCTTTTATTTTATT

CACATAATTTTGTTTTTAATATTTC.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 121. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 121 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 121 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 121 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_9 having the following nucleotide sequence:

(SEQ ID NO: 122)
CATCACATTTAAAAGCATCTCAGCCTACCATGAGAATAAGAGAAAGAAA

ATGAAGATCAAAAGCTTATTCATCTGTTTTTCTTTTTCGTTGGTGTAAA

GCCAACACCCTGTCTAAAAAACATAAATTTCTTTAATCATTTTGCCTCT

TTTCTCT.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 122. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 122 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 122 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 122 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_10 having the following nucleotide sequence:

```
                                          (SEQ ID NO: 123)
ATATTATCCCTAATACCTGCCACCCCACTCTTAATCAGTGGTGGAAGAA

CGGTCTCAGAACTGTTTGTTTCAATTGGCCATTTAAGTTTAGTAGTAAA

AGACTGGTTAATGATAACAATGCATCGTAAAACCTTCAGAAGGAAAGGA

GAATGTTTTGTGGACCACTTTGGTTTTCTTTTTTGCGTGTGGCAGTTTT

AAGTTATTAGTTTTTAAAATCAGTACTTTTTAATGGAAACAACTTGACC

AAAAATTTGTCACAGAATTTTGAGACCCATTAAAAAAGTTAAATGAGAA

A.
```

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 123. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 123 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 123 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 123 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_11 having the following nucleotide sequence:

```
                                          (SEQ ID NO: 124)
GCGCCTGCCCACCTGCCACCGACTGCTGGAACCCAGCCAGTGGGAGGGC

CTGGCCCACCAGAGTCCTGCTCCCTCACTCCTCGCCCCGCCCCCTGTCC

CAGAGTCCCACCTGGGGGCTCTCTCCACCCTTCTCAGAGTTCCAGTTTC

AACCAGAGTTCCAACCAATGGGCTCCATCCTCTGGATTCTGGCCAATGA

AATATCTCCCTGGCAGGGTCCTCTTCTTTTCCCAGAGCTCCACCCCAAC

CAGGAGCTCTAGTTAATGGAGAGCTCCCAGCACACTCGGAGCTTGTGCT

TTGTCTCCACGCAAAGCGATAAATAAAAGCATTGGTGGCCTTA.
```

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 124. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 124 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 124 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 124 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_12 having the following nucleotide sequence:

(SEQ ID NO: 125)
GTGTGTGGAGGACACCCTGAACCCCCCGCTTTCAAACAAGTTTTCAAAT

TGTTTGAGGTCAGGATTTCTCAAACTGATTCCTTTCTTTGCATATGAGT

ATTTGAAAATAAATATTTTCCCAGAATATAAATAAATCATCACATGATT

ATTTTAACTATA.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 125. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 125 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 125 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 125 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_13 having the following nucleotide sequence:

(SEQ ID NO: 126)
GCTGGAGCCTCGGTGGCCTAGCTTCTTGCCCCTTGGGCCTCCCCCCAGC

CCCTCCTCCCCTTCCTGCACCCGTACCCCCGTGGTCTTTGAATAAAGTC

TGAGTGGGCGGCA.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 126. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 126 with one or more T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 126 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 126 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 3' UTR sequence is 3' UTR_14 having the following nucleotide sequence:

(SEQ ID NO: 127)
UUCUAGAGCGGCCGCUUCGAGCCGGUUGAAUCGCUGAUCUCACGCCGUG

GUGAGCUCGCUUUCUUGCUGUCCAAUUUCUAUUAAAGGUUCCUUUGUUC

CCUAAGUCCAACUACUAAACUGGGGGAUAUUAUGAAGGGCCUUGAGCAU

CUGGAUUCUGCCUAAUAAAAAACAUUUAUUUUCAUUGCAAAGUUCCGCG

UACGUACGGCGUC.

In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 127. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 127, with at least about 10%, or at least about 20%, or at least about 30%, or at least about 40%, or at least about 50%, or at least about 60%, or about 100% U residues replaced with T residues, modified U residues or a combination thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 127 with one or more U or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 127 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% U or T nucleotide replaced with a U nucleotide, a modified U nucleotide or a homolog thereof. In embodiments, the 3' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 127 at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the miRNA binding site is inserted within the 3' UTR. In embodiments, the polynucleotide is DNA. In embodiments, the further comprises a spacer sequence between the open reading frame and the miRNA binding site. In aspects, the spacer sequence comprises at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, or at least about 100 nucleotides.

In embodiments, the mmRNA further comprises a 5' UTR. In embodiments, the 5' UTR comprises a nucleic acid sequence at least about 90%, or at least about 95%, or at least about 96%, or at least about 97%, or at least about 98%, or at least about 99%, or about 100% identical to a sequence listed in Table 3 of US Patent Application Publication No. 2019/0114089, or a sequence disclosed in PCT International Application Publication Nos. WO 2017/201325 and WO 2014/164253, each of which is incorporated herein in its entirety. In embodiments, the 5' UTR bears features, which play roles in translation initiation. In embodiments, the 5' UTR harbors signatures like Kozak sequences which are commonly known to be involved in the process by which the ribosome initiates translation of many genes. In embodiments, the 5' UTR forms secondary structures which are involved in elongation factor binding. In embodiments, the 5' UTR of mRNA known to be upregulated in cancers, such as c-myc, may be used to enhance expression of a nucleic acid molecule, such as a polynucleotides, in cancer cells. In embodiments, the 5' UTR of mRNA known to be upregulated in liver and/or spleen may be used to enhance expression of a nucleic acid molecule, such as a polynucleotides, in liver and/or spleen. In embodiments, the mRNA comprises a GC-rich element comprising, or derivatives or analogs thereof, located upstream of a Kozak consensus sequence or a Kozak-like sequence that is located in the 5' UTR. In embodiments, GC-rich element is located at least about 30, or at least about 25, or at least about 20, or at least about 15, or at least about 10, or at least about 5, or at least about 4, or at least about 3, or at least about 2, or at least about 1 nucleotide(s) upstream of a Kozak consensus sequence or a Kozak-like sequence that is located in the 5' UTR. In embodiments, the GC-rich element is located about 15-30, or about 15-20, or about 15-25, or about 10-15, or about 5-10, or about 1-8 nucleotides upstream of a Kozak consensus sequence or a Kozak-like sequence that is located in the 5' UTR. In embodiments, the GC-rich element is located upstream of and immediately abutting to Kozak consensus sequence or a Kozak-like sequence that is located in the 5' UTR. In embodiments, the GC-rich element is about 20-30, about 10-20, about 10-15, about 5-15, or about 3-15 nucleotides long. In embodiments, the GC-rich element comprises a sequence of about 3, or about 4, or about 5, or about 6, or about 7, or about 8, or about 9, or about 10, or about 11, or about 12, or about 13, or about 14, or about 15, or about 16, or about 17, or about 18, or about 19, or about 20 nucleotides long. In embodiments, the GC-rich element is located about 60, or about 55, or about 50, or about 45, or about 40, or about 35, or about 30, or about 25, or about 20, or about 15, or about 10, or about 5, or about 4, or about 3, or about 2, or about 1 nucleotide upstream of the initiation codon. In embodiments, the GC-rich element comprises about 30% to about 50%, or about 40% to about 60%, or about 50% to about 70%, or about 60% to about 80%, or about 70% to about 90% cytosine. In embodiments, the GC-rich element comprises about 30% to about 50%, or about 40% to about 60%, or about 50% to about 70%, or about 60% to about 80%, or about 70% to about 90% guanine. Additional properties of the GC-rich element are described in US Patent Application No. 2020/0208145, which is incorporated herein in its entirety.

In embodiments, the GC-rich element comprises the nucleotide sequence CCCCGGCGCC (SEQ ID NO: 150). In embodiments, the GC-rich element is a variant of CCCCGGCGCC (SEQ ID NO: 150) having one or more nucleotide mutations, independently selected from substitutions, insertions, deletions, and truncations. In embodiments, the GC-rich element has a nucleotide sequence having about 1, 2, 3, 4, 5, 6, 7, 8, 9, or 10 or more nucleotide mutations with respect to the nucleotide sequence CCCCGGCGCC (SEQ ID NO: 150).

In embodiments, the GC-rich element comprises the nucleotide sequence GGGGCGCCCG (SEQ ID NO: 151). In embodiments, the GC-rich element is a variant of GGGGCGCCCG (SEQ ID NO: 151) having one or more nucleotide mutations, independently selected from substitutions, insertions, deletions, and truncations. In embodiments, the GC-rich element has a nucleotide sequence having about 1, 2, 3, 4, 5, 6, 7, 8, 9, or 10 or more nucleotide mutations with respect to the nucleotide sequence GGGGCGCCCG (SEQ ID NO: 151).

Additional GC-rich element sequences are described in US Patent Application No. 2020/0208145, which is incorporated herein in its entirety.

In embodiments, the 5' UTR sequence is 5' UTR_1 having the following nucleotide sequence:

(SEQ ID NO: 128)
ACATTTGCTTCTGACACAACTGTGTTCACTAGCAACCTCAAACAGACAC

C.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 128. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 128 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 128 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 128 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments the 5' UTR sequence is 5' UTR_2 having the following nucleotide sequence:

```
                                     (SEQ ID NO: 129)
ACATTTGCTTCTGACACAACTGTGTTCACTAGCAACCTCAAACAGACAC

CCCCCGGCGCCGCCACCATG.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 129 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, but lacking a GC-rich element. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element comprising the nucleotide sequence CCCCGGCGCC (SEQ ID NO: 150). In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element that is a variant of CCCCGGCGCC (SEQ ID NO: 150) having one or more nucleotide mutations, independently selected from substitutions, insertions, deletions, and truncations.

In embodiments, the 5' UTR sequence is 5' UTR_3 having the following nucleotide sequence:

```
                                     (SEQ ID NO: 130)
ACATTTGCTTCTGACACAACTGTGTTCACTAGCAACCTCAAACAGACAC

CGGGGCGCCCGGCCACCATG.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 130. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 130 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 130 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 130 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element comprising the nucleotide sequence GGGGCGCCCG (SEQ ID NO: 151). In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element that is a variant of GGGGCGCCCG (SEQ ID NO: 151) having one or more nucleotide mutations, independently selected from substitutions, insertions, deletions, and truncations.

In embodiments, the 5' UTR sequence is 5' UTR_4 having the following nucleotide sequence:

```
                                          (SEQ ID NO: 131)
TTGGGGGCGACACTCCACCATAGATCACTCCCCTGTGAGGAACTACTGT

CTTCACGCAGAAAGCGTCTAGCCATGGCGTTAGTATGAGTGTCGTGCAG

CCTCCAGGACCCCCCCTCCCGGGAGAGCCATAGTGGTCTGCGGAACCGG

TGAGTACACCGGAATTGCCAGGACGACCGGGTCCTTTCTTGGATTAACC

CGCTCAATGCCTGGAGATTTGGGCGTGCCCCCGCGAGACTGCTAGCCGA

GTAGTGTTGGGTCGCGAAAGGCCTTGTGGTACTGCCTGATAGGGTGCTT

GCGAGTGCCCCGGGAGGTCTCGTAGACCGTGCATCATGAGCACAAATCC

TAAACCTCAAAGAAAAACCAAACGTAACAAGGGCGAATTCGTTGGTAAA

GCCACC.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 131. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 131 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 131 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 131 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_5 having the following nucleotide sequence:

```
                                          (SEQ ID NO: 132)
TTGGGGGCGACACTCCACCATAGATCACTCCCCTGTGAGGAACTACTGT

CTTCACGCAGAAAGCGTCTAGCCATGGCGTTAGTATGAGTGTCGTGCAG

CCTCCAGGACCCCCCCTCCCGGGAGAGCCATAGTGGTCTGCGGAACCGG

TGAGTACACCGGAATTGCCAGGACGACCGGGTCCTTTCTTGGATTAACC

CGCTCAATGCCTGGAGATTTGGGCGTGCCCCCGCGAGACTGCTAGCCGA

GTAGTGTTGGGTCGCGAAAGGCCTTGTGGTACTGCCTGATAGGGTGCTT

GCGAGTGCCCCGGGAGGTCTCGTAGACCGTGCATCATGAGCACAAATCC

TAAACCTCAAAGAAAAACCAAACGTAACAAGGGCGAATTCGTTGGTAAA

CCCCGGCGCCGCCACC.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 132. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 132 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 132 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 132 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element comprising the nucleotide sequence CCCCGGCGCC (SEQ ID NO: 150). In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element that is a variant of CCCCGGCGCC (SEQ ID NO: 150) having one or more nucleotide mutations, independently selected from substitutions, insertions, deletions, and truncations.

In embodiments, the 5' UTR sequence is 5' UTR_6 having the following nucleotide sequence:

(SEQ ID NO: 133)
TTGGGGGCGACACTCCACCATAGATCACTCCCCTGTGAGGAACTACTGT

CTTCACGCAGAAAGCGTCTAGCCATGGCGTTAGTATGAGTGTCGTGCAG

CCTCCAGGACCCCCCCTCCCGGGAGAGCCATAGTGGTCTGCGGAACCGG

TGAGTACACCGGAATTGCCAGGACGACCGGGTCCTTTCTTGGATTAACC

CGCTCAATGCCTGGAGATTTGGGCGTGCCCCCGCGAGACTGCTAGCCGA

GTAGTGTTGGGTCGCGAAAGGCCTTGTGGTACTGCCTGATAGGGTGCTT

GCGAGTGCCCCGGGAGGTCTCGTAGACCGTGCATCATGAGCACAAATCC

TAAACCTCAAAGAAAAACCAAACGTAACAAGGGCGAATTCGTTGGTAAA

GGGGCGCCCGGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 133. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 133 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 133 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 133 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element comprising the nucleotide sequence GGGGCGCCCG (SEQ ID NO: 151). In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element that is a variant of GGGGCGCCCG (SEQ ID NO: 151) having one or more nucleotide mutations, independently selected from substitutions, insertions, deletions, and truncations.

In embodiments, the 5' UTR sequence is 5' UTR_7 having the following nucleotide sequence:

(SEQ ID NO: 134)
GGGAAATAAGAGAGAAAAGAAGAGTAAGAAGAAATATAAGACCCCGGCG

CCGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 134. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 134 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 134 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 134 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element comprising the nucleotide sequence CCCCGGCGCC (SEQ ID NO: 150). In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 129, and comprising a GC-rich element that is a variant of CCCCGGCGCC (SEQ ID NO: 150) having one or more nucleotide mutations, independently selected from substitutions, insertions, deletions, and truncations.

In embodiments, the 5' UTR sequence is 5' UTR_8 having the following nucleotide sequence:

(SEQ ID NO: 135)
GGGACAUUUGCUUCUGACACAACUGUGUUCACUAGCAACCUCAAACAGA
CACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 135. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 135 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 135 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 135 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_9 having the following nucleotide sequence:

(SEQ ID NO: 136)
TTTAAAATCTGTGTGGCTGTCACTCGGCTGCTTGCTTAGTGCACTCACG

CAGTATAATTAATAACTAATTACTGTCGTTGACAGGACACGAGTAACTC

GTCTATCTTCTGCAGGCTGCTTACGGTTTCGTCCGTGTTGCAGCCGATC

ATCAGCACATCTAGGTTTCGTCCGGGTGTGACCGAAAGGTAAGTTGGAG

AGCCTTGTCCCTGGTTTCAACGAGAAAAC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 136. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 136 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 136 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 136 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_10 having the following nucleotide sequence:

(SEQ ID NO: 137)
GGGAAATAAGAGAGAAAAGAAGAGTAAGAAGAAATATAAGAGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 137. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 137 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 137 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 137 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_11 having the following nucleotide sequence:

```
                                    (SEQ ID NO: 138)
GAGAATAAACTAGTATTCTTCTGGTCCCCACAGACTCAGAGAGAACCCG
CCACC.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 138. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 138 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 138 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 138 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_12 having the following nucleotide sequence:

```
                                    (SEQ ID NO: 139)
GGGAAAAAGAGAGAAAAGAAGAGAAGAAGAAAAAAGAGCCACC.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 139. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 139 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 139 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 139 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_13 having the following nucleotide sequence:

```
                                    (SEQ ID NO: 140)
AACGGCTAGCCTGAGGAGCTGCTGCGACAGTCCACTACCTTTTTCGAGA

GTGACTCCCGTTGTCCCAAGGCTTCCCAGAGCGAACCTGTGCGGCTGCA

GGCACCGGCGCGTCGAGTTTCCGGCGTCCGGAAGGACCGAGCTCTTCTC
```

-continued

GCGGATCCAGTGTTCCGTTTCCAGCCCCCAATCTCAGAGCGGAGCCGAC

AGAGAGCAGGGAACCGGCCCGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 140. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 140 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 140 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 140 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_14 having the following nucleotide sequence:

```
                                        (SEQ ID NO: 141)
TAGTCAGTGTAATATACAGTAACTGACCAAACCACATCCACCGTAAACC
CGCCACC.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 141. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 141 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 141 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 141 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_15 having the following nucleotide sequence:

```
                                        (SEQ ID NO: 142)
GAGACCCAAGCTGGCTAGCGGGAGAAAGCTTACCGGCTAGCGCCGCCAC
C.
```

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 142. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 142 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 142 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 142 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_16 having the following nucleotide sequence:

(SEQ ID NO: 143)
TTTAAAATCTGTGTGGCTGTCACTCGGCTGCTTGCTTAGTGCACTCACG

CAGTATAATTAATAACTAATTACTGTCGTTGACAGGACACGAGTAACTC

GTCTATCTTCTGCAGGCTGCTTACGGTTTCGTCCGTGTTGCAGCCGATC

ATCAGCACATCTAGGTTTCGTCCGGGTGTGACCGAAAGGTAAGTTGGAG

AGCCTTGTCCCTGGTTTCAACGAGAAAACGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 143. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 143 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 143 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 143 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_17 having the following nucleotide sequence:

(SEQ ID NO: 144)
GGGTCAGTGTCACCTCCAGGATACAGACAGCCCCCCTTCAGCCCAGCCC

AGCCAGGTCTCCTACACCGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 144. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 144 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 144 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 144 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_18 having the following nucleotide sequence:

(SEQ ID NO: 145)
ACTCCTCCCCATCCTCTCCCTCTGTCCCTCTGTCCCTCTGACCCTGCAC

TGTCCCAGCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 145. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 145 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 145 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 145 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_19 having the following nucleotide sequence:

(SEQ ID NO: 146)
GGGACTCCCGGGCTGGCAGCAGGGCCCCAGCGGCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 146. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 146 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 146 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 146 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_20 having the following nucleotide sequence:

(SEQ ID NO: 147)
AGCAATCCTTTCTTTCAGCTGGAGTGCTCCTCAGGAGCCAGCCCCACCC
TTAGAAAAG.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 147. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 147 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 147 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 147 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_21 having the following nucleotide sequence:

(SEQ ID NO: 148)
GGGTCAGTGTCACCTCCAGGATACAGACAGCCCCCCTTCAGCCCAGCCC
AGCCAGGTCTCCTACACCGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 148. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 148 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 148 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 148 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, the 5' UTR sequence is 5' UTR_22 having the following nucleotide sequence:

(SEQ ID NO: 149)
TTTAAAATCTGTGTGGCTGTCACTCGGCTGCTTGCTTAGTGCACTCACG

CAGTATAATTAATAACTAATTACTGTCGTTGACAGGACACGAGTAACTC

GTCTATCTTCTGCAGGCTGCTTACGGTTTCGTCCGTGTTGCAGCCGATC

ATCAGCACATCTAGGTTTCGTCCGGGTGTGACCGAAAGGTAAGTTGGAG

AGCCTTGTCCCTGGTTTCAACGAGAAAACGCCACC.

In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 149. In embodiments, the 5' UTR comprises a nucleotide acid sequence that is at least about 90%, or at least about 95%, or at least about 96%, or at least about 97%, or at least about 98%, or at least about 99%, or 100% identical to the nucleotide acid sequence of SEQ ID NO: 149 with one or more T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 149 with at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% T nucleotide replaced with a U nucleotide, a modified U nucleotide or a homolog thereof. In embodiments, the 5' UTR comprises a nucleotide acid sequence that is at least about 90%, or at least about 95%, or at least about 96%, or at least about 97%, or at least about 98%, or at least about 99%, or about 100% identical to the nucleotide acid sequence of SEQ ID NO: 149 having at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the cytosine residues, thymidine residues, adenosine residues and/or guanosine residues are replaced by modified cytidine residues, modified uridine residues, modified adenosine residues and/or modified guanosine residues, respectively.

In embodiments, at least one of the regions of linked nucleosides of A comprises a sequence of linked nucleosides which functions as a 5' UTR and at least one of the regions of linked nucleosides of C comprises a sequence of linked nucleosides which functions as a 3' UTR. In embodiments, the 5' UTR and the 3' UTR are from the same or different species. In embodiments, the 5' UTR and the 3' UTR may be the native untranslated regions from different proteins from the same or different species. In embodiments, the 5' UTR and the 3' UTR may have synthetic sequences.

In embodiments, the mmRNA further comprises a 3' polyadenylation (polyA tail).

In embodiments, the mmRNA further comprises a 5' terminal cap. In embodiments, the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In embodiments, the polynucleotide is in vitro transcribed (IVT). In embodiments, the polynucleotide is chimeric. In embodiments, the polynucleotide is circular.

In embodiments, the polynucleotide is or comprises DNA. In embodiments, the polynucleotide is or comprises a minicircle or a plasmid DNA. In embodiments, the plasmid DNA is devoid of any prokaryotic components. In embodiments, the polynucleotide comprises a tissue-specific control element. In embodiments, the tissue-specific control element is a promoter or an enhancer. In embodiments, the plasmid DNA is an expression vector. In embodiments, the DNA is or comprises a minicircle. In embodiments, the minicircle is a circular molecule, which is optionally small. In embodiments, the minicircle utilizes a cellular transcription and translation machinery to produce an encoded gene product. In embodiments, the minicircle is devoid of any prokaryotic components. In embodiments, the minicircle only comprises substantially only sequences of mammalian origin (or those that have been optimized for mammalian cells). In embodiments, the minicircle lacks or has reduced amount of DNA sequence elements that are recognized by the innate immune system and/or toll-like receptors. In embodiments, the minicircle is produced by excising any bacterial components of from a parental plasmid, thereby making it smaller than a parental DNA sequence. In embodiments, the minicircle is of non-viral origin. In embodiments, the minicircle remains episomal. In embodiments, the minicircle does not replicate with a host cell. In embodiments, expression of the chimeric protein in non-dividing cells harboring a minicircle lasts for at least 2 days, or at least 4 days, or at least 6 days, or at least 8 days, or at least 10 days, or at least 12 days, or at least 14 days, or at least 16 days, or at least 18 days, or at least 20 days, or at least 22 days, or at least 24 days, or longer in dividing cells. In embodiments, expression of the chimeric protein in non-dividing cells harboring a minicircle lasts for at least 4 days, or at least 6 days, or at least 8 days, or at least 10 days, or at least 1 week, or at least 2 weeks, or at least 3 weeks, or at least 4 weeks, or at least 5 weeks, or at least 6 weeks, or at least 1 month, or at least 2 months, or at least 3 months, or at least 4 months, or at least 5 months, or at least 6 months, or at least 8 months, or longer in dividing cells.

In embodiments, the mmRNAs of the present disclosure are produced by means available in the art, including but not limited to in vitro transcription (IVT) and synthetic methods. Enzymatic IVT, solid-phase, liquid-phase, combined synthetic methods, small region synthesis, and ligation methods may be utilized. In embodiments, mmRNAs are made using IVT enzymatic synthesis methods. Methods of making polynucleotides by IVT are known in the art and are described in International Application PCT International Patent Publication No. WO 2013/151666, the contents of which are incorporated herein by reference in their entirety. Accordingly, the present disclosure also includes polynucleotides, e.g., DNA, constructs and vectors that may be used to in vitro transcribe an mRNA described herein.

In embodiments, the polynucleotide is DNA. In embodiments, the polynucleotide comprises a expressed in liver, skin and/or muscle-specific control element. In embodiments, the liver-specific control element is a liver-specific promoter selected from albumin promoter, thyroxine-binding globulin (TBG) promoter, hybrid liver-specific promoter (HLP), human al-antitrypsin promoter, LP1 promoter, and hemopexin promoter. The gene therapy in accordance with the present disclosure can be performed using vector systems. In embodiments, the liver-specific promoter is an LP1 promoter. The LP1 promoter can be a human LP1 promoter, which can be constructed as described, e.g., in Nathwani et al. *Blood* vol. 107(7) (2006):2653-61, which is incorporated herein by reference in its entirety.

In aspects, the present disclosure provides a vector comprising the polynucleotide of any one of the embodiments disclosed herein. In embodiments, the chimeric protein can be provided as an expression vector. In embodiments, the expression vector is a DNA expression vector or an RNA expression vector. In embodiments, the expression vector is a viral expression vector. In embodiments, the expression vector is a non-viral expression vector (without limitation, e.g., a plasmid).

In embodiments, the present non-viral vectors are linear or circular DNA molecules that comprise a polynucleotide encoding a polypeptide and is operably linked to control sequences, wherein the control sequences provide for expression of the polynucleotide encoding the polypeptide. In embodiments, the non-viral vector comprises a promoter sequence, and transcriptional and translational stop signal sequences. In embodiments, the expression vector may include, among others, chromosomal and episomal vectors, e.g., vectors derived from bacterial plasmids, from transposons, from yeast episomes, from insertion elements, from yeast chromosomal elements, and vectors derived from combinations thereof. The present constructs may contain control regions that regulate as well as engender expression.

A vector generally comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. In embodiments, the expression vector is an autonomously replicating plasmid or a virus (e.g., AAV vectors). In embodiments, the expression vector is non-plasmid and non-viral compounds that facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

In embodiments, the polynucleotide or cell therapy may employ expression vectors, which comprise the nucleic acid encoding the chimeric protein operably linked to an expression control region that is functional in the host cell. The expression control region is capable of driving expression of the operably linked encoding nucleic acid such that the chimeric protein is produced in a human cell transformed with the expression vector. Expression control regions are regulatory polynucleotides (sometimes referred to herein as elements), such as promoters and enhancers, which influence expression of an operably linked nucleic acid. An expression control region of an expression vector is capable of expressing operably linked encoding nucleic acid in a human cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. In various embodiments, the chimeric protein expression is inducible or repressible. Typically, the amount of increase or decrease conferred by such elements is proportional to the amount of signal present; the greater the amount of signal, the greater the increase or decrease in expression.

Expression systems functional in human cells are well known in the art and include viral systems. Generally, a promoter functional in a human cell is any DNA sequence capable of binding mammalian RNA polymerase and initiating the downstream (3') transcription of a coding sequence into mRNA. A promoter will have a transcription-initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Where appropriate, gene delivery agents such as, e.g., integration sequences can also be employed. Numerous integration sequences are known in the art (see, e.g., Nunes-Duby et al., *Nucleic Acids Res.* 26:391-406, 1998; Sadwoski, *J. Bacteriol.,* 165:341-357, 1986; Bestor, Cell, 122(3):322-325, 2005; Plasterk et al., TIG 15:326-332, 1999; Kootstra et al., *Ann. Rev. Pharm. Toxicol.,* 43:413-439, 2003). These include recombinases and transposases. Examples include Cre (Sternberg and Hamilton, *J. Mol. Biol.,* 150:467-486, 1981), lambda (Nash, *Nature,* 247, 543-545, 1974), FIp (Broach, et al., *Cell,* 29:227-234, 1982), R (Matsuzaki, et al., *J. Bacteriology,* 172:610-618, 1990), cpC31 (see, e.g., Groth et al., *J. Mol. Biol.* 335:667-678, 2004), sleeping beauty, transposases of the mariner family, and components for integrating viruses such as AAV, retroviruses, and antiviruses having components that provide for virus integration such as the LTR sequences of retroviruses or lentivirus and the ITR sequences of AAV (Kootstra et al., *Ann. Rev. Pharm. Toxicol.,* 43:413-439, 2003). In addition, direct and targeted genetic integration strategies may be used to insert nucleic acid sequences including CRISPR/CAS9, zinc finger, TALEN, and meganuclease gene-editing technologies.

In aspects, the present disclosure provides a host cell comprising the vector of any of the embodiments disclosed herein. A host cell comprising the mmRNA of any of the embodiments disclosed herein.

Pharmaceutical Compositions

In aspects, the present disclosure provides a pharmaceutical composition comprising a pharmaceutically acceptable excipient or carrier, and the chimeric protein of any of the embodiments disclosed herein, the isolated polynucleotide of any of the embodiments disclosed herein, the mmRNA of any of the embodiments disclosed herein, or the vector of any of the embodiments disclosed herein, or the host cell of any of the embodiments disclosed herein. In embodiments, the pharmaceutical composition comprises the mmRNA of any of the embodiments disclosed herein.

Suitable pharmaceutical compositions are disclosed in U.S. Pat. Nos. 8,710,200; 8,822,663; 8,999,380; 9,181,319; 9,254,311; 9,334,328; 9,464,124; 9,950,068; 10,626,400; 10,808,242; 11,020,477, US Patent Application Publication Nos. 2022/0001026, 2021/0318817, 2021/0283262, 2020/0360481, 2020/0113844, 2020/0085758, 2017/0204152, 2019/0114089, 2019/0114090, 2018/0369374, 2018/0318385, 2019/0111003, and PCT International Application Publication Nos. WO/2017112943, WO 2014/028429, WO 2017/201325 the entire contents of which are hereby incorporated by reference.

In aspects, the present disclosure relates to a pharmaceutical composition comprising a pharmaceutically acceptable carrier and the isolated polynucleotide of any of the embodiments disclosed herein, the mmRNA of any of the embodiments disclosed herein, or the vector of any of the embodiments disclosed herein. In embodiments, the pharmaceutically acceptable carrier is mmRNA comprises a modification (e.g., an RNA element), wherein the modification provides a desired translational regulatory activity. Such modifications are described in PCT Application No. PCT International Application Publication No. WO 2018/213789, the entire contents of which are herein incorporated by reference.

In embodiments, the mmRNA further comprises a 3' untranslated region (UTR). In embodiments, the 3' UTR comprises at least one microRNA-122 (miR-122) binding site. In embodiments, the miR-122 binding site is a miR-122-3p binding site or a miR-122-5-binding site. In embodiments, the mmRNA further comprises a spacer sequence between the open reading frame and the miRNA binding site. In embodiments, the spacer sequence comprises at least about 10 nucleotides, at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, or at least about 100 nucleotides.

In embodiments, the mmRNA further comprises a 5' UTR. In embodiments, the 5' UTR harbors a Kozak sequence and/or forms a secondary structure that stimulate elongation factor binding.

In embodiments, the mmRNA further comprises a 5' terminal cap. In embodiments, the 5' terminal cap is a Cap0, Cap1, ARCA, inosine, N1-methyl-guanosine, 2'fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In any of the embodiments disclosed herein, the mmRNA may comprise one or more modifications. In any of the embodiments disclosed herein, the mmRNA may comprise at least one modification. In embodiments, the modification is nucleoside modification. In embodiments, the modification is a base modification. In embodiments, the modification is a sugar-phosphate backbone modification.

In embodiments, the modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and a combination of any two or more thereof. In embodiments, the modifications are selected from pseudouridine ($\Psi$), N1-methylpseudouridine (m1$\Psi$), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1$\Psi$), 5-methoxy-uridine (mo5U), 5-methyl-cytidine (m5C). alpha-thio-guanosine, alpha.-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methylinosine (mi1), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, and a combination of any two or more thereof. In embodiments, modification is selected from pseudouridine, N1-methylpseudouridine, 5-methylcytosine, 5-methoxyuridine, and a combination thereof.

In embodiments, the mmRNA comprises at least one N1-methylpseudouridine. In embodiments, the mmRNA is fully modified with chemically-modified uridines. In embodiments, the mmRNA is a fully modified with N1-methylpseudouridine.

In embodiments, the modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine or a combination of any two or more thereof.

In embodiments, the modifications are selected from 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In embodiments, the modifications are selected from 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyl-adenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In embodiments, the modifications are selected from inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxoguanosine, 7-methyl-8-oxo-guanosine, 1-methyl-6-thio-guanosine, N2-methyl-6-thio-guanosine, and N2,N2-dimethyl-6-thio-guanosine.

In embodiments, the modifications are present on the major groove face. In embodiments, a hydrogen on C-5 of uracil is replaced with a methyl group or a halo group.

In embodiments, the mmRNA further comprises one or more modifications selected from 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine and 5'-O-(1-Thiophosphate)-Pseudouridine.

In embodiments, the pharmaceutical composition is formulated as a lipid nanoparticle (LNP), a lipoplex, or a liposome. In embodiments, the pharmaceutical composition is formulated as a lipid nanoparticle (LNP). In embodiments, the mmRNAs described herein may be formulated in a cationic oil-in-water emulsion where the emulsion particle comprises an oil core and a cationic lipid that can interact with the mRNA anchoring the molecule to the emulsion particle. In embodiments, the mRNAs described herein may be formulated in a water-in-oil emulsion comprising a continuous hydrophobic phase in which the hydrophilic phase is dispersed. Exemplary emulsions can be made by the methods described in PCT International Application Publication Nos. WO 2012/006380 and WO 2010/87791, each of which is herein incorporated by reference in its entirety.

In some embodiments, nucleic acids of the invention (e.g., mRNA) are formulated in a lipid nanoparticle (LNP). Lipid nanoparticles comprise typically comprise ionizable cationic lipid, non-cationic lipid, sterol and PEG lipid components along with the nucleic acid cargo of interest. The lipid nanoparticles of the invention can be generated using components, compositions, and methods as are disclosed, e.g., in PCT International Application Publication Nos. WO 2021/231854, WO 2021/050986, WO 2021/055833, WO 2021/213924, WO 2021/055849, WO 2021/214204, WO 2021/188969, WO 2021/055835, WO 2020/061284, WO 2020/061295, WO 2017/049245, WO 2017/031232, WO 2017/112865, WO 2017/218704, WO 2017/218704, WO 2017/099823, WO 2017/049074, WO 2017/117528, WO 2017/180917, WO 2017/075531, WO 2017/223135, WO 2016/118724, WO 2015/164674, WO 2015/038892, WO 2014/152211, and WO 2013/090648, the entire contents of each which are herein incorporated by reference. PEG-lipids selected from an ionizable lipid (e.g., as known in the art, such as those described in U.S. Pat. No. 8,158,601 and PCT International Application Publication Nos. WO 2012/099755 and WO 2015/130584, which are incorporated herein by reference in their entirety. The ionizable lipid may be selected from, but not limited to, an ionizable lipid described in International Patent Application Publication Nos. WO 2013/086354 and WO 2013116126; the contents of each of which are herein incorporated by reference in their entirety. In embodiments, the lipid may be a cleavable lipid such as those described in PCT International Patent Application Publication No. WO 2012/170889, herein incorporated by reference in its entirety. In embodiments, the lipid may be synthesized by methods known in the art and/or as described in International Patent Application Publication Nos. WO 2013/086354; the contents of each of which are herein incorporated by reference in their entirety. In embodiments, the LNP formulations described herein can additionally comprise a permeability enhancer molecule. Non-limiting permeability enhancer molecules are described in U.S. Patent Application Publication No. US 2005/0222064, herein incorporated by reference in its entirety.

In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNP), a lipoplex, or a liposome. In embodiments, the pharmaceutical composition is formulated as a lipid nanoparticle (LNP). In embodiments, the lipid nanoparticles comprise lipids selected from an ionizable lipid (e.g. an ionizable cationic lipid selected from DLin-DMA, DLin-K-DMA, DLin-KC2-DMA, DLin-MC3-DMA, 98N12-5, and C12-200); a structural lipid (e.g. distearoylphosphatidylcholine (DSPC)); cholesterol, and a polyethyleneglycol (PEG)-lipid (e.g. a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE).

In embodiments, the pharmaceutical composition is formulated as a lipid nanoparticle (LNP). In embodiments, the LNP comprises a molar ratio of about 20-60% ionizable amino lipid, about 5-25% phospholipid, about 25-55% structural lipid, and about 0.5-1.5% PEG lipid. In embodiments, the LNP comprises a molar ratio of about 50% ionizable amino lipid, about 8-12% phospholipid, about 37-40% structural lipid, and about 1-2% PEG lipid. In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE).

In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNP), a lipoplex, or a liposome. In embodiments, the pharmaceutical composition is formulated as a lipid nanoparticle (LNP).

In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA.

In embodiments, the lipid nanoparticles comprise lipids selected from an ionizable lipid; a structural lipid; cholesterol, and a polyethyleneglycol (PEG)-lipid; 1,2-dioleoyl-3-trimethylammoniumpropane (DOTAP); dioleoylphosphatidylethanolamine (DOPE); and the mmRNA. In embodiments, the ionizable lipid is an ionizable cationic lipid selected from DLin-DMA, DLin-K-DMA, DLin-KC2-DMA, DLin-MC3-DMA, 98N12-5, and C12-200. In embodiments, the polyethyleneglycol (PEG)-lipid is selected from a PEG-diacylglycerol (DAG), a PEG-dialkyloxypropyl (DAA), a PEG-phospholipid, a PEG-ceramide (Cer), or a mixture thereof, or a PEG-dilauryloxypropyl (e.g., C12, a PEG-dimyristyloxypropyl (C14), a PEG-dipalmityloxypropyl (C16), or a PEG-distearyloxypropyl (C18)).

In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In any of the embodiments disclosed herein, the pharmaceutical composition is formulated for parenteral administration. In any of the embodiments disclosed herein, the pharmaceutical composition is formulated for topical administration.

In aspects, the present disclosure provides a pharmaceutical composition comprising the mmRNA of any embodiment disclosed herein, or an LNP comprising an mmRNA of any embodiment disclosed herein. In embodiments, the pharmaceutical composition is formulated for parenteral administration.

In embodiments, the pharmaceutical composition comprises a modified mRNA (mmRNA) encoding a heterologous chimeric protein having an amino acid sequence that has at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence selected from the amino acid sequence of SEQ ID NOs: 80-93. In embodiments, the pharmaceutical composition is formulated as an LNP comprising an ionizable amino lipid, a phospholipid, a structural lipid and a PEG lipid.

In embodiments, the pharmaceutical composition is formulated for parenteral administration. In embodiments, the pharmaceutical composition is formulated for topical, dermal, intradermal, intramuscular, intraperitoneal, intraarticular, intravenous, subcutaneous, intraarterial or transdermal administration. In embodiments, the pharmaceutical composition is formulated for topical administration.

In aspects, the present disclosure provides a pharmaceutical composition comprising a pharmaceutically acceptable excipient or carrier, and the chimeric protein of any one of the embodiments disclosed herein, the isolated polynucleotide of any one of the embodiments disclosed herein, the vector of the embodiments disclosed herein, or the host cell of any of the embodiments disclosed herein. In embodiments, the pharmaceutical composition comprises the nucleic acid, e.g., the mmRNA of any one of the embodiments disclosed herein.

In embodiments, the isolated polynucleotide is conjugated polynucleotide sequence that is introduced into cells by various transfection methods such as, e.g., methods that employ lipid particles. In embodiments, a composition, including a gene transfer construct, comprises a delivery particle. In embodiments, the delivery particle comprises a lipid-based particle (e.g., a lipid nanoparticle (LNP)), cationic lipid, or a biodegradable polymer). Lipid nanoparticle (LNP) delivery of gene transfer construct provides certain advantages, including transient, non-integrating expression to limit potential off-target events and immune responses, and efficient delivery with the capacity to transport large cargos. LNPs have been used for delivery of small interfering RNA (siRNA) and mRNA, and for in vitro and in vivo delivering CRISPR/Cas9 components to hepatocytes and the liver. For example, U.S. Pat. No. 10,195,291 describes the use of LNPs for delivery of RNA interference (RNAi) therapeutic agents.

In embodiments, the composition in accordance with embodiments of the present disclosure is in the form of a LNP. In embodiments, the LNP comprises one or more lipids selected from 1,2-dioleoyl-3-trimethylammonium propane (DOTAP); N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB), a cationic cholesterol derivative mixed with dimethylaminoethane-carbamoyl (DC-Chol), phosphatidylcholine (PC), triolein (glyceryl trioleate), and 1,2-distearoyl-sn-glycero-3-phosphoethanolamine-N-[carboxy(polyethylene glycol)-2000] (DSPE-PEG), 1,2-dimyristoyl-rac-glycero-3-methoxypolyethyleneglycol-2000 (DMG-PEG 2K), and 1,2 distearol-sn-glycerol-3phosphocholine (DSPC).

In embodiments, the composition can have a lipid and a polymer in various ratios, wherein the lipid can be selected from, e.g., DOTAP, DC-Chol, PC, Triolein, DSPE-PEG, and wherein the polymer can be, e.g., PEI or Poly Lactic-co-Glycolic Acid (PLGA). Any other lipid and polymer can be used additionally or alternatively. In embodiments, the ratio of the lipid and the polymer is about 0.5:1, or about 1:1, or about 1:1.5, or about 1:2, or about 1:2.5, or about 1:3, or about 3:1, or about 2.5:1, or about 2:1, or about 1.5:1, or about 1:1, or about 1:0.5.

In embodiments, the LNP comprises a cationic lipid, non-limiting examples of which include N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-')amino)ethyl)(2 hydroxydodecyl)amino)ethyl) piperazin-1-yl)ethylazanediyl)didodecan-2-ol (Tech G1), 1,2-Dilinoleyloxo-3-(2-N,N-dimethylamino) ethoxypropane (DLin-EG-DMA), or a mixture thereof.

In embodiments, the LNP comprises one or more molecules selected from polyethylenimine (PEI) and poly(lactic-co-glycolic acid) (PLGA), and N-Acetylgalactosamine (GalNAc), which are suitable for hepatic delivery. In embodiments, the LNP comprises a hepatic-directed compound as described, e.g., in U.S. Pat. No. 5,985,826, which is incorporated by reference herein in its entirety. GalNAc is known to target Asialoglycoprotein Receptor (ASGPR) expressed on mammalian hepatic cells. See Hu et al. *Protein Pept Lett.* 2014; 21(10):1025-30.

In some examples, the isolated polynucleotide can be formulated or complexed with PEI or a derivative thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-tri-GAL) derivatives.

In embodiments, the lipid nanoparticles comprise lipids selected from an ionizable lipid (e.g. an ionizable cationic lipid selected from DLin-DMA, DLin-K-DMA, DLin-KC2-DMA, DLin-MC3-DMA, 98N12-5, and C12-200); a structural lipid (e.g. distearoylphosphatidylcholine (DSPC)); cholesterol, and a polyethyleneglycol (PEG)-lipid (e.g. a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the nucleic acid, e.g., the mmRNA.

In embodiments, the LNP comprises a molar ratio of about 20-60% ionizable amino lipid, about 5-25% phospholipid, about 25-55% structural lipid, and about 0.5-1.5% PEG lipid. In embodiments, the ionizable amino lipid comprises the following formula:

In embodiments, the lipid nanoparticles comprise lipids selected from an ionizable lipid; a structural lipid; cholesterol, and a polyethyleneglycol (PEG)-lipid; 1,2-dioleoyl-3-trimethylammoniumpropane (DOTAP); dioleoylphosphatidylethanolamine (DOPE); and the nucleic acid, e.g., the mmRNA. In embodiments, the ionizable lipid is an ionizable cationic lipid selected from DLin-DMA, DLin-K-DMA, DLin-KC2-DMA, DLin-MC3-DMA, 98N12-5, and C12-200. In embodiments, the polyethyleneglycol (PEG)-lipid is selected from a PEG-diacylglycerol (DAG), a PEG-dialkyloxypropyl (DAA), a PEG-phospholipid, a PEG-ceramide (Cer), or a mixture thereof, or a PEG-dilauryloxypropyl (e.g., C12, a PEG-dimyristyloxypropyl (C14), a PEG-dipalmityloxypropyl (C16), or a PEG-distearyloxypropyl (C18)).

In embodiments, the LNP is a conjugated lipid, non-limiting examples of which include a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl (C12, a PEG-dimyristyloxypropyl (C14), a PEG-dipalmityloxypropyl (C16), or a PEG-distearyloxypropyl (C18).

In embodiments, the LNP formulations may further contain a phosphate conjugate, which can increase in vivo circulation times and/or increase the targeted delivery of the nanoparticle. Phosphate conjugates can be made by the methods described in, e.g., PCT International Patent Application Publication No. WO 2013/033438 or U.S. Pub. No. US 2013/0196948. The LNP formulation can also contain a polymer conjugate (e.g., a water-soluble conjugate) as described in, e.g., U.S. Patent Application Publication Nos. US 2013/0059360, US 2013/0196948, and US 2013/0072709, each of the references is herein incorporated by reference in its entirety.

In embodiments, the LNP formulations may comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., PCT International Patent Application Publication No. WO 2012/109121, herein incorporated by reference in its entirety). In embodiments, the LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Patent Application Publication No. US 2013/0183244, herein incorporated by reference in its entirety. In embodiments, the LNP formulations can be engineered to alter the surface properties of particles so that the lipid nanoparticles can penetrate the mucosal barrier as described in U.S. Pat. No. 8,241,670 or PCT International Patent Application Publication No. WO 2013/110028, each of which is herein incorporated by reference in its entirety. In embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., PCT International Patent Application Publication No. WO 2013/110028, herein incorporated by reference in its entirety.

In embodiments, an mmRNA described herein is formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in PCT International Patent Application Publication No. WO 2013/105101, herein incorporated by reference in its entirety.

In embodiments, a nanoparticle is a particle having a diameter of less than about 1000 nm. In embodiments, nanoparticles of the present disclosure have a greatest dimension (e.g., diameter) of about 500 nm or less, or about 400 nm or less, or about 300 nm or less, or about 200 nm or less, or about 100 nm or less. In embodiments, nanoparticles of the present disclosure have a greatest dimension ranging between about 50 nm and about 150 nm, or between about 70 nm and about 130 nm, or between about 80 nm and about 120 nm, or between about 90 nm and about 110 nm. In embodiments, the nanoparticles of the present disclosure have a greatest dimension (e.g., a diameter) of about 100 nm.

In embodiments, the chimeric protein or the therapeutic nanoparticle comprising mRNA can be formulated for sustained release, which, as used herein, refers to a pharmaceutical composition or compound that conforms to a release rate over a specific period of time. In embodiments, the period of time may include, but is not limited to, hours, days, weeks, months and years. As a non-limiting example, the sustained release nanoparticle of the mRNAs described herein can be formulated as disclosed in PCT International Patent Application Publication No. WO 2010/075072 and U.S. Patent Application Publication Nos. US 2010/0216804, US 2011/0217377, US 2012/0201859 and US 2013/0150295, each of which is herein incorporated by reference in their entirety.

In embodiments, the chimeric protein or the isolated polynucleotide or mmRNA (and/or additional agents) are included various formulations. Any chimeric protein, or the isolated polynucleotide or mmRNA (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In embodiments, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

In embodiments, the present disclosure provides an expression vector, comprising a nucleic acid encoding the chimeric protein described herein. In embodiments, the expression vector comprises DNA or RNA. In embodiments, the expression vector is a mammalian expression vector.

Both prokaryotic and eukaryotic vectors can be used for expression of the chimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and APL. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the chimeric proteins in recombinant host cells.

In embodiments, expression vectors of the disclosure comprise a nucleic acid encoding the chimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, which influence expression of an operably linked nucleic acid. An expression control region of an expression vector of the disclosure is capable of expressing operably linked encoding nucleic acid in a human cell. In embodiments, the cell is a tumor cell. In embodiments, the cell is a non-tumor cell. In embodiments, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In embodiments, the present disclosure contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), FIp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of AAV (Kootstra et al., Ann. Rev. Pharm. Toxicol., 43:413-439, 2003). In addition, direct and targeted genetic integration strategies may be used to insert nucleic acid sequences encoding the chimeric proteins including CRISPR/CAS9, zinc finger, TALEN, and meganuclease gene-editing technologies.

In aspects, the disclosure provides expression vectors for the expression of the chimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (AAV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In embodiments, the disclosure provides methods of transducing a human cell in vivo, comprising contacting a solid tumor in vivo with a viral vector of the disclosure.

In embodiments, the present disclosure provides a host cell, comprising the expression vector comprising the chimeric protein described herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the chimeric proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Where necessary, the formulations comprising the chimeric protein, or the isolated polynucleotide (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the chimeric protein (and/or additional agents) of the present disclosure may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In embodiments, any chimeric protein, or the isolated polynucleotide or mmRNA (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In embodiments, the administering is effected orally or by parenteral injection. In some instances, administration results in the release of any agent described herein into the bloodstream, or alternatively, the agent is administered directly to the site of active disease.

Any chimeric protein, or the isolated polynucleotide (and/or additional agents) described herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In embodiments, the pharmaceutical composition is formulated for parenteral administration. In embodiments, the pharmaceutical composition is formulated for intradermal, intramuscular, intraperitoneal, intraarticular, intravenous, subcutaneous, intraarterial or transdermal administration.

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any chimeric protein, or the isolated polynucleotide or mmRNA (and/or additional agents) described herein as well as the dosing schedule can depend on various parameters, including, but not limited to, the disease being treated, the subject's general health, and the administering physician's discretion. Any chimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In embodiments any chimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days part, 4 days apart, 5 days apart, 6 days apart, 1 week apart, 2 weeks apart, 3 weeks apart, or 4 weeks apart.

The dosage of any chimeric protein, or the isolated polynucleotide or mmRNA (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

In embodiments, delivery can be in a vesicle, in particular a liposome (see Langer, 1990, Science 249:1527-1533; Treat et al., in *Liposomes in the Therapy of Infectious Disease and Cancer*, Lopez-Berestein and Fidler (eds.), Liss, New York, pp. 353-365 (1989).

Any chimeric protein, or the isolated polynucleotide (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In embodiments, polymeric materials can be used (see *Medical Applications of Controlled Release*, Langer and Wise (eds.), CRC Pres., Boca Raton, Florida (1974); *Controlled Drug Bioavailability Drug Product Design and Performance*, Smolen and Ball (eds.), Wiley, New York (1984); Ranger and Peppas, 1983, *J. Macromol. Sci. Rev Macromol. Chem.* 23:61; see also Levy et al., 1985, *Science* 228:190; During et al., 1989, *Ann. Neurol.* 25:351; Howard et al., 1989, *J. Neurosurg.* 71:105).

In embodiments, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein, or the isolated polynucleotide or mmRNA (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein, or the isolated polynucleotide or mmRNA (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the disclosure employed. Any chimeric protein (and/or additional agents) described herein can be administered in a single daily dose, or the total daily dosage can be administered in divided doses of two, three or four times daily. Furthermore, any chimeric protein (and/or additional agents) described herein can be administered continuously rather than intermittently throughout the dosage regimen.

Methods of Treatment or Prevention

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the chimeric protein of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the isolated polynucleotide of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the modified mRNA of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the pharmaceutical composition of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the vector of any of the embodiments disclosed herein.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering to the subject the host cell of any of the embodiments disclosed herein.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition comprising a polynucleotide encoding a chimeric protein having a general structure of: N terminus-(a)-(b)-(c)-C terminus, wherein: (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising a modified mRNA (mmRNA) encoding a chimeric protein having a general structure of: N terminus-(a)-(b)-(c)-C terminus, wherein: (A) (a) is a first domain comprising: (i) a glucagon-like peptide-1 (GLP-1) receptor agonist, or (ii) a fibroblast growth factor 19 (FGF19), FGF21 or a variant thereof, or an analog thereof; (b) is a linker adjoining the first domain and a second domain, optionally wherein the linker comprises one or more protease-cleavable polypeptide linkers, and/or a hinge-CH2-CH3 Fc domain; and (c) is the second domain comprising glucose-dependent insulinotropic polypeptide (GIP) receptor (GIPR) modulator; or (B) (a) is a second domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is a first domain comprising: (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising: (A) (a) a contiguous nucleic acid comprising a 5' translatable region encoding: (i) a glucagon-like peptide-1 (GLP-1) receptor agonist, or (ii) a fibroblast growth factor 19 (FGF19), FGF21 or a variant thereof, or an analog thereof; and (b) a contiguous nucleic acid comprising a 3' translatable region encoding glucose-dependent insulinotropic polypeptide (GIP) receptor (GIPR) modulator; or (B) (a) a contiguous nucleic acid comprising a 5' translatable region encoding a glucose-dependent insulinotropic polypeptide (GIP) receptor (GIPR) modulator; and (b) a contiguous nucleic acid comprising a 3' translatable region encoding: (i) a glucagon-like peptide-1 (GLP-1) receptor agonist, or (ii) a fibroblast growth factor 19 (FGF19), FGF21 or a variant thereof, or an analog thereof, wherein the 5' translatable region and the 3' translatable region are adjoined by an in-frame linker, optionally wherein the linker encodes one or more protease-cleavable polypeptide linkers, and/or a hinge-CH2-CH3 Fc domain.

In embodiments, the GLP-1 receptor agonist is selected from GLP-1, a DPP4 degradation resistant derivative of GLP-1, exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77, 91, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion.

In embodiments, the fibroblast growth factor comprises FGF19, or an analog thereof. In embodiments, the analog of FGF19 is aldafermin (NGM282). In embodiments, the fibroblast growth factor is capable of activating FGFR4, optionally wherein the activating requires R-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence of SEQ ID NOs: 78 or 79.

In embodiments, the fibroblast growth factor comprises FGF21, or an analog thereof. In embodiments, the analog of FGF21 is selected from efruxifermin, LY2405319, FGF21 (RGE) and FGF21 (L146P). In embodiments, the fibroblast growth factor is capable of activating FGFR1c, optionally wherein the activating requires β-Klotho as a coreceptor. In embodiments, the fibroblast growth factor comprises an amino acid sequence that is at least about 90%, or at least about 95%, or at least about 97%, or at least about 98%, or at least about 99% identical to an amino acid sequence selected from SEQ ID NOs: 80-85.

In embodiments, the GIPR modulator comprises GIP (SEQ ID NO: 68), or a variant or analog thereof. In embodiments, the analog of GIP has an amino acid sequence that is selected from the amino acid sequence of SEQ ID NO: 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the GIPR modulator is capable of binding a GIP receptor (GIPR). In embodiments, the GIPR modulator is capable of activating the GIPR. In embodiments, the GIPR modulator is capable of inhibiting the GIPR. In embodiments, the GIPR modulator is capable of modulating the GIPR on the surface of the endocrine pancreas. In embodiments, the GIPR modulator is capable of activating the hypothalamic GIPR. In embodiments, the GIPR modulator comprises an amino acid sequence selected from the amino acid sequence of SEQ ID NOs: 68 or 74 or a variant or an analog thereof having about 1, 2, 3, 4, 5, 6, 7, 8, 9, or 10 or more amino acid mutations independently selected from substitutions, insertions, deletions, and truncations.

In embodiments, the linker comprises a protease-cleavable polypeptide linker. In embodiments, the protease-cleavable polypeptide linkers are cleavable by a protease, wherein the protease is endogenous to a mammalian liver, skin, and/or muscle. In embodiments, the protease is selected from caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain. In embodiments, the protease-cleavable polypeptide linker is N- or C-terminal to the first domain comprising a glucagon-like peptide-1 (GLP-1) receptor agonist. In embodiments, the protease-cleavable polypeptide linker is N- or C-terminal to the first domain comprising a fibroblast growth factor 19 (FGF19), FGF21 or a variant thereof, or an analog thereof. In embodiments, the protease-cleavable polypeptide linker is N- or C-terminal to the second domain comprising glucose-dependent insulinotropic polypeptide (GIP) receptor (GIPR) modulator. In embodiments, the chimeric protein comprises two protease-cleavable polypeptide linkers, such protease-cleavable polypeptide linker independently selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the first protease-cleavable polypeptide linker is C terminal to the first domain and the second domain is protease-cleavable polypeptide linker is N terminal to the second domain.

In embodiments, the hinge-CH2-CH3 Fc domain is derived from IgG1. In embodiments, the IgG1 is human IgG1. In embodiments, the hinge-CH2-CH3 Fc domain is derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113. In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In embodiments, the nucleic acid is a modified mRNA (mmRNA) or mRNA a DNA. In embodiments, the nucleic acid is an mmRNA comprising one or more nucleoside modifications, optionally wherein the mmRNA comprises one or more of 1-methylpseudouridine nucleotides. In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thiopseudouridine, 5-aza-cytidine, pseudoisocytidine, 3-methylcytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof. In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127. In embodiments, the mmRNA further comprises 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) or 3' UTR_6 (SEQ ID NO: 119); 5' UTR_14 (SEQ ID NO: 141) and 3' UTR_10 (SEQ ID NO: 123).

In embodiments, the pharmaceutical composition further comprises a pharmaceutically acceptable carrier. In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNPs), a lipoplex, or a liposome. In embodiments, the pharmaceutical composition is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA. In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising: (i) providing a target cell capable of protein translation, and (ii) introducing into the target cell the target cell the pharmaceutical composition of any of the embodiments disclosed herein.

In embodiments, the target cell is a in vivo cell. In embodiments, the target cell is a muscle, skin or liver cell. In embodiments, the target cell is an in vitro cell extracted from the subject. In embodiments, the target cell is a blood cell, skin cell, or liver cell extracted from the subject. In embodiments, the method further comprises culturing the cell in vitro. In embodiments, the method further comprises administering the cell to the subject.

In aspects, the present disclosure provides a pharmaceutical composition comprising the mmRNA of any of the embodiments disclosed herein, and a pharmaceutically acceptable carrier. In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the pharmaceutical composition is formulated as a lipid nanoparticle (LNPs), a lipoplex, or a liposome. In embodiments, the pharmaceutical composition is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA. In embodiments, the lipid nanoparticles comprise (a) a cationic lipid comprising from 50 mol % to 85 mol % of the total lipid present in the particle;

(b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In embodiments, the pharmaceutical composition is formulated for parenteral administration. In embodiments, the pharmaceutical composition is formulated for intradermal, intramuscular, intraperitoneal, intraarticular, intravenous, subcutaneous, intraarterial or transdermal administration.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition comprising a polynucleotide any one of the embodiments disclosed herein encoding a chimeric protein of any one of the embodiments disclosed herein.

In embodiments, the subject selected for the treatment with the compositions comprising the chimeric protein disclosed herein or the polynucleotides encoding the chimeric protein disclosed herein based on diagnosis symptoms selected from one or more of the subject suffers from one or more symptoms selected from increased urination, increased thirst, increased hunger, increased food intake, increased weight, obesity, weight loss, blurry vision, numbing or tingling hands or feet, very dry skin, increased infections, and diabetic sores. In embodiments, the subject is asymptomatic. In embodiments, the patient has type 1 diabetes. In embodiments, the patient has type 2 diabetes. In embodiments, the patient has gestational diabetes or steroid-induced diabetes.

In embodiments, the chimeric protein disclosed herein or the polynucleotides encoding the chimeric protein disclosed herein is administered to a patient that has an elevated portion of hemoglobin proteins that are glycated, known as the hemoglobin A1c percentage. Normal, in range, A1C percentage is less than about 5.7%. In embodiments, the elevated hemoglobin A1c percentage is one or more of an average hemoglobin A1c percentage value of more than about 5.7%, or more than about 6%, or more than about 6.4%, or more than about 7%, or more than about 8%, or more than about 9%, or more than about 10%, or more than about 11%, or more than about 12%, or more than about 13%, or more than about 14%, or more than about 15%) at the start of treatment with conventional diabetic therapy. In embodiments, the chimeric protein disclosed herein or the polynucleotides encoding the chimeric protein disclosed herein is administered to a patient that has an average glucose of more than about 200 mg/dl, or more than about 210 mg/dl, or more than about 220 mg/dl, or more than about 230 mg/dl, or more than about 240 mg/dl, or more than about 250 mg/dl at the start of treatment with conventional diabetic therapy. In various embodiments, the conventional diabetic therapy is any one of those described herein, including, for example, insulin therapy and non-insulin diabetes agent therapy.

In embodiments, the treatment comprises one or more of a decrease of the blood glucose level, stimulation of peripheral glucose disposal, and inhibition of hepatic glucose production. These biological activities can be assayed in vitro using known methodologies. For example, the effect of the chimeric protein disclosed herein or the polynucleotides encoding the chimeric protein disclosed herein on glucose uptake in 3T3-L1 adipocytes can be measured and compared with that of insulin. Pretreatment of the cells with a biologically active analog may generally produce a dose-dependent increase in 2-deoxyglucose uptake. The ability of the chimeric protein disclosed herein or the polynucleotides encoding the chimeric protein disclosed herein to regulate glucose production may be measured in any number of cell types, for example, H4IIE hepatoma cells. In this assay, pretreatment with a biologically active analog may generally result in a dose-dependent inhibition of the amount of glucose released.

In embodiments, the chimeric protein disclosed herein or the polynucleotides encoding the chimeric protein disclosed herein is administered as an anti-diabetic regimen that decreases blood glucose levels; stimulates peripheral glucose disposal; and/or inhibits hepatic glucose production. In embodiments, the treatment regimen comprises administering the chimeric protein disclosed herein or the polynucleotides encoding the chimeric protein disclosed herein on an insulin-like regimen. For example, in embodiments, the chimeric protein disclosed herein or the polynucleotides encoding the chimeric protein disclosed herein is administered once in the morning or the evening (e.g., at bedtime), or in a twice-daily regimen (e.g., pre-breakfast and pre-evening meal, or as a continuous administration (e.g., analogously to administration of insulin via an insulin pump).

In embodiments, the chimeric protein disclosed herein or the polynucleotides encoding the chimeric protein disclosed herein administration is effective for providing glycemic control. Glycemic control refers to the typical levels of blood sugar (glucose) in a person with diabetes mellitus. Many of the long-term complications of diabetes, including microvascular complications, result from many years of hyperglycemia. Good glycemic control is an important goal of diabetes care. Because blood sugar levels fluctuate throughout the day and glucose records are imperfect indicators of these changes, the percentage of hemoglobin which is glycosylated is used as a proxy measure of long-term glycemic control in research trials and clinical care of people with diabetes. In this test, the hemoglobin A1c or glycosylated hemoglobin reflects average glucose values over the preceding 2-3 months. In non-diabetic persons with normal glucose metabolism glycosylated hemoglobin levels are usually about 4-6% by the most common methods (normal ranges may vary by method). "Perfect glycemic control" indicates that glucose levels are always normal (e.g., about 70-130 mg/dl, or about 3.9-7.2 mmol/L) and indistinguishable from a person without diabetes. In reality, because of the imperfections of treatment measures, even "good glycemic control" describes blood glucose levels that average somewhat higher than normal much of the time. It is noted that what is considered "good glycemic control" varies by age and susceptibility of the patient to hypoglycemia. The American Diabetes Association has advocated for patients and physicians to strive for average glucose and hemoglobin A1c values below 200 mg/dl (11 mmol/I) and 8%. "Poor glycemic control" refers to persistently elevated blood glucose and glycosylated hemoglobin levels, which may range from, e.g., about 200-500 mg/dl (about 11-28 mmol/L, e.g., about 200 mg/dl, or about 250 mg/dl, or about 300 mg/dl, or about 350 mg/dl, or about 400 mg/dl, or about 450 mg/dl, or about 500 mg/dl) and about 9-15% (e.g., about 9%, or about 10%, or about 11%, or about 12%, or about 13%, or about 14%, or about 15%) or higher over months and years before severe complications occur. In some aspects, the present disclosure provides for methods of treatment comprising administering the chimeric protein disclosed herein or the polynucleotides encoding the chimeric protein disclosed herein and/or uses of the chimeric protein disclosed herein or the polynucleotides encoding the chimeric protein disclosed herein in the treatment of or manufacture of a medicament for diabetes and/or glucose intolerance. In embodiments, the present disclosure provides for methods treating diabetes, prediabetes, and/or glucose intolerance, comprising administering an effective amount of the chimeric protein disclosed herein or the polynucleotides encoding the chimeric protein disclosed herein to a patient that suffers from poor glycemic control. In embodiments, the chimeric protein disclosed herein or the polynucleotides encoding the chimeric protein disclosed herein administration is effective for providing an average glucose of below about 200 mg/dl (11 mmol/l). In embodiments, the chimeric protein disclosed herein or the polynucleotides encoding the chimeric protein disclosed herein administration is effective for providing an average glucose of below about 190 mg/dl, or about 180 mg/dl, or about 170 mg/dl, or about 160 mg/dl, or about 150 mg/dl, or about 140 mg/dl, or about 130 mg/dl, or about 120 mg/dl, or about 120 mg/dl, or about 110 mg/dl, or about 100 mg/dl, or about 90 mg/dl, or about 80 mg/dl, or about 70 mg/dl. In embodiments, the chimeric protein disclosed herein or the polynucleotides encoding the chimeric protein disclosed herein administration is effective for providing an average glycosylated hemoglobin levels (hemoglobin A1c) value of about 8%, or about 7%, or about 6%, or about 5%, or about 4%. In embodiments, the chimeric protein disclosed herein or the polynucleotides encoding the chimeric protein disclosed herein administration is effective for providing average glycosylated hemoglobin levels (hemoglobin A1c) values of less than about 8%, or less than about 7%, or less than about 6%, or less than about 5%, or less than about 4%.

In various embodiments, the chimeric protein disclosed herein or the polynucleotides encoding the chimeric protein disclosed herein administration does not cause a patient to experience an increase of insulin upon the administration of the chimeric protein disclosed herein or the polynucleotides encoding the chimeric protein disclosed herein administration. Accordingly, in embodiments, the anti-diabetic effects of the chimeric protein disclosed herein or the polynucleotides encoding the chimeric protein disclosed herein administration are insulin-independent.

In various embodiments, the patient is undergoing treatment with one or more of insulin or an insulin analog. In embodiments, the insulin analog is selected from a rapid acting (e.g., ispro, aspart and glulisine) or a long acting (e.g., glargine or detemir) insulin analog.

In various embodiments, the chimeric protein disclosed herein or the polynucleotides encoding the chimeric protein disclosed herein is administered as an adjuvant therapy. For instance, a diabetic patient may receive treatment with insulin or an insulin analog, or any of the agents listed herein (e.g., sulfonylureas, biguanides, meglitinides, thiazolidinediones, DPP-4 inhibitors, SGLT2 Inhibitors, Alpha-glucosidase inhibitors, and bile acid sequestrants) and the chimeric protein disclosed herein or the polynucleotides encoding the chimeric protein disclosed herein is administered to supplement these treatments. For example, in embodiments, the chimeric protein disclosed herein or the polynucleotides encoding the chimeric protein disclosed herein use an adjuvant therapy with a long-acting insulin offsets the high frequency of hypo- and hyperglycemic excursions and modest reduction in HbA1c seen with these agents.

Further, in embodiments, the chimeric protein disclosed herein or the polynucleotides encoding the chimeric protein disclosed herein administration provides a sustained anti-diabetic effect relative to insulin. There are two phases of insulin release in response to a rise in glucose. The first is an immediate release of insulin. This is attributable to the release of preformed insulin, which is stored in secretory granules. After a short delay, there is a second, more prolonged release of newly synthesized insulin. Once released, insulin is active for only a brief time before it is degraded by enzymes. Insulinase found in the liver and kidneys breaks down insulin circulating in the plasma, and as a result, insulin has a half-life of only about 2-5 minutes. This short duration of action results in rapid changes in the circulating levels of insulin. In embodiments, the chimeric protein disclosed herein or the polynucleotides encoding the chimeric protein disclosed herein solves this short duration of insulin problem by providing a substitute therapy for a diabetes patient.

Furthermore, insulin often multimerizes into dimers and hexamers, which slows its effect and/or reduces the amount of bioavailable agent. In embodiments, the chimeric protein disclosed herein or the polynucleotides encoding the chimeric protein disclosed herein solves this problem by providing a substitute therapy for a diabetes patient.

Furthermore, the chimeric protein disclosed herein or the polynucleotides encoding the chimeric protein disclosed herein may be administered orally to diabetic patients and therefore improves patient quality of life/therapeutic adherence relative to injectable insulin regimens.

Further still, in embodiments, the chimeric protein disclosed herein or the polynucleotides encoding the chimeric protein disclosed herein administration does not cause one or more of common side effects of standard diabetes care, such as hypoglycemia or hypokalemia.

In various aspects, the present methods provide for the treatment of diabetes with the chimeric protein disclosed herein or the polynucleotides encoding the chimeric protein disclosed herein in specific patient populations in need thereof. For example, in various embodiments, the chimeric protein disclosed herein or the polynucleotides encoding the chimeric protein disclosed herein may supplement various agents in a treatment regimen for diabetes, including type 1 or type 2 diabetes, or may supplant various agents in a treatment regimen for diabetes, including type 1 or type 2 diabetes. For example, in embodiments, the chimeric protein disclosed herein or the polynucleotides encoding the chimeric protein disclosed herein is an adjuvant therapy for type 1 or type 2 diabetes.

Type 1 diabetes, once known as juvenile diabetes or insulin-dependent diabetes, is a chronic condition in which the pancreas produces little or no insulin. Treatment is often via intensive insulin regimens, which attempt to mimic the body's normal pattern of insulin secretion, and often involve basal and bolus insulin coverage. For example, one common regimen is the administration of a long-acting insulin (as described herein and including, for example, glargine/detemir) once or twice a day with rapid acting insulin (as described herein and including, for example, aspart, glulisine, lispro) preprandially or postprandially and as needed to correct high blood sugars (as monitored by a glucose meter, for example). Doses administered preprandially or postprandially or as needed to correct high blood sugars may be referred to as bolus administrations. Another common regimen involves dosing, including continuous dosing, via an insulin pump (or continuous subcutaneous insulin infusion device (CSII)) of, for example a rapid acting insulin (as described herein and including, for example, aspart, glulisine, lispro). In various embodiments, the chimeric protein disclosed herein or the polynucleotides encoding the chimeric protein disclosed herein may replace any of the insulins used in various regimens, including instances in which the insulins are not providing effective therapy in the patient. The chimeric protein disclosed herein or the polynucleotides encoding the chimeric protein disclosed herein may cause an increase in patient compliance as it may allow for easier self-dosing relative to various forms of insulin, which must be administered as various doses throughout the day even in the context of an insulin pump, which requires programming. Further, the chimeric protein disclosed herein or the polynucleotides encoding the chimeric protein disclosed herein can offset common frustration of diabetic patient dosing, such as, for example, the dawn phenomenon. Alternatively, the chimeric protein disclosed herein or the polynucleotides encoding the chimeric protein disclosed herein may be used adjuvant to any of the type 1 diabetes treatments described herein to, for example, normalize a patient's regimen and avoid blood sugar "dips" (e.g., hypoglycemia, e.g., blood sugar of below about 70 mg/dL) and "spikes" (e.g., hyperglycemia, e.g., blood sugar of below about 200 mg/dL) that afflict many patients. Accordingly, In embodiments, the chimeric protein disclosed herein or the polynucleotides encoding the chimeric protein disclosed herein may treat or prevent symptoms associated with hypoglycemia, including for example, shakiness, anxiety, nervousness, palpitations, tachycardia, pallor, coldness, clamminess, dilated pupils (mydriasis), hunger, borborygmus, nausea, vomiting, abdominal discomfort, headache, abnormal mentation, impaired judgment, nonspecific dysphoria, paresthesia, negativism, irritability, belligerence, combativeness, rage, personality change, emotional lability, fatigue, weakness, apathy, lethargy, daydreaming, sleep, confusion, amnesia, lightheadedness or dizziness, delirium, staring, "glassy" look, blurred vision, double vision, flashes of light in the field of vision, automatism, difficulty speaking, slurred speech, ataxia, incoordination, focal or general motor deficit, paralysis, hemiparesis, paresthesia, headache, stupor, coma, abnormal breathing, generalized or focal seizures, memory loss, and amnesia. Accordingly, In embodiments, the chimeric protein disclosed herein or the polynucleotides encoding the chimeric protein disclosed herein may treat or prevent symptoms associated with hyperglycemia, including for example, polyphagia, polydipsia, polyuria, blurred vision, fatigue, weight loss, poor wound healing, dry mouth, dry or itchy skin, tingling in feet or heels, erectile dysfunction, recurrent infections, external ear infections (e.g., swimmer's ear), cardiac arrhythmia, stupor, coma, and seizures. In various regimens, a type 1 diabetes may receive additional agents to supplement insulin therapy. In embodiments, the chimeric protein disclosed herein or the polynucleotides encoding the chimeric protein disclosed herein are used in this manner. The chimeric protein disclosed herein or the polynucleotides encoding the chimeric protein disclosed herein may provide additional therapeutic benefits in patients that are struggling to manage type 1 diabetes with insulin therapy alone. In embodiments, patients that are struggling to manage type 1 diabetes with insulin therapy alone have poor glycemic control as described herein.

Patients with type 2 diabetes may be instructed to manage their diabetes with healthy eating and exercise. However, certain non-insulin diabetes agents (e.g., selected from metformin (e.g., GLUCOPHAGE, GLUMETZA); sulfonylureas (e.g., glyburide (e.g., DIABETA, GLYNASE), glipizide (e.g., GLUCOTROL) and glimepiride (e.g., AMARYL)); thiazolidinediones (e.g., rosiglitazone (e.g., AVANDIA) and pioglitazone (e.g., ACTOS)); DPP-4 inhibitors (e.g., sitagliptin (e.g., JANUVIA), saxagliptin (e.g., ONGLYZA) and linagliptin (e.g., TRADJENTA)); GLP-1 receptor agonists (e.g., exenatide (e.g., BYETTA) and liraglutide (e.g., VICTOZA)); and SGLT2 inhibitors (e.g., canagliflozin (e.g., NVOKANA) and dapagliflozin (e.g., FARXIGA))) and/or insulin may be used in treatment. For example, certain patients may be able to manage diabetes with diet and exercise alone (e.g., along with glucose monitoring). However, often this is not the case and therapeutic agents are needed. A first line of treatment may be a non-insulin diabetes agent (e.g., selected from metformin (e.g., GLUCOPHAGE, GLUMETZA); sulfonylureas (e.g., glyburide (e.g., DIABETA, GLYNASE), glipizide (e.g., GLUCOTROL) and glimepiride (e.g., AMARYL)); thiazolidinediones (e.g., rosiglitazone (e.g., AVANDIA) and pioglitazone (e.g., ACTOS)); DPP-4 inhibitors (e.g., sitagliptin (e.g., JANUVIA), saxagliptin (e.g., ONGLYZA) and linagliptin (e.g., TRADJENTA)); GLP-1 receptor agonists (e.g., exenatide (e.g., BYETTA) and liraglutide (e.g., VICTOZA)); and SGLT2 inhibitors (e.g., canagliflozin (e.g., NVOKANA) and dapagliflozin (e.g., FARXIGA)). However, some of these agents provide side effects (e.g., in the case of metformin, abdominal or stomach discomfort, cough or hoarseness, decreased appetite, diarrhea, fast or shallow breathing, fever or chills, general feeling of discomfort, lower back or side pain, muscle pain or cramping, painful or difficult urination, and sleepiness) or negative drug interactions (e.g., in the case of metformin, certain imaging and contrast agents). In embodiments, the chimeric protein disclosed herein or the polynucleotides encoding the chimeric protein disclosed herein are used instead of a non-insulin diabetes agent or in combination with one or more non-insulin diabetes agents (e.g., to lower the dose of the non-insulin diabetes agents and increase their therapeutic windows). In embodiments, the chimeric protein disclosed herein or the polynucleotides encoding the chimeric protein disclosed herein is used to improve an ineffective treatment regimen. In certain embodiments, the chimeric protein disclosed herein or the polynucleotides encoding the chimeric protein disclosed herein increase patient compliance and increase the likelihood of effective type 2 diabetes management. In certain embodiments, the chimeric protein disclosed herein or the polynucleotides encoding the chimeric protein disclosed herein replaces a non-insulin diabetes agent in a patient's treatment regimen in a patient whose diabetes is not well-managed by a non-insulin diabetes agent (e.g., those having uncontrolled, cardiovascular complications and/or blood glucose levels). In embodiments, a patient whose diabetes is not well-managed by a non-insulin diabetes agent has poor glycemic control as described herein.

In some type 2 diabetes patients, diet and exercise and/or non-insulin diabetes agents are insufficient for treatment of diabetes and treatment with insulin therapy is needed. In various embodiments, the chimeric protein disclosed herein or the polynucleotides encoding the chimeric protein disclosed herein may prevent the need to turn to insulin therapy in type 2 diabetes patients or reduce the amount (e.g., frequency of administration) of insulin therapy in type 2 diabetes patients. For example, the chimeric protein disclosed herein or the polynucleotides encoding the chimeric protein disclosed herein may be used in certain type 2 diabetes patient populations that are often at risk for needing insulin therapy, including patients afflicted having: acute infections or other serious illnesses, pregnancy, major surgery, congestive heart failure, kidney disease, liver disease, use of other drugs (e.g., prednisone and some psychiatric medications), overeating or excessive weight gain (including obesity), and progressive loss of beta cell function. In embodiments, the chimeric protein disclosed herein or the polynucleotides encoding the chimeric protein disclosed herein may be administered to patients having onset of diabetes prior to age thirty, or a duration over fifteen years to prevent the need for insulin therapy. Further, In embodiments, the chimeric protein disclosed herein or the polynucleotides encoding the chimeric protein disclosed herein is used to treat diabetes in patients at risk for uncontrolled or poorly controlled type 2 diabetes (overweight and/or obese patients, patients with high abdominal fat distribution, inactive patients, patients with a family history. of type 2 diabetes, patients of certain racial groups (e.g., blacks, Hispanics, American Indians and Asian-Americans), older patients (e.g., over the age of about 45), patients previously afflicted with gestational diabetes and/or who have birthed a baby weighing more than about 9 pounds, and patients having polycystic ovary syndrome).

In embodiments, the chimeric protein disclosed herein or the polynucleotides encoding the chimeric protein disclosed herein is used to treat type 2 diabetes patients that have uncontrolled or poorly controlled type 2 diabetes and are facing a nontraumatic lower extremity amputation (LEA). In embodiments, the chimeric protein disclosed herein or the polynucleotides encoding the chimeric protein disclosed herein is used to treat type 2 diabetes patients that have uncontrolled or poorly controlled type 2 diabetes and have some degree of vision loss and/or blindness (by way of non-limiting example, diabetic retinopathy, which may include one or more of non-proliferative diabetic retinopathy (including, for example, treating microaneurysms) and proliferative diabetic retinopathy (including, for example, treating vitreous, clouding vision, detachment of the retina and glaucoma). In embodiments, the determination of whether a patient is afflicted with or has a high risk for some degree of vision loss and/or blindness comprises diagnostic methods known in the art (e.g., ophthalmoscopy, fluorescein angiography). In embodiments, the chimeric protein disclosed herein or the polynucleotides encoding the chimeric protein disclosed herein is used to treat type 2 diabetes patients that have uncontrolled or poorly controlled type 2 diabetes and have end-stage renal disease (including, for example, end-stage renal disease).

In some aspects the present disclosure relates to a method for treating diabetes and/or prediabetes, glucose intolerance, comprising administering an effective amount of the chimeric protein disclosed herein or the polynucleotides encoding the chimeric protein disclosed herein to a patient in need thereof, wherein the patient is not receiving insulin therapy, optionally comprising treatment with one or more of insulin or an insulin analog. In embodiments, the patient is not receiving one or more of basal, pre-prandial, and postprandial insulin therapy. In embodiments, the patient is not receiving basal insulin therapy but is receiving pre-prandial or postprandial insulin therapy. For example, in embodiments, a patient does not receive basal insulin therapy but is receiving pre-prandial or postprandial insulin therapy and the basal insulin is replaced with the chimeric protein disclosed herein or the polynucleotides encoding the chimeric protein disclosed herein. Such patients, in embodiments, are those that present with at least a partial level of insulin resistance and/or those whose diabetes is not sufficiently controlled with basal insulin therapy. In embodiments, the patient is not receiving preprandial or postprandial insulin therapy but is receiving basal insulin therapy. For example, In embodiments, a patient does not receive preprandial or postprandial insulin therapy but is receiving basal insulin therapy and the preprandial or postprandial insulin therapy is replaced with the chimeric protein disclosed herein or the polynucleotides encoding the chimeric protein disclosed herein. Such patients, in embodiments, are those whose diabetes is not sufficiently controlled with preprandial or postprandial insulin therapy (e.g., experiencing bouts of hypoglycemia and/or hyperglycemia). In embodiments, the patient has not received insulin therapy in up to about 1 hour, or up to about 2 hours, or up to about 3 hours, or up to about 4 hours, or up to about 5 hours, or up to about 6 hours, or up to about 7 hours, or up to about 8 hours, or up to about 12 hours or up to about 16 hours or up to about 20 hours, or up to about 24 hours, up to about 2 days, up to about 3 days, up to about 4 days, up to about 5 days, up to about 6 days, up to about 7 days.

In embodiments, the chimeric protein disclosed herein or the polynucleotides encoding the chimeric protein disclosed herein supplants insulin in the treatment of type 1 or type 2 diabetes. In embodiments, the chimeric protein disclosed herein or the polynucleotides encoding the chimeric protein disclosed herein is used as an insulin replacement therapy. In various embodiments, the patient has experienced one or more instances of lipodystrophy that is caused by injection (e.g., injection of insulin). In embodiments, the patient is afflicted with or is at risk of having hypokalemia. In embodiments, the patient is afflicted with or is at risk of having an insulin allergy or allergy to a an agent, such as zinc, commonly used to formulate insulin (e.g., a patient having or who has previously had an immediate hypersensitive reaction upon insulin injection (e.g., injection site swelling, redness and/or itching; local tender subcutaneous nodules which develop about 0.5 to about 6 hours after an insulin injection; inflammation of the lymph glands, a serum sickness reaction and arthralagia).

In embodiments, the patient is also receiving one or more non-insulin diabetes agents selected from metformin (e.g., GLUCOPHAGE, GLUMETZA); sulfonylureas (e.g., glyburide (e.g., DIABETA, GLYNASE), glipizide (e.g., GLUCOTROL) and glimepiride (e.g., AMARYL)); thiazolidinediones (e.g., rosiglitazone (e.g., AVANDIA) and pioglitazone (e.g., ACTOS)); DPP-4 inhibitors (e.g., sitagliptin (e.g., JANUVIA), saxagliptin (e.g., ONGLYZA) and linagliptin (e.g., TRADJENTA)); GLP-1 receptor agonists (e.g., exenatide (e.g., BYETTA) and liraglutide (e.g., VICTOZA)); and SGLT2 inhibitors (e.g., canagliflozin (e.g., NVOKANA) and dapagliflozin (e.g., FARXIGA)).

In embodiments, the patient is not receiving one or more non-insulin diabetes agents selected from metformin (e.g., GLUCOPHAGE, GLUMETZA); Sulfonylureas (e.g., glyburide (e.g., DIABETA, GLYNASE), glipizide (e.g., GLUCOTROL) and glimepiride (e.g., AMARYL)); thiazolidinediones (e.g., rosiglitazone (e.g., AVANDIA) and pioglitazone (e.g., ACTOS)); DPP-4 inhibitors (e.g., sitagliptin (e.g., JANUVIA), saxagliptin (e.g., ONGLYZA) and linagliptin (e.g., TRADJENTA)); GLP-1 receptor agonists (e.g., exenatide (e.g., BYETTA) and liraglutide (e.g., VICTOZA)); and SGLT2 inhibitors (e.g., canagliflozin (e.g., NVOKANA) and dapagliflozin (e.g., FARXIGA)).

For example, insulin has negative interactions with thiazolidinediones (e.g., rosiglitazone (e.g., AVANDIA) and pioglitazone (e.g., ACTOS)), including, by way of illustration, adipogenesis and fluid retention. In embodiments, the chimeric protein disclosed herein or the polynucleotides encoding the chimeric protein disclosed herein is used in place of insulin to treat a patient with type 2 diabetes with one or more thiazolidinediones (e.g., rosiglitazone (e.g., AVANDIA) and pioglitazone (e.g., ACTOS)). Also, beta-blocker medications (such as, for example, metoprolol, propranolol, glaucoma eye drops, such as timolol) may prevent symptoms indicative of hypoglycemia (e.g., heartbeat) when used with insulin and therefore stifle quick treatment response to hypoglycemia. In embodiments, the chimeric protein disclosed herein or the polynucleotides encoding the chimeric protein disclosed herein is used in patients that are being treated with beta-blocker medications (such as, for example, metoprolol, propranolol, glaucoma eye drops, such as timolol) and, optionally, are experiencing have experienced a substantial number of hypoglycemic symptoms.

In some aspects the present disclosure provides a method for treating type 1 or type 2 diabetes, prediabetes, and/or glucose intolerance, comprising administering an effective amount of the chimeric protein disclosed herein or the polynucleotides encoding the chimeric protein disclosed herein to a patient in need thereof, wherein the chimeric protein disclosed herein or the polynucleotides encoding the chimeric protein disclosed herein stimulates glucose uptake in the patient. In embodiments, the glucose uptake in mediated by glucose transporter type 4 (GLUT4). In embodiments, the glucose uptake is in muscle or fat cells.

In some aspects the present disclosure provides a method for treating type 1 or type 2 diabetes, comprising administering an effective amount of the chimeric protein disclosed herein or the polynucleotides encoding the chimeric protein disclosed herein to a patient in need thereof, wherein the patient is afflicted with or has a high risk for a vascular disease.

In embodiments, the vascular disease is selected from stroke, deep vein thrombosis (DVT), myocardial infarction, coronary artery disease, cerebrovascular disease, peripheral arterial disease, diabetic retinopathy, atrial fibrillation, congestive heart failure, acute coronary syndrome (e.g., Unstable Angina/Non St-Elevation Myocardial Infarction (UA/NSTEMI)), stroke, pulmonary embolism, ischemic complications of peripheral vascular disease, atherosclerosis, and small vessel pathology. Often, aspirin or clopidogrel may be administered to a diabetic patient that is afflicted with or has a high risk for a vascular disease. However, certain patient populations are not suited for treatment with aspirin or clopidogrel because of, for example, various side effects to which they are susceptible or through various "resistance" presentations. In embodiments, the chimeric protein disclosed herein or the polynucleotides encoding the chimeric protein disclosed herein is used in a method of treating type 1 or type 2 diabetes in a patient that is afflicted with or has a high risk for a vascular disease and is not suited for treatment with aspirin or clopidogrel; for example, the patient presents with one or more of an aspirin allergy, asthma related to aspirin, bleeding or clotting disorder, bleeding tendency, anticoagulant therapy, recent gastrointestinal bleeding, and clinically active hepatic disease and/or the patient is less than about 21 years old and/or is a high risk for risk of Reye's syndrome. In embodiments, the determination of whether a patient is afflicted with or has a high risk for is afflicted with or has a high risk for a vascular disease comprises diagnostic methods known in the art (e.g., exercise treadmill testing, ECG stress testing, ankle/brachial index (ABI), duplex ultrasound, and various blood tests to measure, for example, cholesterol levels as well as the levels of other blood lipids).

In embodiments, one may determine whether a type 1 or type 2 diabetes has a high risk for a vascular disease by testing for expression of an early marker of vascular disease in a patient blood sample. In certain embodiments, the early marker is one or more of C-reactive peptide, myeloperoxidase, metalloproteinase-9, soluble CD40 ligand, pregnancy-associated plasma protein A, choline, ischemia-modified albumin, unbound free fatty acids, glycogen phosphorylase isoenzyme BB, placental growth factor and brain natriuretic peptide (BNP).

In some aspects the present disclosure provides a method for treating type 1 or type 2 diabetes, comprising administering an effective amount of the chimeric protein disclosed herein or the polynucleotides encoding the chimeric protein disclosed herein to a patient in need thereof, wherein the patient is afflicted with diabetes and has a high risk for cardiovascular disease or cardiovascular events. In embodiments, the high risk of cardiovascular disease or cardiovascular events is characterized by one or more of an age of greater than about 40 years, smoking, and a family history of cardiovascular disease, hypertension, dyslipidemia, albuminuria, history of myocardial infarction, vascular bypass procedure, stroke or transient ischemic attack, peripheral vascular disease, claudication, and/or angina.

Platelets, play a key role in atherogenesis, and its thrombotic complications and measures, which may lead to blockade of one or multiple pathways modulating platelet activation and aggregation processes, are pivotal in reducing ischemic risk in diabetic subjects. In some aspects the present disclosure provides a method for treating type 1 or type 2 diabetes, comprising administering an effective amount of the chimeric protein disclosed herein or the polynucleotides encoding the chimeric protein disclosed herein to a patient in need thereof, wherein the patient is afflicted with or has a high risk for a platelet dysfunction.

In embodiments, the platelet dysfunction is one or more of platelet hyperreactivity, increased baseline activation and/or reactivity (e.g., aggregation, accumulation, adhesion, and/or cohesion), increased platelet counts. In embodiments, the platelet dysfunction is determined by an increase in protein or nucleic acid levels of soluble P selectin and/or CD40-ligand. In embodiments, platelet counts and/or activity is assessed by methods known in the art. By way of illustration, during Mean Platelet Component (MPC) value determination in patient blood samples, a low MPC value generally corresponds to increased platelet activation (a normal value of MPC for a healthy adult is about 25-30 g/dL. The ADVIA 120 Hematology System's platelet analysis, or other similar automated methods that use one or more of volume and density measurements to derive an accurate platelet count, as well as a platelet density value may be used. In embodiments, the platelet dysfunction is caused by insulin therapy. In embodiments, the chimeric protein disclosed herein or the polynucleotides encoding the chimeric protein disclosed herein causes a reduction in platelet numbers or activation levels. In embodiments, the type 1 or type 2 diabetic patient that is afflicted with or has a high risk for a platelet dysfunction presents with stable or unstable atherosclerotic cardiovascular disease. In embodiments, the type 1 or type 2 diabetic patient that is afflicted with or has a high risk for a platelet dysfunction may not be suited for conventional anti-platelet agents (e.g., cyclooxygenase-1

(COX-1) inhibitors (aspirin), ADP P2Y12 receptor antagonists (thienopyridines), and platelet glycoprotein (GP) IIb/IIIa inhibitors). In embodiments, the chimeric protein disclosed herein or the polynucleotides encoding the chimeric protein disclosed herein is used in place of a conventional anti-platelet agent or is used adjunctive to a conventional anti-platelet agent.

Further, insulin and clopidogrel combination therapy has been shown to increase platelet activation. In embodiments, the chimeric protein disclosed herein or the polynucleotides encoding the chimeric protein disclosed herein replace insulin in the insulin and clopidogrel combination therapy, especially in a type 1 or type 2 diabetic patient that is afflicted with or has a high risk for a platelet dysfunction.

In some aspects the present disclosure provides a method for treating type 1 or type 2 diabetes, comprising administering an effective amount of the chimeric protein disclosed herein or the polynucleotides encoding the chimeric protein disclosed herein to a patient in need thereof, wherein the patient his afflicted with or is at high risk for elevated hematocrit levels. In embodiments, the elevated hematocrit levels are about 0.35, or about 0.40, or about 0.45, or about 0.50, or about 0.55, or about 0.60. Hematocrit measurements are known in the art (e.g., centrifugation, cell counting, etc.).

In embodiments, the administration of the chimeric protein disclosed herein or the polynucleotides encoding the chimeric protein disclosed herein does not substantively change the patient's hematocrit levels.

In some aspects the present disclosure provides a method for treating type 1 or type 2 diabetes, comprising administering an effective amount of the chimeric protein disclosed herein or the polynucleotides encoding the chimeric protein disclosed herein to a patient in need thereof, wherein the patient is afflicted with or is at risk for anemia. In embodiments, the type 1 or type 2 diabetes patient has hemochromatosis and therefore, cannot be treated for anemia by conventional iron supplementation.

In a number of embodiments, including those in which that chimeric protein disclosed herein or the polynucleotides encoding the chimeric protein disclosed herein prevents diabetes and/or treats a pre-diabetic condition, a patient is at risk of diabetes if the patient is characterized by one or more of: being physically inactive; having a parent or sibling with diabetes; having a family background associated with high incidence of diabetes, selected from that is African American, Alaska Native, American Indian, Asian American, Hispanic/Latino, or Pacific Islander American; giving birth to a baby weighing more than 9 pounds; being diagnosed with gestational diabetes; having high blood pressure of about 140/90 mmHg or above; being treated for high blood pressure; having HDL cholesterol level below about 35 mg/dL and/or a triglyceride level above about 250 mg/dL; having polycystic ovary syndrome (PCOS); and having cardiovascular disease.

In some aspects the present disclosure provides methods for inducing weight loss or preventing weight gain, comprising administering an effective amount of the chimeric protein disclosed herein or the polynucleotides encoding the chimeric protein disclosed herein to a patient in need thereof; wherein the patient does not substantially change caloric intake. In some embodiments, the caloric intake is high, relative to guidelines, such as the USDA tables. In some embodiments, the patient's caloric intake is 2000-10000 calories/day, or greater than about 2000 calories/day, or about 2200 calories/day, or about 2400 calories/day, or about 2600 calories/day, or about 2800 calories/day, or about 3000 calories/day, or about 3200 calories/day, or about 3400 calories/day, or about 3600 calories/day, or about 3800 calories/day, or about 4000 calories/day, or about 5000 calories/day, or about 6000 calories/day. In various embodiments, the patient has a high caloric intake and does not gain weight or even loses weight. Therefore, the present disclosure provides for an effect without lifestyle changes that often reduce patient adherence (e.g., failed dieting). In some embodiments, the patient's caloric intake is not restricted by more than about 20%, or not by more than about 10%, or not by more than about 5% of the patient's caloric intake at the start of treatment. In some embodiments, a high proportion of the patient's caloric intake is "empty calories," i.e., calories from solid fats and/or added sugars. In some embodiments, greater than about 15%, or 20%, or 25%, or 30%, or 35%, or 50% of the patient's caloric intake is empty calories. Even in these embodiments, a patient may not gain weight or even lose weight.

In various embodiments, the patient of the present disclosure is overweight or obese. In some embodiments, the patient of the present disclosure suffers from central obesity. In some embodiments, the obesity of one of simple obesity (alimentary obesity; usually resulting from consumption of more calories than the body can utilize), secondary obesity (usually resulting from an underlying medical condition, such as, for example, Gushing's syndrome and polycystic ovary syndrome), and childhood obesity. In some embodiments, the obesity is classified as: Class I, which includes a BMI between 30 and 34.99; Class II, which includes BMIs of 35 to 39.99; and Class III, which includes a BMI of over 40. Further, the present disclosure provides for obesity of any of classes I, II, or II I that is further classified as severe, morbid, and super obesity. In some embodiments, the patient is at risk of further weight gain, as assessed by, for example, daily caloric intake, In various embodiments, the weight management/weight loss/anti-obesity effects of the chimeric protein disclosed herein or the polynucleotides encoding the chimeric protein disclosed herein can be assessed using various techniques and indices. In various embodiments, assessment before, during, and after treatment is undertaken. In some embodiments, body mass index (BMI), a measure of a person's weight taking into account height, may be used. In various embodiments, a patient described herein has a BMI that provides an "overweight" classification, i.e., 25-29.9, such as, for example, about 25, or about 25.5, or about 26, or about 26.5, or about 27, or about 27.5, or about 28, or about 28.5, or about 29, or about 29.5. In various embodiments, a patient described herein has a BMI that provides an "obese" classification, i.e., greater than 30, such as, for example, about 30, or about 31, or about 32, or about 33, or about 34, or about 35, or about 36, or about 37, or about 38, or about 39, or about 40, or about 50. In some embodiments, body volume index (BVI) is used. BVI uses 3D software to create an 3D image of a person so BVI can differentiate between people with the same BMI rating, but who have a different shape and different.

weight distribution. BVI measures where a person's weight and the fat are located on the body, rather than total weight or total fat content and places emphasis on the weight carried around the abdomen, commonly known as central obesity. In some embodiments, whole-body air displacement plethysmography (ADP) is used to assess the weight management/weight loss/anti-obesity effects of the chimeric protein disclosed herein or the polynucleotides encoding the chimeric protein disclosed herein. In some embodiments, simple weighing is used in the present disclosure. In some embodiments, skinfold calipers or "pinch test," bioelectrical impedance analysis, hydrostatic weighing, or dual-energy X-ray absorptiometry (DEXA) may be used.

In some embodiments, simple circumferential measurement of the body may be used. In some embodiments, a patient of the present disclosure has a waist circumference exceeding about 35 inches, or about 36 inches, or about 37 inches, or about 38 inches, or about 39 inches, or about 40 inches, or about 41 inches, or about 42 inches, or about 43 inches, or about 44 inches, or about 45 inches, or about 46 inches, or about 47 inches, or about 48 inches, or about 50 inches, or about 55 inches, or about 60 inches. In some embodiments, the patient is male human with a waist circumference exceeding 40 inches. In some embodiments, the patient is a female human with a waist circumference exceeding 35 inches.

The methods of the disclosure may be used to treat humans having a body fat percentage above the recommended body fat percentage, i.e., at least in the "overweight" range, or at least in the "obese" range. The body fat percentage will differ between women and men. Specifically, for women, the methods of the disclosure may be used to treat a female human having a body fat percentage of at least about 25%, above 25%, at least about 32%, or above 32%. For men, the methods of the disclosure may be used to treat a male human having a body fat percentage of at least about 14%, above 14%, at least about 18%, above 18%, at least about 25%, or above 25%. Body fat percentage may be estimated using any method accepted in the art, including, for example, near infrared interactance, dual energy X-ray absorptiometry, body density measurement, bioelectrical impedance analysis, and the like.

The methods of the disclosure may be used to treat a patient who is a man that is greater than 100 pounds overweight and/or has waist circumference exceeding 40 inches. The methods of the disclosure may be used to treat a patient who is a woman that is greater than 80 pounds overweight" and/or waist circumference exceeding 35 inches.

In some embodiments, the disclosure provides for the chimeric protein disclosed herein or the polynucleotides encoding the chimeric protein disclosed herein being used to treat and/or prevent certain disorders associated with being overweight. For example, the chimeric protein disclosed herein or the polynucleotides encoding the chimeric protein disclosed herein find use in cardiovascular diseases (e.g. high cholesterol, hypercholesterolemia, low HDL, high HDL, hypertension, coronary artery-disease, heart failure), sleep apnea (including obstructive sleep apnea), osteoarthritis, thyroid problems, dementia, gout, asthma, gastroesophageal reflux disease, and chronic renal failure.

In various embodiments, the chimeric protein disclosed herein or the polynucleotides encoding the chimeric protein disclosed herein administration and/or use prevents or reduces the growth of adipose tissue. In some embodiments, the chimeric protein disclosed herein or the polynucleotides encoding the chimeric protein disclosed herein effects one or more of white adipose tissue (WAT) and brown adipose tissue (BAT), including, for example, visceral adipose tissue (VAT), abdominal subcutaneous adipose tissue (ASAT), or ectopic fat. Such an effect may be assessed by, for example, using any of the techniques described herein (e.g., BMI, weight for-stature indexes, skinfold measures, electrical bioimpedance analysis, etc.), as well as various imaging techniques, including computed tomography (CT), magnetic-resonance imaging (MR], including transverse body scans), dual energy X-ray absorptiometry (DXA).

The chimeric protein disclosed herein or the polynucleotides encoding the chimeric protein disclosed herein may also be used in combination with dietary therapy, behavioral therapy, physical therapy, exercise, and weight loss surgery, or a combination of two or more such therapies. In some embodiments, the subject is on a calorie restricted diet. In some embodiments, the subject engages in or is to engage in a physical exercise or physical therapy regimen. In some embodiments, the subject has undergone, or will undergo, weight loss surgery. In some embodiments, the chimeric protein disclosed herein or the polynucleotides encoding the chimeric protein disclosed herein may be in combination with additional agents or may be administered to patient undergoing treatment with various agents.

For example, including, but not limited to, embodiments pertaining to obesity and/or weight reduction/loss, the additional agents may include one or more of orlistat (e.g., ALL1, XENICAL), loracaserin (e.g., BELVIQ), phentermine-topiramate (e.g., QSYMIA), sibutramme (e.g., REDUCTIL or MERJDIA), rimonabant (ACOMPLLA), exenatide (e.g., BYETTA), pramlintide (e.g., SYMLIN) phentermine, benzphetamine, diethylpropion, phendimetrazme, bupropion, and metformin.

Agents that interfere with the body's ability to absorb specific nutrients in food are among the additional agents, e.g., orlistat (e.g., ALU, XENICAL), glucomannan, and guar gum. Agents that suppress appetite are also among the additional agents, e.g., catecholamines and their derivatives (such as phenteimine and other amphetamine-based drugs), various antidepressants and mood stabilizers (e.g., bupropion and topiramate), anorectics (e.g., dexedrine, digoxin). Agents that increase the body's metabolism are also among the additional agents.

In some embodiments, additional agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; dipeptidyl peptidase 4 (DPP-4) antagonists, agents for treating cardiovascular disease, agents for treating elevated triglyceride levels, agents for treating low HDL, agents for treating hypercholesterolemia, and agents for treating hypertension. Some agents for cardiovascular disease include statins (e.g., lovastatin, atorvastatin, fluvastatin, rosuvastatin, simvastatin and pravastatin) and omega-3 agents (e.g., LOVAZA, EPANQVA, VASCEPA, esterified omega-3's in general, fish oils, krill oils, algal oils). In some embodiments, additional agents may be selected from among amphetamines, benzodiazepines, sulfonyl ureas, meglitinides, thiazolidinediones, biguanides, beta-blockers, XCE inhibitors, diuretics, nitrates, calcium channel blockers, phentermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, metformin, pioglitazone, rosiglilazone, and sitagliptin.

In various embodiments, the chimeric protein disclosed herein or the polynucleotides encoding the chimeric protein disclosed herein may be used to treat diabetes in the context of hospitalization. For example, in embodiments, the chimeric protein disclosed herein or the polynucleotides encoding the chimeric protein disclosed herein may be administered to a patient that is in a diabetic coma. In embodiments, the patient may be administered to a patient that has one or more of a severe diabetic hypoglycemia, advanced diabetic ketoacidosis (e.g., advanced enough to result in unconsciousness, contributing factors may include one or more of hyperglycemia, dehydration, shock, and exhaustion), hyperosmolar nonketotic coma (e.g., with one or more of hyperglycemia and dehydration are contributing factors). In these embodiments, the chimeric protein disclosed herein or the polynucleotides encoding the chimeric protein disclosed herein may be used in conjunction with standard treatment regimens of diabetic comas, including administering one or more of glucose, glucagon, insulin, fluids (e.g., saline with potassium and/or other electrolytes), any of which, optionally, are administered intravenously. In embodiments, the chimeric protein disclosed herein or the polynucleotides encoding the chimeric protein disclosed herein may replace insulin in these treatment regimens and, optionally, is administered intravenously.

Further, in, but not limited to, embodiments pertaining to diabetes, the additional agents described herein may be used in the context of combination therapies. Further, any of the methods of treatment described herein may comprise administering the chimeric protein disclosed herein or the polynucleotides encoding the chimeric protein disclosed herein to a patient that is receiving one or more additional agents and/or non-insulin diabetes agents. Additional agents include one or more of a sulfonylurea (e.g., DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g., metformin (GLUCOPHAGE, GLUCOPHAGE XR, RIOMET, FORTAMET, and GLUMETZA)); a thiazolidinedione (e.g., ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose co-transporter 2 (SGLT2) inhibitor (e.g., INVOKANA (canaglifozin)); and a combination pill (e.g., GLUCOVANCE, which combines glyburide (a sulfonylurea) and metformin, METAGLIP, which combines glipizide (a sulfonylurea) and metformin, and AVANDAMET, which uses both metformin and rosiglitazone (AVANDIA) in one pill, KAZANO (alogliptin and metformin), and OSENI (alogliptin plus pioglitazone).

Other additional agents include METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARYI oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROI XL oral, NOVOLIN R injection, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R injection, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human injection, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, and canagliflozin oral.

Other additional agents include Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition comprising a polynucleotide encoding a chimeric protein having a general structure of: N terminus-(a)-(b)-(c)-C terminus, wherein: (A) (a) is a first domain comprising a glucagon-like peptide-1 (GLP-1) receptor agonist, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator, GIP, or a variant thereof, or an analog thereof; or (B) (a) is a first domain comprising a glucose-dependent insulinotropic polypeptide (GIP) receptor (GIPR) modulator, GIP, or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising a modified mRNA (mmRNA) encoding a chimeric protein having a general structure of: N terminus-(a)-(b)-(c)-C terminus, wherein: (A) (a) is a first domain comprising glucagon-like peptide-1 (GLP-1), (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator; or (B) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising glucagon-like peptide-1 (GLP-1).

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising a modified mRNA (mmRNA) encoding a chimeric protein having a general structure of: N terminus-(a)-(b)-(c)-C terminus, wherein: (A) (a) is a first domain comprising glucagon-like peptide-1 (GLP-1), (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator; or (B) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising glucagon-like peptide-1 (GLP-1).

In aspects, the present disclosure provides a method of treating or preventing hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of treating or preventing hyperglycemia in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of treating or preventing diabetes in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of treating or preventing obesity in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of treating or preventing metabolic syndrome in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method reducing blood glucose in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for reducing fed and fasting blood glucose in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for reducing cardiovascular risk in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for decreasing body weight in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for decreasing food intake in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for decreasing liver adiposity in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for decreasing subcutaneous white adipose tissue (sWAT) in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein, wherein the patient has failed, chosen to discontinue, or cannot tolerate peptide-based GLP-1 agonists such as semaglutide.

In aspects, the present disclosure provides a method of treating nonalcoholic fatty liver disease (NAFLD) or non-alcoholic steatohepatitis (NASH) in a subject in need thereof, the method comprising administering pharmaceutical composition comprising chimeric protein or a polynucleotide any one of the embodiments disclosed herein encoding a chimeric protein of any one of the embodiments disclosed herein.

In aspects, the present disclosure provides a method of treating or preventing nonalcoholic fatty liver disease (NAFLD) or non-alcoholic steatohepatitis (NASH) in a subject in need thereof, the method comprising administering a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85.

NAFLD is characterized by hepatic steatosis with no secondary causes of hepatic steatosis including excessive alcohol consumption, other known liver diseases, or long-term use of a steatogenic medication (Chalasani et al., The diagnosis and management of nonalcoholic fatty liver disease: Practice guidance from the American Association for the Study of Liver Diseases, *Hepatology* 2018, 67(1):328-357, which is hereby incorporated by reference in its entirety). In embodiments, the subject has NAFLD selected from non-alcoholic fatty liver (NAFL) and non-alcoholic steatohepatitis (NASH). In embodiments, the subject has NAFL, as indicated by the presence of >5% hepatic steatosis without evidence of hepatocellular injury in the form of hepatocyte ballooning. In embodiments, the subject has NASH as indicated by the presence of >5% hepatic steatosis and inflammation with hepatocyte injury (e.g., ballooning), with or without any liver fibrosis. In embodiments, the subject has NASH, which is associated with hepatic inflammation and liver fibrosis, which optionally has progressed to cirrhosis, end-stage liver disease, and/or hepatocellular carcinoma. In embodiments, the subject has NASH without liver fibrosis. In embodiments, the subject has fibrosis of very low severity of fibrosis.

There are many approaches used to assess and evaluate whether a subject has NAFLD and if so, the severity of the disease including differentiating whether the NAFLD is NAFL or NASH. For example, these approaches include determining one or more of hepatic steatosis (e.g., accumulation of fat in the liver); the NAFLD Activity Score (NAS); hepatic inflammation; biomarkers indicative of one or more of liver damage, hepatic inflammation, liver fibrosis, and/or liver cirrhosis (e.g., serum markers and panels); and liver fibrosis and/or cirrhosis. Accordingly, in embodiments, the subject selected for the treatment with the compositions comprising the chimeric protein disclosed herein or the polynucleotides encoding the chimeric protein disclosed herein based on diagnosis by determining one or more of hepatic steatosis (e.g., accumulation of fat in the liver); the NAFLD Activity Score (NAS); hepatic inflammation; biomarkers indicative of one or more of liver damage, hepatic inflammation, liver fibrosis, and/or liver cirrhosis (e.g., serum markers and panels); and liver fibrosis and/or cirrhosis. In embodiments, the subject selected for the treatment with the chimeric protein and/or compositions disclosed herein based on diagnosis of a physiological indicator of NAFLD selected from liver morphology, liver stiffness, and the size or weight of the subject's liver. In some embodiments, NAFLD in the subject is evidenced by an accumulation of hepatic fat and detection of a biomarker indicative of liver damage. For example, elevated serum ferritin and low titers of serum autoantibodies can be common features of NAFLD. In embodiments, the subject selected for the treatment with the chimeric proteins or compositions disclosed herein based on diagnosis of NAFLD using a technique including, but not limited to, magnetic resonance imaging, either by spectroscopy or by proton density fat fraction (MRI-PDFF) to quantify steatosis, transient elastography (FIBROSCAN®), hepatic venous pressure gradient (HPVG), hepatic stiffness measurement with MRE for diagnosing significant liver fibrosis and/or cirrhosis, and assessing histological features of liver biopsy. In some embodiments, magnetic resonance imaging is used to detect one or more of steatohepatitis (NASH-MRI), liver fibrosis (Fibro-MRI), and steatosis see, for example, U.S. Application Publication Nos. 2016/146715 and 2005/0215882, each of which are incorporated herein by reference in their entireties.

In embodiments, the subject selected for the treatment with the compositions comprising the chimeric protein disclosed herein or the polynucleotides encoding the chimeric protein disclosed herein based on diagnosis symptoms selected from one or more of an enlarged liver, fatigue, pain in the upper right abdomen, abdominal swelling, enlarged blood vessels just beneath the skin's surface, enlarged breasts in men, enlarged spleen, red palms, jaundice, and pruritus. In some embodiments, the subject is asymptomatic.

In embodiments, hepatic steatosis is determined by one or more methods selected from ultrasonography, computed tomography (CT), magnetic resonance imaging, magnetic resonance spectroscopy (MRS), magnetic resonance elastography (MRE), transient elastography (TE) (e.g., FIBROSCAN®), measurement of liver size or weight, or by liver biopsy (see, e.g., Di Lascio et al, Ultrasound Med Biol. 2018; 44(8): 1585-1596; Lv et al, J Clin Transl Hepatol. 2018 Jun. 28; 6(2): 217-221; Reeder, et ah, J Magn Reson Imaging. 2011 October; 34(4): 848-855; and de Ledinghen V, et ah, J Gastroenterol Hepatol. 2016 April; 31(4):848-55, each of which are incorporated herein by reference in their entireties). In embodiments, a subject diagnosed with NAFLD may have more than about 5% hepatic steatosis, for example, about 5% to about 25%, about 25% to about 45%, about 45% to about 65%, or greater than about 65% hepatic steatosis. In embodiments, a subject with about 5% to about 33% hepatic steatosis has stage 1 hepatic steatosis, a subject with about 33% to about 66% hepatic steatosis has stage 2 hepatic steatosis, and a subject with greater than about 66% hepatic steatosis has stage 3 hepatic steatosis.

In embodiments, the amount of hepatic steatosis is determined prior to administration of the combination of (a) the compositions comprising the chimeric protein disclosed herein or the polynucleotides encoding the chimeric protein disclosed herein, and (b) an additional therapeutic agent. In embodiments, the amount of hepatic steatosis is determined during the period of time or after the period of time of administration of the combination of (a) and (b). In embodiments, a reduction in the amount of hepatic steatosis during the period of time or after the period of time of administration of the combination of (a) and (b) compared to prior to administration of the combination of (a) and (b) indicates treatment of NAFLD. For example, a reduction in the amount of hepatic steatosis by about 1% to about 50%, about 25% to about 75%, or about 50% to about 100% indicates treatment of NAFLD. In embodiments, a reduction in the amount of hepatic steatosis by about 5%, bout 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of NAFLD.

In embodiments, treatment of NAFLD can be assessed by measuring hepatic steatosis. In embodiments, treatment of NAFLD comprises a reduction in hepatic steatosis following administration of one or more chimeric proteins or composition encoding the chimeric proteins described herein. In embodiments, the treatment of NAFLD with the chimeric proteins or compositions disclosed herein comprises one or more of a decrease in symptoms; a reduction in the amount of hepatic steatosis; a decrease in the NAS; a decrease in hepatic inflammation; a decrease in the level of biomarkers indicative of one or more of liver damage, inflammation, liver fibrosis, and/or liver cirrhosis; and a reduction in fibrosis and/or cirrhosis, a lack of further progression of fibrosis and/or cirrhosis, or a slowing of the progression of fibrosis and/or cirrhosis. In embodiments, treatment of NAFLD comprises a decrease of one or more symptoms associated with NAFLD in the subject. In embodiments, the total body weight of the subject does not increase. In embodiments, the total body weight of the subject decreases. In embodiments, the body mass index (BMI) of the subject does not increase. In embodiments, the body mass index (BMI) of the subject decreases. In embodiments, the waist and hip (WTH) ratio of the subject does not increase. In embodiments, the waist and hip (WTH) ratio of the subject decreases.

In embodiments, the severity of NALFD can be assessed using the NAS. In embodiments, treatment of NAFLD can be assessed using the NAS. In embodiments, treatment of NAFLD comprises a reduction in the NAS following administration of one or more compounds described herein. In embodiments, the NAS can be determined as described in Kleiner et al., Hepatology. 2005, 41(6): 1313-1321, which is hereby incorporated by reference in its entirety.

In embodiments, the NAS following administration is determined non-invasively, for example, as described in U.S. Application Publication No. 2018/0140219, which is incorporated by reference herein in its entirety. In embodiments, the NAS following administration is determined for a sample from the subject prior to administration of the compositions comprising the chimeric protein disclosed herein or the polynucleotides encoding the chimeric protein disclosed herein. In embodiments, the NAS following administration is determined during the period of time or after the period of time of administration of the compositions comprising the chimeric protein disclosed herein or the polynucleotides encoding the chimeric protein disclosed herein. In embodiments, a lower NAS score during the period of time or after the period of time of administration of the compositions comprising the chimeric protein disclosed herein or the polynucleotides encoding the chimeric protein disclosed herein compared to prior to administration of the compositions comprising the chimeric protein disclosed herein or the polynucleotides encoding the chimeric protein disclosed herein indicates treatment of NAFLD. For example, a decrease in the NAS by 1, by 2, by 3, by 4, by 5, by 6, or by 7 indicates treatment of NAFLD. In embodiments, the NAS following administration of the compositions comprising the chimeric protein disclosed herein or the polynucleotides encoding the chimeric protein disclosed herein is 7 or less. In embodiments, the NAS during the period of time of administration of the compositions comprising the chimeric protein disclosed herein or the polynucleotides encoding the chimeric protein disclosed herein is 5 or less, 4 or less, 3 or less, or 2 or less. In embodiments, the NAS during the period of time of administration of the compositions comprising the chimeric protein disclosed herein or the polynucleotides encoding the chimeric protein disclosed herein is 7 or less. In embodiments, the NAS during the period of time of administration of the compositions comprising the chimeric protein disclosed herein or the polynucleotides encoding the chimeric protein disclosed herein is 5 or less, 4 or less, 3 or less, or 2 or less. In embodiments, the NAS after the period of time of administration of the compositions comprising the chimeric protein disclosed herein or the polynucleotides encoding the chimeric protein disclosed herein is 7 or less. In embodiments, the NAS after the period of time of administration of the compositions comprising the chimeric protein disclosed herein or the polynucleotides encoding the chimeric protein disclosed herein is 5 or less, 4 or less, 3 or less, or 2 or less.

In some embodiments, the presence of hepatic inflammation is determined by one or more methods selected from the group consisting of biomarkers indicative of hepatic inflammation and a liver biopsy sample(s) from the subject. In some embodiments, the severity of hepatic inflammation is determined from a liver biopsy sample(s) from the subject. For example, hepatic inflammation in a liver biopsy sample can be assessed as described in Kleiner et al., Hepatology. 2005, 41(6): 1313-1321 and Brunt et al., Am J Gastroenterol 1999, 94:2467-2474, each of which are hereby incorporated by reference in their entireties.

In some embodiments, the severity of hepatic inflammation is determined prior to administration of the compositions comprising the chimeric protein disclosed herein or the polynucleotides encoding the chimeric protein disclosed herein. In some embodiments, the severity of hepatic inflammation is determined prior to administration of the compositions comprising the chimeric protein disclosed herein or the polynucleotides encoding the chimeric protein disclosed herein. In some embodiments, the severity of hepatic inflammation is determined during the period of time or after the period of time of administration of the compositions comprising the chimeric protein disclosed herein or the polynucleotides encoding the chimeric protein disclosed herein. In some embodiments, a decrease in the severity of hepatic inflammation during the period of time or after the period of time of administration of the compositions comprising the chimeric protein disclosed herein or the polynucleotides encoding the chimeric protein disclosed herein compared to prior to administration of the compositions comprising the chimeric protein disclosed herein or the polynucleotides encoding the chimeric protein disclosed herein indicates treatment of NAFLD. For example, a decrease in the severity of hepatic inflammation by about 1% to about 50%, about 25% to about 75%, or about 50% to about 100% indicates treatment of NAFLD. In some embodiments, a decrease in the severity of hepatic inflammation by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% indicates treatment of NAFLD.

In some embodiments, treatment of NAFLD comprises treatment of fibrosis and/or cirrhosis, e.g., a decrease in the severity of fibrosis, a lack of further progression of fibrosis and/or cirrhosis, or a slowing of the progression of fibrosis and/or cirrhosis. In some embodiments, the presence of fibrosis and/or cirrhosis is determined by one or more methods selected from the group consisting of transient elastography (e.g., FIBROSCAN®), non-invasive markers of hepatic fibrosis, and histological features of a liver biopsy. In some embodiments, the severity (e.g., stage) of fibrosis is determined by one or more methods selected from the group consisting of transient elastography (e.g., FIBROSCAN®), a fibrosis-scoring system, biomarkers of hepatic fibrosis (e.g., non-invasive biomarkers), and hepatic venous pressure gradient (HVPG). Non-limiting examples of fibrosis scoring systems include the NAFLD fibrosis scoring system (see, e.g., Angulo, et al., Hepatology. 2007; 45(4):846-54), the fibrosis scoring system in Brunt et al., Am J Gastroenterol. 1999, 94:2467-2474, the fibrosis scoring system in Kleiner et al., Hepatology. 2005, 41(6): 1313-1321, and the ISHAK fibrosis scoring system (see Ishak et al., J Hepatol. 1995; 22:696-9), the contents of each of which are incorporated by reference herein in their entireties.

In some embodiments, the severity of fibrosis is determined prior to administration of the compositions comprising the chimeric protein disclosed herein or the polynucleotides encoding the chimeric protein disclosed herein. In some embodiments, the severity of fibrosis is determined prior to administration of a combination of (a) the compositions comprising the chimeric protein disclosed herein or the polynucleotides encoding the chimeric protein disclosed herein, and (b) an additional therapeutic agent. In some embodiments, the severity of fibrosis is determined during the period of time or after the period of time of administration of the combination of (a) and (b). In some embodiments, a decrease in the severity of fibrosis during the period of time or after the period of time of administration of the combination of (a) and (b) compared to prior to administration of the combination of (a) and (b) indicates treatment of NAFLD. In some embodiments, a decrease in the severity of fibrosis, a lack of further progression of fibrosis and/or cirrhosis, or a slowing of the progression of fibrosis and/or cirrhosis indicates treatment of NAFLD. In some embodiments, the severity of fibrosis is determined using a scoring system such as any of the fibrosis scoring systems described herein, for example, the score can indicate the stage of fibrosis, e.g., stage 0 (no fibrosis), stage 1, stage 2, stage 3, and stage 4 (cirrhosis) (see, e.g., Kleiner et al). In some embodiments, a decrease in the stage of the fibrosis is a decrease in the severity of the fibrosis. For example, a decrease by 1, 2, 3, or 4 stages is a decrease in the severity of the fibrosis. In some embodiments, a decrease in the stage, e.g., from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 indicates treatment of NAFLD. In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 following administration of the combination of (a) and (b) compared to prior to administration of the combination of (a) and (b). In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 during the period of time of administration of the combination of (a) and (b) compared to prior to administration of the combination of (a) and (b). In some embodiments, the stage of fibrosis decreases from stage 4 to stage 3, from stage 4 to stage 2, from stage 4 to stage 1, from stage 4 to stage 0, from stage 3 to stage 2, from stage 3 to stage 1, from stage 3 to stage 0, from stage 2 to stage 1, from stage 2 to stage 0, or from stage 1 to stage 0 after the period of time of administration of the combination of (a) and (b) compared to prior to administration of the combination of (a) and (b).

In some embodiments, the presence of NAFLD is determined by one or more biomarkers indicative of one or more of liver damage, inflammation, liver fibrosis, and/or liver cirrhosis or scoring systems thereof. In some embodiments, the severity of NAFLD is determined by one or more biomarkers indicative of one or more of liver damage, inflammation, liver fibrosis, and/or liver cirrhosis or scoring systems thereof. The level of the biomarker can be determined by, for example, measuring, quantifying, and monitoring the expression level of the gene or mRNA encoding the biomarker and/or the peptide or protein of the biomarker. Non-limiting examples of biomarkers indicative of one or more of liver damage, inflammation, liver fibrosis, and/or liver cirrhosis and/or scoring systems thereof include the aspartate aminotransferase (AST) to platelet ratio index (APRI); the aspartate aminotransferase (AST) and alanine aminotransferase (ALT) ratio (AAR); the FIB-4 score, which is based on the APRI, alanine aminotransferase (ALT) levels, and age of the subject (see, e.g., McPherson et ah, Gut. 2010; 59(9): 1265-9, which is incorporated by reference herein in its entirety); hyaluronic acid; pro-inflammatory cytokines; a panel of biomarkers consisting of a2-macroglobulin, haptoglobin, apolipoprotein Al, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, a2-macroglobulin combined with the subject's age and sex (e.g., HEPASCORE®; see, e.g., Adams et al., Clin Chem. 2005, 51(10): 1867-73), and a panel of biomarkers consisting of tissue inhibitor of metalloproteinase-1, hyaluronic acid, and a2-macroglobulin (e.g., FIBROSPECT®); a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score, see, e.g., Lichtinghagen R, et al., J Hepatol. 2013 August; 59(2): 236-42, which is incorporated by reference herein in its entirety). In some embodiments, the presence of fibrosis is determined by one or more of the FIB-4 score, a panel of biomarkers consisting of a2-macroglobulin, haptoglobin, apolipoprotein Al, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, a2-macroglobulin combined with the subject's age and sex (e.g., HEPASCORE®; see, e.g., Adams et al., Clin Chem. 2005; 51(10): 1867-73), and a panel of biomarkers consisting of tissue inhibitor of metalloproteinase-1, hyaluronic acid, and a2-macroglobulin (e.g., FIBROSPECT®); and a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score).

In some embodiments, the level of aspartate aminotransferase (AST) does not increase. In some embodiments, the level of aspartate aminotransferase (AST) decreases. In some embodiments, the level of alanine aminotransferase (ALT) does not increase. In some embodiments, the level of alanine aminotransferase (ALT) decreases. In some embodiments, the "level" of an enzyme refers to the concentration of the enzyme, e.g., within blood. For example, the level of AST or ALT can be expressed as Units/L.

In some embodiments, the severity of fibrosis is determined by one or more of the FIB-4 score, a panel of biomarkers consisting of a2-macroglobulin, haptoglobin, apolipoprotein Al, bilirubin, gamma glutamyl transpeptidase (GGT) combined with a subject's age and gender to generate a measure of fibrosis and necroinflammatory activity in the liver (e.g., FIBROTEST®, FIBROSURE®), a panel of biomarkers consisting of bilirubin, gamma-glutamyltransferase, hyaluronic acid, a2-macroglobulin combined with the subject's age and sex (e.g., HEPASCORE®; see, e.g., Adams et al., Clin Chem. 2005 October; 51(10): 1867-73, which is incorporated by reference herein in its entirety), and a panel of biomarkers consisting of tissue inhibitor of metalloproteinase-1, hyaluronic acid, and a2-macroglobulin (e.g., FIBROSPECT®); and a panel of biomarkers consisting of tissue inhibitor of metalloproteinases 1 (TIMP-1), amino-terminal propeptide of type III procollagen (PIIINP) and hyaluronic acid (HA) (e.g., the Enhanced Liver Fibrosis (ELF) score). In some embodiments, hepatic inflammation is determined by the level of liver inflammation biomarkers, e.g., pro-inflammatory cytokines. Non-limiting examples of biomarkers indicative of liver inflammation include interleukin-(IL) 6, interleukin-(IL) 1b, tumor necrosis factor (TNF)-a, transforming growth factor (TGF)-P, monocyte chemotactic protein (MCP)-I, C-reactive protein (CRP), PAI-1, and collagen isoforms such as Collal, Colla2, and Col4al (see, e.g., Neuman, et ah, Can J Gastroenterol Hepatol. 2014 December; 28(11): 607-618 and U.S. Pat. No. 9,872,844, each of which are incorporated by reference herein in their entireties). Liver inflammation can also be assessed by change of macrophage infiltration, e.g., measuring a change of CD68 expression level. In some embodiments, liver inflammation can be determined by measuring or monitoring serum levels or circulating levels of one or more of interleukin-(IL) 6, interleukin-(IL) 1b, tumor necrosis factor (TNF)-a, transforming growth factor (TGF-b, monocyte chemotactic protein (MCP)-I, and C-reactive protein (CRP).

In some embodiments, the level of one or more biomarkers indicative of one or more of liver damage, inflammation, liver fibrosis, and/or liver cirrhosis is determined for a sample from the subject prior to administration of the combination of (a) the compositions comprising the chimeric protein disclosed herein or the polynucleotides encoding the chimeric protein disclosed herein, and (b) an additional therapeutic agent. In some embodiments, the level of one or more biomarkers indicative of one or more of liver damage, inflammation, liver fibrosis, and/or liver cirrhosis is determined during the period of time or after the period of time of administration of the combination of (a) and (b). In some embodiments, a decrease in the level of one or more biomarkers indicative of one or more of liver damage, inflammation, liver fibrosis, and/or liver cirrhosis during the period of time or after the period of time of administration of the combination of (a) and (b) compared to prior to administration of the combination of (a) and (b) indicates treatment of NAFLD. For example, a decrease in the level of one or more biomarkers indicative of one or more of liver damage, inflammation, liver fibrosis, and/or liver cirrhosis by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% indicates treatment of NAFLD. In some embodiments, the decrease in the level of one or more biomarkers indicative of one or more of liver damage, inflammation, liver fibrosis, and/or liver cirrhosis following administration of the combination of (a) and (b) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In some embodiments, the level of one or more biomarkers indicative of one or more of liver damage, inflammation, liver fibrosis, and/or liver cirrhosis during the period of time of administration of the combination of (a) and (b) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. In some embodiments, the level of one or more biomarkers indicative of one or more of liver damage, inflammation, liver fibrosis, and/or liver cirrhosis after the period of time of administration of the combination of (a) and (b) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%.

In some embodiments, the treatment of NAFLD decreases the level of serum bile acids in the subject. In some embodiments, the level of serum bile acids is determined by, for example, an ELISA enzymatic assay or the assays for the measurement of total bile acids as described in Danese et ah, PLoS One. 2017; 12(6): e0179200, which is incorporated by reference herein in its entirety. In some embodiments, the level of serum bile acids can decrease by, for example, 10% to 40%, 20% to 50%, 30% to 60%, 40% to 70%, 50% to 80%, or by more than 90% of the level of serum bile acids prior to administration of (a) and (b). In some embodiments, the NAFLD is NAFLD with attendant cholestasis. In cholestasis, the release of bile, including bile acids, from the liver is blocked. Bile acids can cause hepatocyte damage (see, e.g., Perez M J, Briz O. World J Gastroenterol. 2009 Apr. 14; 15(14): 1677-89) likely leading to or increasing the progression of fibrosis (e.g., cirrhosis) and increasing the risk of hepatocellular carcinoma (see, e.g., Sorrentino P et ah. Dig Dis Sci. 2005; 50(6): 1130-5 and Satapathy S K and Sanyal A J. Semin Liver Dis. 2015, 35(3):221-35, each of which are incorporated by reference herein in their entireties). In some embodiments, the NAFLD with attendant cholestasis is NASH with attendant cholestasis. In some embodiments, the treatment of NAFLD comprises treatment of pruritus. In some embodiments, the treatment of NAFLD with attendant cholestasis comprises treatment of pruritus. In some embodiments, a subject with NAFLD with attendant cholestasis has pruritus.

In some embodiments, treatment of NAFLD comprises an increase in adiponectin. It is thought that the compound of Formula (I) may be a selective activator of a highly limited number of PPARy pathways including pathways regulated by adiponectin. Adiponectin is an anti-fibrotic and anti-inflammatory adipokine in the liver (see e.g., Park et ah, Curr Pathobiol Rep. 2015 Dec. 1; 3(4): 243-252.). In some embodiments, the level of adiponectin is determined by, for example, an ELISA enzymatic assay. In some embodiments, the adiponectin level in the subject is increased by at least about 30%, at least about 68%, at least about 175%, or at least about 200%. In some embodiments, the increase is by at least about 175%. In some embodiments, the level of adiponectin is determined for a sample from the subject prior to administration of the combination of (a) the compositions comprising the chimeric protein disclosed herein or the polynucleotides encoding the chimeric protein disclosed herein, and (b) an additional therapeutic agent. In some embodiments, the level of adiponectin is determined for a sample from the subject prior to administration of the combination of (a) the compositions comprising the chimeric protein disclosed herein or the polynucleotides encoding the chimeric protein disclosed herein, and (b) an additional therapeutic agent. In some embodiments, the level of adiponectin is determined during the period of time or after the period of time of administration of the combination of (a) and (b). In some embodiments, an increase in the level of adiponectin during the period of time or after the period of time of administration of the combination of (a) and (b) compared to prior to administration of the combination of (a) and (b) indicates treatment of NAFLD. For example, an increase in the level of adiponectin by at least about 30%, at least about 68%, at least about 175%, or at least about 200% indicates treatment of NAFLD. In some embodiments, the increase in the level of adiponectin following administration of the combination of (a) and (b) is at least about 200%.

Provided herein are methods of treating non-alcoholic fatty liver disease (NAFLD) in a subject in need thereof comprising or consisting essentially of administering to the subject the compositions comprising the chimeric protein disclosed herein or the polynucleotides encoding the chimeric protein disclosed herein, wherein the amount of the compositions comprising the chimeric protein disclosed herein or the polynucleotides encoding the chimeric protein disclosed herein is effective in treating NAFLD. In some embodiments, a method of treating non-alcoholic fatty liver disease (NAFLD) in a subject in need thereof comprises or consists essentially of administering to the subject the compositions comprising the chimeric protein disclosed herein or the polynucleotides encoding the chimeric protein disclosed herein during a period of time, wherein the amount of the compositions comprising the chimeric protein disclosed herein or the polynucleotides encoding the chimeric protein disclosed herein is effective in treating NAFLD.

Provided herein are methods of treating obesity in a subject in need thereof comprising or consisting essentially of administering to the subject the compositions comprising the chimeric protein disclosed herein or the polynucleotides encoding the chimeric protein disclosed herein, wherein the amount of the compositions comprising the chimeric protein disclosed herein or the polynucleotides encoding the chimeric protein disclosed herein is effective in treating obesity. In some embodiments, a method of treating obesity in a subject in need thereof comprises or consists essentially of administering to the subject the compositions comprising the chimeric protein disclosed herein or the polynucleotides encoding the chimeric protein disclosed herein during a period of time, wherein the amount of the compositions comprising the chimeric protein disclosed herein or the polynucleotides encoding the chimeric protein disclosed herein is effective in treating obesity.

Provided herein are methods of controlling body weight in a subject in need thereof comprising or consisting essentially of administering to the subject a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85. In some embodiments, a method of controlling body weight in a subject in need thereof comprises or consists essentially of administering to the subject the compositions comprising the chimeric protein disclosed herein or the polynucleotides encoding the chimeric protein disclosed herein during a period of time, wherein the amount of the compositions comprising the chimeric protein disclosed herein or the polynucleotides encoding the chimeric protein disclosed herein is effective in controlling body weight.

Also provided herein are methods of treating liver fibrosis in a subject in need thereof comprising or consisting essentially of administering to the subject a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104.

In embodiments, the FGF19, FGF21, FGF23, a variant thereof, and an analog thereof an amino acid sequence that is selected from the amino acid sequence of SEQ ID NOs: 78-85.

Also provided herein are methods of treating steatosis in a subject in need thereof comprising or consisting essentially of administering to the subject a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85.

Also provided herein are methods of treating a subject, the method comprising: selecting a subject having non-alcoholic fatty liver disease (NAFLD); and administering a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85.

Also provided herein are methods of selecting a subject for participation in a clinical trial, the method comprising: identifying a subject having NAFLD; and selecting the identified subject for participation in a clinical trial that comprises administration of the compositions comprising the chimeric protein disclosed herein or the polynucleotides encoding the chimeric protein disclosed herein. In some embodiments, the amount of the compositions comprising the chimeric protein disclosed herein or the polynucleotides encoding the chimeric protein disclosed herein is effective in treating NAFLD.

In aspects, the present disclosure provides a method of treating or preventing non-alcoholic steatohepatitis (NASH) in a subject in need thereof, the method comprising administering a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85.

In aspects, the present disclosure provides a method of treating or preventing nonalcoholic fatty liver disease (NAFLD) in a subject in need thereof, the method comprising administering a pharmaceutical composition comprising a chimeric protein or a nucleic acid encoding the chimeric protein, wherein the chimeric protein comprises a general structure of: N terminus-(a)-(b)-(c)-C terminus, wherein: (A) (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising a fibroblast growth factor selected from fibroblast growth factor 19 (FGF19), FGF21, FGF23, a variant thereof, and an analog thereof; or (B) (a) is a first domain comprising a fibroblast growth factor selected from fibroblast growth factor 19 (FGF19), FGF21, FGF23, a variant thereof, and an analog thereof, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator. In embodiments, the GIPR modulator comprises GIP (SEQ ID NO: 68), or a variant or analog thereof. In embodiments, the GIPR modulator comprises an amino acid sequence that is selected from the amino acid sequence of SEQ ID NOs: 68, 67-69, 97-104, or a variant or an analog thereof having about 1, 2, 3, 4, 5, 6, 7, 8, 9, or 10 or more amino acid mutations with respect to an amino acid sequence selected from the amino acid sequence of SEQ ID NOs: 67-69, 97-104. In embodiments, the FGF19, FGF21, FGF23, a variant thereof, and an analog thereof an amino acid sequence that is selected from the amino acid sequence of SEQ ID NOs: 78-85.

In aspects, the present disclosure provides a method for increasing glucose tolerance in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method for increasing glucose tolerance in a subject in need thereof, the method comprising administering pharmaceutical composition of any one of the embodiments disclosed herein, the isolated polynucleotide of any one of the embodiments disclosed herein, or the pharmaceutical composition of any one of the embodiments disclosed herein, or the host cell of any of the embodiments disclosed herein.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance in a subject in need thereof, the method comprising administering pharmaceutical composition comprising a polynucleotide encoding a chimeric protein having a general structure of: N terminus-(a)-(b)-(c)-C terminus, wherein: A. (a) is a first domain comprising a glucagon-like peptide-1 (GLP-1) receptor agonist, (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator, GIP, or a variant thereof, or an analog thereof; or B. (a) is a first domain comprising a glucose-dependent insulinotropic polypeptide (GIP) receptor (GIPR) modulator, GIP, or a variant thereof, or an analog thereof, (b) is a linker adjoining the first domain and a second domain, optionally wherein the linker comprises one or more protease-cleavable polypeptide linkers, and/or a hinge-CH2-CH3 Fc domain, and (c) is a first domain comprising (i) a glucagon-like peptide-1 (GLP-1) receptor agonist, or (ii) a fibroblast growth factor 19 (FGF19), FGF21 or a variant thereof, or an analog thereof.

In embodiments, the GLP-1 receptor agonist is selected from wherein the GLP-1 receptor agonist is selected from GLP-1, A DPP4 degradation resistant derivative of GLP-1 (without limitation, e.g., GLP-1 7-37, A8G), exenatide, lixisenatide, albiglutide, dulaglutide, or a variant thereof having one or more amino acid mutations, independently selected from substitutions, insertions, deletions, and truncations. In embodiments, the GLP-1 receptor agonist has an amino acid sequence of any one of SEQ ID NOs: 58 to 66, 77, 91, or a variant having about 1, 2, 3, 4, 5, 6, 7, 8, 9, or 10 or more amino acid mutations with respect to an amino acid sequence selected from the amino acid sequence of SEQ ID NOs: 58 to 66. In embodiments, the mutations are independently selected from substitutions, insertions, deletions, and truncations. In embodiments, the GLP-1 receptor agonist is capable of binding a GLP-1 receptor. In embodiments, the GLP-1 receptor agonist is capable of stimulating and/or increasing insulin secretion, and/or inhibiting and/or decreasing glucagon secretion. In embodiments, the GLP-1 receptor agonist is capable of stimulating and/or increasing insulin secretion, and/or inhibiting and/or decreasing glucagon secretion, compared to a chimeric protein lacking the first domain (e.g., having a structure: (a) a second domain comprising a glucose-dependent insulinotropic polypeptide (GIP) receptor (GIPR) modulator of any of the embodiments disclosed herein and optionally (b) a linker comprising one or more protease-cleavable polypeptide linkers and/or a hinge-CH2-CH3 Fc domain In embodiments, the GIPR modulator comprises GIP, or an analog thereof. In embodiments, second domain is capable of modulating a GIP receptor (GIPR). In embodiments, the second domain is capable of binding the GIPR. In embodiments, the GIPR modulator is capable of activating the GIPR. In embodiments, the GIPR modulator is capable of inhibiting the GIPR. In embodiments, GIPR modulator is capable of modulating the GIPR on the surface of the endocrine pancreas. In embodiments, the GIPR modulator is capable of activating the hypothalamic GIPR. In embodiments, the second domain comprises an amino acid sequence that is at least about 90%, or at least about 95%, or at least about 97%, or at least about 98%, or at least about 99% identical to an amino acid sequence selected from the amino acid sequence of SEQ ID NOs: 68 to 74.

In embodiments, the protease-cleavable polypeptide linkers are cleavable by a protease that is endogenous to mammalian liver, skin and/or muscle. In embodiments, the protease being selected from, caspases, kallikreins, cathepsins, legumain, matrix metalloproteinases (MMPs), cathepsin, elastase, plasmin, thrombin, trypsin, urokinase-type plasminogen activator (uPA), matriptase, meprins and hepsin. In embodiments, the chimeric protein comprises one protease-cleavable polypeptide linker selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the protease-cleavable polypeptide linker is C terminal to the first domain or N terminal to the second domain.

In embodiments, the first domain comprises a glucagon-like peptide-1 (GLP-1) receptor agonist and the protease-cleavable polypeptide linker is C terminal to the first domain; or the second domain comprises a glucagon-like peptide-1 (GLP-1) receptor agonist and the protease-cleavable polypeptide linker is N terminal to the second domain. In embodiments, the chimeric protein comprises two protease-cleavable polypeptide linkers, such protease-cleavable polypeptide linker independently selected from HSSKLQ (SEQ ID NO: 70), GPLGVRG (SEQ ID NO: 71), IPVSLRSG (SEQ ID NO: 72), VPLSLYSG (SEQ ID NO: 73), and SGESPAYYTA (SEQ ID NO: 74), RFRS (SEQ ID NO: 75) or a variant thereof having about 1, 2, 3, 4, or more amino acid mutations with respect to an amino acid sequence selected from the amino acid sequence of SEQ ID NOs: 70 to 75. In embodiments, the first protease-cleavable polypeptide linker is C terminal to the first domain and the second domain is protease-cleavable polypeptide linker is N terminal to the second domain.

In embodiments, the hinge-CH2-CH3 Fc domain is derived from IgG1. In embodiments, the IgG1 is human IgG1. In embodiments, the linker further comprises a hinge-CH2-CH3 Fc domain derived from IgG4. In embodiments, the IgG4 is human IgG4. In embodiments, the hinge-CH2-CH3 Fc domain comprises an amino acid sequence that is at least about 95% identical to the amino acid sequence of SEQ ID NO: 1, SEQ ID NO: 2, SEQ ID NO: 3, or SEQ ID NO: 76. In embodiments, the linker further comprises the linker comprises one or more joining linkers, such joining linkers independently selected from SEQ ID NOs: 4 to 50, 92 and 113.

In embodiments, the linker comprises two or more joining linkers each joining linker independently selected from SEQ ID NOs: 4 to 50, 92 and 113; wherein one joining linker is N terminal to the hinge-CH2-CH3-Fc domain and another joining linker is C terminal to the hinge-CH2-CH3-Fc domain.

In embodiments, the polynucleotide is an mmRNA. In embodiments, the mmRNA comprises one or more nucleoside modifications. In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof. In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127. In embodiments, the mmRNA further comprises 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) or 3' UTR_6 (SEQ ID NO: 119); 5' UTR_14 (SEQ ID NO: 141) and 3' UTR_10 (SEQ ID NO: 123).

In embodiments, the pharmaceutical composition further comprises a pharmaceutically acceptable carrier. In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the polynucleotide is formulated as a lipid nanoparticle (LNPs), a lipoplex, or a liposome.

In embodiments, the polynucleotide is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA.

In embodiments, the lipid nanoparticles comprise lipids selected from an ionizable lipid; a structural lipid; cholesterol, and a polyethyleneglycol (PEG)-lipid; 1,2-dioleoyl-3-trimethylammoniumpropane (DOTAP); dioleoylphosphatidylethanolamine (DOPE); and the mmRNA. In embodiments, the ionizable lipid is an ionizable cationic lipid selected from DLin-DMA, DLin-K-DMA, DLin-KC2-DMA, DLin-MC3-DMA, 98N12-5, and C12-200. In embodiments, the polyethyleneglycol (PEG)-lipid is selected from a PEG-diacylglycerol (DAG), a PEG-dialkyloxypropyl (DAA), a PEG-phospholipid, a PEG-ceramide (Cer), or a mixture thereof, or a PEG-dilauryloxypropyl (e.g., C12, a PEG-dimyristyloxypropyl (C14), a PEG-dipalmityloxypropyl (C16), or a PEG-distearyloxypropyl (C18)).

In embodiments, the lipid nanoparticles comprise an ionizable lipid, a PEG-lipid, a phospholipid and a structural lipid. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid. In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle, and/or wherein the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In embodiments, the isolated polynucleotide administered by a parenteral administration. In embodiments, the parenteral administration is selected from intradermal, intramuscular, intraperitoneal, intraarticular, intravenous, subcutaneous, intraarterial or transdermal administration.

In embodiments, the chimeric protein is expressed in liver, skin and/or muscle. In embodiments, the chimeric protein is cleaved in liver, skin and/or muscle. In embodiments, the GLP-1 receptor agonist is released in liver, skin and/or muscle. In embodiments, the GLP-1 receptor agonist enters circulation upon release in liver, skin and/or muscle.

In embodiments, the subject is obese or is at risk of obesity. In embodiments, the subject is suffering from metabolic syndrome or is at risk of suffering from metabolic syndrome. In embodiments, the subject has high blood glucose. In embodiments, the subject is high fed and fasting blood glucose.

In embodiments, an increase in the level of chimeric protein encoded by the isolated polynucleotide may be observed in tissue selected from the liver, spleen, kidney, lung, heart, peri-renal adipose tissue, thymus and muscle and/or in a bodily fluid selected from peripheral blood, serum, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. The increased level of chimeric protein can be observed in the tissue and/or bodily fluid of the subject within 2, 8 and/or 24 hours after administration.

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising a modified mRNA (mmRNA) encoding a chimeric protein having a general structure of: N terminus-(a)-(b)-(c)-C terminus, wherein: A. (a) is a first domain comprising glucagon-like peptide-1 (GLP-1), (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator; or B. (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising glucagon-like peptide-1 (GLP-1).

In aspects, the present disclosure provides a method of preventing or treating hyperglycemia, diabetes, obesity, metabolic syndrome, nonalcoholic fatty liver disease (NAFLD) or non-alcoholic steatohepatitis (NASH) or liver fibrosis, or for reducing blood glucose, or for reducing fed and fasting blood glucose, or for reducing cardiovascular risk, or for decreasing body weight, decreasing food intake, decreasing blood glucose, decreasing liver adiposity, decreasing liver weight, decreasing subcutaneous white adipose tissue (sWAT), or for increasing glucose tolerance, in a subject in need thereof, the method comprising administering a pharmaceutical composition comprising a modified mRNA (mmRNA) encoding a chimeric protein having a general structure of: N terminus-(a)-(b)-(c)-C terminus, wherein: A. (a) is a first domain comprising glucagon-like peptide-1 (GLP-1), (b) is a linker adjoining the first domain and a second domain, optionally wherein the linker comprises one or more protease-cleavable polypeptide linkers, and/or a hinge-CH2-CH3 Fc domain, and (c) is the second domain comprising a glucose-dependent insulinotropic polypeptide (GIP) receptor (GIPR) modulator; or B. (a) is a first domain comprising a glucose-dependent insulinotropic polypeptide (GIP) receptor (GIPR) modulator, (b) is a linker adjoining the first domain and a second domain, optionally wherein the linker comprises one or more protease-cleavable polypeptide linkers, and/or a hinge-CH2-CH3 Fc domain, and (c) is the second domain comprising glucagon-like peptide-1 (GLP-1).

In embodiments, the mmRNA comprises one or more nucleoside modifications. In embodiments, the nucleoside modifications are selected from pyridin-4-one ribonucleoside, 5-aza-uridine, 2-thio-5-aza-uridine, 2-thiouridine, pseudouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methylcytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 2-aminoadenine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

In embodiment, the modified nucleoside of methods and compositions of the present disclosure is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is L (pseudouridine). In another embodiment, the modified nucleoside is Um (2'-O-methyluridine).

In other embodiments, the modified nucleoside is $m^1A$ (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$ isopentenyladenosine); $io^6A$ ($N^6$-(cis-hydroxyisopentenyl)adenosine); $ms^2i6A$ (2-methylthio-$N^6$-(cis-hydroxyisopentenyl)adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); $m^6t^6A$ ($N^6$-methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine);

Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C(N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2{}_2G$ ($N^2,N^2$-dimethylguanosine); $m^2Gm$ ($N^2,2'$-O-dimethylguanosine); $m^2{}_2Gm$ ($N^2,N^2,$2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); $preQ_0$ (7-cyano-7-deazaguanosine); preQ1(7-aminomethyl-7-deazaguanosine); G+(archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6{}_2A$ ($N^6,N^6$-dimethyladenosine); Im (2'-O-methylinosine); $m^4C(N^4$-methylcytidine); $m^4Cm$ ($N^4,2'$-O-dimethylcytidine); $hm^5C$ (5-hydroxymethylcytidine); $m^3U$ (3-methyluridine); $cm^5U$ (5-carboxymethyluridine); $m^6Am$ ($N^6,2'$-O-dimethyladenosine); $m^6{}_2Am$ ($N^6,N^6,$O-2'-trimethyladenosine); $m^{2,7}G$ ($N^2,7$-dimethylguanosine); $m^{227}G$ ($N^2,N^2,7$-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s2U$ (5-taurinomethyl-2-thiouridine)); imG-14 (4-demethylwyosine); imG2 (isowyosine); or $ac^6A$ ($N^6$-acetyladenosine).

In embodiments, the mmRNA further comprises a 5'-cap and/or a poly A tail. In embodiments, the mmRNA further comprises a 5' UTR, optionally comprising a nucleotide sequence that is at least about 90%, or about 95% identical to the nucleotide sequence selected from SEQ ID NOs: 128-149, and/or a 3' UTR, optionally comprising a nucleotide sequence that is at least about 90%, or about 95% identical to the nucleotide sequence selected from SEQ ID NOs: 114-127. In embodiments, the mmRNA further comprises 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) or 3' UTR_6 (SEQ ID NO: 119); 5' UTR_14 (SEQ ID NO: 141) and 3' UTR_10 (SEQ ID NO: 123). In embodiments, the pharmaceutical composition further comprises a pharmaceutically acceptable carrier. In embodiments, the pharmaceutically acceptable carrier is a lipidoid, a liposome, a lipoplex, a lipid nanoparticle, a polymeric nanoparticle, a peptide, a protein, a cell, a nanoparticle mimic, a nanotube, or a conjugate. In embodiments, the polynucleotide is formulated as a lipid nanoparticle (LNPs), a lipoplex, or a liposome. In embodiments, the polynucleotide is formulated as a lipid nanoparticle (LNPs). In embodiments, the lipid nanoparticles comprise lipids selected from an ionizable lipid (e.g., an ionizable cationic lipid selected from DLin-DMA, DLin-K-DMA, DLin-KC2-DMA, DLin-MC3-DMA, 98N12-5, and C12-200); a structural lipid (e.g., distearoylphosphatidylcholine (DSPC)); cholesterol, and a polyethyleneglycol (PEG)-lipid (e.g., a PEG-diacylglycerol (DAG), a PEG-dialkyloxypropyl (DAA), a PEG-phospholipid, a PEG-ceramide (Cer), or a mixture thereof, or a PEG-dilauryloxypropyl (C12, a PEG-dimyristyloxypropyl (C14), a PEG-dipalmityloxypropyl (C16), or a PEG-distearyloxypropyl (C18)); 1,2-dioleoyl-3-trimethylammoniumpropane (DOTAP); dioleoylphosphatidylethanolamine (DOPE); and the mmRNA.

In embodiments, the lipid nanoparticles comprise lipids selected from an ionizable lipid; a structural lipid; cholesterol, and a polyethyleneglycol (PEG)-lipid; 1,2-dioleoyl-3-trimethylammoniumpropane (DOTAP); dioleoylphosphatidylethanolamine (DOPE); and the mmRNA. In embodiments, the ionizable lipid is an ionizable cationic lipid selected from DLin-DMA, DLin-K-DMA, DLin-KC2-DMA, DLin-MC3-DMA, 98N12-5, and C12-200. In embodiments, the polyethyleneglycol (PEG)-lipid is selected from a PEG-diacylglycerol (DAG), a PEG-dialkyloxypropyl (DAA), a PEG-phospholipid, a PEG-ceramide (Cer), or a mixture thereof, or a PEG-dilauryloxypropyl (e.g., C12, a PEG-dimyristyloxypropyl (C14), a PEG-dipalmityloxypropyl (C16), or a PEG-distearyloxypropyl (C18)).

In embodiments, the lipid nanoparticles comprise an ionizable lipid, a PEG-lipid, a phospholipid and a structural lipid. In embodiments, the lipid nanoparticles comprise (a) a cationic lipid comprising from 50 mol % to 85 mol % of the total lipid present in the particle; (b) a non-cationic lipid comprising from 13 mol % to 49.5 mol % of the total lipid present in the particle; and (c) a conjugated lipid that inhibits aggregation of particles comprising from 0.5 mol % to 2 mol % of the total lipid present in the particle. In embodiments, the lipid nanoparticles comprise a lipid selected from SM-102, DLin-DMA, DLin-K-DMA, DLin-KC2-DMA, DLin-MC3-DMA, 98N12-5, and C12-200; a cholesterol; and a PEG-lipid.

In embodiments, the isolated polynucleotide administered by a parenteral administration. In embodiments, the parenteral administration is selected from intradermal, intramuscular, intraperitoneal, intraarticular, intravenous, subcutaneous, intraarterial or transdermal administration. In embodiments, the chimeric protein is expressed in liver, skin and/or muscle. In embodiments, the chimeric protein is cleaved in liver, skin and/or muscle. In embodiments, the GLP-1 receptor agonist is released in liver, skin and/or muscle. In embodiments, the GLP-1 receptor agonist enters circulation upon release in liver, skin and/or muscle.

In embodiments, the treatment of diabetes improves blood sugar control. In embodiments, the treatment of diabetes comprises decreased food intake. In embodiments, the subject has a fasting blood sugar reading of at least about 125 mg/dL, or at least about 150 mg/dL, or at least about 200 mg/dL or more before treatment. In embodiments, the subject's fasting blood sugar reading reaches to less than about 125 mg/dL after treatment. In embodiments, the subject's fasting blood sugar reading reaches to less than about 99 mg/dL aftertreatment. In embodiments, the subject suffers from one or more of increased urination, increased thirst, increased hunger, increased food intake, increased weight, obesity, weight loss, blurry vision, numbing or tingling hands or feet, very dry skin, and diabetic sores.

In embodiments, an increase in the level of chimeric protein encoded by the isolated polynucleotide may be observed in tissue selected from the liver, spleen, kidney, lung, heart, peri-renal adipose tissue, thymus and muscle and/or in a bodily fluid selected from peripheral blood, serum, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. The increased level of chimeric protein can be observed in the tissue and/or bodily fluid of the subject within 2, 8 and/or 24 hours after administration.

Subjects and/or Animals

In embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In embodiments, the subject and/or animal is a non-mammal, such, for example, a zebrafish. In embodiments, the subject and/or animal may comprise fluorescently-tagged cells (with e.g., GFP). In embodiments, the subject and/or animal is a transgenic animal comprising a fluorescent cell.

In embodiments, the subject and/or animal is a human. In embodiments, the human is a pediatric human. In embodiments, the human is an adult human. In embodiments, the human is a geriatric human. In embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In embodiments, the subject is a non-human animal, and therefore the disclosure pertains to veterinary use. In a specific embodiment, the non-human animal is a household pet. In another specific embodiment, the non-human animal is a livestock animal.

Kits

The disclosure provides kits that can simplify the administration of any agent described herein. An illustrative kit of the disclosure comprises any composition described herein in unit dosage form. In embodiments, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In embodiments, the kit comprises a container containing an effective amount of a composition of the disclosure and an effective amount of another composition, such those described herein.

Any aspect or embodiment described herein can be combined with any other aspect or embodiment as disclosed herein.

The disclosure will be further described in the following examples, which do not limit the scope of the disclosure described in the claims.

EXAMPLES

The examples herein are provided to illustrate advantages and benefits of the present technology and to further assist a person of ordinary skill in the art with preparing or using the chimeric proteins of the present technology. The examples herein are also presented in order to more fully illustrate the preferred aspects of the present technology. The examples should in no way be construed as limiting the scope of the present disclosure, as exemplified by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Figure 1B:
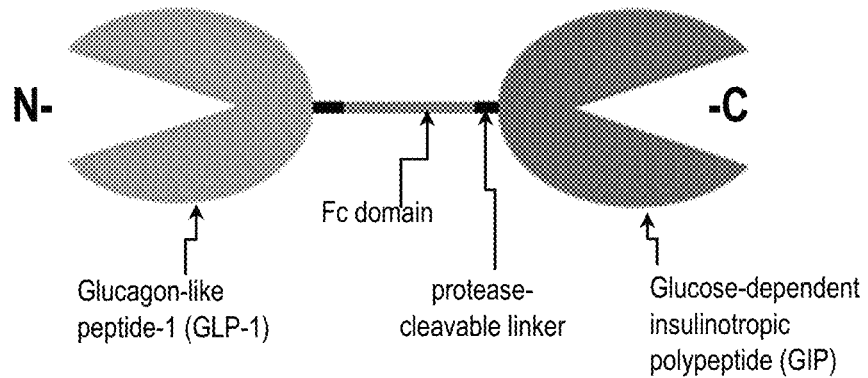

Example 1. Construction and Characterization of an Illustrative GLP-1- and GIP-Based Chimeric Protein A construct encoding a GLP-1- and GIP-based chimeric protein is generated. The "GIP-Fc-GLP-1" construct included GLP-1 fused to GIP via a hinge-CH2-CH3 Fc domain derived from IgG1 and a protease-cleavable polypeptide linker. See, FIG. 1B.

The construct is codon optimized for expression in Chinese Hamster Ovary (CHO) cells, transfected into CHO cells and individual clones were selected for high expression. High expressing clones are then used for small-scale manufacturing in stirred bioreactors in serum-free media and the relevant chimeric fusion proteins are purified with Protein A binding resin columns.

Figure 2A:
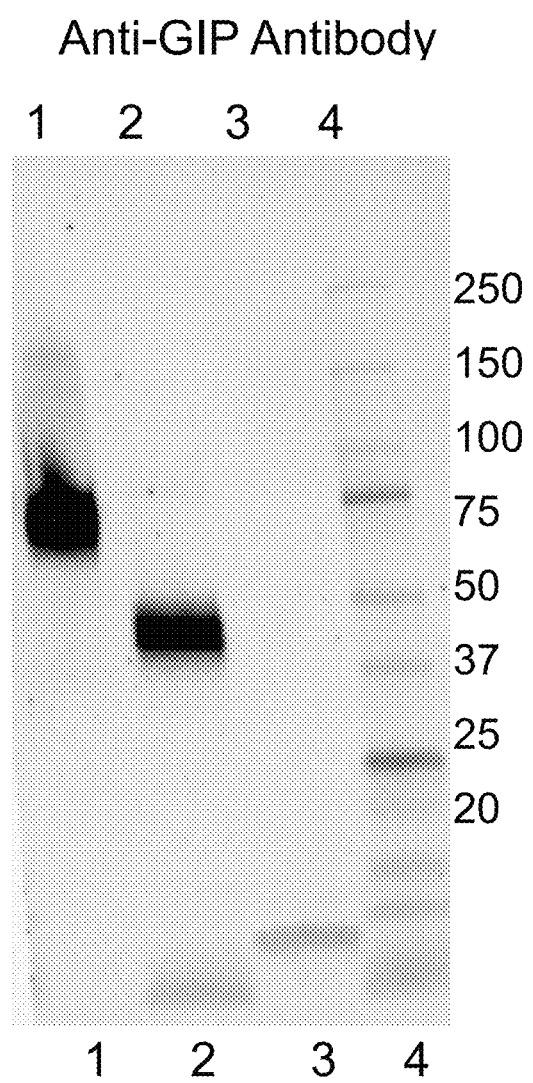
FIG. 2A to FIG. 2E demonstrate the construction of various non-limiting chimeric proteins disclosed herein.

The GIP-Fc-GLP-1construct was transiently expressed in 293 cells and purified using protein-A affinity chromatography. The GIP-Fc-GLP-1 chimeric protein was analyzed by western blots. Briefly, the purified human GIP-Fc-GLP-1protein was boiled in the presence of SDS alone (lane 1 in FIG. 2A), or treated with β-mercaptoethanol and boiled in the presence of SDS (lane 2 in FIG. 2A) and resolved using sodium dodecyl sulfate-polyacrylamide gel electrophoresis (SDS-PAGE). His-GIP peptide was used as a positive control (lane 3 in FIG. 2A). The western blot was probed with an anti-GIP antibody. As shown in FIG. 2A, The chimeric protein ran as a monomer at the predicted molecular weight in the presence of both a reducing agent (R-mercaptoethanol, lane 1 in FIG. 2A). The presence of a band in lane 1 corresponded to a dimer (lane 2 in FIG. 2A).

These results demonstrate, inter alia, that the GIP-Fc-GLP-1 chimeric protein forms a dimer through disulfide bonding.

Example 2. Construction and Characterization of an Illustrative GLP-1- and GIP-Based Chimeric Protein A construct encoding a GLP-1- and GIP-based chimeric protein was generated. The "GIP-Fc-GLP-1" construct included GLP-1 fused to GIP via a hinge-CH2-CH3 Fc domain derived from IgG1 and a protease-cleavable polypeptide linker. See, FIG. 1A.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

The GIP-Fc-GLP-1 construct was transiently expressed in 293 cells and purified using protein-A affinity chromatography. To understand the native structure of the GIP-Fc-GLP-1 chimeric protein, untreated denatured samples (i.e., boiled in the presence of SDS, without a treatment with a reducing agent or a deglycosylation agent) were compared with (i) reduced samples, which were not deglycosylated (i.e. treated only with R-mercaptoethanol, and boiled in the presence of SDS); and (ii) reduced and deglycosylated samples (i.e. treated both with R-mercaptoethanol and a deglycosylation agent, and boiled in the presence of SDS). In addition, to confirm the presence of each domain of the GIP-Fc-GLP-1 chimeric protein, the gels were run in triplicates and probed using an anti-GLP-1 antibody, an anti-IgG+IgM (H+L) antibody, or an anti-GIP antibody.

Example 3. Construction and Characterization of an Illustrative GIP- and GIP Agonist-Based Chimeric Protein A construct encoding a GLP-1 agonist peptide- and a GIP agonist peptide (amino acids 1-42; GIP(Ag))-based chimeric protein was generated. The "GLP-1-Fc-GIP(Ag)" construct included GLP-1 fused to GIP(Ag) via a hinge-CH2-CH3 Fc domain derived from IgG1. See, FIG. 1B.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

Figure 2B:
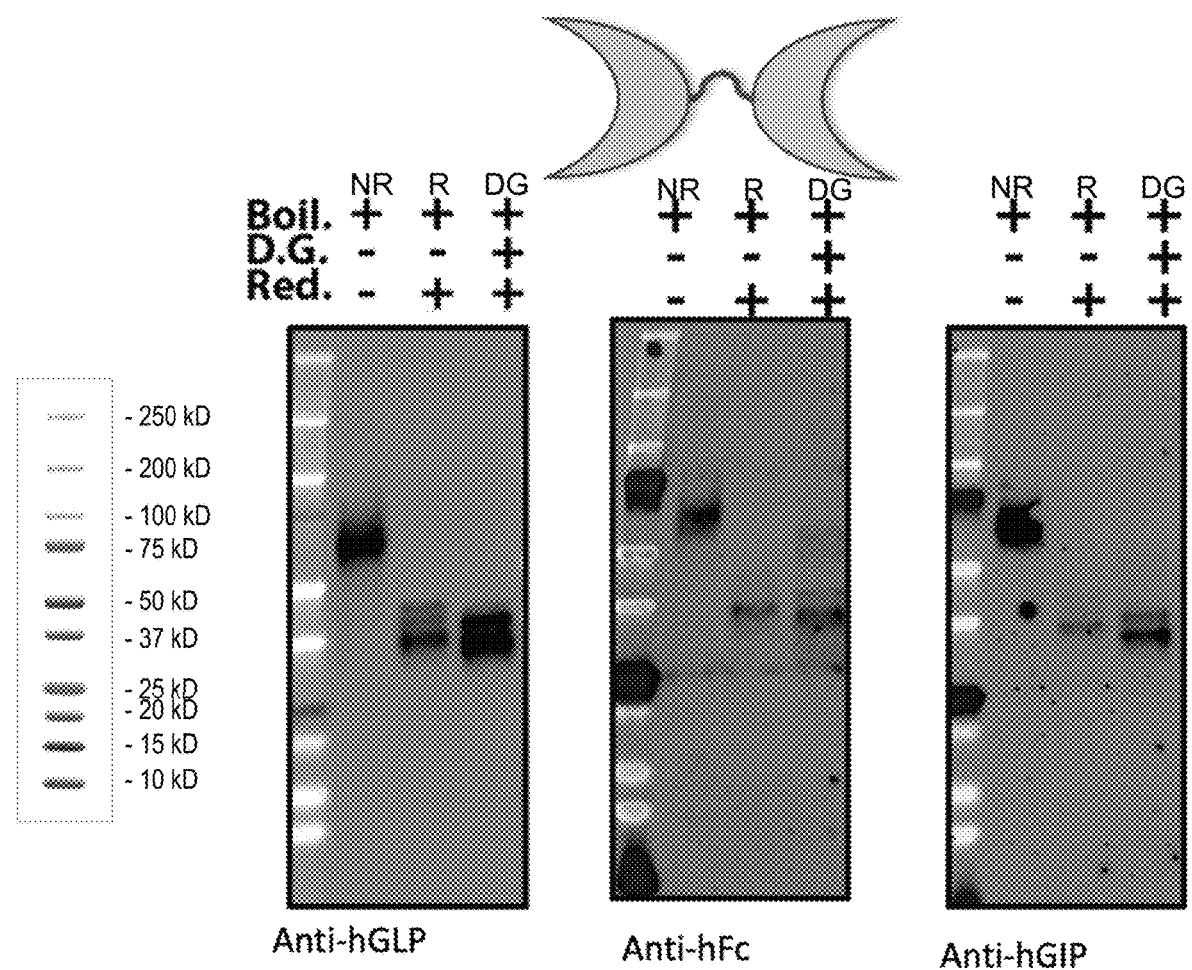

The GLP-1-Fc-GIP(Ag) construct was transiently expressed in 293 cells and purified using protein-A affinity chromatography. To understand the native structure of the GLP-1-Fc-GIP(Ag) chimeric protein, untreated denatured samples (i.e., boiled in the presence of SDS, without a treatment with a reducing agent or a deglycosylation agent) were compared with (i) reduced samples, which were not deglycosylated (i.e. treated only with R-mercaptoethanol, and boiled in the presence of SDS); and (ii) reduced and deglycosylated samples (i.e. treated both with R-mercaptoethanol and a deglycosylation agent, and boiled in the presence of SDS). In addition, to confirm the presence of each domain of the GLP-1-Fc-GIP(Ag) chimeric protein, the gels were run in triplicates and probed using an anti-human GLP-1 antibody (FIG. 2B, left blot), an anti-Fc antibody (FIG. 2B, center blot), or an anti-GIP antibody (FIG. 2B, right blot). The Western blots indicated the presence of a dominant dimer band in the non-reduced lanes (FIG. 2B, lane NR in each blot), which was reduced to a glycosylated monomeric band in the presence of the reducing agent, R-mercaptoethanol (FIG. 2B, lane R in each blot). As shown in FIG. 2B, lane DG in each blot, the chimeric protein ran as a monomer with a slightly increased mobility the presence of both a reducing agent (R-mercaptoethanol) and a deglycosylation agent conditions (lane "R" in FIG. 2B) compared to the protein prepared in the presence of only a reducing agent (lane "DG" in FIG. 2B). The difference in mobility of the GLP-1-Fc-GIP(Ag) chimeric protein prepared under reduced and both reduced and deglycosylated conditions indicated that the GLP-1-Fc-GIP(Ag) chimeric protein is glycosylated.

These results demonstrate, inter alia, that the GLP-1-Fc-GIP(Ag) chimeric protein was successfully constructed and that the GLP-1-Fc-GIP(Ag) chimeric protein is glycosylated and forms a dimer through disulfide bonding.

Example 4. Construction and Characterization of an Illustrative GIP- and GIP Antagonist-Based Chimeric Protein A construct encoding a GLP-1 agonist peptide- and a GIP antagonist peptide (amino acids 1-42 having E3P mutation)-based chimeric protein was generated. The "GLP-1-Fc-GIP (AntPro3)" construct included GLP-1 fused to GIP(AntPro3) via a hinge-CH2-CH3 Fc domain derived from IgG1. See, FIG. 1B.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

Figure 2C:
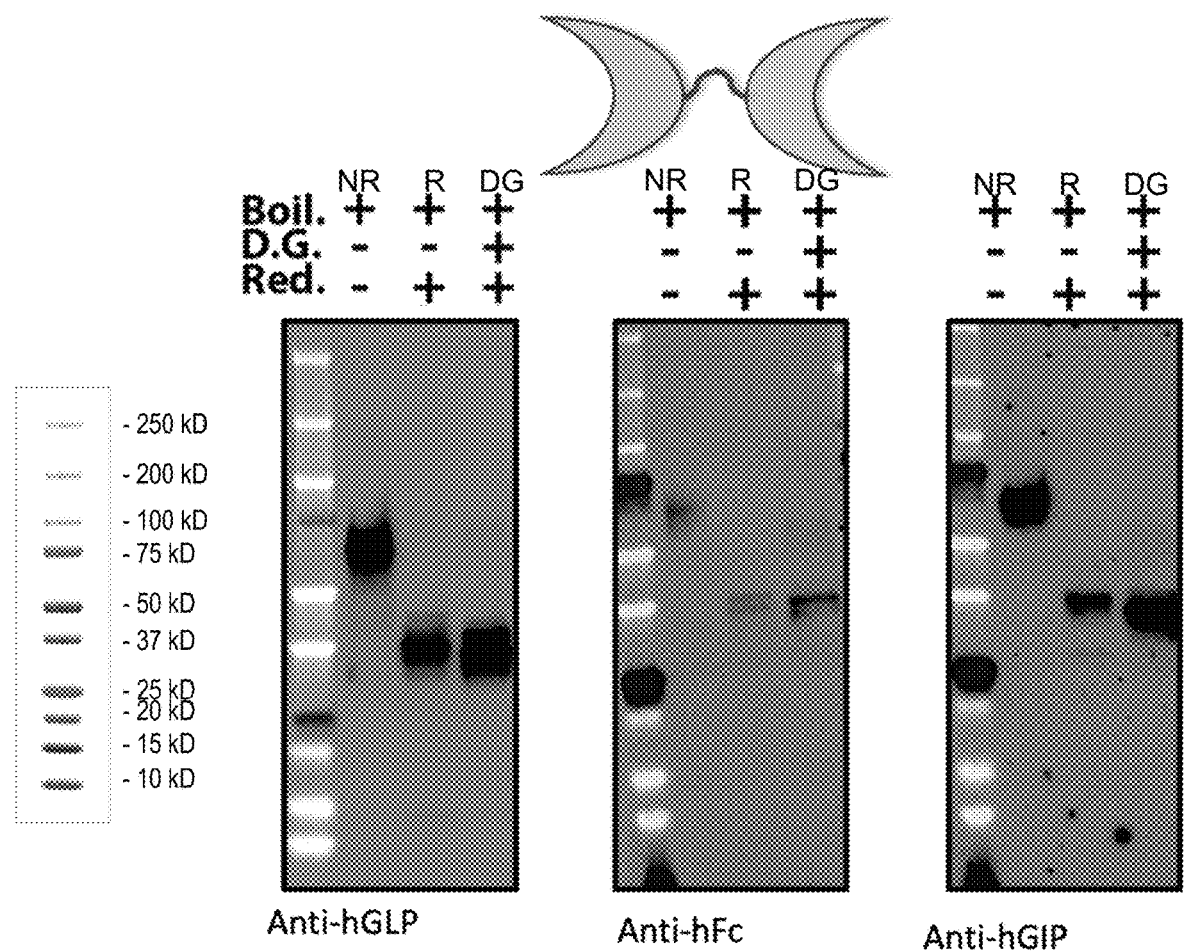

The GLP-1-Fc-GIP(AntPro3) construct was transiently expressed in 293 cells and purified using protein-A affinity chromatography. To understand the native structure of the GLP-1-Fc-GIP(AntPro3) chimeric protein, untreated denatured samples (i.e., boiled in the presence of SDS, without a treatment with a reducing agent or a deglycosylation agent) were compared with (i) reduced samples, which were not deglycosylated (i.e. treated only with R-mercaptoethanol, and boiled in the presence of SDS); and (ii) reduced and deglycosylated samples (i.e. treated both with R-mercaptoethanol and a deglycosylation agent, and boiled in the presence of SDS). In addition, to confirm the presence of each domain of the GLP-1-Fc-GIP(AntPro3) chimeric protein, the gels were run in triplicates and probed using an anti-human GLP-1 antibody (FIG. 2C, left blot), an anti-Fc antibody (FIG. 2C, center blot), or an anti-GIP antibody (FIG. 2C, right blot). The Western blots indicated the presence of a dominant dimer band in the non-reduced lanes (FIG. 2C, lane NR in each blot), which was reduced to a glycosylated monomeric band in the presence of the reducing agent, R-mercaptoethanol (FIG. 2C, lane R in each blot). As shown in FIG. 2C, lane DG in each blot, the chimeric protein ran as a monomer with a slightly increased mobility the presence of both a reducing agent (R-mercaptoethanol) and a deglycosylation agent conditions (lane "R" in FIG.

2C) compared to the protein prepared in the presence of only a reducing agent (lane "DG" in FIG. 2C). The difference in mobility of the GLP-1-Fc-GIP(AntPro3) chimeric protein prepared under reduced and both reduced and deglycosylated conditions indicated that the GLP-1-Fc-GIP(AntPro3) chimeric protein is glycosylated.

These results demonstrate, inter alia, that the GLP-1-Fc-GIP(AntPro3) chimeric protein was successfully constructed and that the GLP-1-Fc-GIP(AntPro3) chimeric protein is glycosylated and forms a dimer through disulfide bonding.

Example 5. Construction and Characterization of an Illustrative Chimeric Protein Based on GIP- and the GIP Antagonist GIP(Ant3-30)

A construct encoding a GLP-1 agonist peptide and a GIP antagonist peptide (amino acids 3-30; GIP(Ant3-30))-based chimeric protein was generated. The "GLP-1-Fc-GIP(Ant 3-30)" construct included GLP-1 fused to GIP(Ant3-30) via a hinge-CH2-CH3 Fc domain derived from IgG1. See, FIG. 1B.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

Figure 2D:
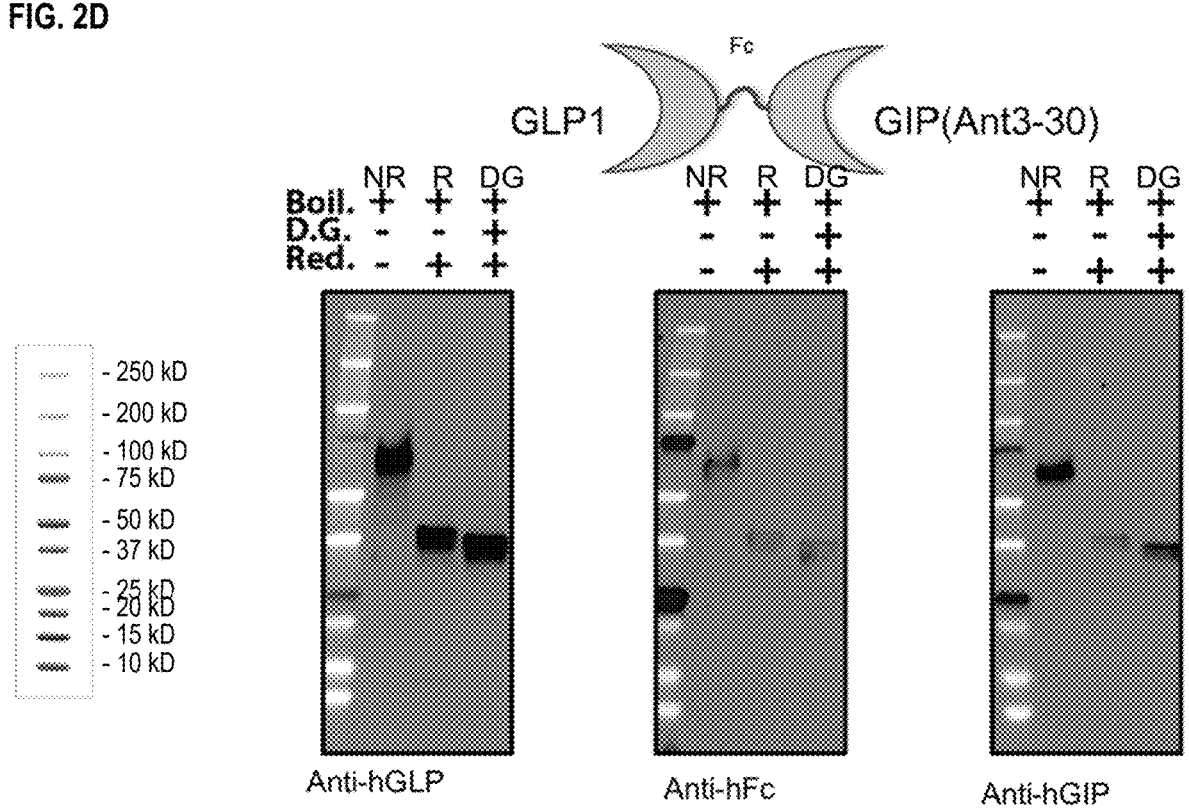

The GLP-1-Fc-GIP(Ant 3-30) construct was transiently expressed in 293 cells and purified using protein-A affinity chromatography. To understand the native structure of the GLP-1-Fc-GIP(Ant 3-30) chimeric protein, untreated denatured samples (i.e., boiled in the presence of SDS, without a treatment with a reducing agent or a deglycosylation agent) were compared with (i) reduced samples, which were not deglycosylated (i.e. treated only with β-mercaptoethanol, and boiled in the presence of SDS); and (ii) reduced and deglycosylated samples (i.e. treated both with β-mercaptoethanol and a deglycosylation agent, and boiled in the presence of SDS). In addition, to confirm the presence of each domain of the GLP-1-Fc-GIP(Ant 3-30) chimeric protein, the gels were run in triplicates and probed using an anti-human GLP-1 antibody (FIG. 2D, left blot), an anti-Fc antibody (FIG. 2D, center blot), or an anti-GIP antibody (FIG. 2D, right blot). The Western blots indicated the presence of a dominant dimer band in the non-reduced lanes (FIG. 2D, lane NR in each blot), which was reduced to a glycosylated monomeric band in the presence of the reducing agent, R-mercaptoethanol (FIG. 2D, lane R in each blot). As shown in FIG. 2D, lane DG in each blot, the chimeric protein ran as a monomer with a slightly increased mobility the presence of both a reducing agent (R-mercaptoethanol) and a deglycosylation agent conditions (lane "R" in FIG. 2D) compared to the protein prepared in the presence of only a reducing agent (lane "DG" in FIG. 2D). The difference in mobility of the GLP-1-Fc-GIP(Ant 3-30) chimeric protein prepared under reduced and both reduced and deglycosylated conditions indicated that the GLP-1-Fc-GIP(Ant 3-30) chimeric protein is glycosylated.

These results demonstrate, inter alia, that the GLP-1-Fc-GIP(Ant 3-30) chimeric protein was successfully constructed and that the GLP-1-Fc-GIP(Ant 3-30) chimeric protein is glycosylated and forms a dimer through disulfide bonding.

Example 6. Construction and Characterization of an Illustrative Chimeric Protein Based on GIP- and the GIP Antagonist GIP(Ant3-30,Pro3)

A construct encoding a GLP-1 agonist peptide and a GIP antagonist peptide (amino acids 3-30; GIP(Ant3-30,Pro3))-based chimeric protein was generated. The "GLP-1-Fc-GIP(Ant 3-30, Pro3)" construct included GLP-1 fused to GIP(Ant3-30,Pro3) via a hinge-CH2-CH3 Fc domain derived from IgG1. See, FIG. 1B.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

Figure 2E:
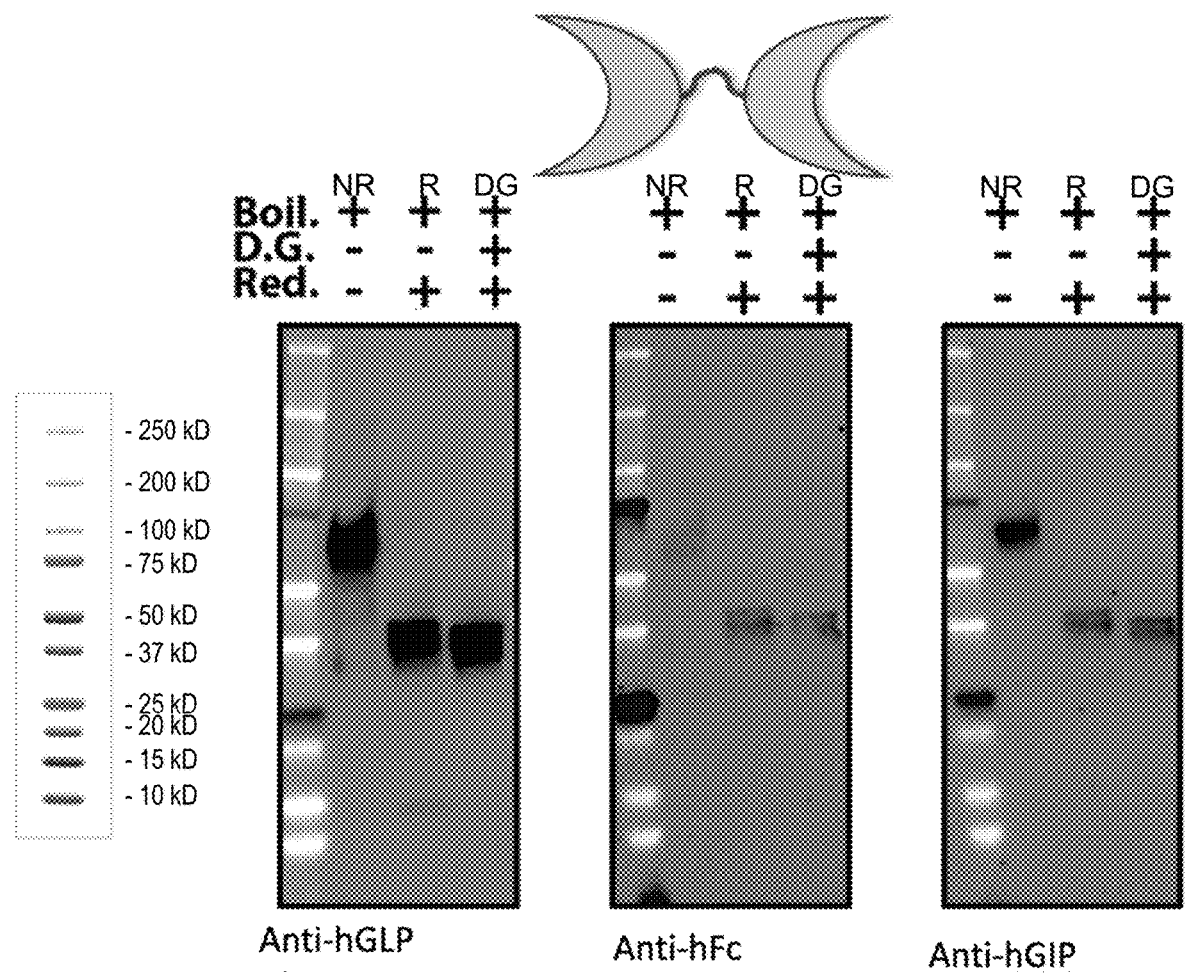

The GLP-1-Fc-GIP(Ant 3-30, Pro3) construct was transiently expressed in 293 cells and purified using protein-A affinity chromatography. To understand the native structure of the GLP-1-Fc-GIP(Ant 3-30, Pro3) chimeric protein, untreated denatured samples (i.e., boiled in the presence of SDS, without a treatment with a reducing agent or a deglycosylation agent) were compared with (i) reduced samples, which were not deglycosylated (i.e. treated only with R-mercaptoethanol, and boiled in the presence of SDS); and (ii) reduced and deglycosylated samples (i.e. treated both with R-mercaptoethanol and a deglycosylation agent, and boiled in the presence of SDS). In addition, to confirm the presence of each domain of the GLP-1-Fc-GIP(Ant 3-30, Pro3) chimeric protein, the gels were run in triplicates and probed using an anti-human GLP-1 antibody (FIG. 2E, left blot), an anti-Fc antibody (FIG. 2E, center blot), or an anti-GIP antibody (FIG. 2E, right blot). The Western blots indicated the presence of a dominant dimer band in the non-reduced lanes (FIG. 2E, lane NR in each blot), which was reduced to a glycosylated monomeric band in the presence of the reducing agent, β-mercaptoethanol (FIG. 2E, lane R in each blot). As shown in FIG. 2E, lane DG in each blot, the chimeric protein ran as a monomer with a slightly increased mobility the presence of both a reducing agent (β-mercaptoethanol) and a deglycosylation agent conditions (lane "R" in FIG. 2E) compared to the protein prepared in the presence of only a reducing agent (lane "DG" in FIG. 2E). The difference in mobility of the GLP-1-Fc-GIP(Ant 3-30, Pro3) chimeric protein prepared under reduced and both reduced and deglycosylated conditions indicated that the GLP-1-Fc-GIP(Ant 3-30, Pro3) chimeric protein is glycosylated.

These results demonstrate, inter alia, that the GLP-1-Fc-GIP(Ant 3-30, Pro3) chimeric protein was successfully constructed and that the GLP-1-Fc-GIP(Ant 3-30, Pro3) chimeric protein is glycosylated and forms a dimer through disulfide bonding.

Example 7. Construction and Characterization of an Illustrative GIP- and FGF19-Based Chimeric Protein A construct encoding a GIP- and FGF19-based chimeric protein was generated. The "GIP-Fc-FGF19" construct included GIP fused to FGF19 via a hinge-CH2-CH3 Fc domain derived from IgG1 and a protease-cleavable polypeptide linker. See, FIG. 1B.

The construct was codon optimized for expression in Chinese Hamster Ovary (CHO) cells, transfected into CHO cells and individual clones were selected for high expression. High expressing clones were then used for small-scale manufacturing in stirred bioreactors in serum-free media and the relevant chimeric fusion proteins were purified with Protein A binding resin columns.

The GIP-Fc-FGF19 construct was transiently expressed in 293 cells and purified using protein-A affinity chromatography. To understand the native structure of the GIP-Fc-FGF19 chimeric protein, untreated denatured samples (i.e., boiled in the presence of SDS, without a treatment with a reducing agent or a deglycosylation agent) were compared with (i) reduced samples, which were not deglycosylated (i.e. treated only with R-mercaptoethanol, and boiled in the presence of SDS); and (ii) reduced and deglycosylated samples (i.e. treated both with R-mercaptoethanol and a deglycosylation agent, and boiled in the presence of SDS). In addition, to confirm the presence of each domain of the GIP-Fc-FGF19 chimeric protein, the gels were run in triplicates and probed using an anti-GIP antibody, an anti-IgG+ IgM (H+L) antibody, or an anti-FGF19 antibody.

Figure 3A:
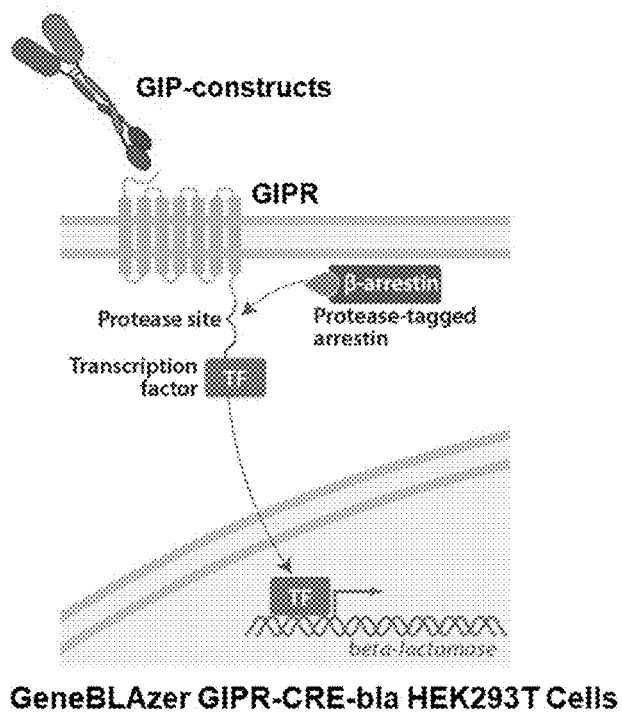
FIG. 3A and FIG. 3B show the results of a reporter assay demonstrating the activation of GIPR by the chimeric proteins disclosed herein.

Example 8. The Purified Chimeric Proteins and the Culture Supernatants of Cells Transfected with the Modified mRNA (mmRNA) Disclosed Herein Activate GIP Receptor The activity of GLP-1 receptor was assayed using the GeneBLAzer® GIPR-CRE-bla HEK293T cell-based assay (ThermoFisher) and purified proteins. This assay is diagrammatically represented in FIG. 3A. Upon binding of a glucose-dependent insulinotropic polypeptide receptor (GIPR) agonist to the targeting construct, a transcriptional cascade is initiated that produces R-lactamase (FIG. 3A). In the presence of the β-lactamase LiveBLAzer™ substrate, cells expressing R-lactamase fluoresce blue (460 nm), while those not expressing β-lactamase fluoresce green (530 nm); higher 460/530 ratio indicates the activation of GIPR.

Figure 3B:
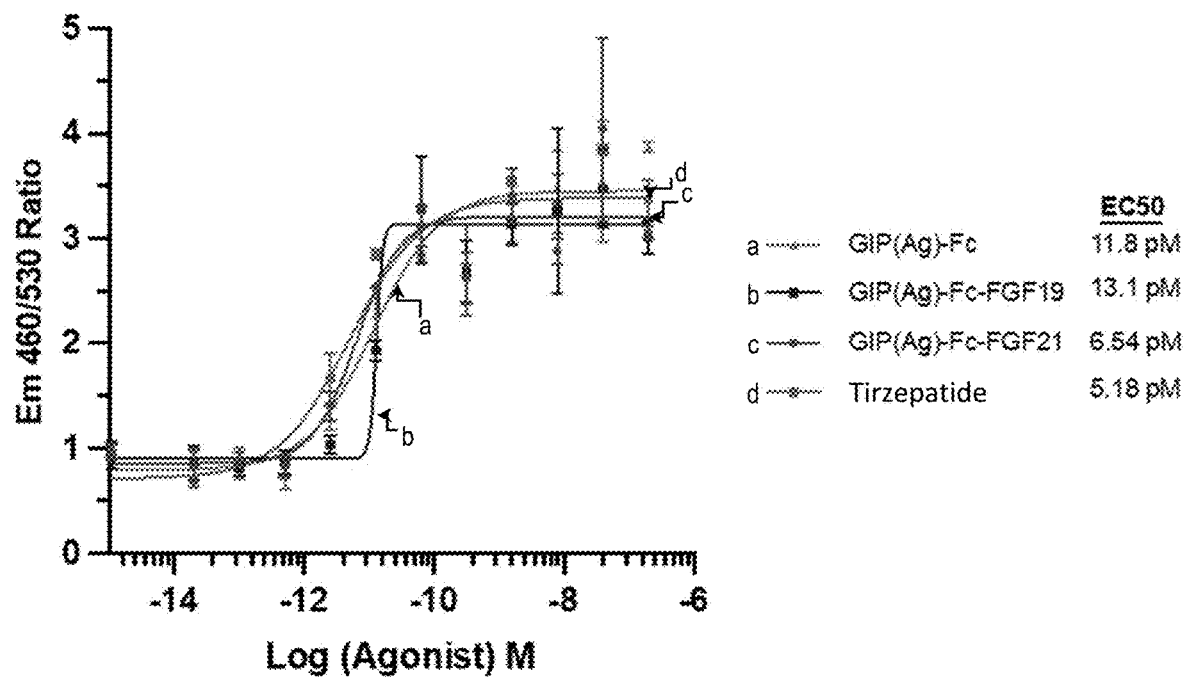

Briefly, GeneBLAzer® GIPR-CRE-bla HEK293T cells were added to wells of black-wall assay plates. Medium alone (negative control) or increasing amounts of the GIP (Ag)-Fc fusion protein, tirzepatide, or the purified GIP(Ag)-Fc-FGF19, or GIP(Ag)-Fc-FGF21 chimeric proteins were added to the plates and the plates were incubated in a humidified 37° C./5% C02 incubator for 5 hours. The GIP(Ag)-Fc fusion protein was used as a positive control. To each well, LiverBLAzer-FRET B/G substrate mixture was added. The plate was covered with plate sealer and incubated at room temperature for 2 hours in the dark. Fluorescence emission was measured on SpectraMax plate reader at 460 nm and 530 nm with excitation set to 409 nm. After subtraction of background, average value at 460 nm (blue color) was divided by average value at 530 nm (green color) to obtain the 460/530 ratio. As shown in FIG. 3B, each of the tirzepatide, the GIP(Ag)-Fc fusion protein and the purified GIP(Ag)-Fc-FGF19, or GIP(Ag)-Fc-FGF21 chimeric proteins produced a dose-dependent and saturable increase in 460/530 ratio, indicative of the activation of GIPR. Tirzepatide, GIP(Ag)-Fc protein and the purified GIP(Ag)-Fc-FGF19, or GIP(Ag)-Fc-FGF21 chimeric proteins activated GIPR with $EC_{50}$ values of 5.18 pM, 11.8 pM, 13.1 pM, and 6.54 pM, respectively (FIG. 3B). Surprisingly, the purified GIP(Ag)-Fc-FGF21 chimeric protein activated GIPR with an $EC_{50}$ that is greater than that of the GIP(Ag)-Fc fusion protein (FIG. 3B).

These results indicate, inter alia, that chimeric proteins disclosed herein cause GIP-receptor engagement and activation of downstream signaling.

Figure 4A:
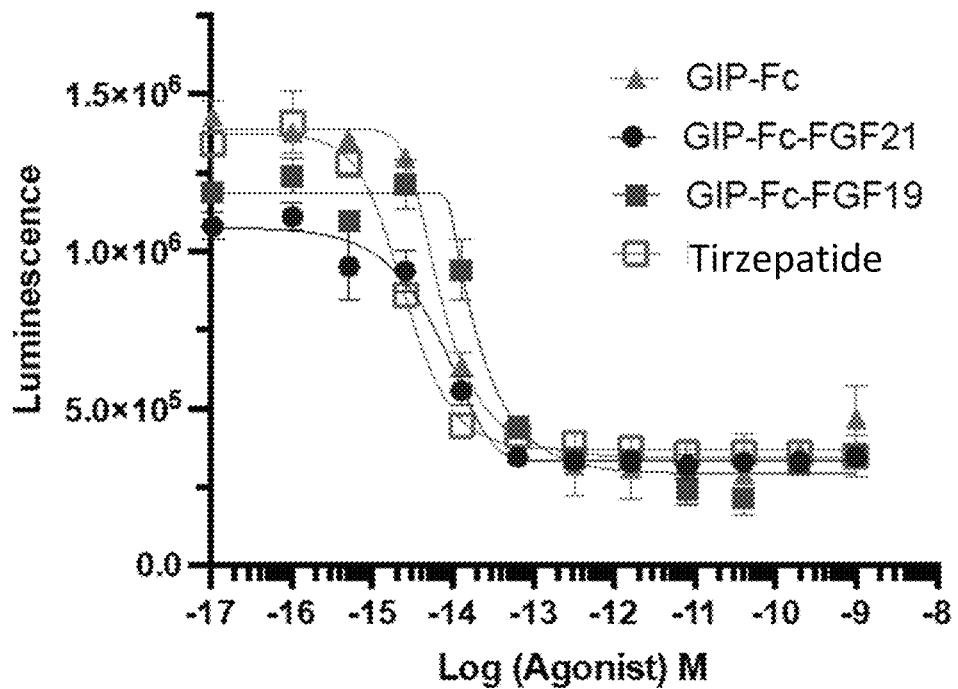
FIG. 4A and FIG. 4B demonstrate the activation of GIP receptor (GIPR) and glucose-stimulated insulin secretion (GSIS) induced by the chimeric proteins disclosed herein.

Example 9. The Purified Chimeric Proteins Disclosed Herein Activate GIP Receptor A derivative of the rat INS-1 insulinoma cell line, which is a commonly used model to study pancreatic islet beta cell function following glucose stimulation, was used to study the activation of GIP receptor (GIPR) and glucose-stimulated insulin secretion (GSIS) in vitro. Rat insulinoma INS-1 cells harboring a cAMP-luciferase reporter gene were used to study the activation of GIPR. Without wishing to be bound by theory, the activation of GIPR leads to temporary depletion of ATP because of consumption of ATP in cyclization reaction to produce cAMP as well as by phosphorylation by protein kinase A of its substrate. Without wishing to be bound by theory, the temporary depletion of ATP leads to an inhibition of luciferase activity, which needs ATP as a substrate. Briefly, the rat insulinoma INS-1 cells harboring a cAMP-luciferase reporter gene were stimulated for 1 hour with glucose, followed by a 2 hour incubation with increasing amounts of GIP-Fc fusion protein, the GIP-Fc-FGF19 or GIP-Fc-FGF21 chimeric proteins, or tirzepatide and luciferase activity was measured using the cAMP-Glo™ assay (Promega). As shown in FIG. 4A, each of the GIP-Fc fusion protein, the GIP-Fc-FGF19 or GIP-Fc-FGF21 chimeric proteins, and tirzepatide caused a dose-dependent and saturable inhibition of luciferase with similar potency.

These results indicate, inter alia, that the GIP-Fc-FGF19 or GIP-Fc-FGF21 chimeric proteins activate the GIP receptor.

Figure 4B:
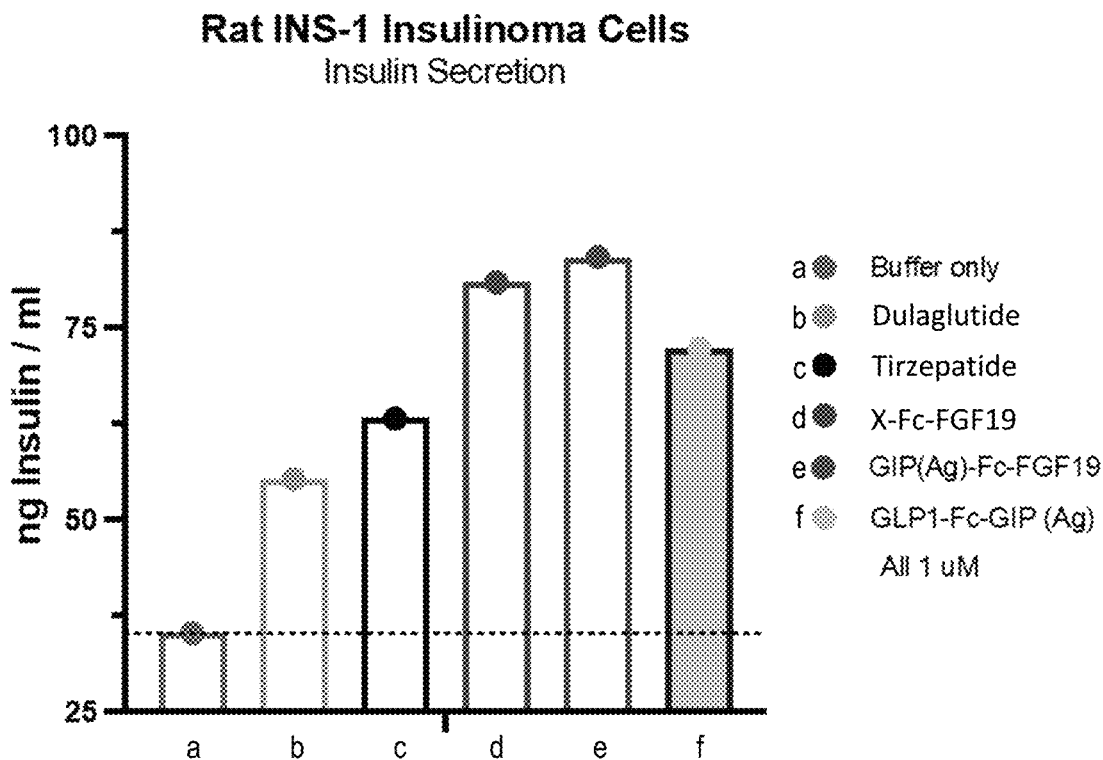

Rat insulinoma INS-1 cells harboring a cAMP-luciferase reporter gene were used to study in vitro glucose-stimulated insulin secretion (GSIS). Briefly, the rat insulinoma INS-1 cells harboring a cAMP-luciferase reporter gene were stimulated for 1 hour with glucose, followed by a 2 hour incubation with increasing amounts of dulaglutide, tirzepatide, the GIP-Fc-FGF19 or GLP-1-Fc-GIP(Ag) chimeric proteins, or a X-Fc-FGF19 chimeric protein. X is a known inducer of GSIS. Dulaglutide, tirzepatide, and X-Fc-FGF19 were used as positive controls and buffer alone was used as a negative control. After 2 hours of incubation, insulin was quantitated in the culture supernatant using ELIZA. As shown in FIG. 4B, the GIP(Ag)-Fc-FGF19 or GLP-1-Fc-GIP(Ag) chimeric proteins, stimulated insulin production to a similar, if not greater magnitude than dulaglutide or tirzepatide.

These results indicate, inter alia, that the GIP-Fc-FGF19 or GIP(Ag)-Fc-FGF19 chimeric proteins induce insulin production by pancreatic islet beta cells.

Example 10. Identification of GIP Receptor Antagonists and Agonists

A series of GIP antagonist peptides were evaluated at blocking human GIP (hGIP) agonism and the induction of cAMP. Briefly, rat INS-1 cells having pGloSensor-22F (Promega) were constructed and used to evaluate GIPR agonism and antagonism. These cells express a circularly permuted luciferase enzyme, which is inactive, and which undergoes a conformational change upon binding to cAMP. The conformational change leads to the activation of the luciferase enzyme, thereby allowing detection of activation of GIPR, which produces cAMP upon activation.

Figure 5A:
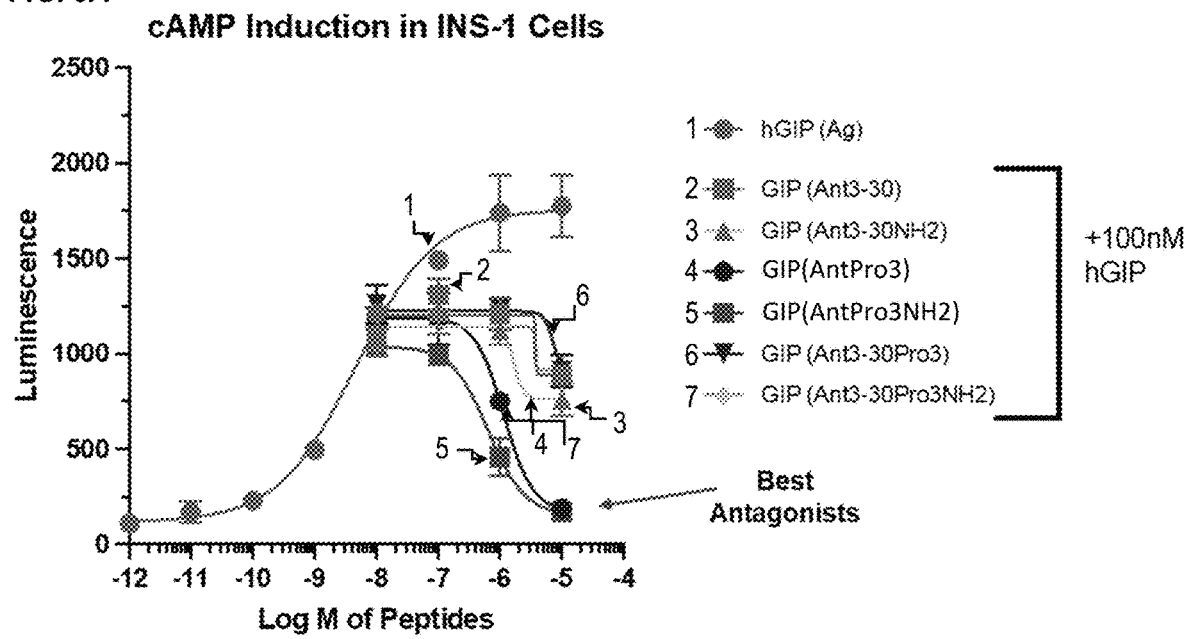
FIG. 5A and FIG. 5B demonstrate the agonistic and antagonistic activities of various GIP agonist and antagonist peptides.

To assay for GIPR agonism, rat INS-1 cells having pGloSensor-22F biosensor were treated with increasing concentrations of GIP(Ag). Immediately after the addition, the luminescence of the cells was measured, normalized using the basal luminescence and plotted. As shown in FIG. 5A, GIP(Ag) caused a dose-dependent activation of the cAMP-luciferase reporter gene.

GIPR antagonism was measured as the inhibition of GIP(Ag)-induced activation of the cAMP-luciferase reporter gene in rat INS-1 cells having pGloSensor-22F biosensor. The following GIP derivatives accessed in this assay for GIPR antagonism: GIP(Ant 3-30), GIP(Ant 3-30NH2), (GIP (Ant 3-30) having amidated carboxy terminus), GIP(Ant-Pro3), GIP(AntPro3NH2), GIP(Ant3-30, Pro3) and GIP (Ant3-30, Pro3NH2). Briefly, rat INS-1 cells having pGloSensor-22F were treated with increasing doses of the above various GIP derivatives, mixed with 100 mM GIP (Ag). Immediately after the addition, the luminescence of the cells was measured, normalized using the basal luminescence and plotted. As shown in FIG. 5A, GIP(AntPro3) and GIP(AntPro3NH2) caused maximal level of a dose-dependent inhibition of GIP(Ag)-induced activation of the cAMP-luciferase reporter gene in rat INS-1 cells having pGloSensor-22F biosensor.

Figure 5B:
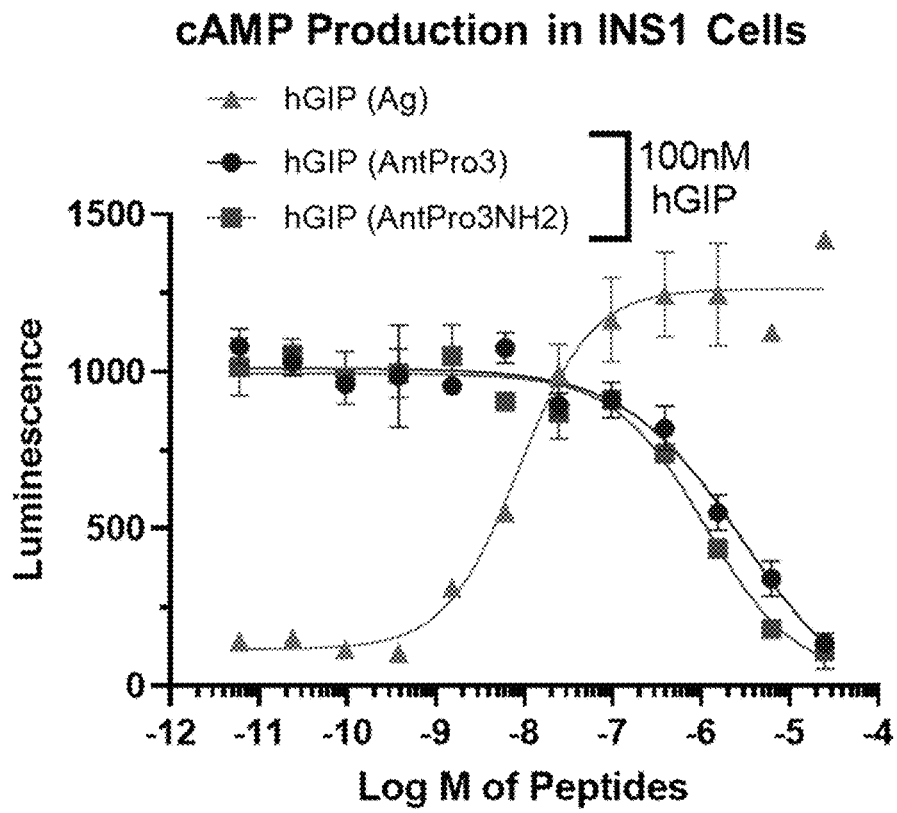

The GIP(Ag) was re-evaluated across a broader concentration range. Rat INS-1 cells having pGloSensor-22F biosensor were treated with increasing concentrations of GIP (Ag). Immediately after the addition, the luminescence of the cells was measured, normalized using the basal luminescence and plotted. As shown in FIG. 5B, GIP(Ag) caused a dose-dependent activation of the cAMP-luciferase reporter gene.

The GIP(AntPro3) and GIP(AntPro3NH2) were re-evaluated across a broader concentration range. Briefly, rat INS-1 cells having pGloSensor-22F were treated with increasing doses of GIP(AntPro3) and GIP(AntPro3NH2), mixed with 100 mM GIP(Ag). Immediately after the addition, the luminescence of the cells was measured, normalized using the basal luminescence and plotted. As shown in FIG. 5B, GIP(AntPro3) and GIP(AntPro3NH2) caused a dose-dependent inhibition of GIP(Ag)-induced activation of the cAMP-luciferase reporter gene in rat INS-1 cells having pGloSensor-22F biosensor.

These results indicate, inter alia, that GIP (Agonist) is a GIPR agonist.

These results further indicate, inter alia, that the GIP (AntPro3) and GIP (AntPro3NH2) are GIPR antagonists.

Figure 6A:
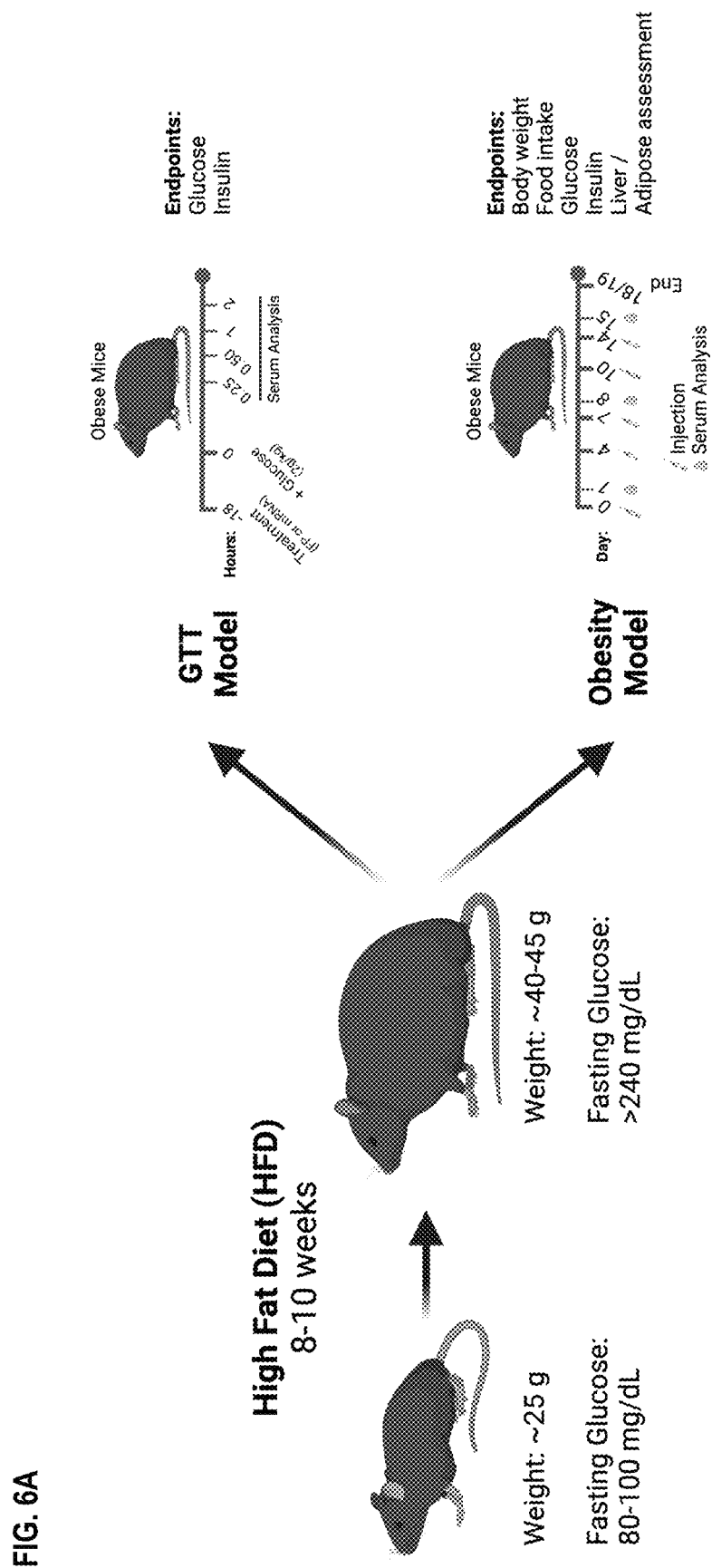
FIG. 6A shows the schematic representation of generation of a mouse model and in vivo experiments conducted to study the efficacy of the chimeric proteins disclosed herein in a glucose tolerance test (GTT) or against obesity.

Example 11. In Vivo Induction of Insulin Production and Control of Blood Glucose by the Purified Chimeric Proteins and Modified mRNA (mmRNA) Encoding the Chimeric Proteins Disclosed Herein GLP-1/GIP fusion protein and mRNA constructs were assessed in commonly used models of obesity/type 2 diabetes shown in FIG. 6A. Briefly, mice (Male C57BL/6) were of approximately 13 weeks of age were housed 4 mice per cage. Following 2 weeks of acclimatation, mice were introduced to 60% kcal HFD (Research Diets D12492). Cages were changed once, then changed once a week. Weekly body weights and non-fasted blood glucose were collected. The glucose tolerance test (GTT) model is acute and assesses tolerance to a bolus glucose injection and subsequent insulin production (FIG. 6A). The longer-term obesity model assesses a number of end points associated with obesity related type 2 diabetes (FIG. 6A).

Figure 6B:
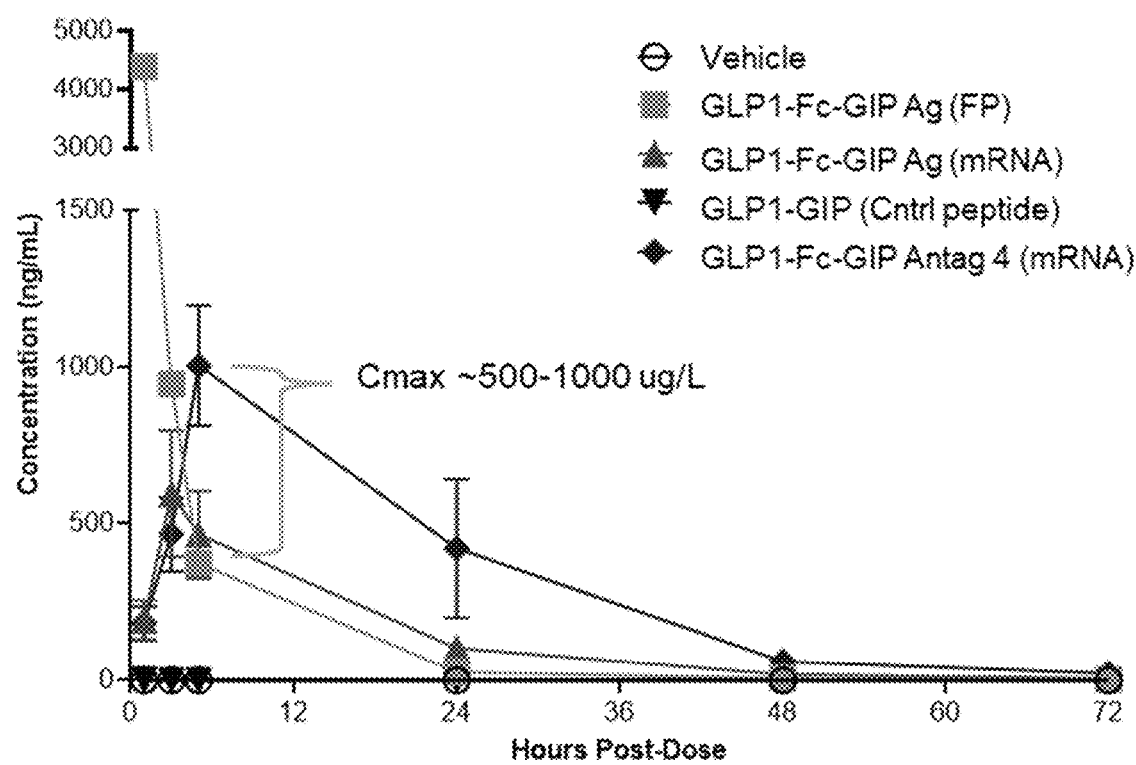
FIG. 6B shows the pharmacokinetics of the GLP-1-Fc-GIP(Ag) chimeric protein, GLP-1-GIP synthesized peptide, or mRNA encoding the GLP-1-Fc-GIP(Ag) chimeric protein or GLP-1-Fc-GIP synthetic peptide.

Pharmacokinetics of the chimeric proteins delivered as purified fusion proteins and as mmRNA was determined. Briefly, the HFD-fed mice were treated with the GLP-1-Fc-GIP(Ag) chimeric protein, GLP-1-GIP synthesized peptide, or mRNA encoding the GLP-1-Fc-GIP(Ag) chimeric protein or GLP-1-Fc-GIP synthetic peptide. The mRNA/LNP formulation were administered dose of 0.5 mpk/200 µL, and the purified fusion protein were administered at a dose of 5 mpk/400 ul. The levels of the GLP-1-Fc-GIP(Ag) chimeric protein and GLP-1-Fc-GIP in serum were determined using an ELISA-based assay. As shown in FIG. 6B, the pharmacokinetics (PK) of the purified fusion protein (FP) showed a rapid post-dose clearance. On the other hand, the mRNA-encoded protein accumulated between 6-24 hours post-dose and was detectable 48-72 hours after a single treatment (FIG. 6B).

These results indicate, inter alia, that the Fc-containing chimeric proteins disclosed herein or mRNA disclosed herein provide superior PK profiles as compared to the synthesized peptide constructs.

The GTT model in the HFD-fed mice was used to access insulin production and control of blood glucose by the purified chimeric proteins and modified mRNA (mmRNA) encoding the chimeric proteins disclosed herein (FIG. 6A). Upon induction of obesity using high fat diet, the mice were randomly divided in the following 6 treatment groups (6 mice per group):

Group #1 Glucose only+PBS (400ul per mouse, n=6)
Group #2 Glucose+Human tirzepatide (1.25 mpk/250 nm/kg bw, 400ul, n=6)
Group #3 hGLP-1-Fc-GIP (Ag)-fusion protein (5 mpk/400ul): n=6
Group #4 hGLP-1-Fc-GIP (Ag)-mRNA (1 mpk/400ul): n=6
Group #5 hGLP-1-Fc-GIP (AntPro3)-Fusion Protein (5 mpk/400ul): n=6
Group #6 hGLP-1-Fc-GIP (AntPro3)-mRNA (1 mpk/400ul): n=6

The mice administered the above treatment by i.v. injections. The mice were then fasted for 18 hours and administered a dose of 2 g/kg glucose by i.v. injections. Blood samples were drawn by tail clip bleeding at 15, 30 and 60 minutes post dosing and cardiac bleeding was used at 2 hours after glucose injection as end-point. The blood samples were analyzed for serum glucose and serum insulin concentrations.

Figure 7A:
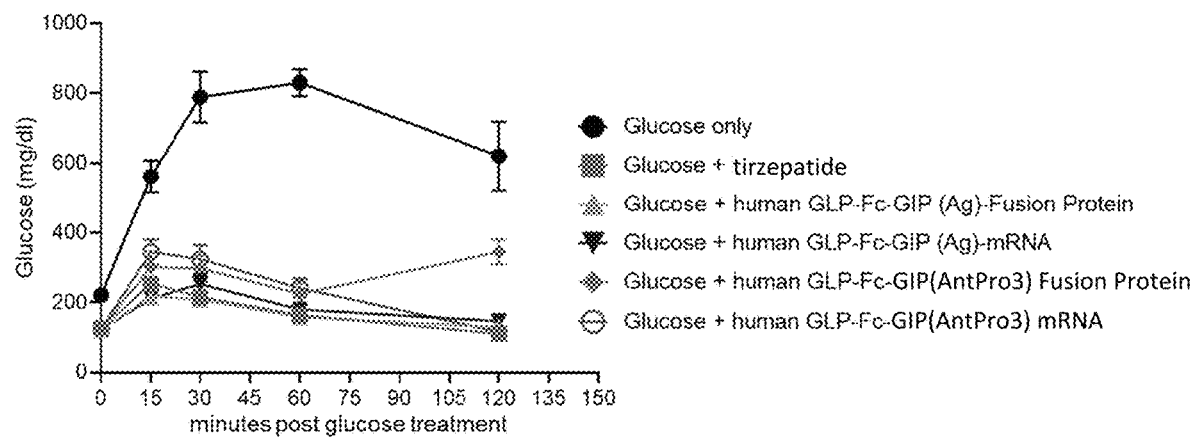
FIG. 7A to FIG. 7D demonstrate the control of blood glucose and insulin production in the mouse model treated with tirzepatide, the GLP-1-Fc-GIP (Ag) and GLP-1-Fc-GIP (AntPro3) chimeric proteins, or mRNA encoding the GLP-1-Fc-GIP (Ag) or GLP-1-Fc-GIP (AntPro3) chimeric proteins.
Figure 7B:
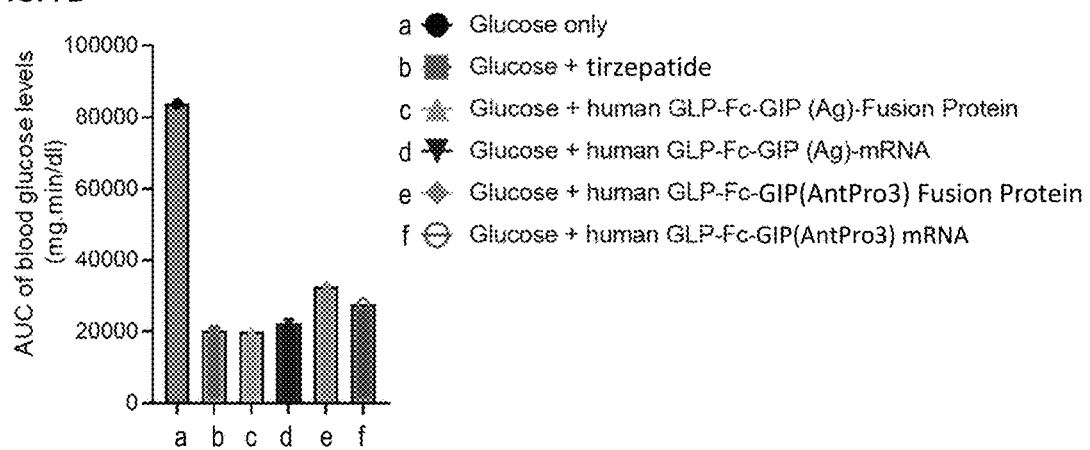

As shown in FIG. 7A, the serum glucose levels increase from 200 mg/dl to about 800 mg/dl following glucose administration in control mice that received only PBS (Group 1, closed circles in FIG. 7A). On the other hand, the treatment with each of tirzepatide (Group 2, squares in FIG. 7A), the hGLP-1-Fc-GIP (Ag) fusion protein (Group 3, triangles in FIG. 7A), the hGLP-1-Fc-GIP (AntPro3) fusion protein (Group 5, diamonds in FIG. 7A), the mmRNA encoding the hGLP-1-Fc-GIP (Ag) fusion protein (Group 4, inverted triangles in FIG. 7A), and the mmRNA encoding the hGLP-1-Fc-GIP (AntPro3) fusion protein (Group 6, open circles in FIG. 7A) showed a much smaller increase in serum glucose. Areas under curve were calculated and plotted. As shown in FIG. 7B, each of the treatments provided control of blood glucose to about 25 to 33% compared to control mice that received only PBS (Group 1).

Figure 7C:
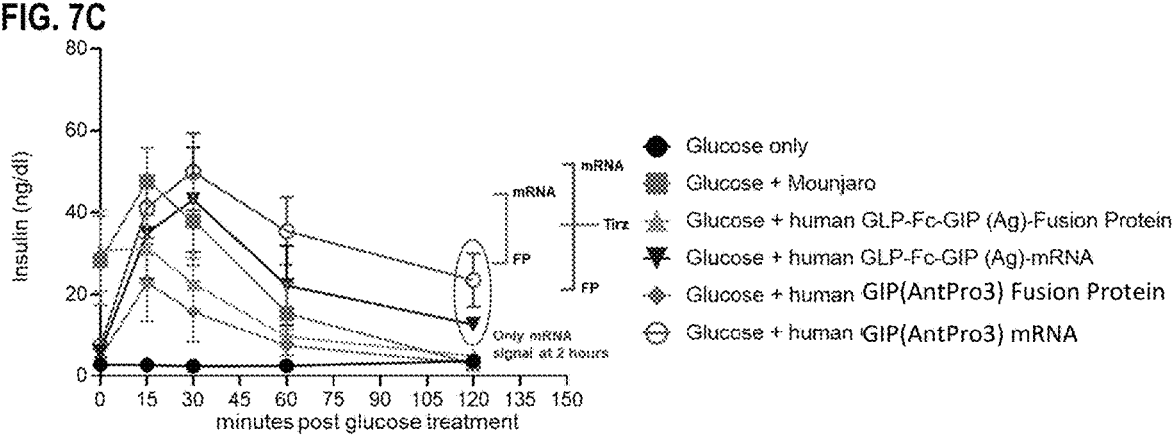
Figure 7D:
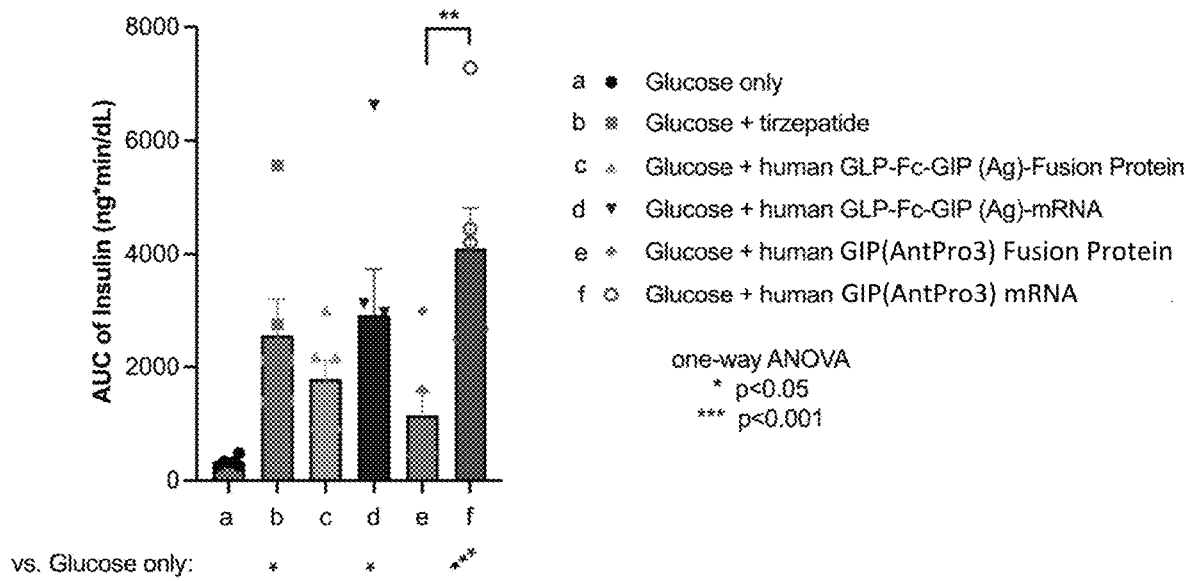

As shown in FIG. 7C, the serum insulin levels in control mice that received only PBS remained unchanged following glucose administration (Group 1, closed circles in FIG. 7C), showing that these mice were diabetic. On the other hand, the treatments with each of tirzepatide (Group 2, squares in FIG. 7C), the hGLP-1-Fc-GIP (Ag) fusion protein (Group 3, triangles in FIG. 7C), the hGLP-1-Fc-GIP (Ant Pro3) fusion protein (Group 5, diamonds in FIG. 7C), the mmRNA encoding the hGLP-1-Fc-GIP (Ag) fusion protein (Group 4, inverted triangles in FIG. 7C), and the mmRNA encoding the hGLP-1-Fc-GIP (Ant Pro3) fusion protein (Group 6, open circles in FIG. 7C) induced a rapid induction of insulin. The kinetics of insulin induction were delayed with the mRNA encoded hGLP-1-Fc-GIP(Ag) and hGLP-1-Fc-GIP (Ant) groups in comparison to the recombinant protein treated groups, which mirrors the prolonged exposure observed in the pharmacokinetic profile as shown in FIG. 6B. In addition, serum insulin concentrations were maintained at a significantly elevated level in the mRNA GLP-1-Fc-GIP(AntPro3) group in comparison to all other groups, suggesting that this combination may provide extended benefit in controlling serum glucose. Areas under curve were calculated and plotted. As shown in FIG. 7C, each of the treatments induced insulin secretion.

These results indicate, inter alia, that the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein showed improved glucose tolerance. These results further indicate, inter alia, that the mmRNA encoding the hGLP-1-Fc-GIP (Ag) fusion protein and the mmRNA encoding the hGLP-1-Fc-GIP (AntPro3) fusion protein showed prolonged insulin secretion, particularly in case of the hGLP-1-Fc-GIP (AntPro3) fusion protein. These results further indicate, inter alia, that a prolonged exposure to the fusion proteins disclosed herein when nucleic acids (without limitation, e.g., mmRNA) encoding the fusion proteins is administered.

Example 12. In Vivo Control of Obesity and Type 2 Diabetes by the Purified Chimeric Proteins and Modified mRNA (mmRNA) Encoding the Chimeric Proteins Disclosed Herein The longer-term obesity model was used to assess the efficacy of the purified chimeric proteins and modified mRNA (mmRNA) encoding the chimeric proteins disclosed herein against obesity and type 2 diabetes (FIG. 6A). Mice (Male C57BL/6) were of approximately 13 weeks of age were housed 4 mice per cage. Following 2 weeks of acclimation, mice were introduced to 60% kcal HFD (Research Diets D12492). Cages were changed once, then changed once a week. Weekly body weights and non-fasted blood glucose were collected. Upon induction of obesity using high fat diet, the mice were randomly divided in the following 7 treatment groups (12 mice per group):

Group #1 Untreated
Group #2 dulaglutide (1 mpk/18 nmol/kg, 200ul, n=12): dose weekly
Group #3 tirzepatide (0.5 mpk/100 nmol/kg, 200 ul, n=12): dose weekly
Group #4 Human GLP-Fc-GIP(Ag)-Fusion protein (5 mpk, 200ul, n=12)
Group #5 Human GLP-Fc-GIP(Ag)-mRNA (1 mpk, 200ul, n=12)
Group #6 Human GLP-Fc-GIP(AntPro3)-Fusion Protein (5 mpk, 200ul, n=12)
Group #7 Human GLP-Fc-GIP(AntPro3)-mRNA (1 mpk, 200ul, n=12)

Figure 8A:
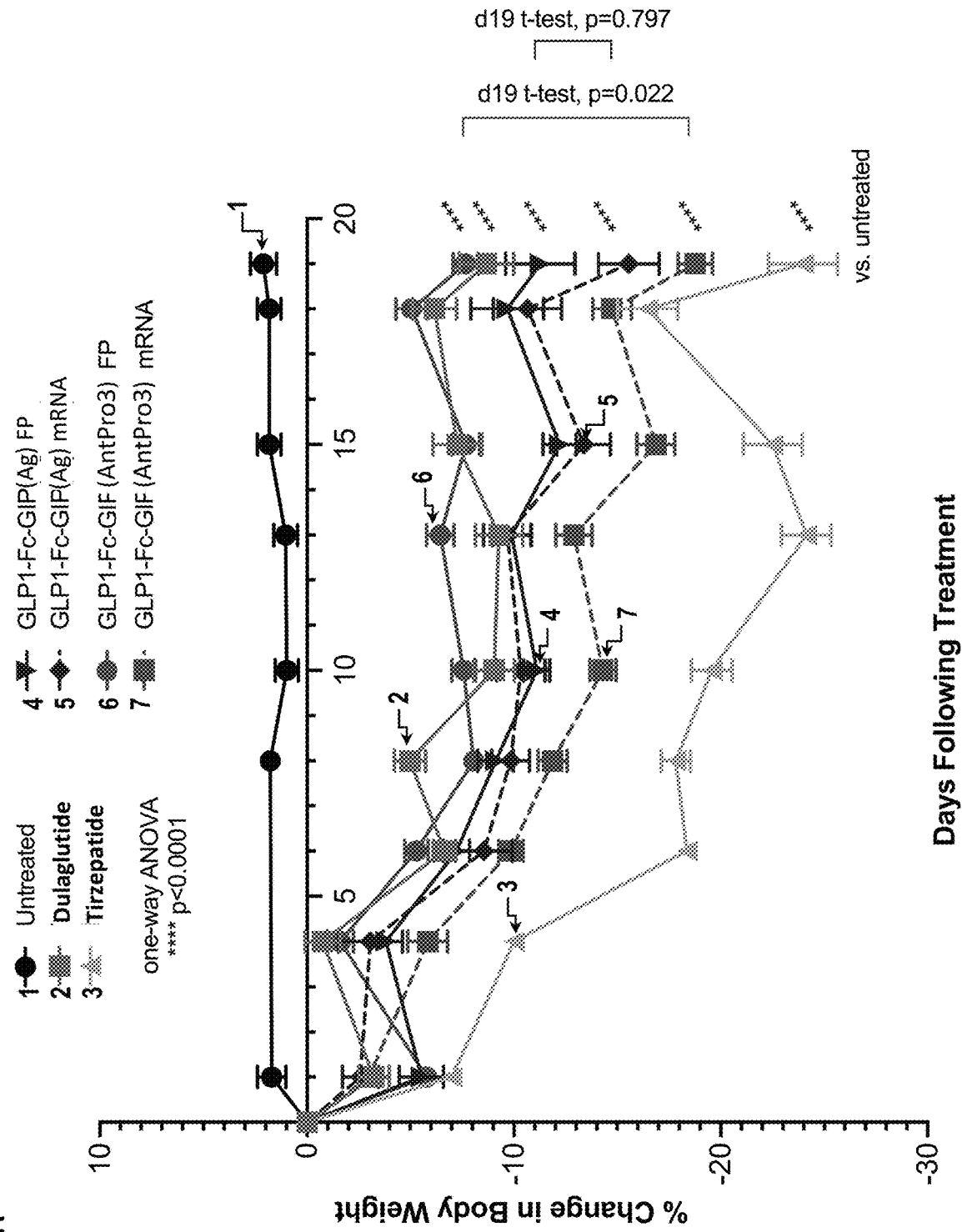

Mice were injected by tail vein with vehicle or the drugs on Day 0, Day 4, Day 7, Day 10, Day 14, and Day 18. Body weights were measured every 2 days. Change in body weight was calculated and plotted. As shown in FIG. 8A, the body weights of control mice that received only PBS remained unchanged during the course of the experiment (Group 1, closed circles in FIG. 8A). On the other hand, the treatment with each of each of dulaglutide, tirzepatide, the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein induced a progressive weight loss (FIG. 8A). To note, tirzepatide treated animals were moribund, lethargic, scruffy, and consumed significantly less food and water immediately post dose, which may be reminiscent of the nausea and GI distress found in human patients treated with tirzepatide. The absence of these symptoms in the mRNA treated groups, despite achieving a higher maximum serum concentration, are potentially related to the prolonged rise in the serum concentration when the GLP-1-Fc-GIP(Ag or AntPro3) constructs are produced in vivo from mRNA as compared to a bolus injected protein.

Dulaglutide, the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein were well tolerated and no overt toxicities were noted.

Figure 8B:
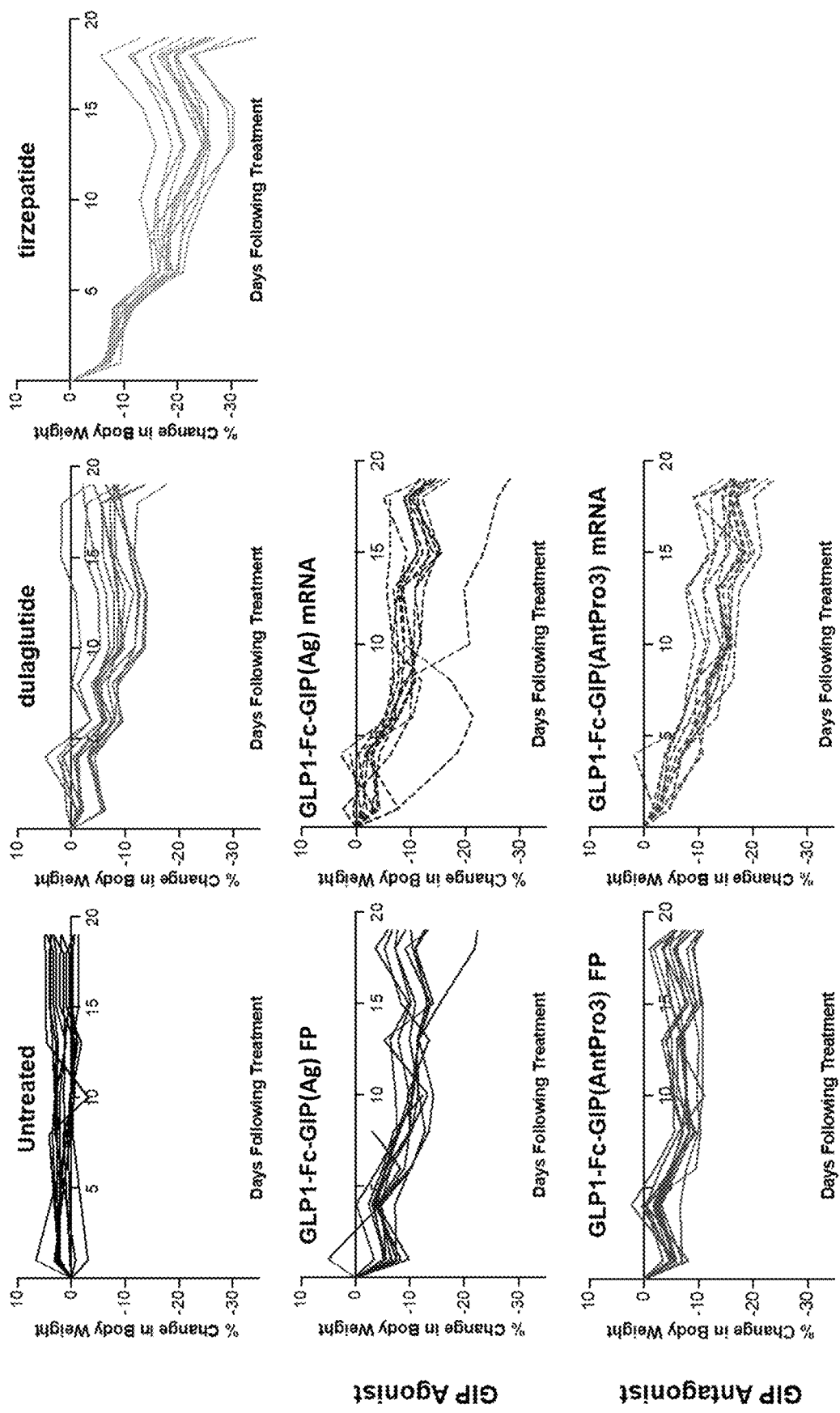

Weights of individual mice were plotted (FIG. 8B). As shown in FIG. 8B, the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein induced weight loss, consistent with the activity observed using the control GLP-1R-agonist dulaglutide and the dual GLP-1R/GIPR-agonist tirzepatide.

Figure 8C:
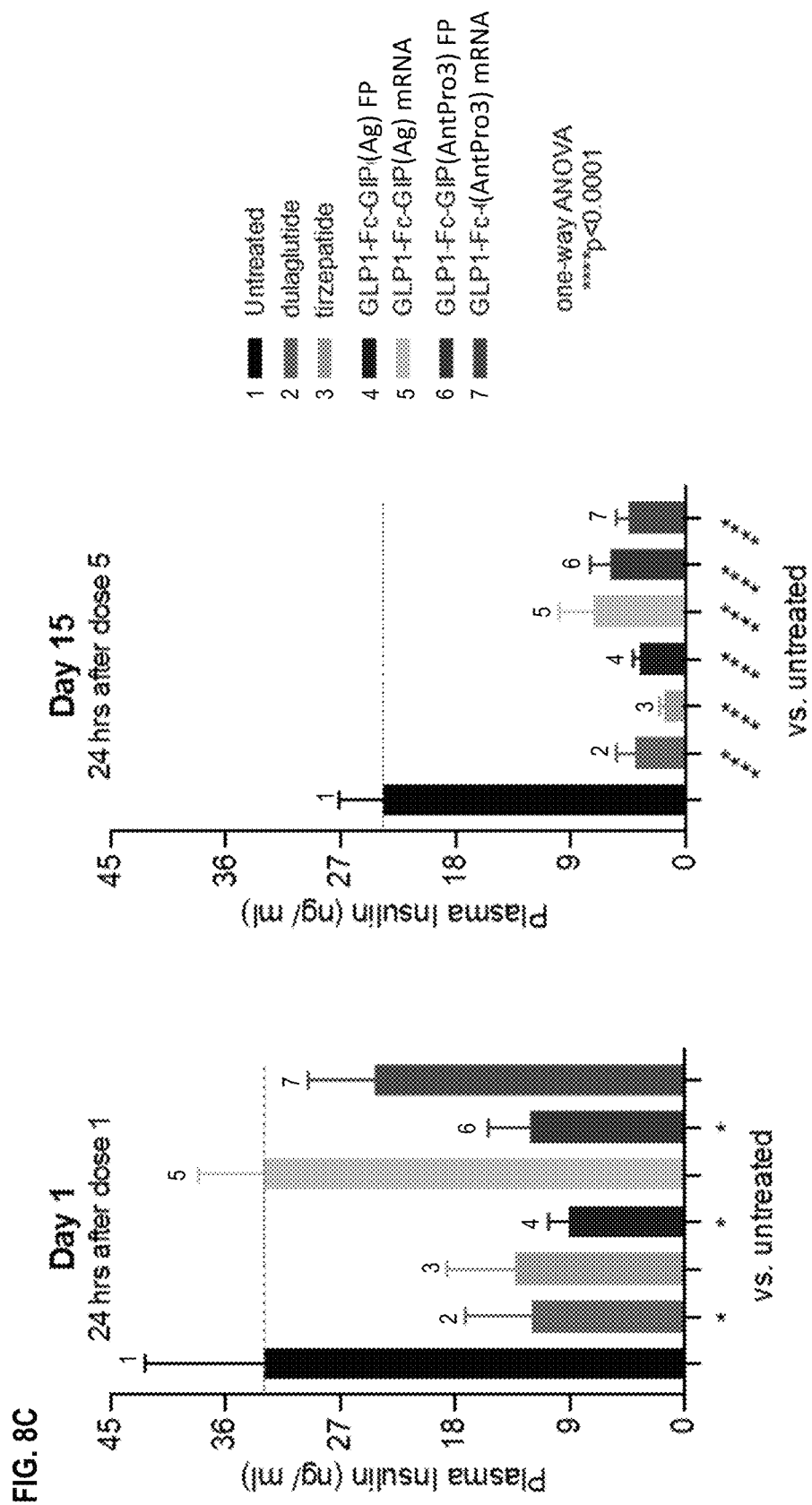

Plasma insulin levels were measured on Day 1 (between 15 and 120 minutes after treatment) and Day 15. As shown in FIG. 8C (left panel), dulaglutide, the hGLP-1-Fc-GIP (Ag) fusion protein, and the hGLP-1-Fc-GIP (AntPro3) fusion protein caused a rapid decrease in insulin levels (one way ANOVA p<0.05). The mmRNA encoding the hGLP-1-Fc-GIP (Ag) fusion protein, and the mmRNA encoding the hGLP-1-Fc-GIP (AntPro3) fusion protein did not cause a significant decrease, if any, in 15-120 minutes of treatment (FIG. 8C (left panel)). Without wishing to be bound by theory, this may be because the accumulation of protein that following mRNA integration into cells.

As shown in FIG. 8C (left panel), each of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein caused a significant decrease in the levels of insulin (one way ANOVA p<0.0001, FIG. 8C (right panel)). Without wishing to be bound by theory, this is consistent with the activity of the mmRNA-delivered drugs that need the accumulation of protein that following mRNA integration into cells.

While insulin was transiently higher (between 15 and 120 minutes after treatment) in response to treatment to tolerize animals to increased glucose (e.g. GTT assay), the drug-induced lowering of glucose longer-term (>=24 hours, FIG. 8E) resulted in a decrease in observed insulin after drug administration. The kinetics of insulin reduction with in mice treated with the mmRNA encoding the hGLP-1-Fc-GIP (Ag) fusion protein, and the mmRNA encoding the hGLP-1-Fc-GIP (AntPro3) fusion protein was consistent with PK and other PD readouts, and is delayed from that observed with the other biologics, due to the accumulation of protein that follows mRNA integration into cells (FIG. 8C).

Figure 8D:
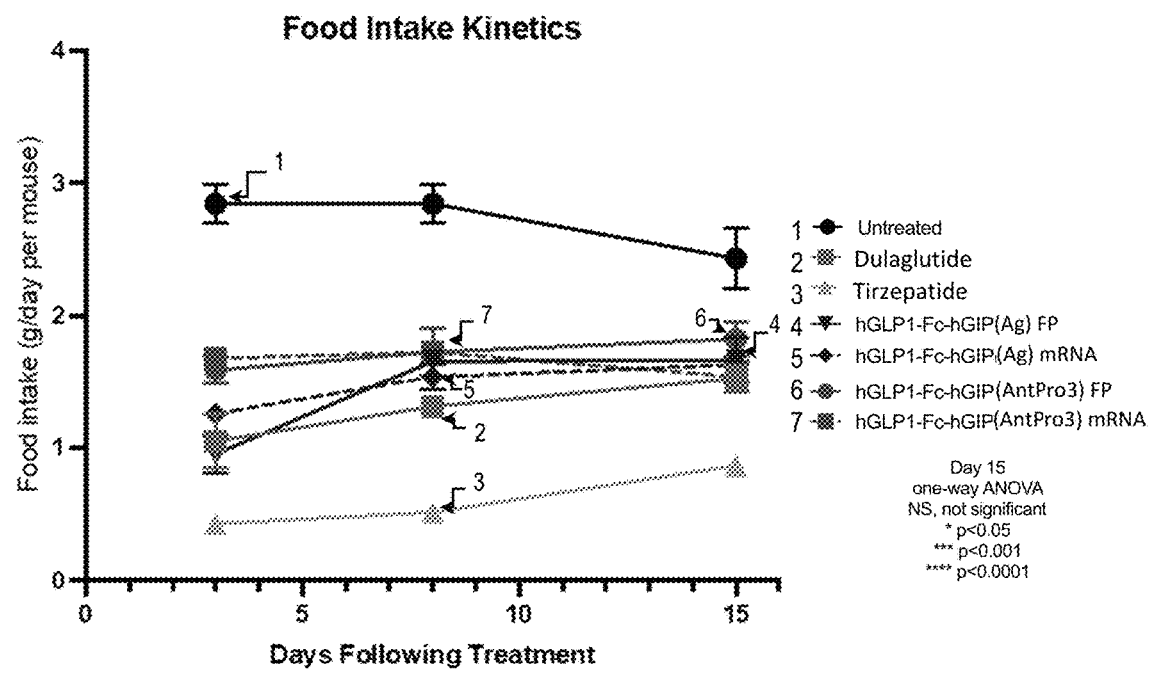

Cumulative food intake was measured between day 0 and 3, between day 4 and 7, between day 7 and day 11, and between day 11 and day 14, and represented as average daily food intake. For food consumption, remaining food was weighed on days 3, 8, and 15, and subtracted from the starting weight. This value was then normalized to the number of mice in the cage, and the number of days the mice had access to the food prior to weighing. As shown in FIG. 8D, the food intake of control mice that received only PBS remained unchanged during the course of the experiment. On the other hand, each of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein caused a decrease in food intake (FIG. 8D) compared to the untreated mice.

Figure 8E:
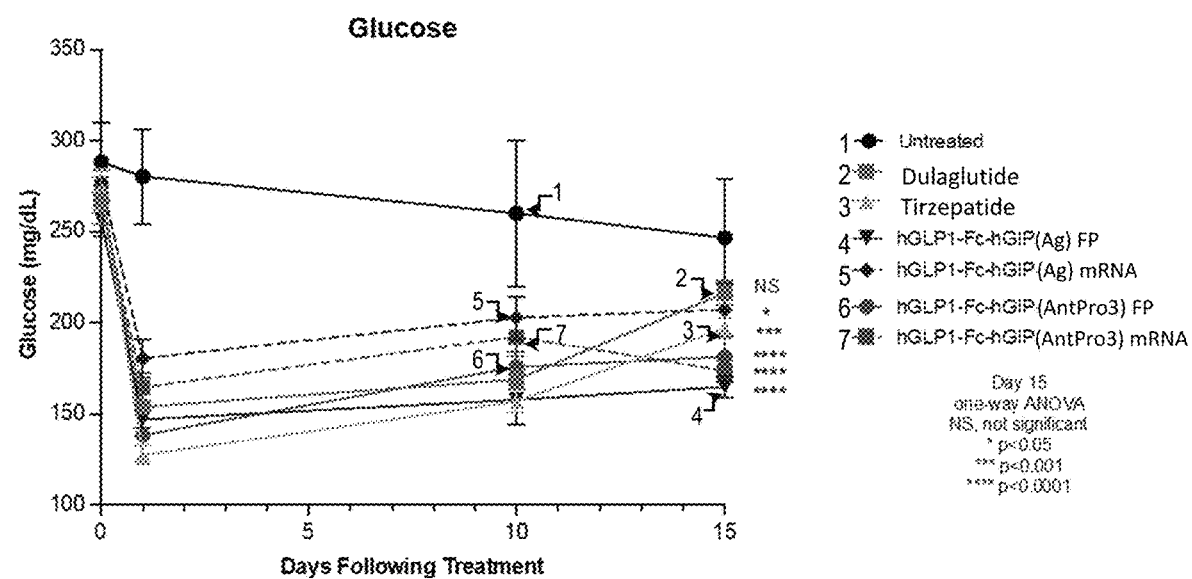

Blood glucose levels were measured on Days 0, 1, 10 and 15 and plotted. As shown in FIG. 8E, the blood glucose levels in control mice that received only PBS slightly decreased during the course of the experiment. On the other hand, each of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein caused a decrease in blood glucose (FIG. 8D) compared to the untreated mice.

Figure 8F:
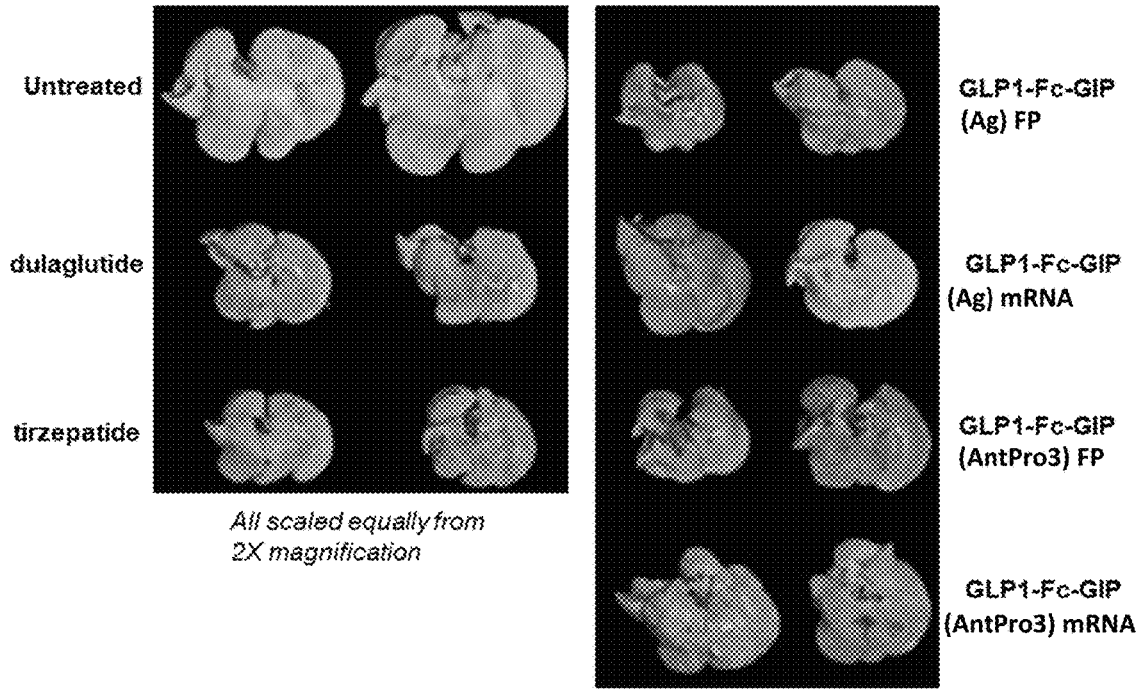

On day 19 during terminal necropsy, liver and subcutaneous white adipose tissue were recovered weighed from treated animals. FIG. 8F shows photographs of livers recovered from representative mice. As shown in FIG. 8F, the livers of control mice that received only PBS appeared enlarged and whitish in color, indicating an increase in adiposity. By contrast, the livers of mice receiving the treatments were pinkish in color and smaller in size, showing a decrease in adiposity (FIG. 8F).

Figure 8G:
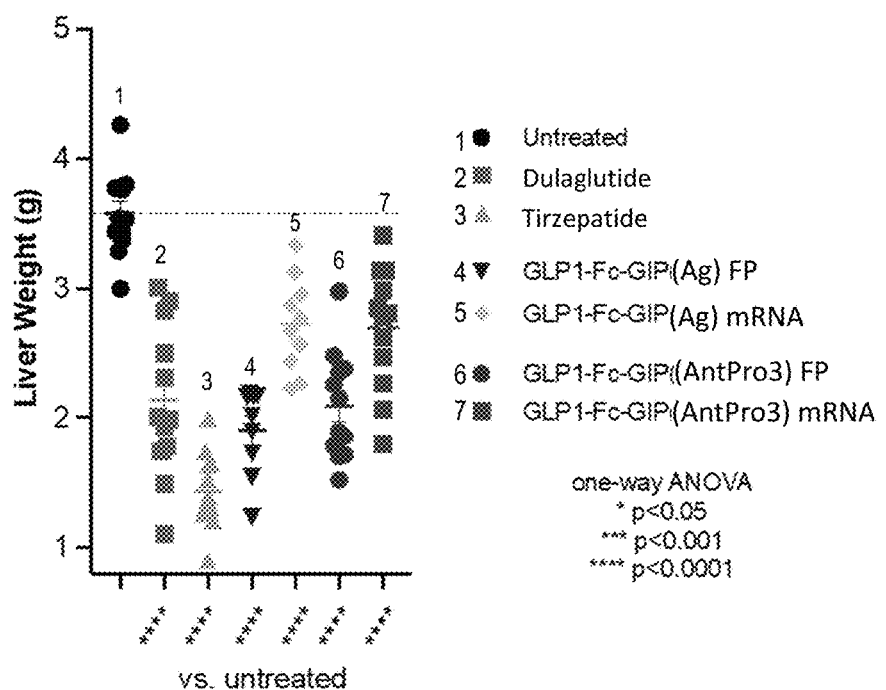

The livers were weighed. As shown in FIG. 8G, the livers of control mice that received only PBS were much heavier compared to the mice receiving treatments with one of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein (FIG. 8G).

Figure 8H:
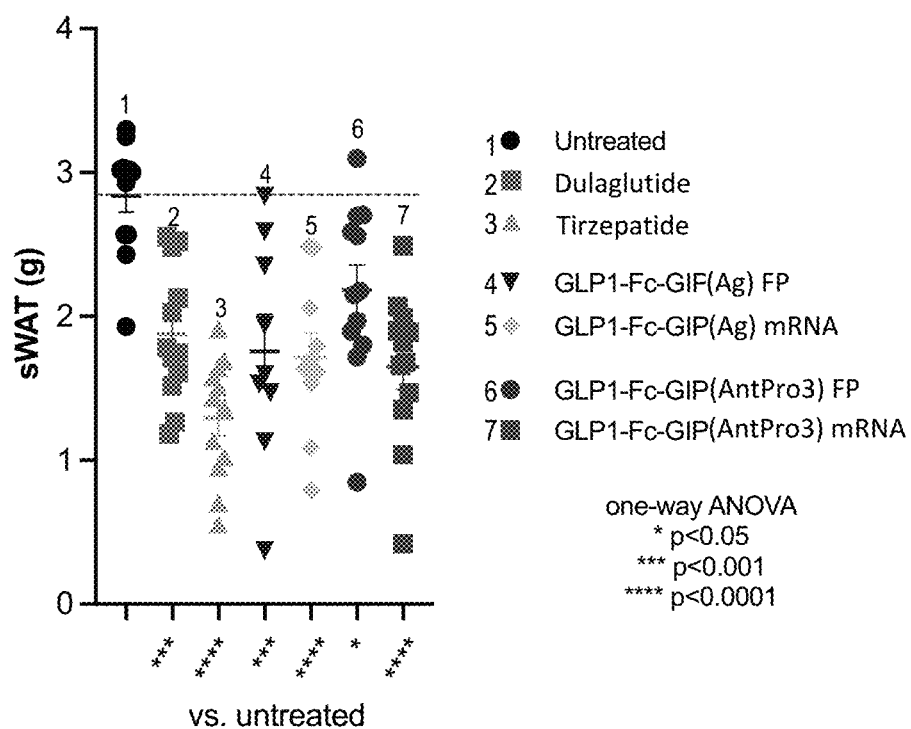

The subcutaneous white adipose tissue (sWAT) recovered from the mice was weighed. As shown in FIG. 8H, the control mice that received only PBS had accumulated a substantial amount of sWAT, which decreased in the mice receiving treatments with one of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein (FIG. 8H).

Figure 8I:
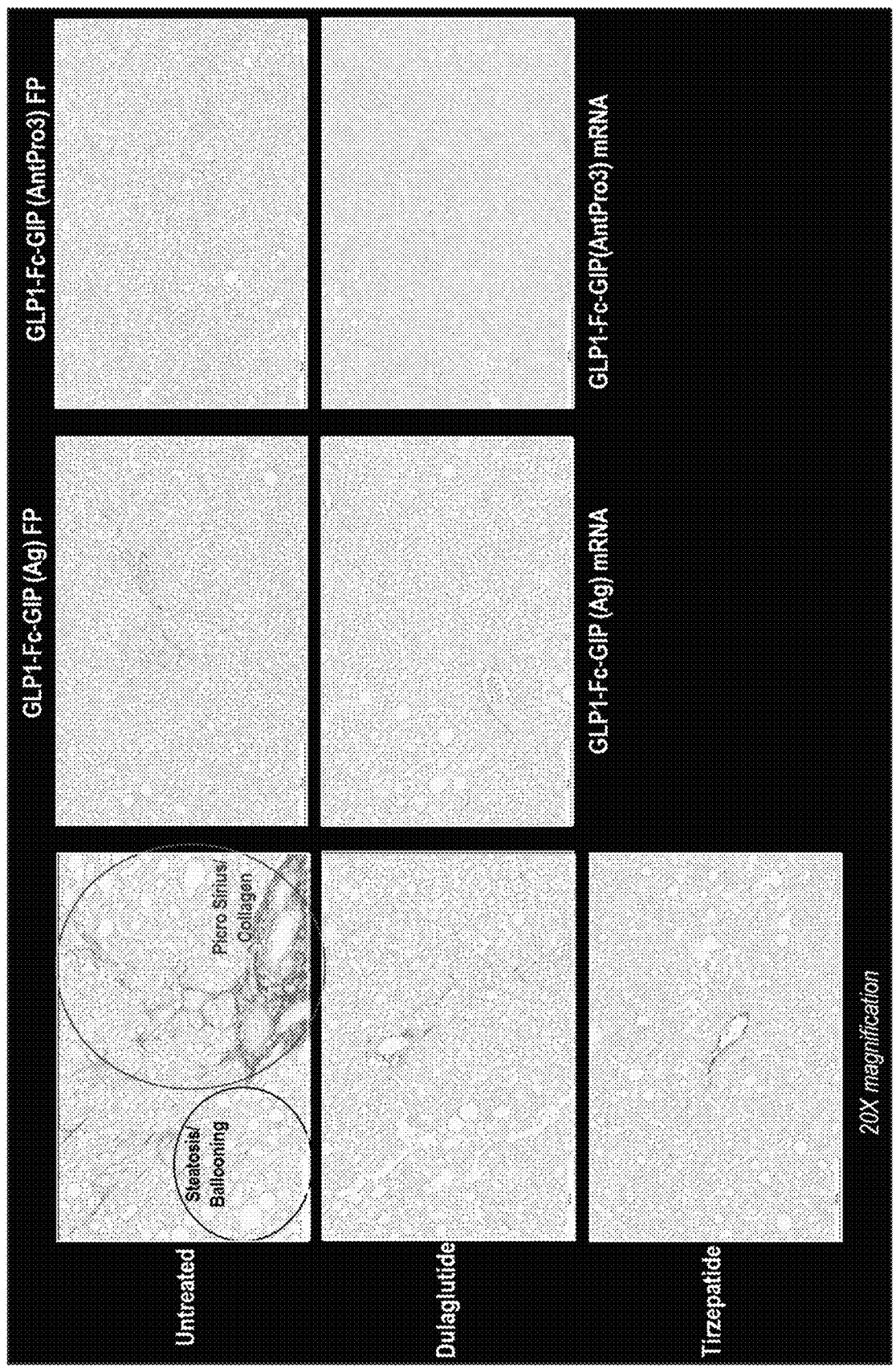
Figure 8K:
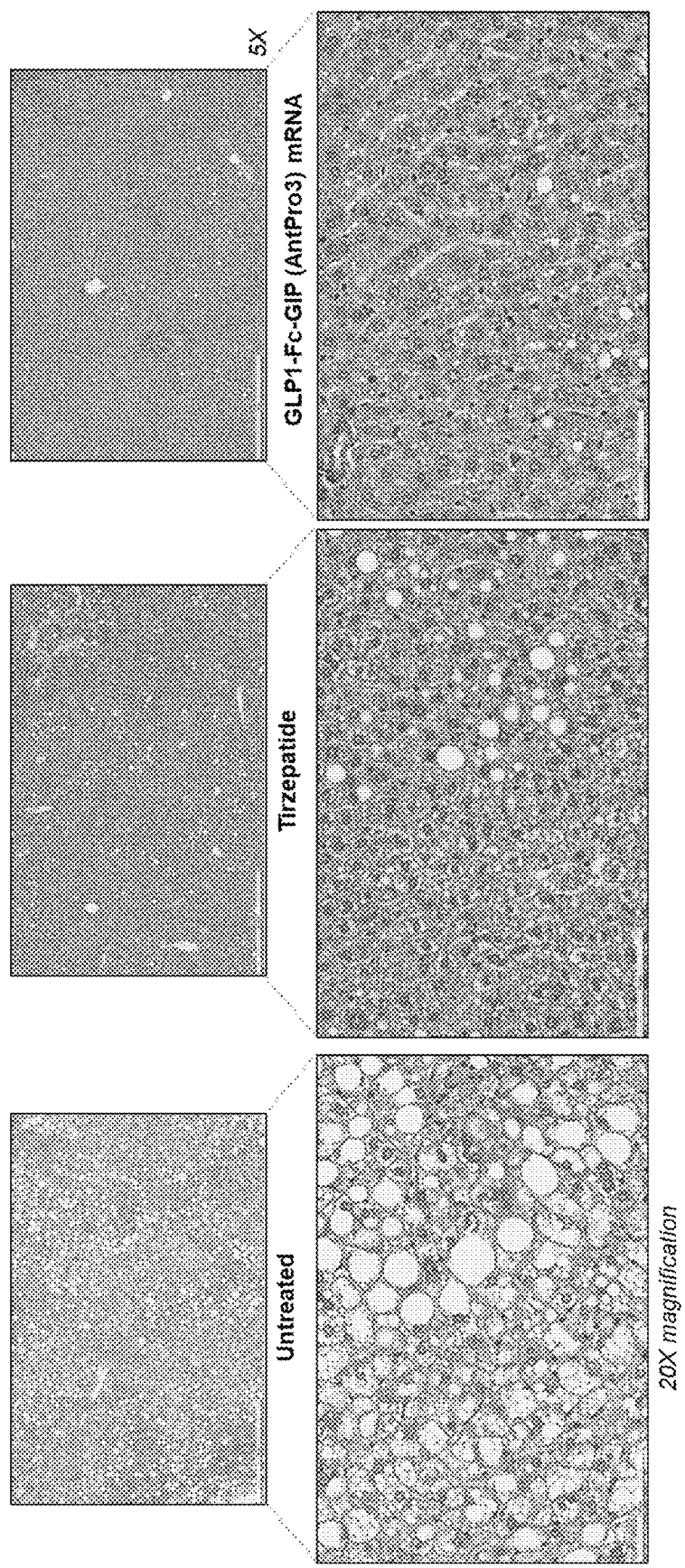

To further analyze the changes in liver, histopathological analysis was conducted. Briefly, the liver tissue was stained with hematoxylin and eosin (H&E) and evaluated using standard techniques. Liver tissue samples were obtained from the mice treated with one of tirzepatide, dulaglutide, the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein. FIG. 8J shows representative images. As shown in FIG. 8J, the liver tissue from vehicle-treated mice showed enlarged cells with rarefied cytoplasm and hepatocellular ballooning, which is associated with fat droplet accumulation and steatosis. The livers from mice treated with tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, or the mmRNA encoding the hGLP-1-Fc-GIP (AntPro3) fusion protein showed a decrease in hepatocellular ballooning and steatosis (FIG. 8J), indicating, inter alia, that each of these treatments decreased hepatocellular ballooning and steatosis. To further evaluate the treatment with mmRNA encoding the hGLP-1-Fc-GIP (AntPro3) fusion protein in comparison the treatment with tirzepatide, the H&E-stained images were observed under higher magnifications. As shown in FIG. 8K, compared to the liver tissue from untreated animals, the liver tissue from the animals treated with mmRNA encoding tirzepatide or the hGLP-1-Fc-GIP (AntPro3) fusion protein showed a significant decrease in hepatocellular ballooning and steatosis. Interestingly, livers from mice treated with the mmRNA encoding the hGLP-1-Fc-GIP (AntPro3) fusion protein showed a decrease in hepatocellular ballooning and steatosis that was greater than the decrease observed in mice that received tirzepatide (FIG. 8K).

To assess whether the observed hepatocellular ballooning was associated with fibrosis, liver sections stained with picrosirius red (PSR) were analyzed. FIG. 8I shows representative images. As shown in FIG. 8I, the liver tissue from vehicle-treated mice showed hepatocellular ballooning, steatosis as well as collagen staining, which is indicative of existence of fibrosis. The livers from mice treated with each of tirzepatide, dulaglutide, the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, or the mmRNA encoding the hGLP-1-Fc-GIP (AntPro3) fusion protein showed a decrease in collagen staining, indicating a decrease in fibrosis (FIG. 8I). Interestingly, the livers from mice treated with the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, or the mmRNA encoding the hGLP-1-Fc-GIP (AntPro3) fusion protein caused greater decrease in collagen staining compared to the livers from mice treated with tirzepatide or dulaglutide, indicating a greater decrease in fibrosis (FIG. 8I). These results indicate, inter alia, that the hGLP-1-Fc-GIP (Ag) fusion protein, and the hGLP-1-Fc-GIP (AntPro3) fusion protein, the mmRNA encoding the hGLP-1-Fc-GIP (Ag) fusion protein, or the mmRNA encoding the hGLP-1-Fc-GIP (AntPro3) fusion protein are effective in decreasing hepatocellular ballooning, steatosis, and liver fibrosis, and therefore, are useful for the treatment of, inter alia, nonalcoholic fatty liver disease (NAFLD) and non-alcoholic steatohepatitis (NASH).

Collectively, these results indicate, inter alia, that the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein control body weight, plasma insulin, food intake, blood glucose, liver adiposity, liver weight and subcutaneous white adipose tissue (sWAT) weight. These results further indicate, inter alia, that the hGLP-1-Fc-GIP (Ag) fusion protein, the hGLP-1-Fc-GIP (AntPro3) fusion protein, the mmRNA encoding the hGLP-1-Fc-GIP (Ag) fusion protein, and the mmRNA encoding the hGLP-1-Fc-GIP (AntPro3) fusion protein are useful to treat nonalcoholic fatty liver disease (NAFLD), non-alcoholic steatohepatitis (NASH), diabetes, obesity, Type II diabetes, metabolic syndrome and related ailments. These results further indicate, inter alia, that the fusion proteins and the mmRNA encoding the fusion proteins disclosed herein do not cause nausea and GI distress.

Example 13. Evaluation of Differences in Pharmacokinetics Between Intravenous and Intramuscular Delivery of Fusion Proteins and mRNA/LNP Formulations To evaluate pharmacokinetics of the fusion proteins and nucleic acids disclosed herein, mice were divided in nine groups and treated as follows:
Group 1: Mice were administered a single dose of vehicle-only control (control),
Group 2: Mice were administered a single intravenous (IV) injection of a 1 mg/kg dose of the purified GLP-1-Fc-GIP(AntPro3) fusion protein,
Group 3: Mice were administered a single IV injection of a 0.3 mg/kg dose of the purified GLP-1-Fc-GIP(AntPro3) fusion protein,
Group 4: Mice were administered a single intramuscular (IM) injection of a 1 mg/kg dose of the purified GLP-1-Fc-GIP(AntPro3) fusion protein,
Group 5: Mice were administered a single intramuscular (IM) injection of a 0.3 mg/kg dose of the purified GLP-1-Fc-GIP(AntPro3) fusion protein,
Group 6: Mice were administered a single intravenous (IV) injection of a 1 mg/kg dose of a lipid nanoparticle (LNP) formulation comprising the mmRNA encoding the GLP-1-Fc-GIP(AntPro3) fusion protein,
Group 7: Mice were administered a single IV injection of a 0.3 mg/kg dose of the LNP formulation comprising the mmRNA encoding the GLP-1-Fc-GIP(AntPro3) fusion protein,
Group 8: Mice were administered a single intramuscular (IM) injection of a 1 mg/kg dose of the LNP formulation comprising the mmRNA encoding the GLP-1-Fc-GIP(AntPro3) fusion protein, and
Group 9: Mice were administered a single intramuscular (IM) injection of a 0.3 mg/kg dose of the LNP formulation comprising the mmRNA encoding the GLP-1-Fc-GIP(AntPro3) fusion protein.

Figure 9:
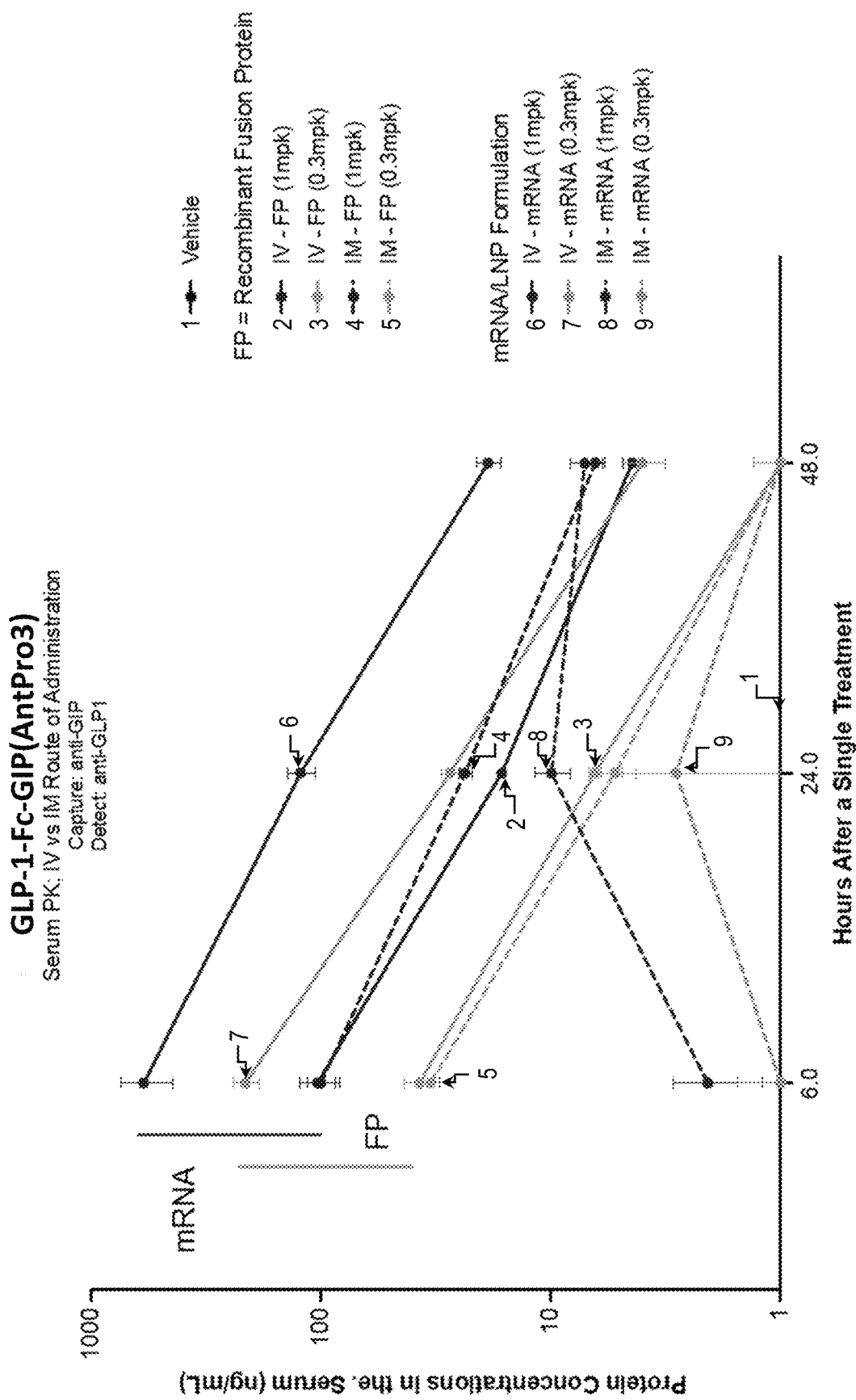
FIG. 9 is a line graph showing the differences in pharmacokinetics between intravenous and intramuscular delivery of the GLP-1-Fc-GIP(AntPro3) chimeric protein, or mRNA encoding the GLP-1-Fc-GIP(AntPro3) chimeric protein.

Blood samples were collected 6, 24, and 48 hours after treatment and serum samples were prepared. The GLP-1-Fc-GIP(AntPro3) fusion protein was quantitated in the serum samples using a dual Meso Scale Discovery (MSD) platform-based assay. Briefly, an anti-GIP antibody was coated on a plate. The serum samples were added to the plate for capture by the plate-bound anti-GIP antibody. Increasing amounts of the purified GLP-1-Fc-GIP(AntPro3) fusion protein were also added in a series of wells in the plate for generating a standard curve. The protein captured by the plate-bound anti-GIP antibody was detected using an anti-GLP-1 antibody and a SULFO-TAG conjugated secondary antibody. The standard curve generated using the purified GLP-1-Fc-GIP(AntPro3) fusion protein was used to quantitate amount of GLP-1-Fc-GIP(AntPro3) fusion protein present in the serum samples and plotted. The results are shown in FIG. 9. As shown in FIG. 9, more GLP-1-Fc-GIP(AntPro3) fusion protein was detected in sera of the mice that received IV injections of the mmRNA encoding the GLP-1-Fc-GIP(AntPro3) fusion protein compared the sera of the mice that received IV injections of the purified GLP-1-Fc-GIP(AntPro3) fusion protein itself. These results indicated, inter alia, that IV injections of the mmRNA encoding fusion proteins disclosed herein produced an increased exposure, as indicated by $C_{max}$ and AUC compared to the IV injections of the fusion proteins disclosed herein.

Serum samples from the mice that received IM injections of the mmRNA encoding the GLP-1-Fc-GIP(AntPro3) fusion protein showed lower levels of the GLP-1-Fc-GIP(AntPro3) fusion protein at 6 hours compared to the mice that received IM injections of the purified GLP-1-Fc-GIP(AntPro3) fusion protein (FIG. 9). However, serum samples from the mice that received IM injections of the mmRNA encoding the GLP-1-Fc-GIP(AntPro3) fusion protein showed an increase at 24 hours compared to 6 hours, which further increased at 48 hours in mice that received a 1 mg/kg dose (FIG. 9). These results indicated, inter alia, that IM delivery of mmRNA encoding the fusion proteins disclosed herein took time to produce the GLP-1-Fc-GIP(AntPro3) fusion protein that enters into the circulation and it is expected that the GLP-1-Fc-GIP(AntPro3) fusion protein would be expected to continue to be detected well past 48 hours. These results indicated, inter alia, that IM injections of the mmRNA encoding fusion proteins disclosed herein produced an increased exposure, as indicated by AUC, compared to the IV injections of the fusion proteins disclosed herein.

Example 14. Characterization of mmRNA Constructs Encoding the GLP-1-Fc-GIP Chimeric Protein and Harboring Different 5' UTR and 3'UTR Sequences Several mmRNA constructs harboring different 5' UTR and/or 3'UTR sequences were prepared to evaluate the expression of the GLP-1-Fc-GIP(AntPro3) chimeric protein. Some constructs also included codon optimization performed using alternate algorithms. A control mRNA also included an mmRNA construct having a scrambled UTR sequence. The tested constructs included the following combinations of UTR sequences:
5' UTR_1 (SEQ ID NO: 128) and 3' UTR_1 (SEQ ID NO: 114),
5' UTR_1 (SEQ ID NO: 128) and 3' UTR_2 (SEQ ID NO: 115),
5' UTR_2 (SEQ ID NO: 129) and 3' UTR_1 (SEQ ID NO: 114),
5' UTR_3 (SEQ ID NO: 130) and 3' UTR_1 (SEQ ID NO: 114),
5' UTR_4 (SEQ ID NO: 131) and 3' UTR_1 (SEQ ID NO: 114),
5' UTR_4 (SEQ ID NO: 131) and 3' UTR_2 (SEQ ID NO: 115),
5' UTR_5 (SEQ ID NO: 132) and 3' UTR_1 (SEQ ID NO: 114),
5' UTR_6 (SEQ ID NO: 133) and 3' UTR_1 (SEQ ID NO: 114),
5' UTR_7 (SEQ ID NO: 134) and 3' UTR_3 (SEQ ID NO: 116),
5' UTR_8 (SEQ ID NO: 135) and 3' UTR_4 (SEQ ID NO: 117),
5' UTR_9 (SEQ ID NO: 136) and 3' UTR_1 (SEQ ID NO: 114),
5' UTR_10 (SEQ ID NO: 137) and 3' UTR_1 (SEQ ID NO: 114),
5' UTR_11 (SEQ ID NO: 138) and 3' UTR_5 (SEQ ID NO: 118),
5' UTR_1 (SEQ ID NO: 128) and 3' UTR_1 (SEQ ID NO: 114) with codon optimization 2, 5' UTR_1 (SEQ ID NO: 128) and 3' UTR_1 (SEQ ID NO: 114) with codon optimization 3,
5' UTR_7 (SEQ ID NO: 134) and 3' UTR_3 (SEQ ID NO: 116) with codon optimization 3,
5' UTR_8 (SEQ ID NO: 135) and 3' UTR_4 (SEQ ID NO: 117) with codon optimization 3,
5' UTR_12 (SEQ ID NO: 139) and 3' UTR_6 (SEQ ID NO: 119),
5' UTR_13 (SEQ ID NO: 140) and 3' UTR_7 (SEQ ID NO: 120),
5' UTR_1 (SEQ ID NO: 128) and 3' UTR_8 (SEQ ID NO: 121),
5' UTR_13 (SEQ ID NO: 140) and 3' UTR_9 (SEQ ID NO: 122),
5' UTR_13 (SEQ ID NO: 140) and 3' UTR_10 (SEQ ID NO: 123),
5' UTR_14 (SEQ ID NO: 141) and 3' UTR_10 (SEQ ID NO: 123),
5' UTR_15 (SEQ ID NO: 142) and 3' UTR_7 (SEQ ID NO: 120), and
5' UTR_9 (SEQ ID NO: 136) and 3' UTR_1 (SEQ ID NO: 114).

Figure 10:
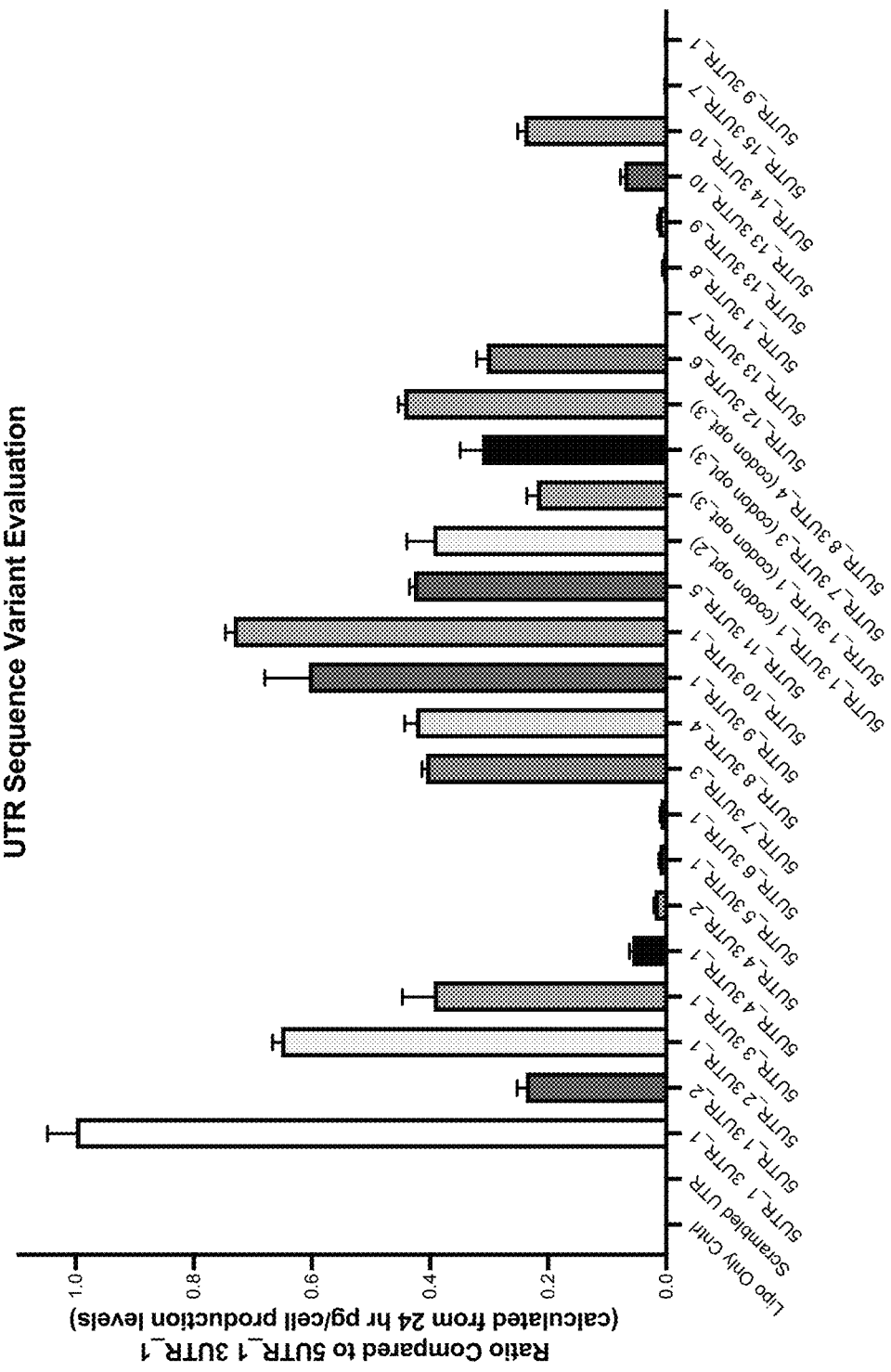
FIG. 10 is a bar graph comparing the production of the GLP-1-Fc-GIP (AntPro3) chimeric protein by cells transfected with mRNA constructs encoding the GLP-1-Fc-GIP (AntPro3) chimeric protein and harboring different 5' untranslated region (5' UTR) sequences and 3' untranslated region (3' UTR) sequences.

Some constructs also included codon optimization performed using alternate algorithms. A control mRNA also included an mmRNA construct having a scrambled UTR sequence. The expression of the GLP-1-Fc-GIP(AntPro3) chimeric protein driven by these constructs was evaluated in HEK293T cells. Briefly, HEK293T cells were transfected with each mRNA construct using lipofectamine 2000. Lipofectamine 2000 only was used as another control. After 24 hours, cell culture supernatants were collected and the level of production of the GLP-1-Fc-GIP(AntPro3) chimeric protein was assessed using a Meso Scale Discovery (MSD) platform-based assay. Briefly, an anti-GIP antibody was coated on a plate. The cell culture supernatants were added to the plate for capture by the plate-bound anti-GIP antibody. Increasing amounts of the purified GLP-1-Fc-GIP(AntPro3) fusion protein were also added in a series of wells in the plate for generating a standard curve. The protein captured by the plate-bound anti-GIP antibody was detected using an anti-GLP-1 antibody and a SULFO-TAG conjugated secondary antibody. The standard curve generated using the purified GLP-1-Fc-GIP(AntPro3) fusion protein was used to quantitate amount of the GLP-1-Fc-GIP(AntPro3) fusion protein present in the cell culture supernatants and plotted as a bar graph and normalized with the level of the GLP-1-Fc-GIP(AntPro3) fusion protein produced by the mmRNA comprising the combination of 5' UTR_1 and 3' UTR_1. As shown in FIG. 10, the following combinations of UTR sequences provided better expression levels compared to the controls and other sequences: 5' UTR_1 (SEQ ID NO: 128) and 3' UTR_1 (SEQ ID NO: 114); 5' UTR_1 (SEQ ID NO: 128) and 3' UTR_2 (SEQ ID NO: 115); 5' UTR_2 (SEQ ID NO: 129) and 3' UTR_1 (SEQ ID NO: 114); 5' UTR_3 (SEQ ID NO: 130) and 3' UTR_1 (SEQ ID NO: 114); 5' UTR_7 (SEQ ID NO: 134) and 3' UTR_3 (SEQ ID NO: 116); 5' UTR_8 (SEQ ID NO: 135) and 3' UTR_4 (SEQ ID NO: 117); 5' UTR_9 (SEQ ID NO: 136) and 3' UTR_1 (SEQ ID NO: 114); 5' UTR_10 (SEQ ID NO: 137) and 3' UTR_1 (SEQ ID NO: 114); 5' UTR_11 (SEQ ID NO: 138) and 3' UTR_5 (SEQ ID NO: 118); 5' UTR_12 (SEQ ID NO: 139) and 3' UTR_6 (SEQ ID NO: 119); 5' UTR_14 (SEQ ID NO: 141) and 3' UTR_10 (SEQ ID NO: 123). As shown in FIG. 10, the mmRNA comprising the combination of 5' UTR_1 (SEQ ID NO: 128) and 3' UTR_1 (SEQ ID NO: 114) produced the most amount of the GLP-1-Fc-GIP(AntPro3) fusion protein. Alternate algorithms of codon optimization also generated intriguingly enhanced results (FIG. 10). The mmRNA comprising scrambled UTR sequences produced the very little the GLP-1-Fc-GIP(AntPro3) fusion protein (FIG. 10).

These results demonstrate, inter alia, that sequence elements such as 5' UTR and 3' UTR enhance the expression of the fusion proteins disclosed herein. These results demonstrate, inter alia, that engineering the present nucleic acid sequence is useful to enhance the expression of the fusion proteins disclosed herein.

Example 15. Construction and Characterization an Illustrative GLP-1- and ACVR2B-Based Chimeric Protein A construct encoding a GLP-1- and activin receptor type-2B (ACVR2B)-based chimeric protein was generated. The "GLP-1-Fc-ACVR2B" construct included GLP-1 fused to ACVR2B via a hinge-CH2-CH3 Fc domain derived from IgG1.

Several mmRNA constructs harboring different 5' UTR and/or 3'UTR sequences were prepared to evaluate the expression of the GLP-1-Fc-ACVR2B chimeric protein. The tested constructs included the following combinations of UTR sequences:
5' UTR_1 (SEQ ID NO: 132) and 3' UTR_1 (SEQ ID NO: 118),
5' UTR_7 (SEQ ID NO: 138) and 3' UTR_3 (SEQ ID NO: 120),
5' UTR_8 (SEQ ID NO: 139) and 3' UTR_4 (SEQ ID NO: 121),
5' UTR_9 (SEQ ID NO: 140) and 3' UTR_1 (SEQ ID NO: 118),
5' UTR_10 (SEQ ID NO: 141) and 3' UTR_2 (SEQ ID NO: 119),
5' UTR_11 (SEQ ID NO: 142) and 3' UTR_5 (SEQ ID NO: 122),
5' UTR_17 (SEQ ID NO: 148) and 3' UTR_11 (SEQ ID NO: 128), and
5' UTR_1 (SEQ ID NO: 132) and 3' UTR_1 (SEQ ID NO: 118) with codon optimization 2,
5' UTR_1 (SEQ ID NO: 132) and 3' UTR_1 (SEQ ID NO: 118) with codon optimization 2,
5' UTR_7 (SEQ ID NO: 138) and 3' UTR_3 (SEQ ID NO: 120) with codon optimization 2,
5' UTR_8 (SEQ ID NO: 139) and 3' UTR_4 (SEQ ID NO: 121) with codon optimization 2,
5' UTR_10 (SEQ ID NO: 141) and 3' UTR_1 (SEQ ID NO: 118) with codon optimization 2,
5' UTR_11 (SEQ ID NO: 142) and 3' UTR_5 (SEQ ID NO: 122) with codon optimization 2, and
5' UTR_4 (SEQ ID NO: 135) and 3' UTR_1 (SEQ ID NO: 118),
5' UTR_17 (SEQ ID NO: 148) and 3' UTR_11 (SEQ ID NO: 128).

Figure 11A:
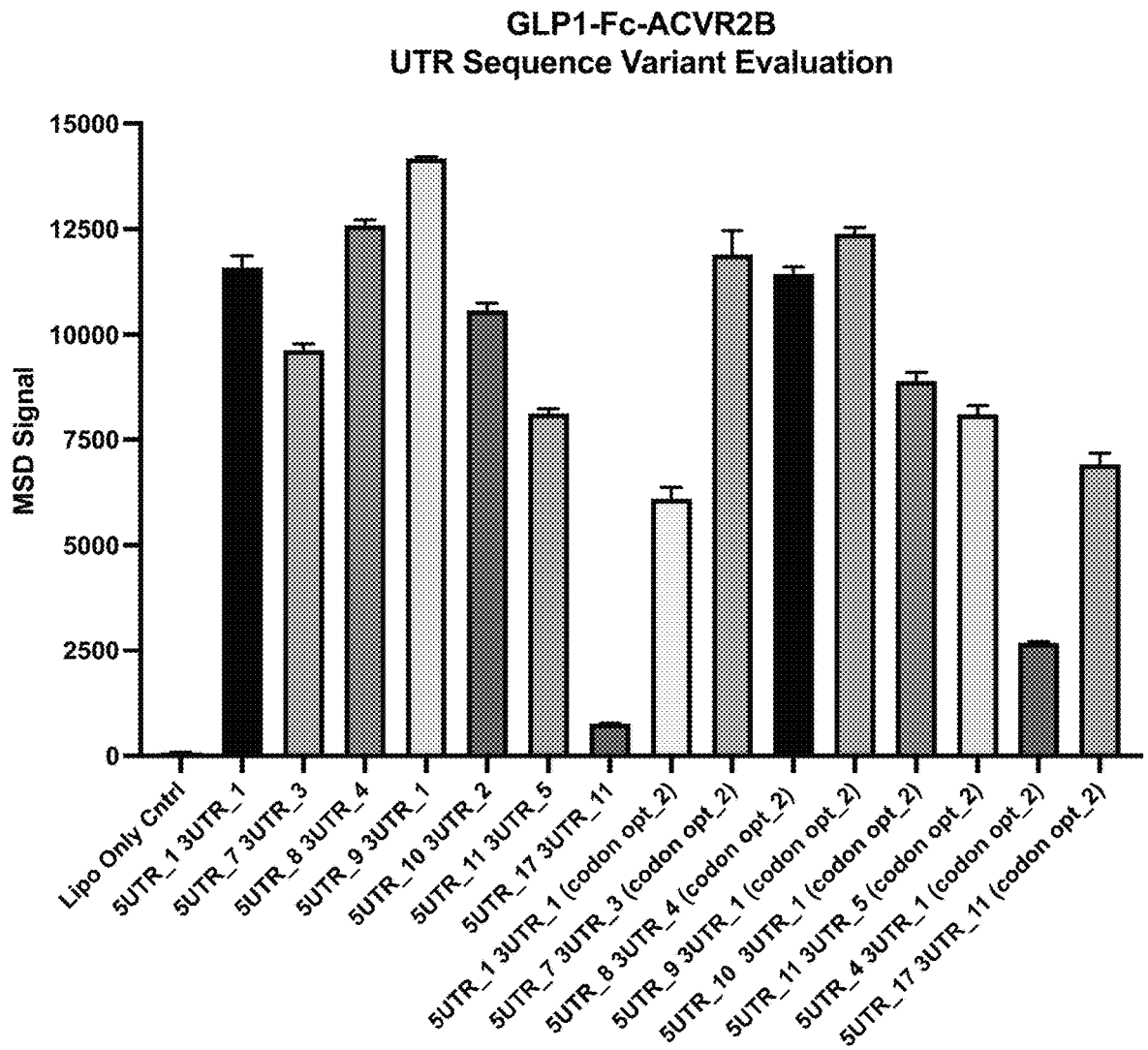
FIG. 11A to FIG. 11E show the characterization of mRNA constructs encoding the GLP-1-Fc-Activin receptor type-2B (ACVR2B) chimeric protein.

Some constructs also included codon optimization performed using alternate algorithms. The expression of the GLP-1-Fc-ACVR2B chimeric protein driven by these constructs was evaluated in HEK293T cells. Briefly, HEK293T cells were transfected with each mRNA construct using lipofectamine 2000. Lipofectamine 2000 only was used as a control. After 48 hours, cell culture supernatants were collected and the level of production of the GLP-1-Fc-ACVR2B chimeric protein was assessed using a Meso Scale Discovery (MSD) platform-based assay. Briefly, an anti-ACVR2B antibody was coated on a plate. The cell culture supernatants were added to the plate for capture by the plate-bound anti-ACVR2B antibody. The protein captured by the plate-bound anti-ACVR2B antibody was detected using an anti-GLP-1 antibody and a SULFO-TAG conjugated secondary antibody. The MSD signals generated by the culture supernatants of HEK293T cells transfected with different mmRNA constructs were normalized with the level of the GLP-1-Fc-ACVR2B fusion protein produced by cells transfected with the mmRNA comprising the combination of 5' UTR_1 and 3' UTR_1 and plotted. The results are shown in FIG. 11A. As expected, lipofectamine 2000 only produced no signal corresponding to the GLP-1-Fc-ACVR2B fusion protein (FIG. 11A). As shown in FIG. 11A, the mmRNA comprising the combination of 5' UTR_9 and 3' UTR_1 produced the most amount of the GLP-1-Fc-ACVR2B fusion protein. Alternate algorithms of codon optimization also generated intriguingly enhanced expression in some cases. See, e.g., the combination of 5' UTR_17 (SEQ ID NO: 148) and 3' UTR_11 (SEQ ID NO: 128) with usual and alternative codon optimization (FIG. 11A).

These results demonstrate, inter alia, that sequence elements such as 5' UTR and 3' UTR enhance the expression of the fusion proteins disclosed herein. These results demonstrate, inter alia, that engineering the present nucleic acid sequence is useful to enhance the expression of the fusion proteins disclosed herein.

These results demonstrate, inter alia, that sequence elements such as 5' UTR and 3' UTR enhance the expression of the fusion proteins disclosed herein. These results demonstrate, inter alia, that different methods to codon optimize the nucleic acid sequence may be used to enhance the expression of the fusion proteins disclosed herein.

Figure 11B:
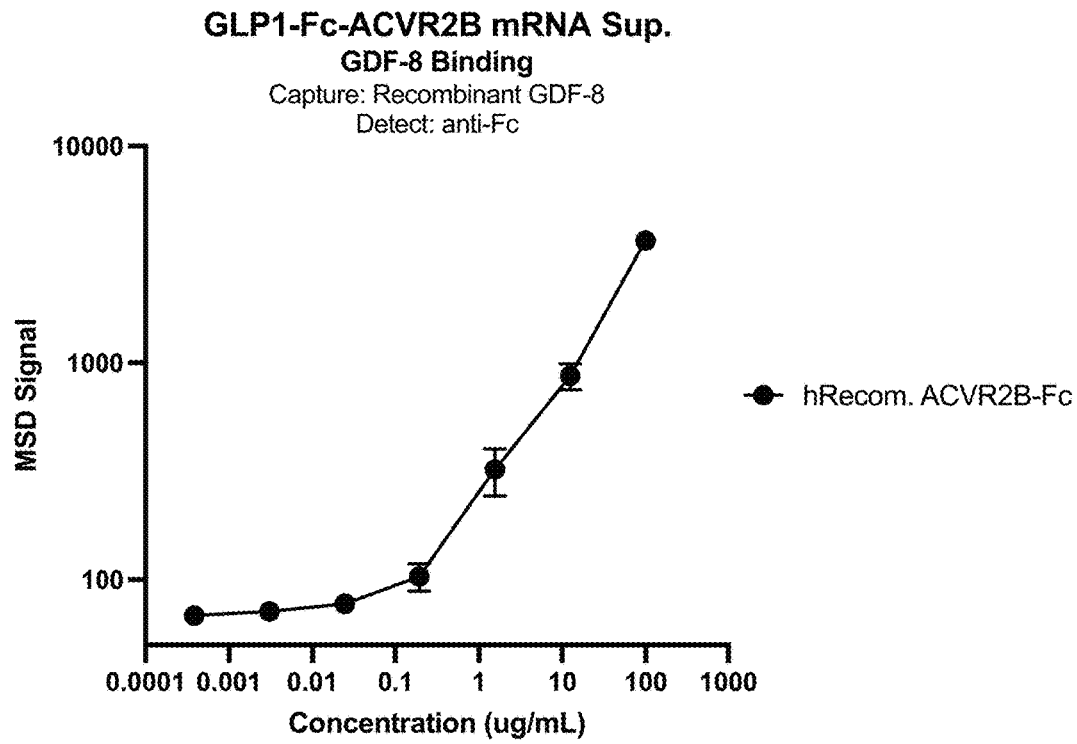

The binding by a recombinant human ACVR2B-Fc fusion protein to activin A (also known as Inhibin beta A) was characterized using a Meso Scale Discovery (MSD) platform-based assay. Briefly, Activin A was coated on a plate and 8× serial dilutions of the purified recombinant human ACVR2B-Fc fusion protein were also added in a series of wells. The protein captured by the plate-bound Activin A was detected using an anti-human Fc antibody and a SULFO-TAG conjugated secondary antibody. As shown in FIG. 11B, the recombinant human ACVR2B-Fc fusion protein exhibited a dose-dependent binding to Activin A.

Figure 11C:
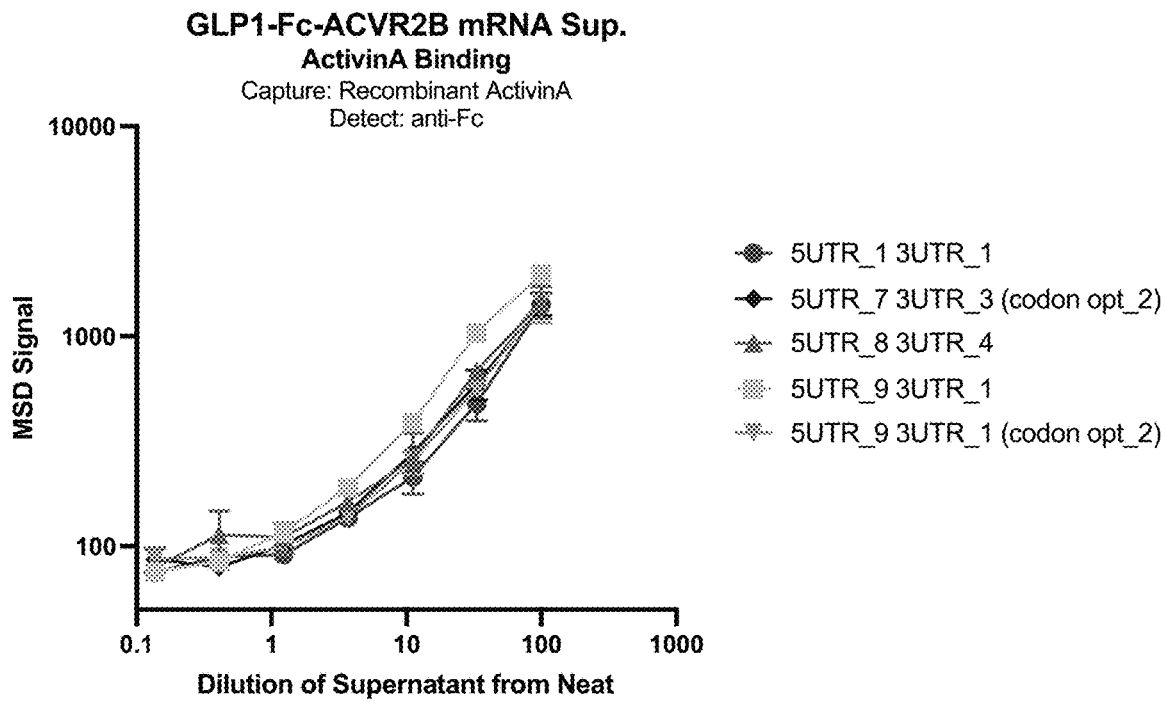
Figure 11D:
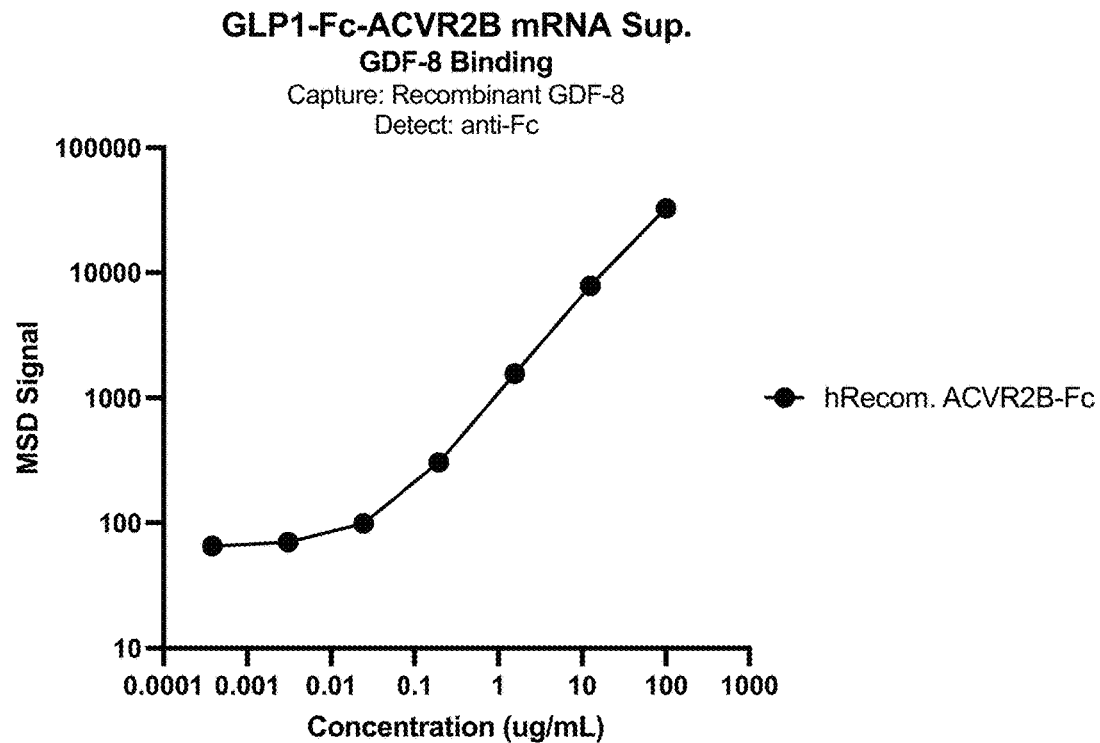
Figure 11E:
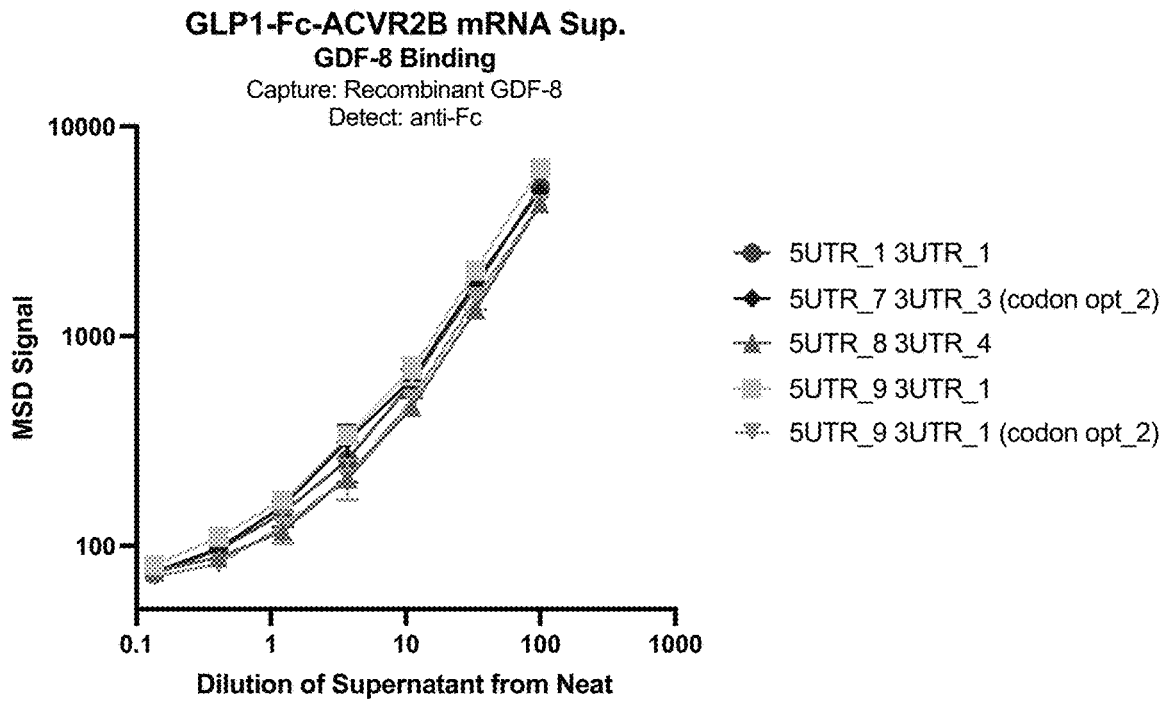

The binding to Activin A by the GLP-1-Fc-ACVR2B fusion protein produced using the mmRNA constructs was investigated using a Meso Scale Discovery (MSD) platform-based assay. Briefly, HEK293T cells were transfected with each mRNA construct using lipofectamine 2000, and culture supernatants were collected after 48 hours. Activin A was coated on a plate, and 3× serial dilutions of the culture supernatants were added to the plate for capture by the plate-bound Activin A. The protein captured by the plate-bound Activin A was detected using an anti-human Fc antibody and a SULFO-TAG conjugated secondary antibody. The MSD signals generated by the culture supernatants of HEK293T cells transfected with different mmRNA constructs were plotted as a line graph. The results are shown in FIG. 11C. These results demonstrate, inter alia, that the purified GLP-1-Fc-ACVR2B chimeric protein secreted in culture supernatants by HEK293T cells transfected with different mmRNA constructs binds to the human Activin A.

The binding by a recombinant human ACVR2B-Fc fusion protein to GDF-8 (also known as myostatin) was characterized using a Meso Scale Discovery (MSD) platform-based assay. Briefly, GDF-8 was coated on a plate and 8× serial dilutions of the purified recombinant human ACVR2B-Fc fusion protein were also added in a series of wells. The protein captured by the plate-bound GDF-8 was detected using an anti-human Fc antibody and a SULFO-TAG conjugated secondary antibody. As shown in FIG. 11B, the recombinant human ACVR2B-Fc fusion protein exhibited a dose-dependent binding to GDF-8.

The binding to GDF-8 by the GLP-1-Fc-ACVR2B fusion protein produced using the mmRNA constructs was investigated using a Meso Scale Discovery (MSD) platform-based assay. Briefly, HEK293T cells were transfected with each mRNA construct using lipofectamine 2000, and culture supernatants were collected after 48 hours. GDF-8 was coated on a plate, and 3× serial dilutions of the culture supernatants were added to the plate for capture by the plate-bound GDF-8. The protein captured by the plate-bound GDF-8 was detected using an anti-human Fc antibody and a SULFO-TAG conjugated secondary antibody. The MSD signals generated by the culture supernatants of HEK293T cells transfected with different mmRNA constructs were plotted as a line graph. The results are shown in FIG. 11C. These results demonstrate, inter alia, that the purified GLP-1-Fc-ACVR2B chimeric protein secreted in culture supernatants by HEK293T cells transfected with different mmRNA constructs binds to the human GDF-8.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present technology is not entitled to antedate such publication by virtue of prior disclosure.

As used herein, all headings are simply for organization and are not intended to limit the disclosure in any manner. The content of any individual section may be equally applicable to all sections.

EQUIVALENTS

While the disclosure has been disclosed in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

Those skilled in the art will recognize, or be able to ascertain, using no more than routine experimentation, numerous equivalents to the specific embodiments disclosed specifically herein. Such equivalents are intended to be encompassed in the scope of the following claims.

What is claimed is:

1. An mRNA encoding a chimeric protein having a general structure of:

N terminus-(a)-(b)-(c)-C terminus, wherein:
   (a) is a first domain comprising a glucagon-like peptide-1 (GLP-1) receptor agonist comprising the amino acid sequence of SEQ ID NO: 91;
   (b) is a linker adjoining the first domain and a second domain wherein the linker comprises a hinge-CH2-CH3 Fc domain; and
   (c) is the second domain comprising glucose-dependent insulinotropic polypeptide (GIP) receptor (GIPR) modulator comprising the amino acid sequence of SEQ ID NO: 97.

* * * * *